(12) United States Patent
Serrano Marugan et al.

(10) Patent No.: US 9,993,554 B2
(45) Date of Patent: Jun. 12, 2018

(54) USE OF P13K INHIBITORS FOR THE TREATMENT OF OBESITY, STEATOSIS AND AGEING

(75) Inventors: Manuel Serrano Marugan, Madrid (ES); Joaquin Pastor Fernández, Madrid (ES); Sonia Martínez González, Madrid (ES); Ana Ortega Molina, Madrid (ES); James R. Bischoff, Madrid (ES); Julen Oyarzabal Santamarina, Madrid (ES)

(73) Assignee: CENTRO NACIONAL DE INVESTIGACIONES ONCOLOGICAS (CNIO), Madrid (ES)

( * ) Notice: Subject to any disclaimer, the term of this patent is extended or adjusted under 35 U.S.C. 154(b) by 0 days. days.

(21) Appl. No.: 13/880,893

(22) PCT Filed: Jun. 1, 2011

(86) PCT No.: PCT/GB2011/051030
§ 371 (c)(1),
(2), (4) Date: Jan. 1, 2014

(87) PCT Pub. No.: WO2012/052730
PCT Pub. Date: Apr. 26, 2012

(65) Prior Publication Data
US 2014/0154232 A1 Jun. 5, 2014

(30) Foreign Application Priority Data

Oct. 21, 2010 (EP) .................................. 10381033.8

(51) Int. Cl.
| | | |
|---|---|---|
| A61K 31/5377 | (2006.01) | |
| A61K 31/35 | (2006.01) | |
| A61K 45/06 | (2006.01) | |
| C07D 471/10 | (2006.01) | |
| C07D 487/04 | (2006.01) | |
| A61K 31/4985 | (2006.01) | |

(52) U.S. Cl.
CPC .............. *A61K 45/06* (2013.01); *A61K 31/35* (2013.01); *A61K 31/4985* (2013.01); *A61K 31/5377* (2013.01); *C07D 471/10* (2013.01); *C07D 487/04* (2013.01)

(58) Field of Classification Search
CPC combination set(s) only.
See application file for complete search history.

(56) References Cited

U.S. PATENT DOCUMENTS

| | | |
|---|---|---|
| 4,376,110 A | 3/1983 | David et al. |
| 4,486,530 A | 12/1984 | David et al. |
| 8,642,660 B2 | 2/2014 | Goldfarb |
| 2003/0139427 A1 | 7/2003 | Castelhano et al. |

FOREIGN PATENT DOCUMENTS

| | | |
|---|---|---|
| WO | 1988/04298 A1 | 6/1988 |
| WO | 1999/66401 A1 | 12/1999 |
| WO | 2002/010140 A1 | 2/2002 |
| WO | 2002/060492 A1 | 8/2002 |
| WO | 2002/062800 A1 | 8/2002 |
| WO | 2004/022562 A1 | 3/2004 |
| WO | 2004/072080 A1 | 8/2004 |
| WO | 2004/072081 A1 | 8/2004 |
| WO | 2006/046040 A1 | 5/2006 |
| WO | 2007/028051 A2 | 3/2007 |
| WO | 2007/096764 A2 | 8/2007 |
| WO | 2007/127175 A2 | 8/2007 |
| WO | 2008/059373 A1 | 5/2008 |
| WO | 2008/156614 A1 | 12/2008 |
| WO | 2009/007029 A1 | 1/2009 |
| WO | 2010/119264 A1 | 10/2010 |

OTHER PUBLICATIONS

Aubin (Phosphoinositide 3-kinase is required for human adipocyte differentiation in culture, International Journal of Obesity, 2005, 29, pp. 1006-1009).*
Gaal (Efficacy and Safety of Rimonabant for Improvement of Multiple Cardiometabolic Risk Factors in Overweight/Obeses Patients, 2008, Diabetes Care, Suppl 2, pp. S229-S240).*
Spalding, et al. "Dynamics of fat cell turnover in humans" ResearchGate, Nature, vol. 453/5 Jun. 2008, pp. 784-787.
Engelman, Jeffrey; "Targeting PI3K signalling in cancer: opportunities, challenges and limitations;" Reviews, Aug. 2009, vol. 9, 550-562.
Wikipedia, "Phosphoinositide 3-kinase inhibitor," 1-5.
Gustafson, et al.; Restricted Adipogenesis in Hypertrophic ObesityThe Role of WISP2, WNT, and BMP4; Diabetes, vol. 62, Sep. 2013, 2997-3004.
Krishna M. Vasudevan: "AKT-IndependentSignalingDownstreamofOncogenic PIK3CA Mutations in Human Cancer," Cancer Cell 16, 21-32, Jul. 7, 2009 " 2009 Elsevier Inc., 21-32.
Gustafson, et al.; "Insulin resistance and impaired adipogenesis," Trends in Endocrinology and Metabolism, Apr. 2015, vol. 26, No. 4, 193-200.
Widipedia, "Phosphoinositide 3-kinase inhibitor" Sep. 14, 2011, pp. 1-4.

(Continued)

*Primary Examiner* — Kathrien A Cruz
(74) *Attorney, Agent, or Firm* — McDonnell Boehnen Hulbert & Berghoff LLP

(57) ABSTRACT

The first aspect of the invention relates to a phosphoinositide 3-kinase inhibitor for use in the treatment or prevention of a disease or condition associated with the expression of peroxisome proliferator-activated receptor gamma coactivator 1-α (Pgd1α) and/or uncoupling protein 1 (Thermogenin/Ucp1) in brown adipocytes. The disease or condition may be positive energy imbalance-associated, for example, obesity, an obesity-associated disease or condition, steatosis and biological aging (performance aging). Another aspect of the invention provides the use of a phosphoinositide 3-kinase inhibitor for promoting weight loss in an individual.

12 Claims, 43 Drawing Sheets

(56) References Cited

OTHER PUBLICATIONS

Figure 1:
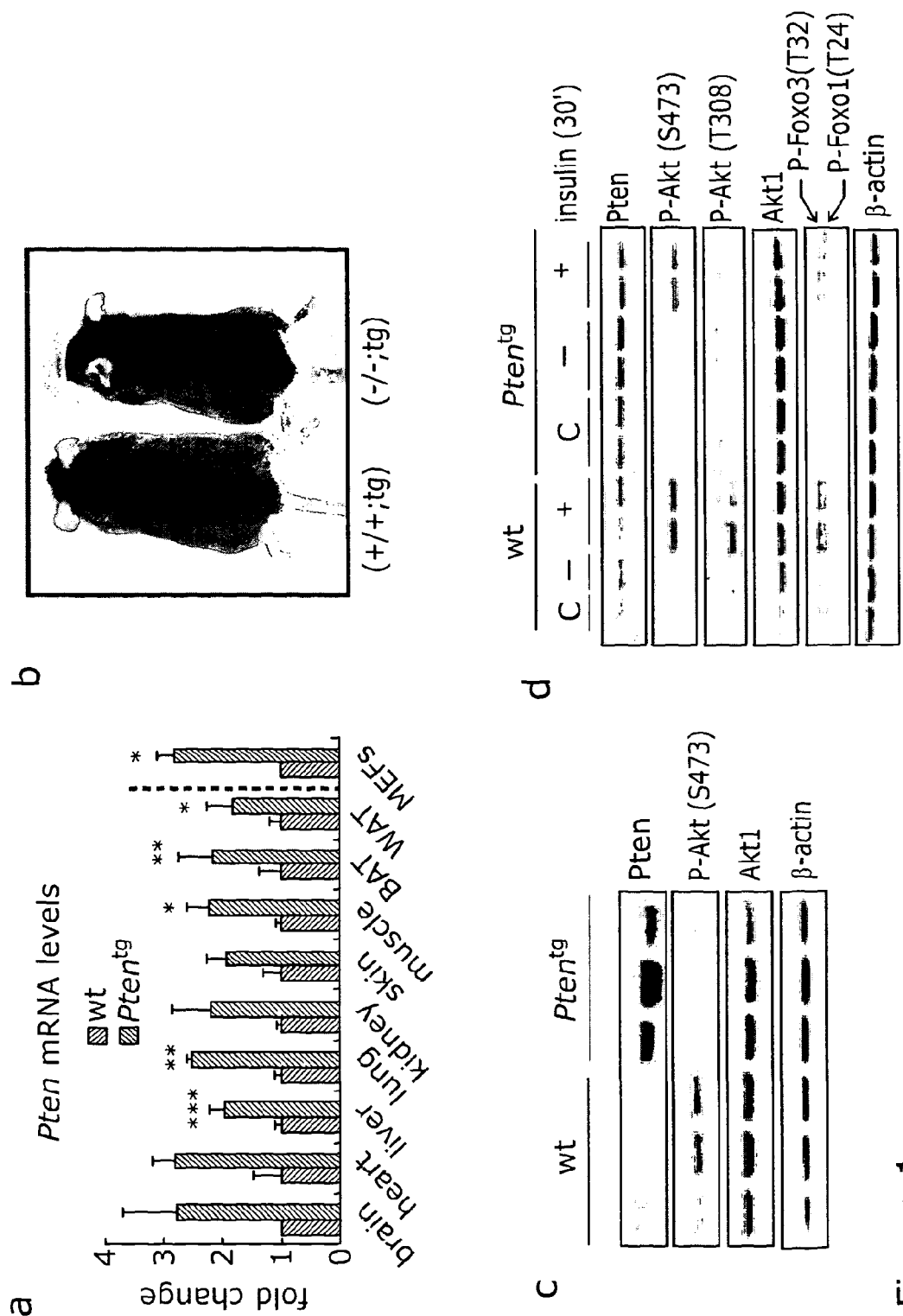
Figure 1:
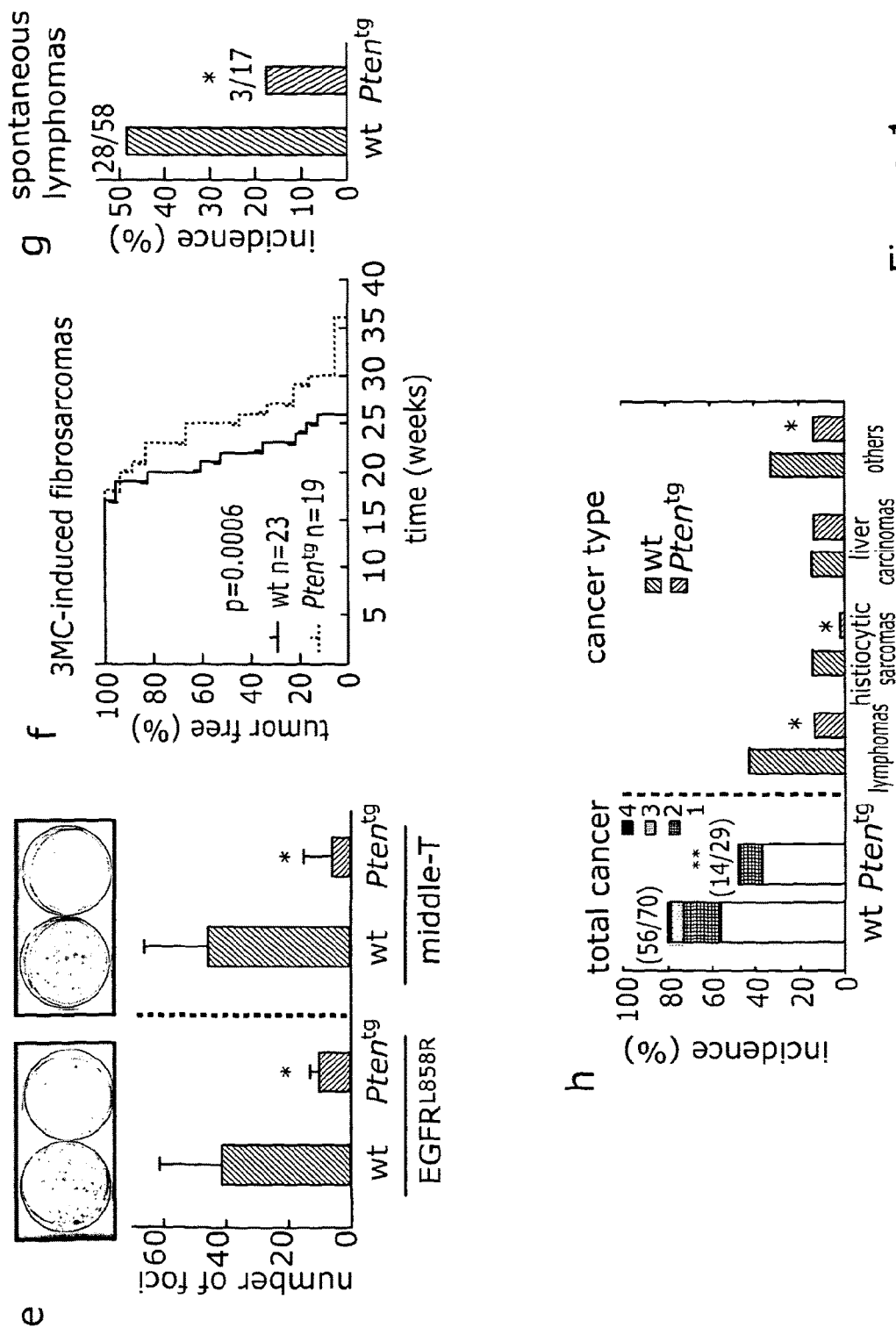

Bartke, Andrzej "Impact of reduced insulin-like growth factor1/Insulin signalling on aging in mammals: novel findings" Aging Cell (2008) vol. 7, pp. 285-290.

Carracedo, A. & Pandolfi, P. P. "The PTEN-PI3K pathway: of feedbacks and cross-talks" Oncogene (2008) vol. 27, pp. 5527-5541.

Chaloub, N. et al., "PTEN and the PI3-kinase pathway in cancer" Annu Rev Pathol. (2009) vol. 4, pp. 127-150.

Daitoku, H. et al., "Regulation of PGC-I promoter activity by protein kinase B and the forkhead transcription factor FKHR" Diabetes (2003) vol. 52, pp. 642-649.

David, Gary S. et al., "Protein iodination with solid state lactoperoxidase" Biochemistry (1974) vol. 13(5), pp. 1014-1021.

Di Cristofano, Antonio et al., "Pten is essential for embryonic development and tumour suppression" Nature Genetics (1998) vol. 19, pp. 348-355.

Dorman, Jennie B. et al., "The age-1 and daf-2 genes function in a common pathway to control the lifespan of Caenorhabditis elegans" Genetics (1995) vol. 141, pp. 1399-1406.

Easton, JB et al., "mTOR and cancer therapy" Oncogene (2006) vol. 25, pp. 6436-6446.

Fontana, L. et al., "Dietary restriction, growth factors and aging: from yeast to humans" Science (2010) vol. 328(5976), pp. 321-326.

Geroldi et al"Perifosine may be of therapeutic usefulness in morbid obese females via inhibition of the PI3K/Akt signaling pathway" Medical Hypotheses (2006) vol. 68(1), p. 236.

Greulich, H. et al., "Oncogenic transformation by inhibitor-sensitive and -resistant EGFR mutants" PLoS Med (2005) vol. 2(11) e313, pp. 1167-1176.

Hempenstall, S.et al., "The impact of acute caloric restriction on the metabolic phenotype in male C57BU6 and DBN2 mice" Mechanisms Ageing and Development (2010) vol. 131, pp. 111-118.

Hennessey, Bryan T. et al., " Exploiting the PI3K/AKT pathway for cancer drug discovery" Nature Rev. Drug Discovery (2005) vol. 4, pp. 988-1004.

Hipkiss, Alan R. "Energy metabolism, altered proteins, sirtuins and ageing: converging mechanisms?" Biogerontology (2008) vol. 9, pp. 49-55.

Ingram, Donald K. et al., "Assessing the predictive validity of psychomotor tests as measures of biological age in mice" Experimental Aging Research (1986) vol. 12(3), pp. 155-162.

Jiang, Weiqin et al. "Dietary energy restriction modulates the activity of AMPK, Akt, and mTor in mammary carcinomas, mammary gland, and liver" Cancer Res. (2008) vol. 68, pp. 5492-5499.

Kajimura, S. et al. "Initiation of myoblast/brown fat switch through a PRDM16-C/EBP-beta transcriptional complex" Nature (2009) vol. 460(7259), pp. 1154-1158.

Kenyon, C. J. "The genetics of ageing" Nature (2010) vol. 464, pp. 504-512.

Kops, G. J. et al. "Direct control of the Forkhead transcription factor AFX by protein kinase B" Nature (1999) vol. 398, pp. 630-634.

Kozak, L. P. et al. "UCPI: its involvement and utility in obesity" Int J Obes (Lond) (2008) vol. 32 Suppl 7, pp. S32-S38.

Li, X. et al., "Akt/PKB regulates hepatic metabolism by directly inhibiting PGC-I alpha transcription coactivator" Nature (2007) vol. 447, pp. 1012-1016.

Lidell, M. E. et al., "Brown adipose tissue—a new role in humans?" Nat Rev Endocrinol (2010) vol. 6, pp. 319-325.

Matheu, A et al. "Regulation of the INK4a1ARF locus by histone deacetylase inhibitors" J Bioi Chem (2005) vol. 280 (51), pp. 42433-42441.

Matheu, A. et al. "Anti-aging activity of the Ink4/Arf locus" Aging Cell (2009) vol. 8, pp. 152-161.

Matheu, A. et al. "Delayed ageing through damage protection by the Arf/p53 pathway" Nature (2007) vol. 448(19), pp. 375-379.

Matsumoto, M. et al. "Dual role of transcription factor FoxOI in controlling hepatic insulin sensitivity and lipid metabolism" Journal of Clinical Investigation (2006) vol. 116(9), pp. 2464-2472.

Matsumoto, M. et al. "Impaired regulation of hepatic glucose production in mice lacking the forkhead transcription factor Foxo1 in liver" Cell Metabolism (2007) vol. 6, pp. 208-216.

Mihaylova, V. T. et al. "The PTEN tumor suppressor homolog in Caenorhabditis elegans regulates longevity and dauer brmation in an insulin receptor-like signaling pathway" Proc Natl Acad Sci USA(1999) vol. 96, pp. 7427-7432.

Moore, T. et al. "Dietary energy balance modulates signaling through the Akt/mammalian target of rapamycin pathways in multiple epithelial tissues" Cancer Prevention Research (2008) vol. 1(1), pp. 65-76.

Morris, Jason Z. et al. "A phosphatidylinositol-3-¬OH kinase family member regulating longevity and diapause in Caenorhabditis elegans" Nature (1996) vol. 382(8), pp. 536-539.

Nedergaard, Jan et al. "The changed metabolic world with human brown adipose tissue: therapeutic visions" Cell Metabolism (2010) vol. 11, pp. 268-272.

Palmero, I. et al. "Induction of senescence by oncogenic Ras" Methods Enzymology (2001) vol. 333, pp. 247-256.

Parsons et al. "Mutatins in a signalling pathway" Nature (2005), vol. 436, p. 792.

Podsypanina, K. et al. "Mutation of Pten/Mmacl in mice causes neoplasia in multiple organ systems" Proc Natl Acad Sci USA (1999) vol. 96, pp. 1563-1568.

Puig, Oscar et al. "Transcriptional feedback control of insulin receptor by dFOXO/FOXO1" Genes Development (2005) vol. 19, pp. 2435-2446.

Puigserver, P. et al. "Peroxisome proliferator-activated receptor-gamma coactivator 1 alpha (PGC-I alpha): tanscriptional coactivator and metabolic regulator" Endocrine Reviews (2003) vol. 24(1), pp. 78-90.

Puigserver, P. et al. "A cold-inducible coactivator of nuclear receptors linked to adaptive thermogenesis" Cell (1998) vol. 92, pp. 829-839.

Puigserver, P. et al. "Insulin-regulated hepatic gluconeogenesis through FOXO1-PGC-1alpha interaction" Nature (2003) vol. 423, pp. 550-555.

Renner, Oliver et al. "Mouse models to decipher the PI3K signalling network in human cancer" Current Molecular Medicine (2009) vol. 9, pp. 612-625.

Seale, P. et al. "Transcriptional control of brown fat determination by PRDMI6" Cell Metab (2007) vol. 6(1), pp. 38-54.

Selman, C. et al. "Ribosomal protein S6 kinase 1 signalling regulates mammalian lifespan" Science (2009) vol. 326 (5949), pp. 140-144.

Serrano, M. et al. "Cancer and ageing: convergent and divergent mechanisms" Nat Rev Mol Cell Bioi (2007) vol. 8, pp. 715-722.

Stambolic, V. et al. "High incidence of breast and endometrial neoplasia resembling human Cowden syndrome in pten +/- mice" Cancer Research (2000) vol. 60, pp. 3605-3611.

Um, S. H. et al. "Absence of S6KI protects against age- and diet-induced obesity while enhancing insulin sensitivity" Nature (2004) vol. 431, pp. 200-205.

Um, S. H. et al. "Nutrient overload, insulin resistance, and ribosomal protein S6 kinase 1, S6K1" Cell Metabolism (2006) vol. 3, pp. 393-402.

Utermark, T. et al. "The p110 alpha isoform of phosphatidylinositol 3-kinase is essential for polyomavirus middle T antigen-mediated transformation" Journal of Virology (2007) vol. 81(13), pp. 7069-7076.

Van der Horst, A. et al. "Stressing the role of Foxo proteins in lifespan and disease" Nature Reviews Moleular Cell Biology (2007) vol. 8, pp. 440-450.

Kamagate, A. et al. "FoX01 Links Hepatic Insulin Action to Endoplasmic Reticulum Stress" Endocrinology (2010) vol. 15(8), pp. 3521-3535.

Zhang et al. "The Role of AEBP1 in Sex-specific diet-induced obesity" Mol Med (2005) vol. 11, pp. 39-47.

Zhao, J. J. et al "The p110alpha isoform of PI3K is essential for proper growth factor signalling and oncogenic transformation" Proc Natl Acad Sci USA (2006) vol. 103, pp. 16296-16300.

(56) References Cited

OTHER PUBLICATIONS

Gomes et al., "Dexclining NAD+ Induces a pseudohypoxic state disrupting nuclear-mitochondrial communication during aging" Cell. (2013) vol. 155(7), pp. 1624-1638.
Abdel-Magid A. F., et al., "Reductive Amination of Aldehydes and Ketones with Sodium Triacetoxyborohydride. Studies on Direct and Indirect Reductive Amination Procedures" J. Org. Chem. (1996) vol. 61, pp. 3849-3862.
Abdel-Magid A. F., et al., "Reductive Amination of Aldehydes and Ketones with Wealky basic Anilines using Sodium Triacetoxyborohydride" Synthesis (1990), pp. 537-539.
Abignente E. et al., "Research on Heterocyclic compounds, XXVII, Synthesis and Antilnflammatory activity of 2-Phenylimidaxo[1,2-b]Pyridazine-3-Carboxylic Acids" II Farmaco (1990) vol. 45(10), pp. 1075-1087.
Gadad, Andanappa K. et al., "Synthesis and anti-tubercular activity of a series of 2-sulfonamido/trifluoromethyl-6-substituted imidazo-[2,1-b]-1,3,4-thiadiazole derivatives" Bioorg. Med. Chem. (2004) vol. 12, pp. 5651-5659.
Marin, Asunción et al., Synthesis and anthelmintic activity of carbamates derived from imidazo[2,1-b][1,3,4] thiadiazole and imidazol[2,1-b]thiazole(*)' Farmaco (1992) vol. 47(1), pp. 63-75.
Bellamy, F.D., et al., Selective reduction of aromatic nitro compounds with stannous chloride in non acidic and non aqueous medium Tetrahedron Letters (1984) vol. 25(8), pp. 839-842.
Bretonnet, Anne-Sophie et al., "NMR screening applied to the fragment-based generation of inhibitors of creatine kinase exploiting an new interaction proximate to the ATP binding site" J. Med. Chem. (2007) vol. 50, pp. 1865-1875.
Cohen, Philip "The development and therapeutic potential of protein kinase inhibitors" Current Opinion in Chemical Biology (1999) vol. 3, pp. 459-465.
Defacqz N., et al., "Synthesis of C5-substituted imidazolines" Tetrahedron Letters 44 (2003), pp. 9111-9114.
Dermer O. C., "Metallic salts of alcohols and alcohol analogs" Chem. Rev. (1934) vol. 14, pp. 385-430.
El-Sherbeny, M.A. et al., "Synthesis and cardiotonic activity of certain imidazo[2,1-b]-1,3,4-thiadiazole derivatives" Boll. Chim. Farm. (1997) vol. 136, pp. 253-256.
Fabio, P. F. et al., "Synthesis of carvon-14 and deuterium labeled 3-nitro-6-propoxyimidazo [1,2-B]pyridazine—an antiparasitic agent" Journal of Labelled Compounds and Pharmaceuticals (1978) vol. 15, pp. 407-412.
Gregson, Stephen J. et al., "Linker length modulates DNA crosslinking reactivity and cytotoxic potency of C8/C/' ether-linked C2-exo-unsatureated pyrrolo[2,1-c][1,4]benzodiazepine (PBD) Dimers" J. Med. Chem. (2004) vol. 47, pp. 1161-1174.
Han So-Yeop et al., "Recent development of peptide coupling reagents in organic synthesis" Tetrahedron (2004) vol. 60, pp. 2447-2467.
Ikemoto T., et al., "Reactions with N-chlorosuccinimide of various 5-methylimidazo[1,2-a]pyridine derivatives with an electron-withdrawings group substituted at the 3-position" Heterocycles (2001) vol. 55(1), pp. 99-108.
Ikemoto T. et al., "A Practical Synthesis of the Chronic Renal Disease Agent, 4,5-Dihydro-3H -1,4,8b-triazaacenaphthylen-3-one Derivatives, Using Regioselective Chlorination of Ethyl 5-methylimidazo[1,2-a ]pyridine-3-carboxylate with N-Chlorosuccinimide" Tetrahedron (2000) vol. 56, pp. 7915-7921.
Katritzky, Alan R. et al., "Regiospecific synthesis of 3-substituted imidazol[1,2-a]pyridines, imidazo[1,2-a]pyrimidines, and imidazo[1,2-c]pyrimidine" J. Org. Chem (2003) vol. 68, pp. 4935-4937.
Katrizky, Alan R. et al., "A novel method for the synthesis of symmetrical vicinal tertiary and secondary diamines" J. Org. Chem. (1990) vol. 55(10), pp. 3209-3213.
Katso, Roy et al., "Cellular function of phosphoinositide 3-kinases: implications for development, immunity, homeostasis, and Cancer" Annu. Rev. Cell. Dev. Boil. (2001) vol. 17, pp. 615-675.
Kobe J. et al., "Synthesis of pyridazine derivatives-XV some electrophilic substitutions on imidazo[1,2-b]-pyridazines" Tetrahedron (1968) vol. 24, pp. 239-245.
Kuwahara M. et al., "Synthetic studies on condensed-azole derivatives. IV. synthesis and anti-asthmatic activities of ω-Sulfamoylalkyloxyimidazo[1,2-b]pyridazines" Chem. Pharm Bull. (1996) vol. 44(1), pp. 122-131.
Lainton J. A. H. et al., "Design and synthesis of a diverse morpholine template library" J. Comb. Chem. (2003) vol. 2, pp. 400-407.
Leslie, Nick R. et al., "Phosphoiositide-regulated kinases and phosphoinositide phosphatases" Chem. Rev. (2001) vol. 101(8), pp. 2365-2380.
Lumma W. C., et al. ", Piperazinylimidazo[1,2-a ]pyrazines with Selective Affinity for in Vitro a-Adrenergic Receptor Subtypes" J. Med. Chem. (1983) vol. 26 (3), pp. 357-363.
Paul, Heinz et al., "Uber einige Umsetzungen von 2,5-Diamino-sowie 2-Amino-1,3,4-thiadiazolen mit α-Ilalogenketonen zu Imidazo [2,1--b] -1,3,4-thiadiazolen" Monatshefte fur Chemie (1977) vol. 108, pp. 665-680.
Plotkin, M. et al. "A practical approach to highly functionalized benzodihydrofurans" Tetrahedron Letters (2000) vol. 41, pp. 2269-2273.
Schlosser M. et al. "Organometallics in Synthesis a Manual" (M. Schlosser, Ed.), Wiley & Sons Ltd: Chichester, UK, 2002.
Severinsen, R. et al. "Versatile strategies for the solid phase synthesis of small heterocyclic scaffolds: [1,3,4]-thiadiazoles and [1,3,4]-oxadiazoles" Tetrahedron (2005) vol. 61, pp. 5565-5575.
Seyden-Penne, J. "Reductions by the Alumino and Borohydrides in Organic Synthesis" VCH, NY, (1991).
Shintani, R., et al. "Carbon-carbon bond-forming enantioselective synthesis of chiral organosilicon compounds by rhodium/chiral diene-catalyzed asymmetric 1,4-addition reaction" Org. Lett. (2005) vol. 7(21), pp. 4757-4759.
Toker, A. "Phosphoinositides and signal transduction" Cellular and Molecular Life Sciences (2002) vol. 59, pp. 761-779.
Vanhaesebroeck, B. et al. "signaling by distinct classes of phosphoinositide 3-kinases" Exp. Cell Research (1999) vol. 253, pp. 239-254.
Vanhaesebroeck, Bart et al. "Phosphoinositide 3-kinases: a conserved family of signal transducers" Trends Biochem. Sci. (1997) vol. 22, pp. 267-272.
Vitse, O. et al. "New imidazo[1,2-a]pyrazines derivatives with bronchodilatory and cyclic nucleotide phosphodiesterase inhibitory activities" Bioorganic & Medicinal Chemistry (1999) vol. 7, pp. 1059-1065.
Lin, Wengwei L. et al., "Preparation of highly functionalized arylmagnesium reagents by the addition of magnesium phenylselenide to arynes" Tetrahedron Letters (2006) vol. 47, pp. 1941-1944.
Werber, G. et al. "The synthesis and reactivity of some 2-amino-5-bromo-1,3,4-thiadiazoles and the corresponding Δ2-1,3,4-thiadiazolines" J. Heterocycl. Chem. (1977) vol. 14, pp. 823-827.
Wiggins, J. M. "A convenient procedure for the reduction of diarylmethanols with disclorodimethylsilane/sodium iodide" Synthetic Communications (1988) vol. 18(7), pp. 741-749.
Wipf, P. et al. "Formal total synthesis of (+)-diepoxin σ" J. Org. Chem. (2000) vol. 65(20), pp. 6319-6337.

\* cited by examiner i j

USE OF PI3K INHIBITORS FOR THE TREATMENT OF OBESITY, STEATOSIS AND AGEING

This application is a U.S. national phase of International Application No. PCT/GB2011/051030, filed Jun. 1, 2011, and claims the benefit of European Patent Application No. 10380133.8, filed Oct. 21, 2010, the disclosures of both of which are hereby incorporated by reference in their entireties.

FIELD OF THE INVENTION

The present invention relates to phosphoinositide 3-kinase (PI3K) inhibitors for use in the treatment or prevention of diseases or conditions associated with the expression of peroxisome proliferator-activated receptor gamma coactivator 1-α (Pgc1α) and/or uncoupling protein 1 (Thermogenin or Ucp1) in brown adipocytes. Such diseases include obesity, obesity-associated diseases or conditions, steatosis and biological aging (performance aging) and are associated with positive energy imbalance. The invention also relates to the use of a phosphoinositide 3-kinase inhibitor for promoting weight loss.

BACKGROUND

Energy Imbalance-Associated Diseases/Conditions Such as Obesity and Related Diseases Obesity is a medical condition associated with excess body fat, and may be treated by dieting or exercise or by the use of anti-obesity drugs, which may act by altering/suppressing appetite, metabolism or absorption of calories. There may not be any current medicament that seeks to treat obesity (or associated conditions) by e.g. increasing the rate of energy expenditure.

PI3K Inhibitors

Phosphatidylinositol 3-kinases (PI3Ks) are a family of lipid and serine/threonine kinases that catalyze the phosphorylation of the membrane lipid phosphatidylinositol (PI) on the 3'-OH of the inositol ring to produce phosphoinositol-3-phosphate (PIP), phosphoinositol-3,4-diphosphate ($PIP_2$) and phosphoinositol-3,4,5-triphosphate ($PIP_3$), which act as recruitment sites for various intracellular signalling proteins, which in turn form signalling complexes to relay extracellular signals to the cytoplasmic face of the plasma membrane. These 3'-phosphoinositide subtypes function as second messengers in intracellular signal transduction pathways (see e.g. Trends Biochem. Sci 22 87,267-72 (1997) by Vanhaesebroeck et al.; Chem. Rev. 101 (8), 2365-80 (2001) by Leslie et al (2001); Annu. Rev. Cell. Dev. Boil. 17, 615-75 (2001) by Katso et al; and Cell. Mol. Life. Sci. 59 (5), 761-79 (2002) by Toker et al).

Multiple PI3K isoforms categorized by their catalytic subunits, their regulation by corresponding regulatory subunits, expression patterns and signalling specific functions (p110α, β, δ, γ) perform this enzymatic reaction (Exp. Cell. Res. 25 (1), 239-54 (1999) by Vanhaesebroeck and Katso et al., 2001, above).

The closely related isoforms p110α and β are ubiquitously expressed, while δ and γ are more specifically expressed in the haematopoietic cell system, smooth muscle cells, myocytes and endothelial cells (see e.g. Trends Biochem. Sci. 22 (7), 267-72 (1997) by Vanhaesebroeck et al). Their expression might also be regulated in an inducible manner depending on the cellular, tissue type and stimuli as well as disease context. Inductibility of protein expression includes synthesis of protein as well as protein stabilization that is in part regulated by association with regulatory subunits.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain containing p85 adapter subunit. Class Ia PI3Ks are activated through tyrosine kinase signalling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p110 regulatory subunit. PI3Kγ is regulated by G protein coupled receptors (GPCRs) via association with βγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

These observations show that deregulation of phosphoinositol-3-kinase and the upstream and downstream components of this signalling pathway is one of the most common deregulations associated with human cancers and proliferative diseases (see e.g. Parsons et al., Nature 436:792 (2005); Hennessey et al., Nature Rev. Drug Discovery 4: 988-1004 (2005).

Several PI3K inhibitors are currently undergoing clinical trials for use in the treatment of certain cancers. Certain inhibitors are also disclosed in unpublished international patent application PCT/GB2010/000773.

mTOR Inhibitors

The mammalian target of rapamycin (mTOR) also known as FK506 binding protein 12-rapamycin associated protein 1 (FRAP1) is a protein which in humans is encoded by the FRAP1 gene. mTOR is a serine/threonine protein kinase that regulates cell growth, cell proliferation, cell motility, cell survival, protein synthesis, and transcription. The inhibition of mTORs are believed to be useful for treating various diseases/conditions, such as cancer (for example, as described in Easton et al. (2006). "mTOR and cancer therapy". *Oncogene* 25 (48): 6436-46).

Dual PI3K and mTOR inhibitors are currently undergoing clinical trials for use in the treatment of certain cancers. Certain inhibitors are also disclosed in unpublished international patent application PCT/GB2010/000773.

The Pten Protein

Pten, which together with p53, Ink4a and Arf, constitute the four more important tumour suppressors in mammals as deduced by their high frequency of inactivation and the large range of tumour types where they are inactivated.

The most prominent function of Pten is to counteract the activity of phosphatidylinositol 3-kinases type I, hereby abbreviated as $PI3K^3$. These kinases mediate signals triggered by insulin, insulin-like growth factors, and many other molecules generally involved in cellular growth and proliferation. Activation of PI3K is followed by the activation of Akt, which, in turn, triggers a complex cascade of events that includes the inhibition of Foxo transcription factors, as well as, feedback loops that ensure that the activity of the pathway is kept within limits[13-17]. A number of genetically-modified animals with decreased activity of the Insulin and Igf1 Signalling (IIS) axis are characterized by an extended longevity[1,2,18]. In the case of the nematode *Caenorhabditis elegans*, decreased PI3K (AGE-1) activity[19] or increased Pten (DAF-18) activity[20], both result in extended longevity and both participate in the same longevity pathway as the IIS axis[21]. However, in the case of mammals, nothing is known about the impact of PI3K signalling on healthspan or aging. Although severe inhibition of PI3K/Akt activity results in pathological defects, diseases and premature lethality[22].

The predominant molecular symptom of ageing is the accumulation of altered gene products. Nutritional studies show that ageing in animals can be significantly influenced by dietary restriction. Genetic analyses have revealed that ageing may be controlled by changes in intracellular NAD/NADH ratio regulating sirtuin activity. Physiological and other approaches indicate that mitochondria may also regulate ageing. A mechanism is proposed which links diet and mitochondria-dependent changes in NAD/NADH ratio to intracellular generation of altered proteins. It is suggested that excessive feeding conditions decrease NAD availability which also decreases metabolism of the triose phosphate glycolytic intermediates, glyceraldehyde-3-phosphate and dihydroxyacetone-phosphate, which can spontaneously decompose into methylglyoxal (MG). MG is a highly toxic glycating agent and a major source of protein advanced-glycosylation end-products (AGEs). MG and AGEs can induce mitochondrial dysfunction and formation of reactive oxygen species (ROS), as well as affect gene expression and intracellular signalling. In dietary restriction—induced fasting, NADH would be oxidised and NAD regenerated via mitochondrial action. This would not only activate sirtuins and extend lifespan but also suppress MG formation[44].

Geroldi et al. (2006, Medical Hypotheses, 68(1):236) is a brief letter suggesting that the use of the Akt activation inhibitor perifosine could be investigated as a speculative treatment for certain diseases. Geroldi et al., state that Zhang et al. (Mol Med 2005; 11:39-47) have shown links between certain disease states and the PI3K/Akt pathway, and on that basis mention some further proposals. Zhang et al. (2005) discloses that AEBP1-overexpressing on female mice (which also have reduced Pten expression, among other things) may display a certain phenotype.

However, it should be noted that Geroldi et al., and Zhang et al., fail to demonstrate that AEBP1-mediated adiposity regulation is regulated by Pten in any way (rather, it speculatively refers to regulation via MAPK activation).

There is no disclosure in the prior art that PI3K and/or mTOR inhibitors may be useful in the treatment of obesity or associated conditions.

DISCLOSURE OF THE INVENTION

The present invention relates to the surprising finding that Pten promotes weight loss, reduced total adiposity and longevity.

Insulin and Igf1 levels modulate the rate of aging across animal evolution[1,2]. In worms and flies, the effects of insulin/Igf1 on longevity are intracellularly mediated by the PI3K/Akt/Foxo pathway[1,2]. However, in mammals, nothing is known about the impact of reduced PI3K pathway activity on aging. Here, we have generated transgenic mice with moderate overexpression of Pten under its own transcriptional regulatory elements. The tumour suppressor Pten counteracts PI3K activity[3] and, accordingly, Pten$^{tg}$ mice have lower levels of PI3K signalling and are protected from cancer. Interestingly, Pten$^{tg}$ mice present a remarkable extension of lifespan (~25% increase in median lifespan). Physiological analyses of these mice showed an elevated rate of energy expenditure, accompanied by severely decreased adiposity and protection from high-fat diet-induced liver steatosis. Accounting for the elevated energy expenditure, we found that brown and white adipose tissues from Pten$^{tg}$ mice express high levels of the uncoupling protein Ucp1 and its transcriptional activator Pgc1α. Also, the brown adipose tissue of Pten$^{tg}$ mice contains lower levels of active (i.e., phosphorylated) Akt, which is a negative regulator of both Pgc1α and its critical partner Foxo1[4-7]. Moreover, in vivo administration of a synthetic PI3K inhibitor elevates the expression of Pgc1α and Ucp1 in the brown adipose tissue. Finally, Pten$^{tg}$ fibroblasts programmed in vitro with Prdm16 and C/Ebpβ, master factors for brown adipocyte differentiation[8,9], formed ectopic subcutaneous brown adipose pads more efficiently than non-transgenic controls, indicating that the effects of Pten on brown adipocytes are cell autonomous. Together, these observations extend to mammals the evolutionary conserved modulation of longevity by the PI3K pathway and uncover a role of Pten in promoting nutrient combustion by brown adipocytes. Combustion of nutrients (i.e., energy expenditure) by brown adipocytes decreases the systemic damage associated to elevated calorie intake and may be a mechanism for Pten-mediated longevity.

Excessive calorie consumption (positive energy imbalance) is associated with numerous other diseases and conditions, including obesity and obesity-associated diseases. Obesity is a disease characterized by the excessive accumulation of corporal fat, which produces deleterious effects to the health.

There will now be described new uses for a phosphoinositide 3-kinase inhibitor, which may be referred to herein as the "use(s) of the invention".

The first aspect of the present invention relates to a phosphoinositide 3-kinase inhibitor for use in the treatment or prevention of a disease or condition associated with the expression of peroxisome proliferator-activated receptor gamma coactivator 1-α (Pgc1α) and/or uncoupling protein 1 (Thermogenin or Ucp1) in brown adipocytes (e.g. a disease or condition that would benefit from the over-expression, or up-regulation, of such proteins). The disease or condition may be associated with the expression of peroxisome proliferator-activated receptor gamma coactivator 1-α and uncoupling protein 1 in brown adipocytes (e.g. the disease or condition may benefit from the over-expression, or up-regulation, of both proteins).

The expression of high levels of the uncoupling protein Ucp1 and/or its transcriptional activator Pgc1α may account for an elevated rate of energy expenditure, decreased adiposity and/or protection from high fat diet-induced liver steatosis in mammals. Hence, the use of the invention includes the treatment or prevention of any disease or condition that may benefit from these effects.

Peroxisome proliferator-activated receptor gamma coactivator 1-α (PGC1α) is transcriptional coactivator that, in humans, is encoded by the PPARGC1 gene (also know as LEM6, PGC-1(alpha), PGC-1v, PGC1, PGC1A and PPARAGC1A). Exemplary protein and mRNA sequences include NM_013261 (human mRNA), NP_037393 (human protein), NM_008904 (mouse mRNA) and NP_032930 (mouse protein).

Uncoupling protein 1 (called uncoupling protein by its discoverers and now known UCP1 or Thermogenin) is an uncoupling protein found in the mitochondria of brown adipose tissue (BAT). It is used to generate heat by non-shivering thermogenesis. Non-shivering thermogenesis is the primary means of heat generation in hibernating mammals and in human infants. Exemplary protein and mRNA sequences include NM_021833 (human mRNA), NP_068605 (human protein), NM_009463 (mouse mRNA) and NP_033489 (mouse protein).

In one embodiment the disease or condition is treatable by the overexpression of peroxisome proliferator-activated receptor gamma coactivator 1-α and/or uncoupling protein 1 in brown adipocytes in brown adipocytes. The disease or condition may be treatable by the overexpression of peroxisome proliferator-activated receptor gamma coactivator 1-α and uncoupling protein 1 in brown adipocytes.

The disease or condition to be treated by the use of the invention may also be associated with decreased levels of Igf1 (which may be resultant of the effect of the PI3K inhibition). This may promote calorific restriction, and this factor may therefore be useful in the treatment of the diseases mentioned herein.

In a further embodiment, the disease or condition is an energy expenditure-associated disease or condition. Oxygen consumption is a classical means of assessing energy expenditure, the major component of energy balance. When energy balance is positive (i.e. the body consumes more energy than it expends), weight increases. This is observed during the dynamic phase of obesity and during body composition changes with aging. Hence, by "energy expenditure-associated disease or condition" we mean any disease or condition associated with the rate of energy consumption in an individual. Such diseases or conditions include obesity and obesity-associated diseases or conditions.

Thus, the disease or condition may be an energy imbalance-associated disease or condition (i.e. a disease or condition associated with an excess or a deficiency of energy in an individual). Preferably, the disease or condition is associated with a positive energy imbalance-associated disease or condition (i.e. a gaining energy imbalance). However, although less preferred, the disease or condition may also be associated with a negative energy imbalance (i.e. a losing energy imbalance). Diseases and conditions associated with such physiological states include obesity, an obesity-associated disease or condition, steatosis and biological aging (performance aging). In particular, the disease or condition that may be treated is obesity associated with a positive energy imbalance (e.g. the obesity may be treated or prevented by promoting energy expenditure).

In a preferred embodiment the energy expenditure-associated disease or condition is obesity. By "obesity" we mean an accumulation of excess body fat to the extent that it may have an adverse effect on health. In humans, body mass index (BMI) is commonly used to define obesity. BMI is calculated according to the following formula—BMI=kilograms/meters$^2$. A BMI of 25.0-29.9 indicates an individual is overweight, a BMI of 30.0-34.9 indicates Class I obesity, a BMI of 35.0-39.9 indicates Class II obesity and a BMI of ≥40.0 indicates Class II obesity, according to World Health Organisation guidelines.

The disease or condition may also be obesity-associated. Obesity is generally deleterious to health and can lead to a number of associated conditions including Type 2 (adult-onset) diabetes, high blood pressure, stroke heart attack, heart failure, gallstones gout and gouty arthritis, osteoarthritis, sleep apnea and pickwickian syndrome. For the avoidance of doubt, the obesity-associated diseases and conditions may not be cancer (although, given that obesity may be considered a risk for cancer, the prevention of cancer may occur as an indirect consequence of the treatment). Hence, the disease or condition to be treated/prevented is directly associated with energy imbalance, and is therefore preferably obesity itself. However, in an embodiment, the disease or condition to be treated may include in addition to obesity itself a further obesity-associated condition (such as one mentioned hereinbefore or e.g. cancer, given that the treatment or prevention of obesity may ultimately prevent (as an indirect consequence) such obesity-associated diseases/conditions).

The study of energy expenditure has deep roots in understanding aging and lifespan in all species. In humans, total energy expenditure decreases substantially in advanced age resulting from parallel changes in resting metabolic rate (RMR) and active energy expenditure. For RMR, this reduction appears to be due to a reduction in organ mass and specific metabolic rates of individual tissues. However, these anatomical changes explain very little regarding the decline in activity energy expenditure, which is governed by both genetic and environmental sources. Recent evidence suggests that activity EE has an important role in dictating lifespan and thus places emphasis on future research to uncover the underlying biological mechanisms. Thus, in one embodiment the energy expenditure-associated disease or condition is biological aging (performance aging).

By "biological aging", also known as performance aging, we mean the change in the biology of an organism as it ages after its initial maturity (e.g. childhood). Hence, by "treating biological aging" we mean that the biological/performance age of an individual is reduced relative to their chronological age (i.e. one or more biomarker of biological aging is improved, relative to the value predicted for the individual's chronological age). There are numerous methods for determining biological age, for a detailed review see Biological Aging Methods and Protocols (Methods in Molecular Biology), 2007, Trygve O. Tollefsbol (ed.), Humana Press. However, two reliable methods include measurement of neuromuscular coordination testing (such as the "tightrope test" for rodents) and/or insulin resistance. For specific protocols, see the present Examples section. In one embodiment "biological aging" includes both measured parameters of performance aging and perceived parameters of aging. Other measurements of biological aging include wound healing, hair graying, hair regrowth and osteoporosis.

In an alternative embodiment, the energy expenditure-associated disease or condition is steatosis, in particular, liver steatosis. Steatosis is the abnormal and excessive accumulation of cellular lipids.

In one embodiment of the first aspect of the invention the phosphoinositide 3-kinase inhibitor of the invention is a Class I phosphoinositide 3-kinase inhibitors, Class II phosphoinositide 3-kinase inhibitors or Class III phosphoinositide 3-kinase inhibitors. Class I phosphoinositide 3-kinase inhibitors of the invention may be a Class IA or a Class1B phosphoinositide 3-kinase inhibitor. For example Class IA phosphoinositide 3-kinase inhibitors may inhibit isoform p110α, isoform p110β and/or isoform p110δ. Preferably, isoform p110α and isoform p110δ are inhibited. Alternatively, where the phosphoinositide 3-kinase inhibitor is a Class IB inhibitor, preferably isoform p110γ is inhibited.

A compound that is a PI3K inhibitor (e.g. class I PI3K inhibitor, such as PI3Kα) may be easily determined by the skilled person. For instance, it will include any substance/compound that exhibits a PI3K inhibitory effect as may be determined in a test described herein. In particular, a compound/substance may be classed as a PI3K inhibitor if it is found to exhibit 50% inhibition at a concentration of 200 μM or below (for example at a concentration of below 100 μM, e.g. below 50 μM, or even below 10 μM, such as below 1 μM).

For example, a compound/substance may be classed as a PI3K inhibitor if it is found to exhibit:
(i) in the in vitro PI3K activity assay described hereinafter 50% inhibition at a concentration of 200 μM or below, in particular below 50 μM, e.g below 10 μM (most preferably below 1 μM, or even below 0.1 μM); and/or
(ii) in the AKT phosphorylation inhibition cell assay (Western Blot analysis) 50% inhibition at a concentration of 100 μM or below, in particular below 50 μM, e.g below 10 μM (most preferably below 1 μM, or even below 0.1 μM).

For the purposes of this invention the PI3K inhibitor may also act as an inhibitor of another protein or lipid kinase, such as mTOR. Hence, in an embodiment, the PI3K inhibitor is a single inhibitor and in a separate embodiment it may also be a "dual inhibitor", i.e. it may also inhibit mTOR (as may be determined in a test known to the skilled person, e.g. such as that described herein).

Thus, the phosphoinositide 3-kinase inhibitor of the invention may be selected from the group consisting of wortmannin, demethoxyviridin, LY294002, PX-866, palomid 529, GSK615, 1087114, phosphatase and tensin homolog (Pten) and any of the phosphoinositide 3-kinase inhibitors listed in Table A (which PI3K inhibitors may also inhibit mTOR), below.

TABLE A

| Chemical Structure | Name/Code | Company |
|---|---|---|
| 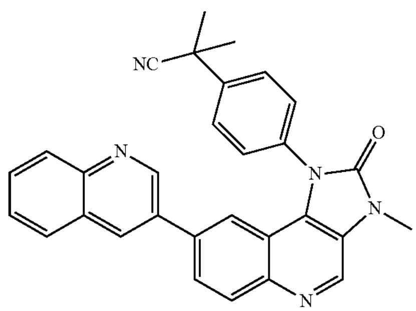 [SMILES: Cn1c(=O)n(-c2ccc(C(C)(C)C#N)cc2)c2c3cc(-c4cnc5ccccc5c4)ccc3ncc21] | BEZ-235 | Novartis AG |
| 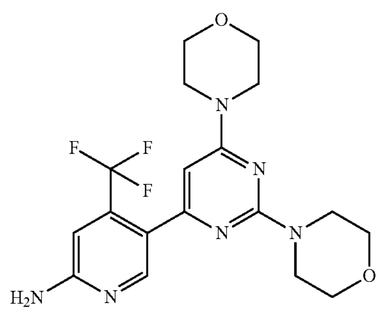 | BKM-120 | Novartis AG |
| 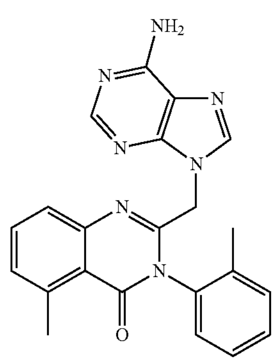 [SMILES: Cc1ccccc1-n1c(Cn2cnc3c(N)ncnc32)nc2cccc(C)c2c1=O] | CAL-101 | ICOS Corp |
| | CAL-263 | ICOS Corp |
| | XL-147 | Exelixis |
| | XL-765 | Exelixis |

TABLE A-continued

| Chemical Structure | Name/Code | Company |
|---|---|---|
| 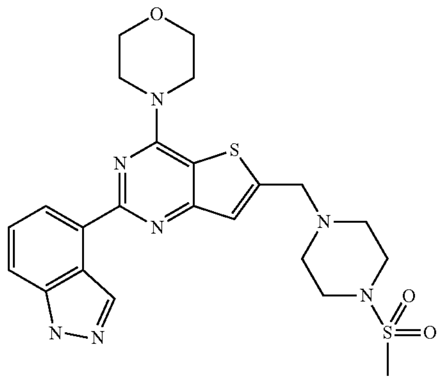 [SMILES: CS(=O)(=O)N1CCN(Cc2cc3nc(-c4cccc5[nH]ncc45)nc(N4CCOCC4)c3s2)CC1] | GDC-0941 | Genentech |
| | PI3K inhibitor, Bayer | Bayer |
| 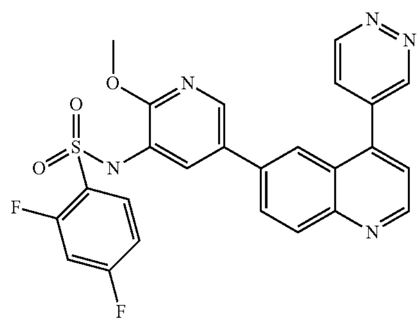 [SMILES: COc1ncc(-c2ccc3nccc(-c4ccnnc4)c3c2)cc1NS(=O)(=O)c1ccc(F)cc1F] | GSK2126458 | GSK |
| 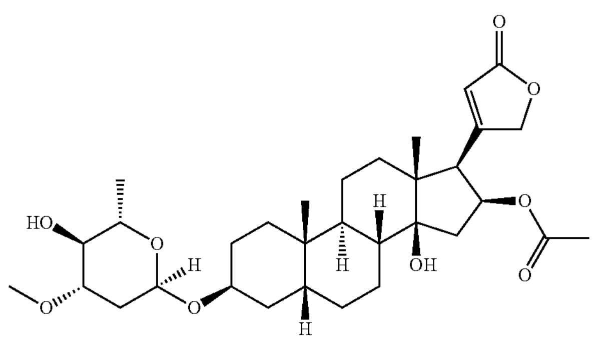 | PBI-05204 | Phoenix Biotechnology Inc |
| 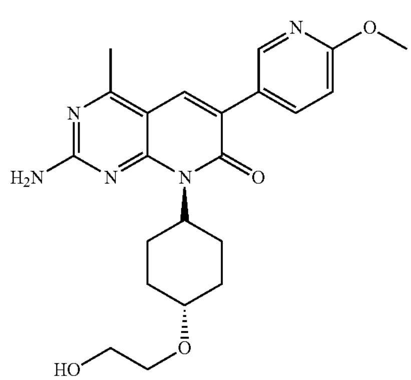 | PF-4691502 | Pfizer |

TABLE A-continued

PI3K inhibitors

| Chemical Structure | Name/Code | Company |
|---|---|---|
| 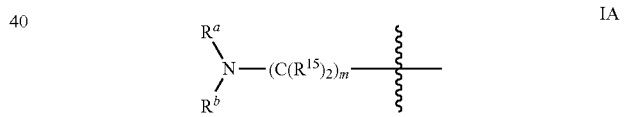 | SF-1126 | Semafore |
| 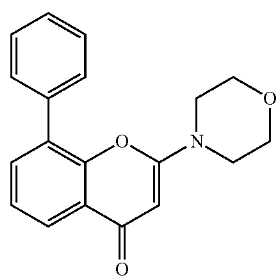 [SMILES: O=c1cc(N2CCOCC2)oc2c(-c3ccccc3)cccc12] | LY294002 | Lilly |

The PI3K inhibitors mentioned in Table A above may be known and are currently in clinical trials.

The PI3-K inhibitor of the invention may also be a compound of formula I:

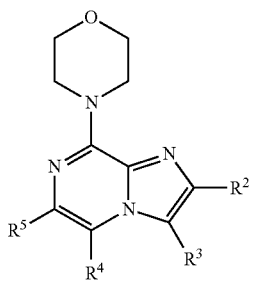

I wherein:
$R^2$ and $R^3$ independently represent:
(i) hydrogen;
(ii) $Q^1$;
(iii) $C_{1-12}$ alkyl optionally substituted by one or more substituents selected from =O, =S, =N($R^{10a}$) and $Q^2$; or $R^2$ or $R^3$ may represent a fragment of formula IA,

IA m represents 0, 1, 2, 3, 4, 5 or 6;
each $R^{15}$ represents hydrogen, halo (e.g. fluoro) or $C_{1-6}$ alkyl optionally substituted by one or more substituents selected from $E^1$; or
the two $R^{15}$ groups may linked together to form (along with the requisite carbon atom to which those $R^{15}$ groups are necessarily attached) a 3- to 6-membered (spiro-cyclic) ring, which ring optionally contains one or more double bonds, and optionally contains a further heteroatom selected from nitrogen, sulfur and oxygen, and which ring is optionally substituted by one or more substituents selected from $E^2$;
$R^a$ and $R^b$ are linked together, along with the requisite nitrogen atom to which they are necessarily attached, to form a first 3- to 7-membered cyclic group, optionally containing one further heteroatom selected from nitrogen, sulfur and oxygen, and which ring:
(a) is fused to a second ring that is either a 3- to 7-membered saturated heterocycloalkyl group containing one to four heteroatoms selected from oxygen, sulfur and nitrogen (preferably oxygen and nitrogen), a 3- to 12-membered saturated carbocyclic ring, or an unsaturated 5- to 12-membered carbocyclic or heterocyclic ring (in which the heteroatoms are preferably selected from sulfur and, especially, nitrogen and oxygen);

(b) comprises a linker group —$(C(R^x)_2)_p$— and/or —$(C(R^x)_2)_r$—O—$(C(R^x)_2)_s$— (wherein p is 1 or 2; r is 0 or 1; s is 0 or 1; and each $R^x$ independently represents hydrogen or $C_{1-6}$ alkyl), linking together any two non-adjacent atoms of the first 3- to 7-membered ring (i.e. forming a bridged structure); or (c) comprises a second ring that is either a 3- to 12-membered saturated carbocyclic ring or a 3- to 7-membered saturated heterocycloalkyl group containing one to four heteroatoms selected from oxygen and nitrogen, and which second ring is linked together with the first ring via a single carbon atom common to both rings (i.e. forming a spiro-cycle), all of which cyclic groups, defined by the linkage of $R^a$ and $R^b$, are optionally substituted by one or more substituents selected from =O and $E^3$;

$R^4$ represents hydrogen or a substituent selected from halo, —CN, —$OR^{10b}$, —$N(R^{10b})R^{11b}$, —$C(O)N(R^{10b})R^{11b}$, —$C(O)R^{10b}$, $C_{1-6}$ alkyl and heterocycloalkyl (e.g. a 3- to 7-membered heterocycloalkyl), which latter two groups are optionally substituted by one or more substituents selected from $E^4$ and =O;

but wherein at least one of $R^2$, $R^3$ and $R^4$ represents a substituent other than hydrogen;

$R^5$ represents aryl or heteroaryl (both of which are optionally substituted by one or more substituents selected from $E^5$);

each $Q^1$ and $Q^2$ independently represents, on each occasion when used herein:

halo, —CN, —$NO_2$, —$N(R^{10a})R^{11a}$, —$OR^{10a}$, —C(=Y)—$OR^{10a}$, —C(=Y)—$OR^{10a}$, —C(=Y)$N(R^{10a})R^{11a}$, —OC(=Y)—$R^{10a}$, —OC(=Y)—$OR^{10a}$, —OC(=Y)$N(R^{10a})R^{11a}$, —$OS(O)_2OR^{10a}$, —OP(=Y)$(OR^{10a})(OR^{11a})$, —OP$(OR^{10a})(OR^{11a})$, —$N(R^{12a})C(=Y)R^{11a}$, —$N(R^{12a})C(=Y)OR^{11a}$, —$N(R^{12a})C(=Y)N(R^{10a})R^{11a}$, —$NR^{12a}S(O)_2R^{10a}$, —$NR^{12a}S(O)_2N(R^{10a})R^{11a}$, —$S(O)_2N(R^{10a})R^{11a}$, —SC(=Y)$R^{10a}$, —$S(O)_2R^{10a}$, —$SR^{10a}$, —$S(O)R^{10a}$, $C_{1-12}$ alkyl, heterocycloalkyl (which latter two groups are optionally substituted by one or more substituents selected from =O, =S, =$N(R^{10a})$ and $E^6$), aryl or heteroaryl (which latter two groups are optionally substituted by one or more substituents selected from $E^7$);

each $R^{10a}$, $R^{11a}$, $R^{12a}$, $R^{10b}$, $R^{11b}$ and $R^{12b}$ independently represent, on each occasion when used herein, hydrogen, $C_{1-12}$ alkyl, heterocycloalkyl (which latter two groups are optionally substituted by one or more substituents selected from =O, =S, =$N(R^{20})$ and $E^{10}$), aryl or heteroaryl (which latter two groups are optionally substituted by one or more substituents selected from $E^{11}$); or any relevant pair of $R^{10a}$, $R^{11a}$ and $R^{12a}$ (for example, when attached to the same atom, adjacent atom (i.e. 1,2-relationship) or to atoms that are two atom atoms apart, i.e. in a 1,3-relationship) and/or any pair of $R^{10b}$ and $R^{11b}$ may be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (preferably, double bonds), and which ring is optionally substituted by one or more substituents selected from =O, =S, =$N(R^{20})$ and $E^{12}$;

each $E^1$, $E^2$, $E^3$, $E^4$, $E^5$, $E^6$, $E^7$, $E^{10}$, $E^{11}$ and $E^{12}$ independently represents, on each occasion when used herein:

(i) $Q^4$;

(ii) $C_{1-12}$ alkyl optionally substituted by one or more substituents selected from =O and $Q^5$; or any two $E^1$, $E^2$, $E^3$, $E^4$, $E^5$, $E^6$, $E^7$, $E^{10}$, $E^{11}$ or $E^{12}$ groups, for example on $C_{1-12}$ alkyl groups, e.g. when they are attached to the same or adjacent carbon atoms or on aryl groups, e.g. when attached to adjacent carbon atoms, may be linked together to form a 3- to 12-membered ring, optionally containing one or more (e.g. one to three) unsaturations (preferably, double bonds), and which ring is optionally substituted by one or more substituents selected from =O and $J^1$;

each $Q^4$ and $Q^5$ independently represent, on each occasion when used herein:

halo, —CN, —$NO_2$, —$N(R^{20})R^{21}$, —$OR^{20}$, —C(=Y)—$R^{20}$, —C(=Y)—$OR^{20}$, —C(=Y)$N(R^{20})R^{21}$, —OC(=Y)—$R^{20}$, —OC(=Y)—$OR^{20}$, —OC(=Y)$N(R^{20})R^{21}$, —$OS(O)_2OR^{20}$, —OP(=Y)$(OR^{20})(OR^{21})$, —OP$(OR^{20})(OR^{21})$, —$N(R^{22})C(=Y)R^{21}$, —$N(R^{22})C(=Y)OR^{21}$, —$N(R^{22})C(=Y)N(R^{20})R^{21}$, —$NR^{22}S(O)_2R^{20}$, —$NR^{22}S(O)_2N(R^{20})R^{21}$, —$S(O)_2N(R^{20})R^{21}$, —SC(=Y)$R^{20}$, —$S(O)_2R^{20}$, —$SR^{20}$, —$S(O)R^{20}$, $C_{1-6}$ alkyl, heterocycloalkyl (which latter two groups are optionally substituted by one or more substituents selected from =O and $J^2$), aryl or heteroaryl (which latter two groups are optionally substituted by one or more substituents selected from $J^3$);

each Y independently represents, on each occasion when used herein, =O, =S, =$NR^{23}$ or =N—CN;

each $R^{20}$, $R^{21}$, $R^{22}$ and $R^{23}$ independently represent, on each occasion when used herein, hydrogen, $C_{1-6}$ alkyl, heterocycloalkyl (which latter two groups are optionally substituted by one or more substituents selected from $J^4$ and =O), aryl or heteroaryl (which latter two groups are optionally substituted by one or more substituents selected from $J^5$); or any relevant pair of $R^{20}$, $R^{21}$ and $R^{22}$ may (for example, when attached to the same atom, adjacent atom (i.e. 1,2-relationship) or to atoms that are two atom atoms apart, i.e. in a 1,3-relationship) be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (preferably, double bonds), and which ring is optionally substituted by one or more substituents selected from $J^6$ and =O; each $J^1$, $J^2$, $J^3$, $J^4$, $J^5$ and $J^6$ independently represents, on each occasion when used herein:

(I) $Q^7$;

(ii) $C_{1-6}$ alkyl or heterocycloalkyl, both of which are optionally substituted by one or more substituents selected from =O and $Q^8$;

each $Q^7$ and $Q^8$ independently represents, on each occasion when used herein:

—CN or, preferably, halo, —$N(R^{50})R^{51}$, —$OR^{50}$, —C(=$Y^a$)—$R^{50}$, —C(=$Y^a$)—$OR^{50}$, —C(=$Y^a$)$N(R^{50})R^{51}$, —$N(R^{52})C(=Y^a)R^{51}$, —$NR^{52}S(O)_2R^{50}$, —$S(O)_2R^{50}$, —$SR^{50}$, —$S(O)R^{50}$ or $C_{1-6}$ alkyl optionally substituted by one or more fluoro atoms;

each $Y^a$ independently represents, on each occasion when used herein, =O, =S, =$NR^{53}$ or =N—CN;

each $R^{50}$, $R^{51}$, $R^{52}$ and $R^{53}$ independently represents, on each occasion when used herein, hydrogen or $C_{1-6}$ alkyl optionally substituted by one or more substituents selected from fluoro, —$OR^{60}$ and —$N(R^{61})R^{62}$; or any relevant pair of $R^{50}$, $R^{51}$ and $R^{52}$ may (for example when attached to the same or adjacent atoms) be linked together to form, a 3- to 8-membered ring, optionally containing one or more heteroatoms (for example, in addition to those that may already be present, heteroatoms selected from oxygen, nitrogen and sulfur), optionally containing one or more unsaturations (preferably, double bonds), and which ring is optionally substituted by one or more substituents selected from =O and $C_{1-3}$ alkyl;

$R^{60}$, $R^{61}$ and $R^{62}$ independently represent hydrogen or $C_{1-6}$ alkyl optionally substituted by one or more fluoro atoms;

or a pharmaceutically acceptable ester, amide, solvate or salt thereof, which compounds, esters, amides, solvates and salts may be referred to hereinafter as "the compounds of the invention".

Compounds of the invention may be tested for PI3K inhibition in a test known to the skilled person, for instance a test described hereinafter. Other compounds that are known PI3K inhibitors may also have been tested in such tests.

As mentioned above, in one embodiment biological aging (performance aging) is reduced. Thus, one or more biomarker value associated with biological aging of an individual being treated is improved compared to the biomarker value of an otherwise equivalent individual that has not been treated with the phosphoinositide 3-kinase inhibitor. Preferably biological aging (performance aging) is reduced by at least 5%, for example at least 10%, 15%, 20%, 25%, 30%, 35%, 40%, 45%, 50%, 55%, 60%, 65%, 70% or at least 75%.

In a further embodiment, neuromuscular coordination is improved. Thus, neuromuscular coordination of an individual being treated is preferably improved by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the neuromuscular coordination of an otherwise equivalent individual that has not been treated with the phosphoinositide 3-kinase inhibitor.

In yet further embodiment insulin resistance is reduced. Thus, insulin resistance of an individual being treated is preferably reduced by at least 5%, for example at least 10%, 15%, 20%, 25%, 30%, 35%, 40%, 45%, 50%, 55%, 60%, 65%, 70% or at least 75% compared to the insulin resistance of an otherwise equivalent individual that has not been treated with the phosphoinositide 3-kinase inhibitor.

In a further embodiment, the lifespan of the individual being treated is increased compared to the lifespan of an otherwise equivalent individual that has not been treated with the phosphoinositide 3-kinase inhibitor. Preferably, lifespan is increased by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140% or at least 150%.

Preferably, lifespan is increased independently of cancer development in the individual. For example, lifespan may be increased independently of lymphoma development in the individual.

In a further embodiment the biological energy expenditure of an individual being treated is increased compared to the energy expenditure of an otherwise equivalent individual that has not been treated with the phosphoinositide 3-kinase inhibitor. Preferably, biological energy expenditure is increased by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500%.

Biological energy expenditure (i.e. the number of calories consumed by an organism in a specified time period) can be determined by any suitable means known in the art. A suitable method, disclosed in U, D'Alession & Thomas, 2006, Cell. Metab. 3:393-402, is indirect calorimetry (see also, the metabolic measurements section of the present Examples). Other measures of biological energy expenditure include weight vs ingested food, $O_2$ consumption related to $CO_2$ production.

In a preferred embodiment biological energy expenditure is only increased in individuals being treated that have an excess of corporal fat (i.e., overweight or obese individuals) and/or individuals undergoing positive energy balance. Hence, in one embodiment biological energy expenditure is not increased in individuals being treated that do not have an excess of corporal fat (i.e., non-overweight or non-obese individuals) or are not undergoing energy balance. The positive energy balance may be acute or chronic.

In one embodiment, total adiposity (i.e. the total adipocytes content of an individual) is decreased compared to the total adiposity of an otherwise equivalent individual that has not been treated with the phosphoinositide 3-kinase inhibitor. Total adiposity can be determined by any suitable means known in the art such as body mass index (BMI), bioimpedence, calliper measurements or computerised tomography. However, a suitable means is dual energy x-ray absorpitometry using a region of interest comprising the whole body (see the metabolic measurements section of the present Examples).

Preferably, total adiposity is decreased by at least 5%, for example at least 10%, 15%, 20%, 25%, 30%, 35%, 40%, 45%, 50%, 55%, 60%, 65%, 70%, 75%, 80% or at least 85% compared to the total adiposity of an otherwise equivalent individual that has not been treated with the phosphoinositide 3-kinase inhibitor.

In a further preferred embodiment total adiposity is only decreased in individuals being treated that have an excess of corporal fat (i.e., overweight or obese individuals). Hence, in one embodiment total adiposity is not reduced in individuals being treated that do not have an excess of corporal fat (i.e., non-overweight or non-obese individuals).

In an additional embodiment, brown adipocyte number is increased compared to the total adiposity of an otherwise equivalent individual that has not been treated with the phosphoinositide 3-kinase inhibitor. Preferably, brown adipocyte number in an individual being treated is increased by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the brown adipocyte number of an otherwise equivalent individual that has not been treated with the phosphoinositide 3-kinase inhibitor.

In one embodiment, brown adipose tissue (BAT) weight is increased compared to the brown adipose tissue weight of an otherwise equivalent individual that has not been treated with the phosphoinositide 3-kinase inhibitor. Thus, it is preferred that brown adipose tissue (BAT) weight in an individual being treated is increased by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500%.

In an additional embodiment, white adipose tissue (WAT) number in an individual being treated is decreased compared to the white adipose tissue number of an otherwise equivalent individual that has not been treated with the phosphoinositide 3-kinase inhibitor. Accordingly, white adipose tissue (WAT) number may be decreased by at least 5%, for example at least 10%, 15%, 20%, 25%, 30%, 35%, 40%, 45%, 50%, 55%, 60%, 65%, 70%, 75%, 80% or at least 85%.

In an additional embodiment, white adipose tissue (WAT) weight in an individual being treated is decreased compared to the white adipose tissue weight of an otherwise equivalent individual that has not been treated with the phosphoinositide 3-kinase inhibitor. Accordingly, white adipose tissue (WAT) weight may be decreased by at least 5%, for example at least 10%, 15%, 20%, 25%, 30%, 35%, 40%, 45%, 50%, 55%, 60%, 65%, 70%, 75%, 80% or at least 85%.

In a further preferred embodiment white adipose tissue (WAT) weight and/or number is only decreased in individuals being treated that have an excess of corporal fat (i.e., overweight or obese individuals). Hence, in one embodiment white adipose tissue (WAT) weight and/or number is not reduced in individuals being treated that do not have an excess of corporal fat (i.e., non-overweight or non-obese individuals).

In one embodiment, the expression of peroxisome proliferator-activated receptor gamma coactivator 1-α (Pgc1α) is increased in brown adipocytes. Preferably, the expression of peroxisome proliferator-activated receptor gamma coactivator 1-α in an individual being treated is increased in brown adipocytes by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the expression of an otherwise equivalent individual that has not been treated with the phosphoinositide 3-kinase inhibitor.

Protein concentration can be measured directly or indirectly (via measurement of associated nucleic acids).

Methods of detecting and/or measuring the concentration of protein and/or nucleic acid are well known to those skilled in the art, see for example Sambrook and Russell, 2001, Cold Spring Harbor Laboratory Press.

Preferred methods for detection and/or measurement of protein include Western blot, North-Western blot, immunosorbent assays (ELISA), antibody microarray, tissue microarray (TMA), immunoprecipitation, in situ hybridisation and other immunohistochemistry techniques, radioimmunoassay (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference. Antibody staining of cells on slides may be used in methods well known in cytology laboratory diagnostic tests, as well known to those skilled in the art.

Typically, ELISA involves the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemi-luminescent systems based on enzymes such as luciferase can also be used.

Conjugation with the vitamin biotin is frequently used since this can readily be detected by its reaction with enzyme-linked avidin or streptavidin to which it binds with great specificity and affinity.

Preferred methods for detection and/or measurement of nucleic acid (e.g. mRNA) include southern blot, northern blot, polymerase chain reaction (PCR), reverse transcriptase PCR(RT-PCR), quantitative real-time PCR (qRT-PCR), nanoarray, microarray, macroarray, autoradiography and in situ hybridisation.

In a further embodiment the expression of uncoupling protein 1 (also known as Thermogenin or Ucp1) is increased in brown adipocytes. It is preferred that the expression of uncoupling protein 1 in an individual being treated is increased in brown adipocytes by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the expression of an otherwise equivalent individual that has not been treated with the phosphoinositide 3-kinase inhibitor.

In a yet further embodiment, the level of active v-akt murine thymoma viral oncogene homolog 1 (also known as Akt or PKB) is decreased in brown adipocytes. Preferably, the level of active v-akt murine thymoma viral oncogene homolog 1 in an individual being tested is decreased by at least 5%, for example at least 10%, 15%, 20%, 25%, 30%, 35%, 40%, 45%, 50%, 55%, 60%, 65%, 70%, 75%, 80% or at least 85% compared to the expression of an otherwise equivalent individual that has not been treated with the phosphoinositide 3-kinase inhibitor.

In one embodiment the level of active forkhead box protein O1 (FOXO1) is increased in brown adipocytes. Preferably, the level of active forkhead box protein O1 (FOXO1) is increased in an individual being treated by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the expression of an otherwise equivalent individual that has not been treated with the phosphoinositide 3-kinase inhibitor.

In an additional embodiment, the level of active forkhead box protein O3 (FOXO3) is increased in brown adipocytes. It is preferred that is increased in an individual being treated by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the expression of an otherwise equivalent individual that has not been treated with the phosphoinositide 3-kinase inhibitor.

In a further embodiment the level of Ser/Thr phosphorylated Irs1 is decreased in white adipocytes. It is preferred that is increased in an individual being treated by at least 5%, for example at least at least 10%, 15%, 20%, 25%, 30%, 35%, 40%, 45%, 50%, 55%, 60%, 65%, 70%, 75%, 80% or at least 85% compared to the level of an otherwise equivalent individual that has not been treated with the phosphoinositide 3-kinase inhibitor.

In one instance the brown adipocytes are situated in Brown Adipose Tissue (BAT). However, in a preferred instance the brown adipocytes are situated in White Adipose Tissue (WAT). Even more preferably, the brown adipocytes are situated in both Brown Adipose Tissue (BAT) and White Adipose Tissue (WAT).

It will be appreciated that the phosphoinositide 3-kinase inhibitor of the inention may be administered together with (either concurrently or consecutively) one or more additional pharmaceutical compounds. Preferably, it is administered with an anti-obesity medication. Suitable anti-obesity medications include orlistat, sibutramine, rimonabant, metformin, exenatide, pramlintide and lorcaserin.

The second aspect of the present provides a method of treating or preventing of a disease or condition associated with the expression of peroxisome proliferator-activated receptor gamma coactivator 1-α (Pgc1α) and/or uncoupling protein 1 (Thermogenin or Ucp1) in brown adipocytes in an individual comprising administering an effective amount of a phosphoinositide 3-kinase inhibitor. The disease or condition may be associated with the expression of peroxisome proliferator-activated receptor gamma coactivator 1-α and uncoupling protein 1 in brown adipocytes and may be associated with the overexpression of either or both.

The disease or condition may be an energy expenditure-associated disease or condition, especially a positive energy imbalance-associated disease or condition such as obesity, an obesity-associated disease or condition, steatosis and biological aging (performance aging).

Preferably the disease or condition is obesity. In an equally preferred embodiment, the disease or condition is obesity-associated, for example, Type 2 (adult-onset) diabetes, High blood pressure, Stroke Heart attack, Heart failure, Gallstones Gout and gouty arthritis, Osteoarthritis, Sleep apnea and Pickwickian syndrome. In one embodiment, the obesity-associated diseases and condition is not cancer.

In a further embodiment the disease or condition is biological aging (performance aging). Alternatively, the disease or condition may be steatosis (i.e. the abnormal and excessive accumulation of cellular lipids), in particular, liver steatosis.

The phosphoinositide 3-kinase inhibitor of the invention may be a Class I phosphoinositide 3-kinase inhibitors, Class II phosphoinositide 3-kinase inhibitors or Class III phosphoinositide 3-kinase inhibitors. Class I phosphoinositide 3-kinase inhibitors of the invention may be a Class IA or a Class1B phosphoinositide 3-kinase inhibitor. For example Class IA phosphoinositide 3-kinase inhibitors may inhibit isoform p110α, isoform p110β and/or isoform p110δ. Preferably, isoform p110α and isoform p110δ are inhibited. Alternatively, where the phosphoinositide 3-kinase inhibitor is a Class IB inhibitor, preferably isoform p110γ is inhibited. The phosphoinositide 3-kinase inhibitor may be selected from the group consisting of wortmannin, demethoxyviridin, LY294002, BEZ235, CAL101, SF1126, PX-866, GDC-0941, BKM120, XL147, XL765, palomid 529, GSK615, IC87114, CAL263, phosphatase and tensin homolog (Pten) and the other PI3K inhibitors mentioned hereinbefore (in Table A and the compound of formula I (compounds of the invention). In an embodiment, the PI3K inhibitor is an inhibitor of PI3Kα.

In one embodiment biological aging (performance aging) is reduced, Thus, one or more indicator (i.e. biomarker) associated with biological aging is improved compared to the same indicator/biomaker of an otherwise equivalent individual that has not been treated with the phosphoinositide 3-kinase inhibitor. Preferably biological aging (performance aging) is reduced by at least 5%, for example at least 10%, 15%, 20%, 25%, 30%, 35%, 40%, 45%, 50%, 55%, 60%, 65%, 70% or at least 75%.

Accordingly, neuromuscular coordination may be improved, preferably by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the neuromuscular coordination of an otherwise equivalent individual that has not been treated with the phosphoinositide 3-kinase inhibitor.

In a further embodiment insulin resistance is reduced, preferably, by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the insulin resistance of an otherwise equivalent individual that has not been treated with the phosphoinositide 3-kinase inhibitor.

In a one embodiment, the lifespan of the individual being treated is increased compared to the lifespan of an otherwise equivalent individual that has not been treated with the phosphoinositide 3-kinase inhibitor. It is preferred that, lifespan is increased by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500%. Preferably, lifespan is increased independently of cancer development in the individual. For example, lifespan may be increased independently of lymphoma development in the individual.

In another embodiment the biological energy expenditure of an individual being treated is increased compared to the energy expenditure of an otherwise equivalent individual that has not been treated with the phosphoinositide 3-kinase inhibitor. Preferably, biological energy expenditure is increased by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500%.

In yet another embodiment, total adiposity (i.e. the total adipocytes content of an individual) is decreased. Preferably, total adiposity is decreased by at least 5%, for example at least 10%, 15%, 20%, 25%, 30%, 35%, 40%, 45%, 50%, 55%, 60%, 65%, 70%, 75%, 80% or at least 85% compared to the total adiposity of an otherwise equivalent individual that has not been treated with the phosphoinositide 3-kinase inhibitor.

In one embodiment, brown adipocyte number is increased. Preferably, brown adipocyte number in an individual being treated is increased by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the brown adipocyte number of an otherwise equivalent individual that has not been treated with the phosphoinositide 3-kinase inhibitor.

Alternatively or additionally, brown adipose tissue (BAT) weight may be increased compared to the brown adipose tissue weight of an otherwise equivalent individual that has not been treated with the phosphoinositide 3-kinase inhibitor. Thus, it is preferred that brown adipose tissue (BAT) weight in an individual being treated is increased by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 50%, 300%, 350%, 400%, 450% or at least 500%.

Also alternatively or additionally, white adipose tissue (WAT) weight in an individual being treated may be decreased compared to the white adipose tissue weight of an otherwise equivalent individual that has not been treated with the phosphoinositide 3-kinase inhibitor. Accordingly, white adipose tissue (WAT) weight may be decreased by at least 5%, for example at least 10%, 15%, 20%, 25%, 30%, 35%, 40%, 45%, 50%, 55%, 60%, 65%, 70%, 75%, 80% or at least 85%.

In one embodiment, the expression of peroxisome proliferator-activated receptor gamma coactivator 1-α (Pgc1α) is increased in brown adipocytes. Preferably, the expression of peroxisome proliferator-activated receptor gamma coactivator 1-α in an individual being treated is increased in brown adipocytes by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the expression of an otherwise equivalent individual that has not been treated with the phosphoinositide 3-kinase inhibitor.

In a further embodiment the expression of uncoupling protein 1 (also known as Thermogenin or Ucp1) is increased in brown adipocytes. It is preferred that the expression of uncoupling protein 1 in an individual being treated is increased in brown adipocytes by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the expression of an otherwise equivalent individual that has not been treated with the phosphoinositide 3-kinase inhibitor.

In a yet further embodiment, the expression of v-akt murine thymoma viral oncogene homolog 1 (also known as Akt, Akt1 or PKB) is decreased in brown adipocytes. Exemplary protein and mRNA sequences include NM_001014431 (human mRNA), NP_001014431 (human protein), NM_009652 (mouse mRNA) and NP_033782 (mouse protein). Preferably, the expression of v-akt murine thymoma viral oncogene homolog 1 in an individual being tested is decreased by at least 5%, for example at least 10%, 15%, 20%, 25%, 30%, 35%, 40%, 45%, 50%, 55%, 60%, 65%, 70%, 75%, 80% or at least 85% compared to the expression of an otherwise equivalent individual that has not been treated with the phosphoinositide 3-kinase inhibitor.

In one embodiment, the expression of v-akt murine thymoma viral oncogene homolog 2 (also known as Akt2) is decreased in brown adipocytes. Exemplary protein and mRNA sequences include NM_001626 (human mRNA), NP_001617 (human protein), XM_001000182 (mouse mRNA) and XP_001000182 (mouse protein). Preferably, the expression of v-akt murine thymoma viral oncogene homolog 2 in an individual being tested is decreased by at least 5%, for example at least 10%, 15%, 20%, 25%, 30%, 35%, 40%, 45%, 50%, 55%, 60%, 65%, 70%, 75%, 80% or at least 85% compared to the expression of an otherwise equivalent individual that has not been treated with the phosphoinositide 3-kinase inhibitor.

In another embodiment, the expression of v-akt murine thymoma viral oncogene homolog 3 (also known as Akt3) is decreased in brown adipocytes. Exemplary protein and mRNA sequences include NM_005465 (human mRNA), NP_005456 (human protein), NM_011785 (mouse mRNA) and NP_035915 (mouse protein). Preferably, the expression of v-akt murine thymoma viral oncogene homolog 3 in an individual being tested is decreased by at least 5%, for example at least 10%, 15%, 20%, 25%, 30%, 35%, 40%, 45%, 50%, 55%, 60%, 65%, 70%, 75%, 80% or at least 85% compared to the expression of an otherwise equivalent individual that has not been treated with the phosphoinositide 3-kinase inhibitor.

In one embodiment the expression of forkhead box protein O1 (FOXO1) is increased in brown adipocytes. Exemplary protein and mRNA sequences include NM_002015 (human mRNA), NP_002006 (human protein), NM_019739 (mouse mRNA) and NP_062713 (mouse protein). Preferably, the expression of forkhead box protein O1 (FOXO1) is increased in an individual being treated by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the expression of an otherwise equivalent individual that has not been treated with the phosphoinositide 3-kinase inhibitor.

In an additional embodiment, the expression of forkhead box protein O3 (FOXO3) is increased in brown adipocytes. Exemplary protein and mRNA sequences include NM_001455 (human mRNA), NP_001446 (human protein), XM_001000298 (mouse mRNA) and XP_001000298 (mouse protein). It is preferred that is increased in an individual being treated by at least 5%, for example at least 10%, 15%, 20%, 25%, 30%, 35%, 40%, 45%, 50%, 55%, 60%, 65%, 70%, 75%, 80%, 90%, 100%, 110%, 120%, 130%, 140%, 150%, 200%, 250%, 300%, 350%, 400%, 450% or at least 500% compared to the expression of an otherwise equivalent individual that has not been treated with the phosphoinositide 3-kinase inhibitor.

By "an otherwise equivalent individual that has not been treated with the phosphoinositide 3-kinase inhibitor" we mean, an otherwise equivalent individual that has not been treated with the PI3K inhibitor and individuals or groups wherein all parameters other than the parameter being tested have been standardised or adjusted to a standard level for the group or individual. For example, adipose tissue weight would effectively be measured relative to total organism weight (rather than measuring absolute adipose tissue weight alone). Standardisation or control of non-test parameters is standard experimental procedure. Hence, the relevant parameters requiring standardisation would be clear to a skilled person in respect of each parameter to be tested. Hence "an otherwise equivalent individual that has not been treated with the phosphoinositide 3-kinase inhibitor" may refer to a control individual or group of control individuals. Alternatively, it may refer to the individual being treated prior to treatment began (preferably, immediately prior to treatment began).

In one instance the brown adipocytes are situated in Brown Adipose Tissue (BAT). However, in a preferred instance the brown adipocytes are situated in White Adipose Tissue (WAT). Even more preferably, the brown adipocytes are situated in both Brown Adipose Tissue (BAT) and White Adipose Tissue (WAT).

It will be appreciated that for the use of the invention the phosphoinositide 3-kinase inhibitor of the invention should be administered in an effective amount. It may be administered together with (either concurrently or consecutively) one or more additional pharmaceutical compounds, for instance another anti-obesity medication. Suitable anti-obesity medications include orlistat, sibutramine, rimonabant, metformin, exenatide, pramlintide and lorcaserin.

The term 'effective amount' as used herein, refers to that amount which provides a sufficiently detectable signal for a given administration regimen. This is a predetermined quantity of active material calculated to produce a desired signal strength in association with the required additive and diluent, i.e. a carrier or administration vehicle. As is appreciated by those skilled in the art, the amount of a compound may vary depending on its specific activity. Suitable dosage amounts may contain a predetermined quantity of active composition calculated to produce the desired signal strength in association with the required diluent. In the methods and use for manufacture of compositions of the invention, an effective amount of the active component is provided. An effective amount can be determined by the ordinary skilled medical or veterinary worker based on patient characteristics, such as age, weight, sex, condition, complications, other diseases, etc., as is well known in the art.

Administration may be oral, intravenous, subcutaneous, buccal, rectal, dermal, nasal, tracheal, bronchial, sublingual, or any other parenteral route or via inhalation, in a pharmaceutically acceptable dosage form.

Administration may be via by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Dosage forms to be administered should also be standard. For instance, a medical practitioner, or other skilled person, will be able to determine routinely the actual dosage, which will be most suitable for an individual patient.

It is intended that the methods of the second aspect of the invention comprise at least the same or equivalent embodiments as the first aspect of the invention.

A third aspect of the present invention relates to a phosphoinositide 3-kinase inhibitor as defined in the first aspect of the invention, for use in promoting weight loss in an individual in need thereof. The individual being treated may or may not be clinically obese.

Preferred compounds of the invention (i.e. preferred PI3K inhibitors for the use of the invention) include those in which:

$R^2$ and $R^3$ independently represent(s) hydrogen, a fragment of formula IA, $C_{1-6}$ alkyl (optionally substituted by one or more (e.g. one) substituent(s) selected from $Q^2$) or a substituent selected from $Q^1$;

$Q^1$ represents halo (e.g. bromo, chloro, iodo)-CN, —N($R^{10a}$)$R^{11a}$, —C(=Y)O$R^{10a}$, —C(=Y)—$R^{10a}$, —C(=Y)—N($R^{10a}$)$R^{11a}$, $C_{1-6}$ alkyl (optionally substituted by one or more (e.g. one) substituent(s) selected from $E^6$) and heterocycloalkyl (e.g. a 5-, 7- or, preferably, a 6-membered heterocycloalkyl group, which preferably contains one or two heteroatoms (e.g. selected from nitrogen, oxygen and sulfur), and which may contain one unsaturation, e.g a double bond, so forming e.g. azepanyl or, preferably, piperazinyl (e.g. 1-piperazinyl), morpholinyl, thiomorpholinyl, piperidinyl (e.g. 4-piperidinyl, for example in which the 1,2-position optionally contains a double bond) or tetrahydropyranyl (e.g. 4-tetrahydropyranyl), which heterocycloalkyl group is optionally substituted by one or more substituents selected from =O (which may be present on a sulfur atom to form e.g. a —S(O)$_2$— moiety) and, preferably, $E^6$ (e.g. in which the $E^6$ substituent is located on a nitrogen heteroatom);

when $R^2$ or $R^3$ represents a fragment of formula IA, then it is preferably $R^2$ that represents such a fragment;

when $R^2$ or $R^3$ represents a fragment of formula IA (in an embodiment of the invention one of $R^2$ and $R^3$, e.g. $R^2$, represents a fragment of formula IA), then preferably m represents 1 and each $R^{15}$ independently represent hydrogen (so forming a fragment —CH$_2$—N($R^a$)($R^b$));

$R^a$ and $R^b$ are linked together to form a 4-, 5- or 6-membered cyclic group (preferably containing no further heteroatoms, and so forming a azetidinyl, pyrrolidinyl, piperidinyl or piperazinyl group), which further comprises: (a) a fused 6- or preferably 5-membered heterocycloalkyl (e.g. pyrrolidinyl) group (preferably containing one heteroatom, e.g. nitrogen, so forming e.g. a 5,5-fused bicycle); (b) a —CH$_2$—CH$_2$— linker group (thereby forming a bridged cyclic structure) or (c) a 4-, 5- or 6-membered heterocycloalkyl group (in which there is preferably one nitrogen heteroatom, so forming e.g. pyrrolidinyl or piperidinyl) linked together via a single common carbon atom to form a spiro-cycle (e.g. 2,8-diaza-spiro[4,5]-decane-8-yl, 2,8-diaza-spiro[4,5]-decane-2-yl, 3,9-diaza-spiro[5,5]undecane-3-yl, 2,7-diaza-spiro[3.5]nonane-7-yl or 2,7-diaza-spiro[3.5]nonane-2-yl), which rings are optionally substituted by one or more substituents selected from =O and $E^3$ (for instance the second ring may be substituted with such substituents);

when $R^2$ or $R^3$ represents $C_{1-12}$ (e.g. $C_{1-6}$) alkyl, then it may be straight-chained, e.g. acyclic $C_{1-3}$ alkyl (e.g. methyl) or $C_{3-6}$ cycloalkyl (e.g. cyclopropyl), all of which are optionally substituted by one or more fluoro atoms (so forming for example a trifluoromethyl group);

$R^4$ represents hydrogen, chloro, bromo, iodo, —CN, —C(O)$R^{10b}$ (e.g. —C(O)H) or methyl optionally substituted by one or more (e.g. one) substituent(s) selected from $E^4$ (in which $E^4$ preferably represents heteroaryl (e.g. imidazolyl) or, especially, —O$R^{20}$, so forming e.g. a —CH$_2$OH group or a —CH$_2$-heteroaryl moiety);

one of $R^2$ and $R^3$ represents a substituent as defined herein, and the other represents hydrogen or a substituent as defined herein;

$R^5$ represents aryl (e.g. phenyl) or heteroaryl (e.g. a 5- or 6-membered monocyclic heteroaryl group, or a 10- or, preferably, 9-membered bicyclic heteroaryl group, in which, in both cases, there is one or two heteroatom(s) present, preferably selected from nitrogen, so forming e.g. pyrazolyl, pyridyl, indazolyl, indolyl, pyrimidinyl, indolonyl or pyrrolopyridine, such as pyrrolo[2,3]pyridine), both of which $R^5$ groups are optionally substituted by one or more (e.g. one or two) substituents selected from $E^5$;

each $Q^2$ independently represents halo (e.g. fluoro; and hence when substituted on alkyl, may form e.g. a —CF$_3$ group), —O$R^{10a}$ (in which $R^{10a}$ preferably represents hydrogen or $C_{1-2}$ alkyl), —N($R^{10a}$)$R^{10b}$), —C(=Y)O$R^{10a}$, —C(=Y)$R^{10a}$, —C(=Y)N($R^{10a}$)$R^{10b}$, —S(O)$_2$R$^{10a}$, $C_{1-6}$ alkyl (e.g. $C_{1-3}$ alkyl; optionally substituted by one or more fluoro atoms), heterocycloalkyl (optionally substituted by one or more substituents selected from =O and $E^6$), aryl and/or heteroaryl (e.g. pyrimidinyl; which latter two aryl and heteroaryl groups are optionally substituted by one or more substituents selected from $E^7$);

each $R^{10a}$, $R^{11a}$, $R^{12a}$, $R^{10b}$, $R^{11b}$ and $R^{12b}$ (e.g. each $R^{10a}$ and $R^{11a}$) independently represents hydrogen or $C_{1-6}$ alkyl (e.g. ethyl or propyl or $C_{3-6}$ cycloalkyl, such as cyclohexyl) optionally substituted by one or more (e.g. one) substituent(s) selected from $E^{10}$; or one of $R^{10a}$ and $R^{11a}$ may represent heterocyloalkyl (e.g. a 5- or preferably 6-membered heterocycloalkyl group e.g. containing one heteroatom, so forming e.g. a piperidinyl or a tetrahydropyranyl group; which heterocycloalkyl group is optionally substituted by one or more (e.g. one) substituent selected from $E^{10}$); or any relevant pair of $R^{10a}$, $R^{11a}$ and $R^{12a}$ (e.g. $R^{10a}$ and $R^{11a}$) may (e.g. when both are attached to the same nitrogen atom) be linked together to form a 5-, 6- or 7-membered ring, optionally containing a further heteroatom (preferably selected from nitrogen, oxygen and sulfur), which ring is preferably saturated (so forming, for example, a pyrrolidinyl, piperidinyl, azepanyl, piperazinyl, morpholinyl or thiomorpholinyl group), and optionally substituted by one or more substituents selected from =O and $E^{12}$ (which $E^{12}$ substituent may be situated on a nitrogen heteroatom; and/or $E^{12}$ is preferably halo (e.g. fluoro), —N($R^{20}$)$R^{21}$, —O$R^{20}$, —C(O)O$R^{20}$, —OC(O)$R^{20}$, —C(O)$R^{20}$, —C(O)$R^{20}$, —S(O)$_2$$R^{20}$ or $C_{1-3}$ alkyl optionally substituted by one or more fluoro atoms or substituents selected from $Q^5$);

each $E^1$, $E^2$, $E^3$, $E^4$, $E^5$, $E^6$, $E^7$, $E^{10}$, $E^{11}$ and $E^{12}$ (e.g. each $E^5$ and $E^6$) independently represents a substituent selected from $Q^4$ or $C_{1-2}$ alkyl optionally substituted by one or more substituents selected from $Q^5$ and =O;

$Q^4$ represents halo (e.g. fluoro or chloro), —CN, —O$R^{20}$, —N($R^{20}$)$R^{21}$, —C(=Y)O$R^{20}$, —C(=Y)$R^{20}$, —C(=Y)N($R^{20}$)$R^{21}$, —N($R^{22}$)—C(=Y)—$R^{21}$, —N$R^{22}$S(O)$_2$$R^{20}$, —S(O)$_2$$R^{20}$, —N($R^{22}$)C(=Y)N($R^{20}$)$R^{21}$, —OC(O)$R^{20}$, $C_{1-6}$ alkyl (e.g. $C_{1-3}$ alkyl; optionally substituted by one or more fluoro atoms), aryl (which latter group, when attached to an alkyl group may form e.g. a benzyl moiety) or heteroaryl (e.g. imidazolyl), which latter two aryl and heteroaryl groups are optionally substituted by one or more $J^3$ substituents;

$Q^5$ represents halo (e.g. fluoro), —N($R^{20}$)$R^{21}$, —O$R^{20}$ and —O—C(O)$R^{20}$;

each $E^3$ independently represents —C(=Y)O$R^{20}$ or —S(O)$_2$$R^{20}$;

each $E^4$ independently represents halo (e.g. fluoro), —O$R^{20}$ (e.g. —OH) or heteroaryl (e.g. imidazolyl);

each $E^5$ independently represents halo (e.g. fluoro or chloro), —CN, —O$R^{20}$, —N($R^{20}$)$R^{21}$, —C(=Y)O$R^{20}$, —C(=Y)N($R^{20}$)$R^{21}$, —N($R^{22}$)—C(=Y)—$R^{21}$, —N$R^{22}$S(O)$_2$$R^{20}$, —N($R^{22}$)C(=Y)N($R^{20}$)$R^{21}$ and/or $C_{1-6}$ alkyl (e.g. $C_{1-3}$ alkyl) optionally substituted by one or more fluoro atoms;

each $E^6$ independently represents halo (e.g. fluoro), —O$R^{20}$ (in which $R^{20}$ preferably represents hydrogen or $C_{1-2}$ alkyl), —N($R^{20}$)$R^{21}$, —C(=Y)O$R^{20}$, —C(=Y)$R^{20}$, —C(=Y)N($R^{20}$)$R^{21}$, —S(O)$_2$$R^{20}$ and/or $C_{1-6}$ alkyl (e.g. $C_{1-3}$ alkyl) optionally substituted by one or more fluoro atoms;

each $E^7$ independently represents —N($R^{20}$)$R^{21}$;

each $E^{10}$ (which is preferably located on a nitrogen heteroatom, when a substituent on a heterocycloalkyl group) represents —S(O)$_2$$R^{20}$, —O$R^{20}$, —N($R^{20}$)$R^{21}$, —N($R^{22}$)—C(O)—$R^{21}$, —C(O)—O$R^{20}$ or aryl (which latter group, when attached to an alkyl group may form e.g. a benzyl moiety; and which may be substituted by one or more $J^3$ substituents);

each Y represents, on each occasion when used herein, =S, or preferably =O;

each $R^{20}$, $R^{21}$, $R^{22}$ (e.g. each $R^{20}$ and $R^{21}$) independently represents hydrogen, $C_{1-4}$ (e.g. $C_{1-3}$) alkyl (e.g. tert-butyl, ethyl or methyl; which alkyl group is optionally substituted by one or more substituents selected from $J^4$) or aryl (e.g. phenyl; especially in the case of —S(O)$_2$$R^{20}$, and which aryl group is optionally substituted by one or more $J^5$ substituents); or any relevant pair of $R^{20}$, $R^{21}$ and $R^{22}$ (e.g. $R^{20}$ and $R^{21}$) may (e.g. when both are attached to the same nitrogen atom) may be linked together to form a 5- or 6-membered ring, optionally containing a further heteroatom (preferably selected from nitrogen and oxygen), which ring is preferably saturated (so forming, for example, a pyrrolidinyl, piperazinyl or morpholinyl group), and optionally substituted by one or more substituents selected from =O and $J^6$ (which $J^6$ substituent may be situated on a nitrogen heteroatom);

$R^{22}$ represents $C_{1-3}$ alkyl or, preferably, hydrogen;

each $J^1$, $J^2$, $J^3$, $J^4$, $J^5$ and $J^6$ independently represent a substituent selected from $Q^7$;

each $Q^7$ and $Q^8$ independently represent halo, —N($R^{50}$)$R^{51}$, —C(=$Y^a$)—O$R^{50}$, —C(=$Y^a$)—N($R^{50}$)$R^{51}$, —C(=$Y^a$)—$R^{50}$, —S(O)$_2$$R^{50}$ or $C_{1-3}$ alkyl optionally substituted by one or more fluoro atoms;

each $Y^a$ independently represents =S or, preferably, =O;

each $R^{50}$ and $R^{51}$ independently represents hydrogen, $C_{1-4}$ alkyl (e.g. tert-butyl or methyl) or $R^{50}$ and $R^{51}$, when attached to the same carbon atom, may be linked together to form a 5- or preferably, 6-membered ring (e.g. containing a further heteroatom, so forming e.g. piperazinyl) optionally substituted by methyl (e.g. which substituent is located in the additional nitrogen heteroatom).

Other preferred compounds of the invention that may be mentioned include:

$R^2$ represents a substituent other than hydrogen, and $R^3$ and $R^4$ independently represent hydrogen or a substituent other than hydrogen;

$R^2$ represents a substituent other than hydrogen;

$R^2$ represents $Q^1$ or $C_{1-2}$ alkyl (e.g. methyl) optionally substituted by $Q^2$ (e.g. at the terminal position of the methyl group);

$R^3$ and $R^4$ independently represent $C_{1-2}$ alkyl or, preferably, hydrogen or $Q^1$ (e.g. in which $Q^1$ preferably represents halo (e.g. chloro) or heterocycloalkyl optionally substituted by one or more $E^6$ groups);

at least one of $R^3$ and $R^4$ represent hydrogen;

$R^5$ represents: (a) phenyl (which is preferably substituted e.g. by one $E^5$ substituent located preferably at the meta position); (b) a 5- or 6-membered (e.g. 6-membered) monocyclic heteroaryl group (e.g. containing one or two heteroatoms preferably selected from nitrogen, so forming e.g. pyrimidinyl, such as 5-pyrimidinyl, or pyridyl, such as 3-pyridyl), which monocyclic heteroaryl group is optionally substituted e.g. by one or two $E^5$ substituent(s) (e.g. located at the 2-position (and optionally 6-position), when $R^5$ represents pyrimidinyl, or, at the 6-position when $R^5$ represents 3-pyridyl; in each case a substituent is preferably at the position para relative to the point of attachment to the requisite imidazopyrazine of formula I); or (c) a 9- or 10-membered (e.g. 9-membered) bicyclic heteroaryl group (e.g. indazolyl, such as 4-indazolyl, or azaindolyl, such as 7-azaindolyl i.e. pyrrolo[2,3-b]pyridyl, such as 7-azaindol-5yl), which bicyclic heteroaryl group is preferably unsubstituted;

$Q^1$ represents —C(O)N($R^{10a}$)$R^{11a}$ or —C(O)O$R^{10a}$ (e.g. in which $R^{10a}$ is $C_{1-2}$ alkyl);

$Q^2$ represents fluoro, —N($R^{10a}$)$R^{11a}$ or heterocycloalkyl (e.g. piperazinyl or morpholinyl) optionally (and preferably) substituted by one or more (e.g. one) substituent(s) (preferably located on a nitrogen heteroatom) selected from =O and, preferably, $E^6$;

$R^{10a}$ and $R^{11a}$ (for instance when $Q^1$ represents —C(O)N($R^{10a}$)$R^{11a}$) independently represent hydrogen, acyclic $C_{1-3}$ (e.g. $C_{1-2}$) alkyl (e.g. methyl or ethyl) (optionally substituted by one or more (e.g. one) $E^{10}$ substituent), $C_{5-6}$ cycloalkyl (e.g. cyclohexyl) (optionally substituted by one or more (e.g. one) $E^{10}$ substituent) or heterocycloalkyl (e.g. a 5- or 6-membered heterocycloalkyl group (e.g. containing one heteroatom, so forming e.g. piperidinyl, such as 4-piperidinyl, or tetrahydropyranyl, such as 4-tetrahydropyranyl) (optionally substituted by one or more (e.g. one) $E^{10}$ substituent, which may be located on a nitrogen heteroatom);

when $Q^2$ represents —N($R^{10a}$)$R^{11a}$, then $R^{10a}$ and $R^{11a}$ are preferably linked together to form a 5- or preferably 6-membered ring preferably containing a further (e.g. nitrogen, oxygen or sulfur) heteroatom (so forming, e.g., piperazinyl, morpholinyl or thiomorpholinyl) optionally (and preferably)

substituted by one or more (e.g. one) substituent(s) (optionally located on a nitrogen heteroatom) selected from =O, $E^{12}$ and $C_{1-2}$ alkyl (e.g. methyl) optionally substituted by one or more fluoro atoms (and, e.g. in the case of rings containing S, with one or more (e.g. one or two) =O, which carbonyl group(s) are located on the S to form e.g. a —S(O)$_2$— moiety);

when $E^5$ represents a substituent on phenyl, then it is preferably $Q^4$ (e.g. —OR$^{20}$);

when $E^5$ represents a substituent on monocyclic heteroaryl, then it is preferably $Q^4$ (e.g. —N(R$^{20}$)R$^{21}$) or $C_{1-2}$ alkyl (e.g. methyl) optionally substituted by one or more fluoro atoms (so forming e.g. a —CF$_3$ group);

$E^6$ and $E^{12}$ preferably represent $Q^4$;

$E^{10}$ represents $Q^4$;

for instance when $E^5$ represents $Q^4$, then $Q^4$ represents —OR$^{20}$ or —N(R$^{20}$)R$^{21}$;

for instance when $E^6$ and $E^{12}$ represent $Q^4$, then $Q^4$ represents —S(O)$_2$R$^{20}$ (e.g. —S(O)$_2$C$_{1-4}$ alkyl), —C(O)R$^{20}$ or —OC(O)R$^{20}$;

$E^{10}$ represents —N(R$^{20}$)R$^{21}$, —OR$^{20}$ or —C(O)OR$^{20}$;

for instance when $E^{10}$ represents $Q^4$ (and $E^{10}$ is a substituent on an alkyl or cycloalkyl group), then $Q^4$ represents —N(R$^{20}$)R$^{21}$ or —OR$^{20}$ (e.g. —OCH$_3$ or —OH);

for instance when $E^{10}$ represents $Q^4$ (and $E^{10}$ is a substituent on a heterocycloalkyl group), then $Q^4$ represents —C(O)OR$^{20}$;

$R^{20}$ and $R^{21}$ independently represent hydrogen or $C_{1-4}$ alkyl (e.g. methyl, ethyl or butyl (e.g isobutyl)), which alkyl group may (e.g. in the case when $E^{12}$ represents —C(O)R$^{20}$) be substituted with a $J^4$ substituent; or for instance, when $E^{10}$ represents —N(R$^{20}$)R$^{21}$, then R$^{20}$ and R$^{21}$ may be linked together to form a 5- or preferably 6-membered ring, optionally containing a further heteroatom (e.g. oxygen, so forming e.g. morpholinyl);

$J^4$ represents $Q^7$;

$Q^7$ represents —N(R$^{50}$)R$^{51}$;

$R^{50}$ and $R^{51}$ independently represent hydrogen, or, preferably, $C_{1-2}$ alkyl (e.g. methyl).

The most preferred compound of the invention (i.e. PI3-K inhibitor for the use of the invention) is:

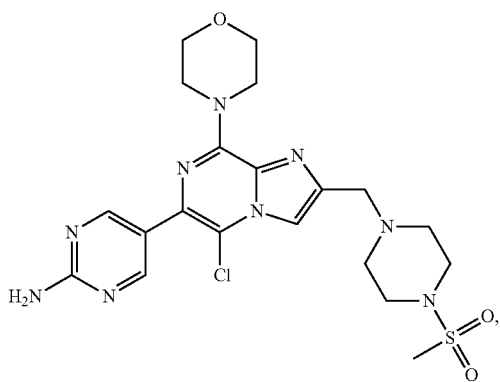 [SMILES: CS(=O)(=O)N1CCN(Cc2cn3c(Cl)c(-c4cnc(N)nc4)nc(N4CCOCC4)c3n2)CC1]

referred to herein as "Compound A".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable ester, amide, solvate or salt thereof", we include salts of pharmaceutically acceptable esters or amides, and solvates of pharmaceutically acceptable esters, amides or salts. For instance, pharmaceutically acceptable esters and amides such as those defined herein may be mentioned, as well as pharmaceutically acceptable solvates or salts.

Pharmaceutically acceptable esters and amides of the compounds of the invention are also included within the scope of the invention. Pharmaceutically acceptable esters and amides of compounds of the invention may be formed from corresponding compounds that have an appropriate group, for example an acid group, converted to the appropriate ester or amide. For example, pharmaceutically acceptable esters (of carboxylic acids of compounds of the invention) that may be mentioned include optionally substituted $C_{1-6}$ alkyl, $C_{5-10}$ aryl and/or $C_{5-10}$ aryl-$C_{1-6}$ alkyl-esters. Pharmaceutically acceptable amides (of carboxylic acids of compounds of the invention) that may be mentioned include those of the formula —C(O)N(R$^{z1}$)R$^{z2}$, in which R$^{z1}$ and R$^{z2}$ independently represent optionally substituted $C_{1-6}$ alkyl, $C_{5-10}$ aryl, or $C_{5-10}$ aryl-$C_{1-6}$ alkylene-. Preferably, $C_{1-6}$ alkyl groups that may be mentioned in the context of such pharmaceutically acceptable esters and amides are not cyclic, e.g. linear and/or branched.

Further compounds of the invention that may be mentioned include carbamate, carboxamido or ureido derivatives, e.g. such derivatives of existing amino functional groups.

For the purposes of this invention, therefore, prodrugs of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. I-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and for substrate tissue distribution assays. Tritiated ($^{3}H$) and carbon-I4 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}O$ and $^{18}F$ are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise stated, the term $C_{1-q}$ alkylene (where q is the upper limit of the range) defined herein may be straight-chain or, when there is a sufficient number of carbon atoms, be saturated or unsaturated (so forming, for example, an alkenylene or alkynylene linker group). However, such $C_{1-q}$ alkylene groups may not be branched.

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i.e. a minimum of four) such cycloalkyl groups may also be part cyclic.

The term "halo", when used herein, preferably includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolanyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N— or S— oxidised form. Heterocycloalkyl mentioned herein may be stated to be specifically monocyclic or bicyclic.

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring.

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N— or S— oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group.

It may be specifically stated that the heteroaryl group is monocyclic or bicyclic. In the case where it is specified that the heteroaryl is bicyclic, then it may be consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulfur.

For the avoidance of doubt, where it is stated herein that a group (e.g. a $C_{1-12}$ alkyl group) may be substituted by one or more substituents (e.g. selected from $E^6$), then those substituents (e.g. defined by $E^6$) are independent of one another. That is, such groups may be substituted with the same substituent (e.g. defined by $E^6$) or different substituents (defined by $E^6$).

For the avoidance of doubt, in cases in which the identity of two or more substituents in a compound of the invention may be the same, the actual identities of the respective substituents are not in any way interdependent. For example, in the situation in which there is more than one $Q^1$ (or e.g. $E^6$) substituent present, then those $Q^1$ (or e.g. $E^6$) substituents may be the same or different. Further, in the case where there are two $Q^1$ (or two $E^6$) substituents present, in which one represents —$OR^{10a}$ (or e.g. —$OR^{20}$, as appropriate) and the other represents —$C(O)_2R^{10a}$ (or e.g. —$C(O)_2R^{20}$, as appropriate), then those $R^{10a}$ or $R^{20}$ groups are not to be regarded as being interdependent. Also, when e.g. there are two —$OR^{10a}$ substituents present, then those —$OR^{10a}$ groups may be the same or different (i.e. each $R^{10a}$ group may be the same or different).

For the avoidance of doubt, when a term such as "$E^1$ to $E^{12}$" is employed herein, this will be understood by the skilled person to mean $E^1$, $E^2$, $E^3$, $E^4$, $E^5$, $E^6$, $E^7$, $E^8$ (if present), $E^9$ (if present), $E^{10}$, $E^{11}$ and $E^{12}$, inclusively.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Compounds of the invention (and intermediates) may be prepared in accordance with the following scheme (Scheme I), in which $R^1$ represents unsubstituted 4-morpholinyl (i.e. linked to the requisite bicycle via the nitrogen atom).

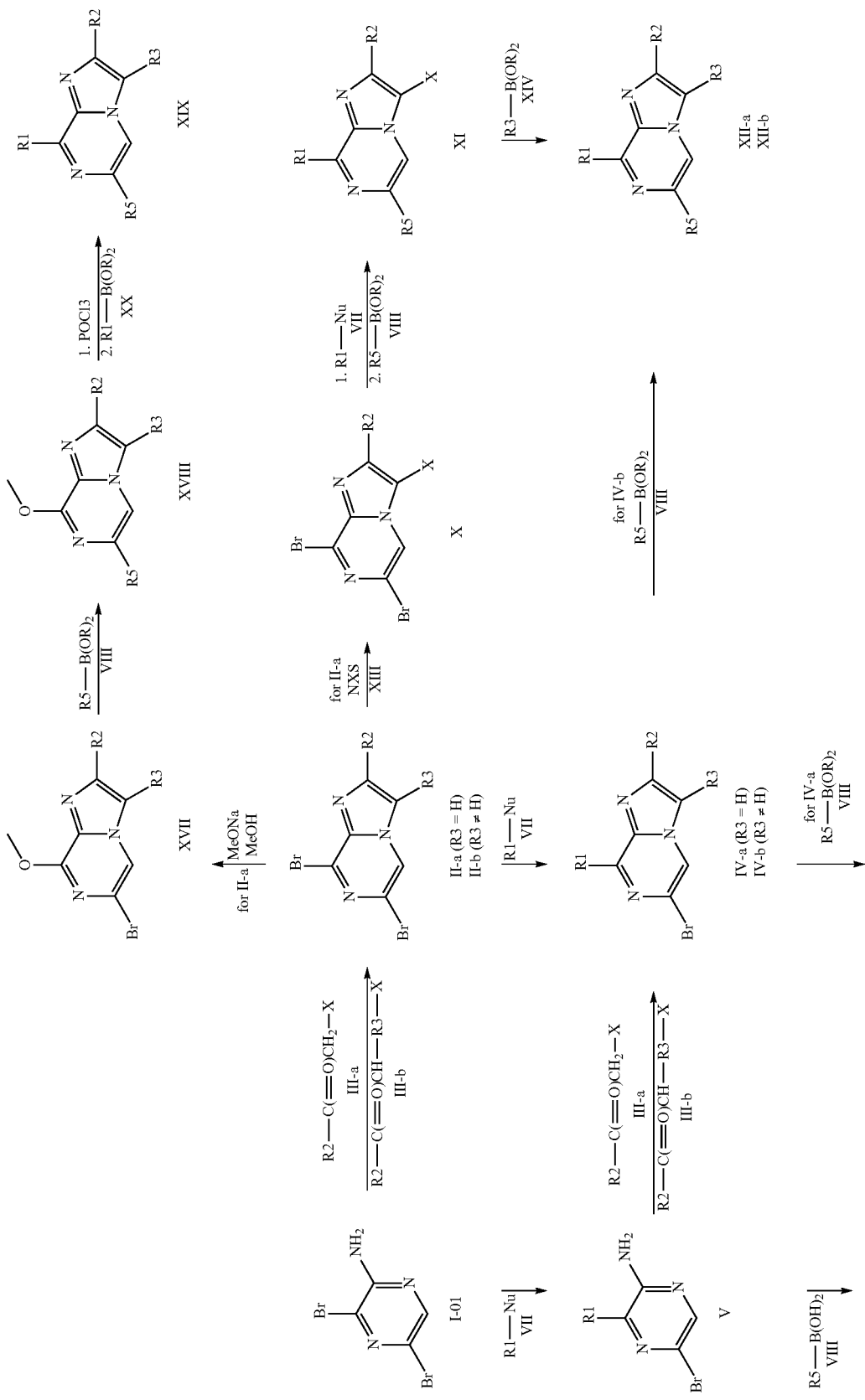

-continued
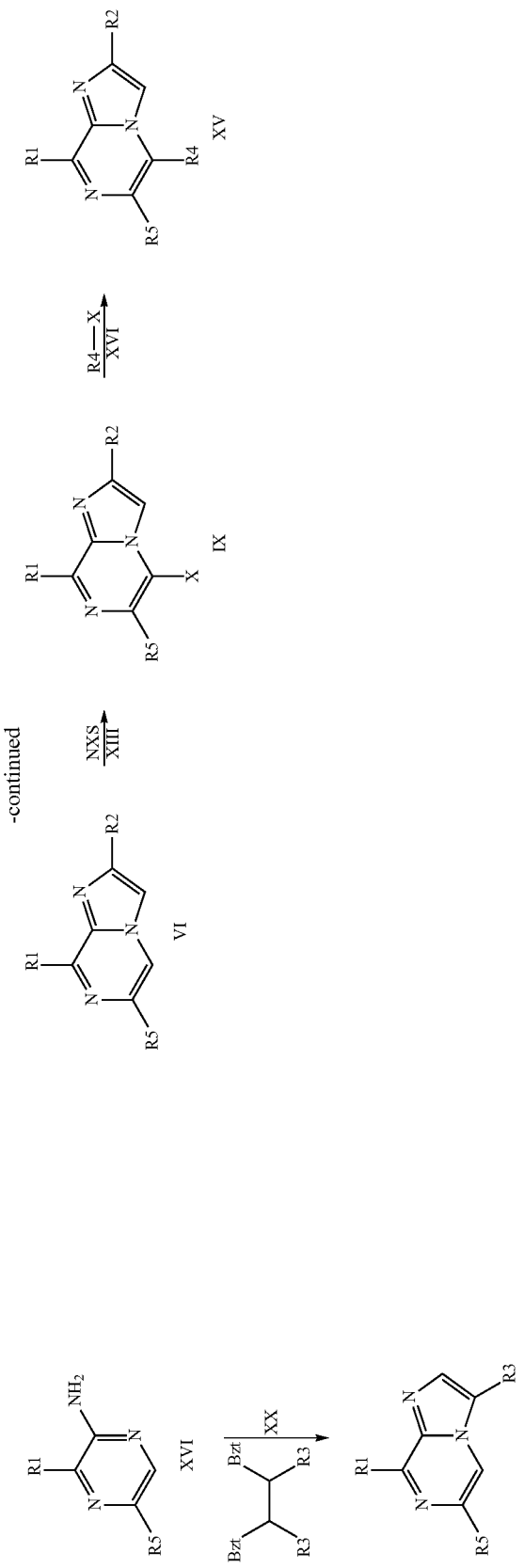

Compound I-01 was reacted with an intermediate (III-a) of formula $R^2$—C(=O)—$CH_2$—X or an intermediate (III-b) of formula $R^2$—C(=O)—CH—$R^3$—X, where $R^2$ and $R^3$ are as hereinbefore defined and X represents a suitable leaving group (e.g. a halide), without solvent or in the presence of a suitable reaction solvent such as DME or 2-propanol, at a convenient temperature, typically heating at 90° C., to obtain compounds of formula (II-a) or formula (II-b).

Compounds of formula (II-a) can be reacted with a halogenating agent, such as N-bromoSuccinimide, N-iodosuccininide, N-chlorosuccinimide or others, and X represents an halogen group such as Cl, Br or Iodine atom, in the presence of a suitable reaction solvent such as $CHCl_3$, typically heating at a convenient temperature, either by conventional heating under reflux or under microwave irradiation, for a period of time to ensure the completion of the reaction, to obtain compounds of formula (X).

Compounds of formula (X) can react with an intermediate (VII) of formula $R^1$—Nu, where $R^1$ is unsubstituted 4-morpholinyl as hereinbefore defined and Nu represents a nucleophilic group, such as an amine (and $R^1$—Nu together form the group that is to be linked to the imidazopyrazine) in a suitable solvent such as DCM, dioxane at room temperature or by heating at a convenient temperature, for a period of time to ensure the completion of the reaction. Further, reaction may be with an intermediate (VIII) of formula $R^5$—$B(OR)_2$, which R is H or $C_1$-$C_6$ alkyl or the two groups OR form, together with the boron atom to which they are attached a pinacolato boronate ester group, and where $R^5$ is as defined before, in a suitable solvent such as DME or DMF, in the presence of a suitable base, such as an inorganic aqueous base $Na_2CO_3$ or $K_2CO_3$, in the presence of a metal catalyst, such as palladium, and a suitable ligand, such us $PdCl_2(dppf).DCM$, $Pd(PPh_3)_4$ by heating at a convenient temperature, such as 130° C. under microwave irradiation or reflux temperature under traditional heating, for a period of time that allows the completion of reaction, to obtain compounds of formula (XI).

Compounds of formula (XI) can react with an intermediate (XIV) of formula $R^3$—$B(OR)_2$, in which the —$B(OR)_2$ moiety is as defined above, and $R^3$ is as hereinbefore defined, under conditions such as those described hereinbefore (e.g. reaction of (X) with (VIII); e.g. microwave irradiation conditions at about 140° C. may be deployed), to obtain compounds of formula (XII-a).

Compounds of formula (II-b) can react with an intermediate (VII) of formula $R^1$—Nu (as hereinbefore defined), in a suitable solvent such as DCM, dioxane at room temperature or by heating, for a period of time to ensure the completion of the reaction to afford compounds of formula (IV-b).

Compounds of formula (IV-b) can react with an intermediate (VIII) of formula $R^5$—$B(OR)_2$ as hereinbefore defined, under reaction conditions hereinbefore described (e.g. the reaction of (X) with (VIII)), to obtain compounds of formula (XII-b).

Compound I-01 can react with an intermediate (VII) of formula $R^1$—Nu (as hereinbefore defined), at a convenient temperature, such us 120° C., for a period of time that allows the completion of reaction, to afford compound (V).

Compound (V) was reacted with an intermediate (III-a) of formula $R^2$—C(=O)—$CH_2$—X or an intermediate (III-b) of formula $R^2$—C(=O)—CH—$R^3$—X, both of which are as hereinbefore defined, under reaction conditions hereinbefore described (e.g. the reaction of (I-01) with (III-a) or (III-b)), to obtain compounds of formula (IV-a).

Compounds of formula (IV-a) can react with an intermediate (VIII) of formula $R^5$—$B(OR)_2$, as hereinbefore defined, e.g. under reaction conditions hereinbefore described (e.g. the reaction of (X) with (VIII)), to obtain compounds of formula (VI).

Compounds of formula (VI) can be reacted with a halogenating agent, for example as described hereinbefore (e.g. reaction of (II-a) to (X)), to obtain compounds of formula (IX).

The halogen atom X of compounds of formula (IX) can be substituted via a coupling reaction with an intermediate (XVI) of formula $R^4$—$B(OR)_2$, in which the —$B(OR)_2$ moiety is as hereinbefore defined, and $R^4$ is as hereinbefore defined, e.g. under reaction conditions hereinbefore described (e.g. the reaction of (X) with (VIII)), for a period of time that allows the completion of reaction, to obtain compounds of formula XV.

The halogen atom X of compounds of formula (IX) can be substituted via coupling reaction of a CN group, by treatment with $Zn(CN)_2$, in a suitable solvent such as DMF, AcCN and in the presence of a Pd catalyst, such us $Pd(PPh_3)_4$ or $PdCl_2(dppf)_2$. Additionally an inorganic aqueous base can be added such as $Na_2CO_3$ aq. Heating at a convenient temperature, such as 130° C. under microwave irradiation or reflux temperature under traditional heating, for a period of time that allows the completion of reaction, to obtain compounds of formula XV.

Compounds of formula (V) can react with an intermediate (VIII) of formula $R^5$—$B(OR)_2$ as hereinbefore defined, e.g. under reaction conditions hereinbefore described (e.g. the reaction of (X) with (VIII)), to obtain compounds of formula (XVI).

Compounds of formula (XVI) can react with an intermediate of formula XX, in which Bzt is Benzotriazol, following similar conditions reported in literature (*J. Org. Chem.* 1990, 55, 3209-3213, *J. Org. Chem.*, 2003, 68, 4935-4937), in a suitable solvent, such as DCE, heating at a convenient temperature, in a period of time to ensure completion of the reaction, typically at reflux for 5 h. Additionally an inorganic base can be added to ensure completion of the reaction.

Compounds of formula (II-a) can react with sodium methoxide in the presence of methanol, at room temperature or by heating at a convenient temperature, such as 60° C., to obtain compounds of formula (XVII).

Compounds of formula (XVII) can react with an intermediate (VIII) of formula $R^5$—$B(OR)_2$ as hereinbefore defined, e.g. under reaction conditions hereinbefore described (e.g. the reaction of (X) with (VIII)), to obtain compounds of formula (XVIII).

Compound of formula (XVIII) can react with $POCl_3$ by heating, typically to reflux, for a period of time to ensure the completion of the reaction, to afford the replacement of the methoxy group by chlorine atom. Coupling of the chlorine atom with an intermediate (XX) of formula $R^1$—$B(OR)_2$ in which the —$B(OR)_2$ moiety and $R^1$ are as hereinbefore defined (i.e. $R^1$ is unsubstituted 4-morpholinyl), e.g. under reaction conditions hereinbefore described (e.g. the reaction of (X) with (VIII)), to obtain compounds of formula (XIX).

Preferred, non-limiting examples which embody certain aspects of the invention will now be described, with reference to the following figures:

FIG. 1. Generation and characterization of Pten$^{tg}$ mice.
a. Relative Pten mRNA levels of the indicated tissues. Bars represent mean±sd (n=3 per genotype). Statistical significance was determined by the two-tailed Student's t-test.
b. Representative Pten transgenic mouse homozygously null for the resident Pten alleles.

c. Immunoblot of the indicated proteins in growing cultures of primary MEFs. Each lane corresponds to an independent MEF preparation.
d. Lysates from normal growing (C), serum starved (−) or starved and stimulated with insulin (+) immunoblotted to detect the indicated proteins.
e. Neoplastic foci in MEFs retrovirally transduced with the viral oncoprotein E6 and either one of the indicated PI3K-dependent oncogenes, EGFRL858R or polyoma virus middle-T. Bars represent mean±sd (n=3 independent MEF preparations per genotype). Representative plates are shown in the top. Statistical significance was determined by the two-tailed Student's t-test.
f. Chemical carcinogenesis with 3-methyl-cholanthrene (3MC). Tumour-free Kaplan-Meier curves post-3MC injection were compared using the logrank test.
g. Incidence of lymphomas in old moribund mice (mice that died with lymphoma vs. total dead mice). Statistical significance was determined by the Fisher's exact test.
h. Incidence of cancers. Left, percentage of mice with 1 cancer, or more (2-4), as indicated. Right, percentage of mice with the indicated type of cancer. Statistical significance was determined by the Fisher's exact test. See FIG. 1(f).

$*p<0.05$, $p<0.01$, $*p<0.001$

Figure 2:
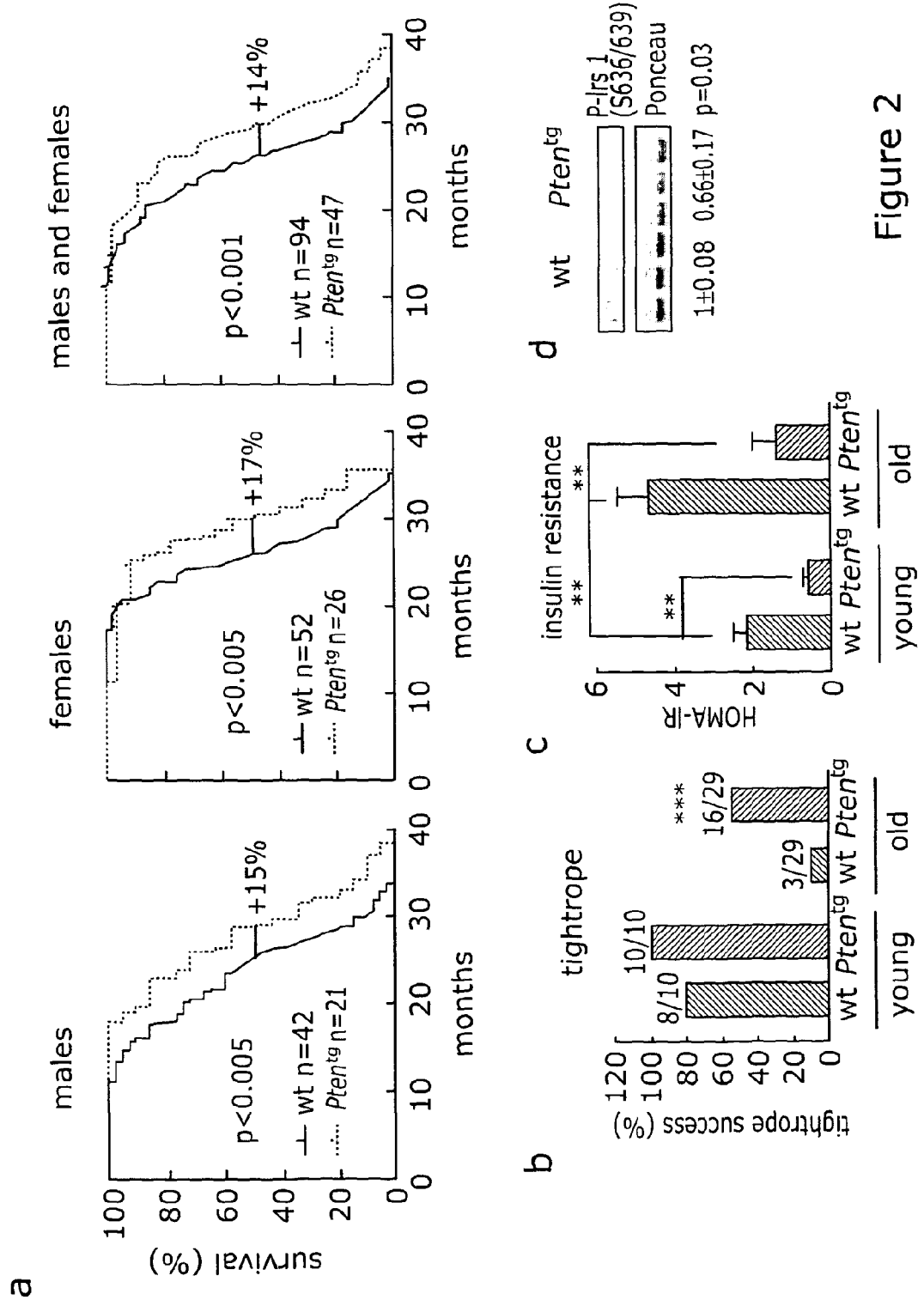
Figure 2:
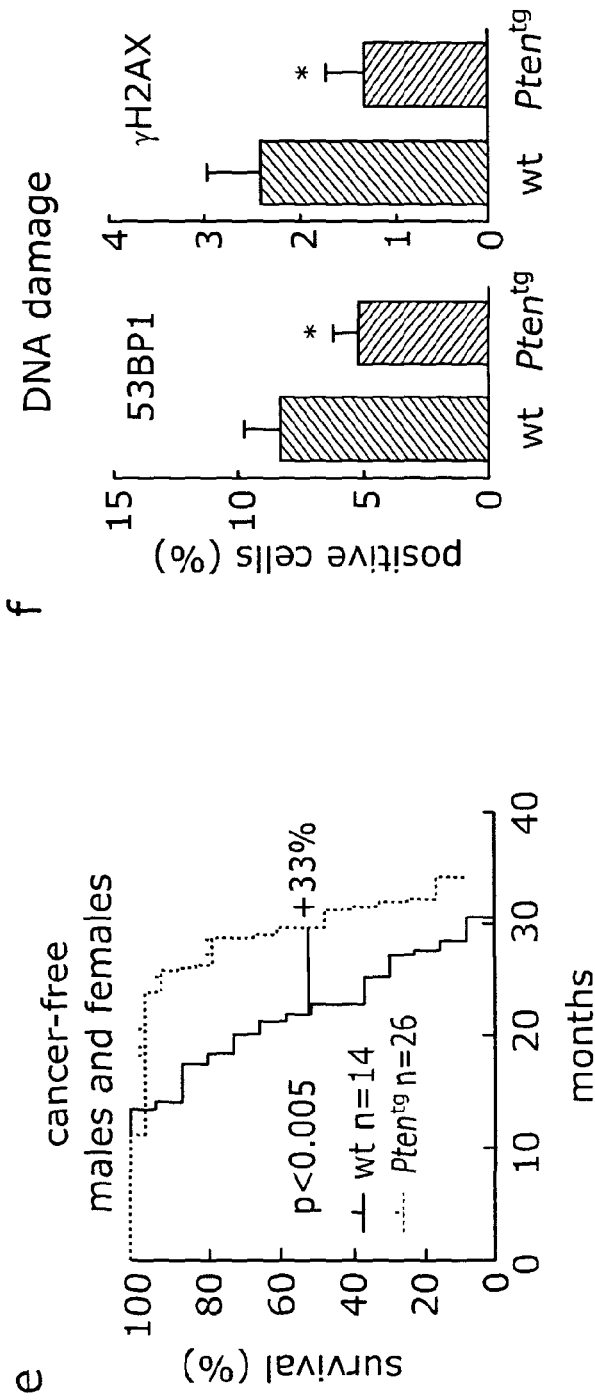

FIG. 2. Extended longevity and improved healthspan in Pten$^{tg}$.

a. Kaplan-Meier survival curves. Statistical significance was determined by the logrank test. See FIG. 2(a).
b. Neuromuscular coordination assessed by the tightrope assay in young (<6 month) and old (1.5-2 years) mice of the indicated genotypes (number of mice that passed the test vs. total number of tested mice). Statistical significance was determined by the Fisher's exact test.
c. Insulin resistance measured as the HOMA-IR index determined from fasting insulin and glucose concentrations (see FIG. 6b). Bars represent mean±sd (n=5-7 male mice per genotype and per age group; young: less that 6 months old; old: 1.5-2 years old). Statistical significance was determined by the two-tailed Student's t-test.
d. Levels of phosphorylated Irs1 in epididymal WAT (n=3 male mice for each genotype). Blots were quantified relative to the Ponceau staining and mean±sd is indicated. Statistical significance was determined by the two-tailed Student's t-test.
e. Kaplan-Meier survival curves of those mice that were free of detectable cancer at the time of death. Statistical significance was determined by the logrank test. See FIG. 2(b).
f. DNA damage in the liver of old mice (1.5-2 years old; n=4 males per genotype). Percentage of positive nuclei by immunofluorescence using the indicated markers (mean±sd). Statistical significance was determined by the two-tailed Student's t-test. See FIG. 2(c).

$*p<0.05$, $p<0.01$, $*p<0.001$.

Figure 3:
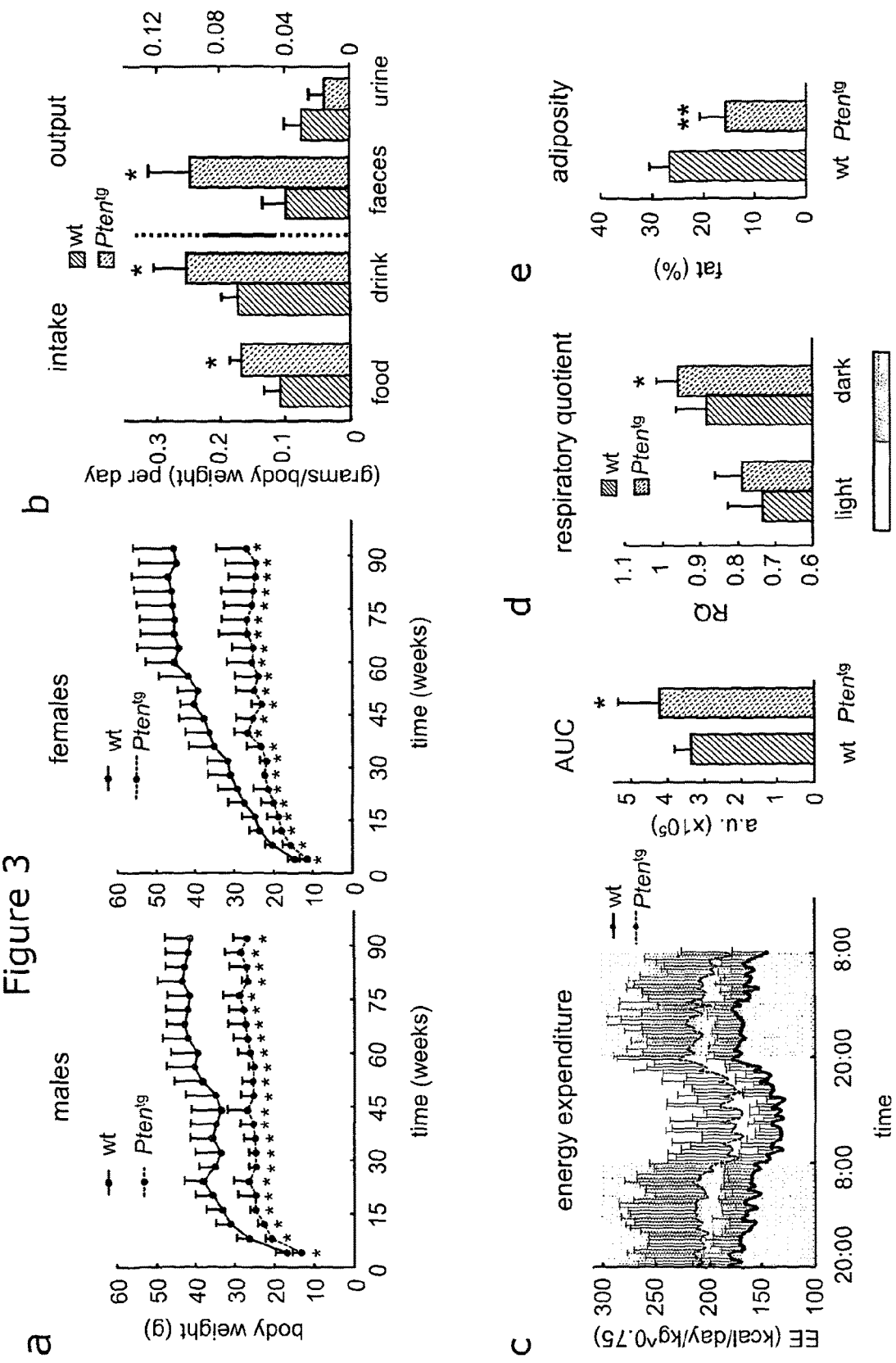
Figure 3:
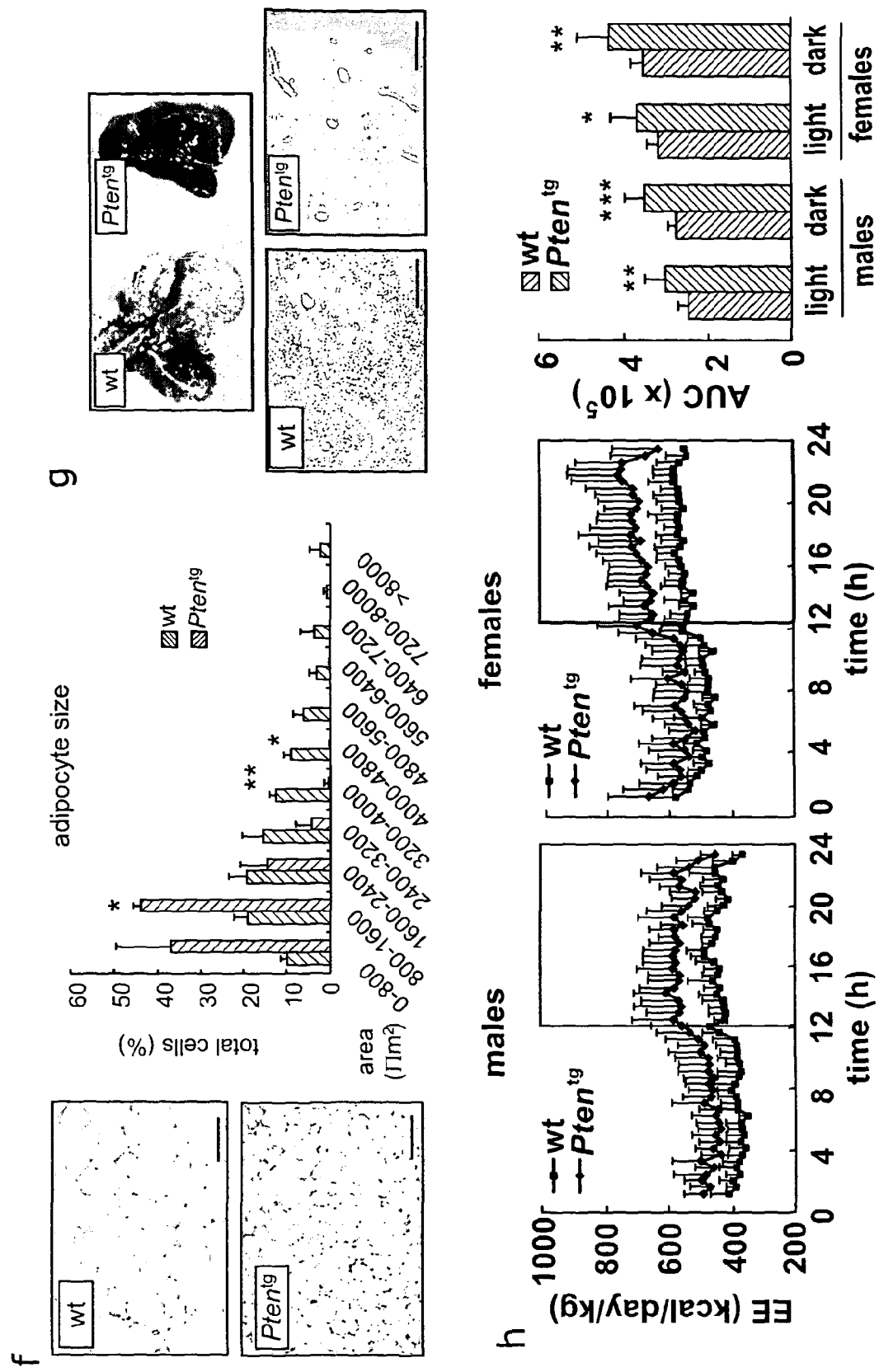
Figure 3:
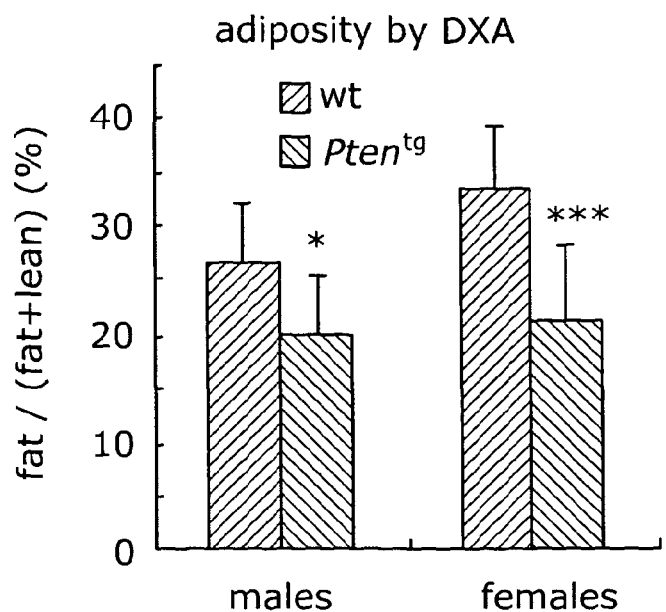
Figure 3:
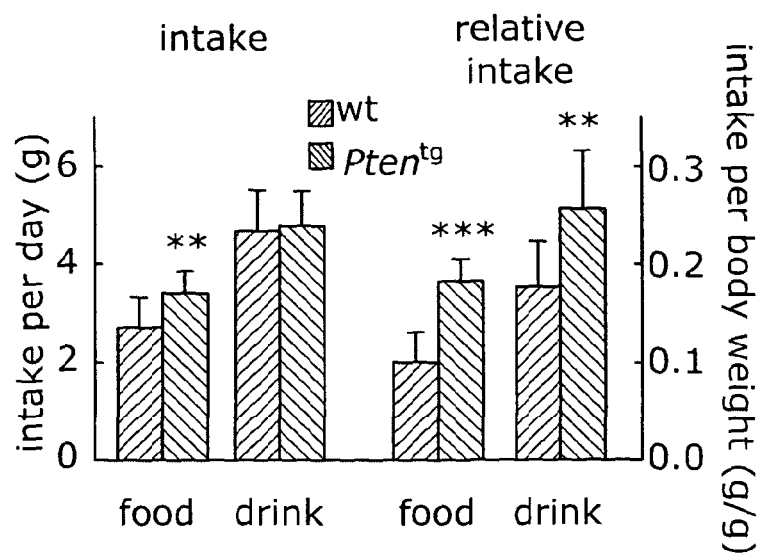

FIG. 3. Elevated energy expenditure, decreased adiposity and protection from diet-induced steatosis in Pten$^{tg}$ mice.

a. Weight curves (n=15 for each genotype and sex).
b. Intake and output normalized by body weight (3-4 months old; n=4 male mice per genotype).
c. Energy expenditure measured in young males (2-4 moths old; n=8 per genotype) during a 36 hr recording (two dark periods and one light period). Similar results were obtained in an independent recording. The bar graph at the right side represents the average Area Under the .curve (AUC) over the 36 hr period.
d. Respiratory quotient ($VCO_2/VO_2$) during one nocturnal phase and one diurnal phase.
e. Adiposity in young males (2-3 months old; n=6 per genotype) measured by Dual energy X-ray Absorptiometry (DXA). Values correspond to the mean±sd of the percentage of fat relative to the sum of lean and fat masses.
f. Representative picture of epididymal WAT. Samples correspond to young males and were stained with hematoxylin and eosin (bar indicates 100 µm). Adipocyte area distribution is shown in the right graph (n=2 per genotype; >500 cells per genotype).
g. Macroscopic views of representative livers 6 months after high-fat diet feeding (top) and microscopic sections stained with hematoxylin and eosin (bottom, bar indicates 500 µm).
h. Energy expenditure measured in adult males and females (6-8 moths old; n=8-10 per genotype and per sex). The bar graph at the right side represents the average Area Under the Curve (AUC) over the indicated 12 hr period. See FIG. 3(c).
i. Adiposity in young mice (6-8 moths old; n=8-10 per genotype and per sex) measured by Dual energy X-ray Absorptiometry (DXA). Values correspond to the percentage of fat relative to the sum of lean and fat masses. See FIG. 3(d).
j. Food intake in absolute values (left) and normalized by body weight (right) (n=8 males per genotype; 3-4 months old). See FIG. 3(b).

Values represent mean±sd, and statistical significance was determined by the two-tailed Student's t-test. $*p<0.05$, $p<0.01$, $*p<0.001$.

Figure 4:
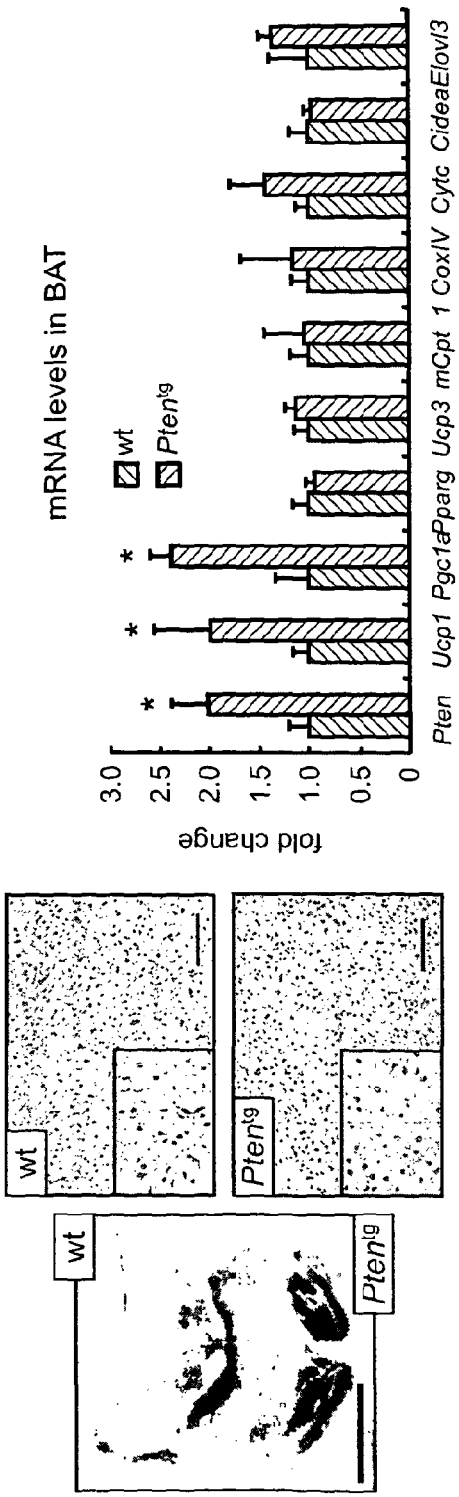
Figure 4:
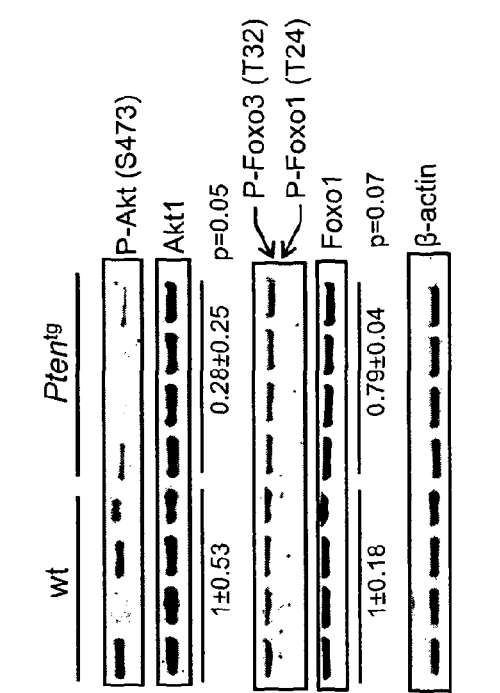
Figure 4:
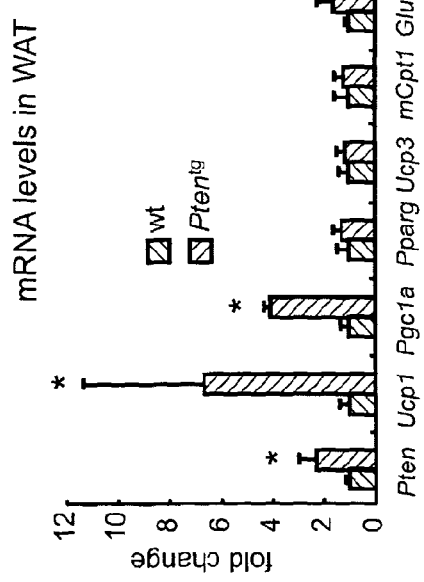
Figure 4:
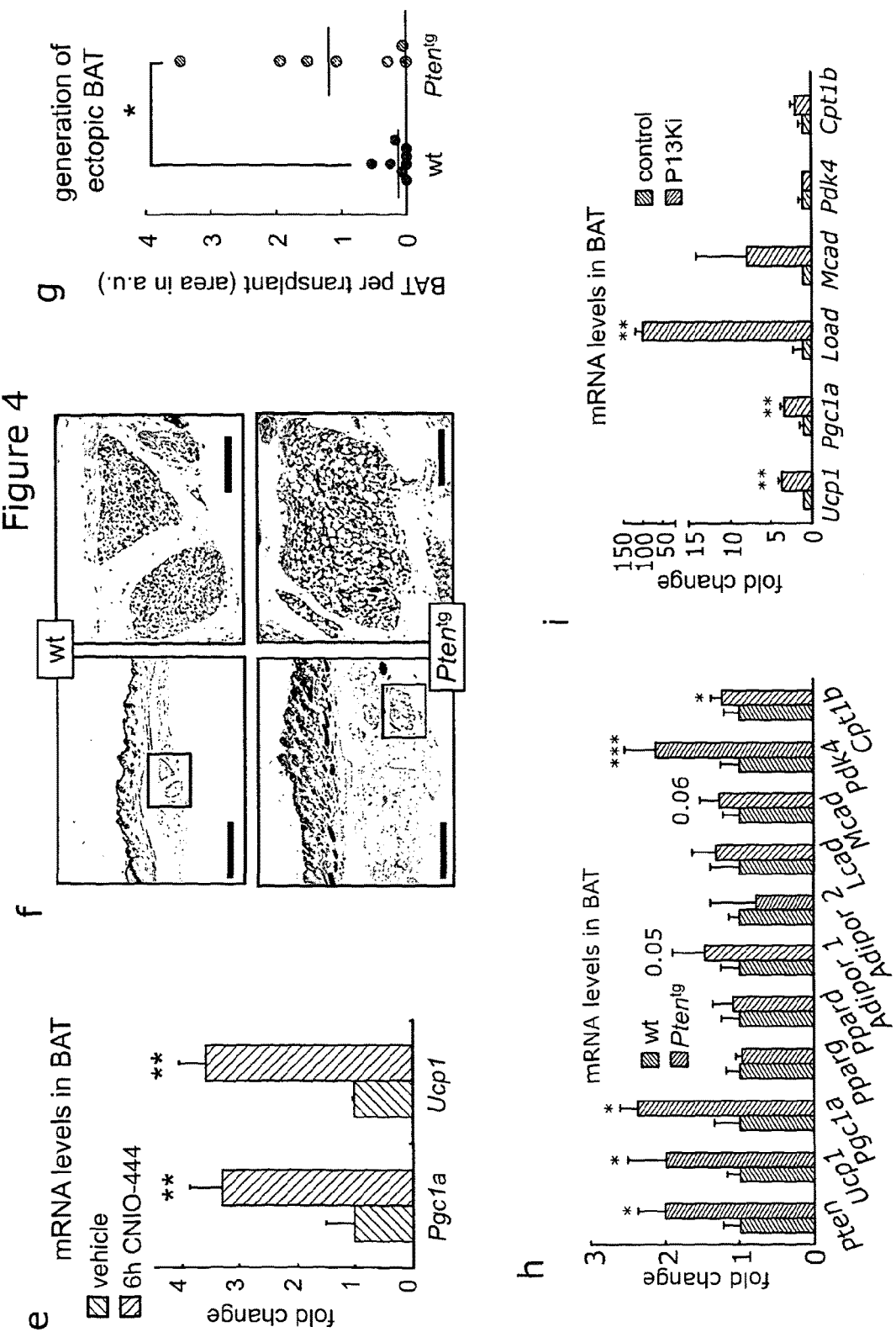
Figure 8:
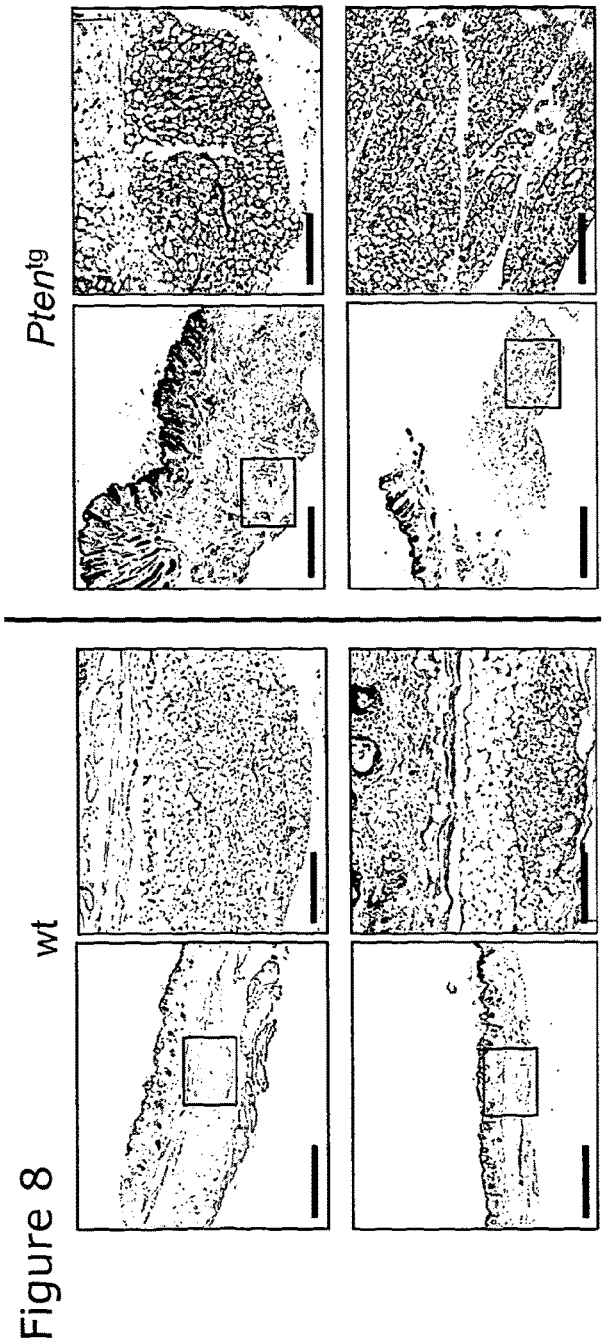

FIG. 4. Elevated uncoupling activity in Ptentg brown adipose tissue (BAT).

a. Representative macroscopic pictures of brown adipose tissue (BAT) (left, bar indicates 1 cm). Microscopic pictures of BAT stained with hematoxylin and eosin (bars indicate 100 µm). Samples correspond to males (5 months old).
b. Relative gene expression in BAT (5 months old; n=3 males per genotype).
c. Relative gene expression in epididymal WAT (5 months old; n=3 males per genotype).
d. Immunoblot of BAT lysates (5 months old; n=4 males per genotype). Levels of phospho-Akt were quantified relative to total Akt1, and phospho-Foxo1 levels were quantified relative to total Foxo1.
e. Relative mRNA levels in BAT after Compound A or vehicle administration (3 months old; n=3 males C57BL6 per group). Samples were analyzed 6 h after gavage.
f. Representative microscopic pictures of ectopic BAT derived from Prdm16/Cebpb-programmed wt or Pten$^{tg}$ fibroblasts. Low magnification, bars corresponds to 1 mm; high magnification, bars correspond to 200 µm. Additional pictures are shown in FIG. 8.
g. Amount of BAT formation by Prdm16/Cebpb-programmed wt or Pten$^{tg}$ fibroblasts. Each value corresponds to the area of BAT (in arbitrary units) measured in the fat pads formed per injection site (n=8 for wt, and n=7 for Pten$^{tg}$).
h. Relative gene expression in BAT (5 months old; n=3-6 males per genotype). See FIG. 4(b).
i. Relative mRNA levels in BAT upon PI3Ki "CNIO-compound A" (15 mg per kg of body weight) or vehicle administration, by gavage (3 months old; n=3 males C57BL6 per group). Samples were analyzed 6 h after administration. See FIG. 4(e).

Values represent mean±sd, and statistical significance was determined by the two-tailed Student's t-test. *p<0.05, **p<0.01.

Figure 5:
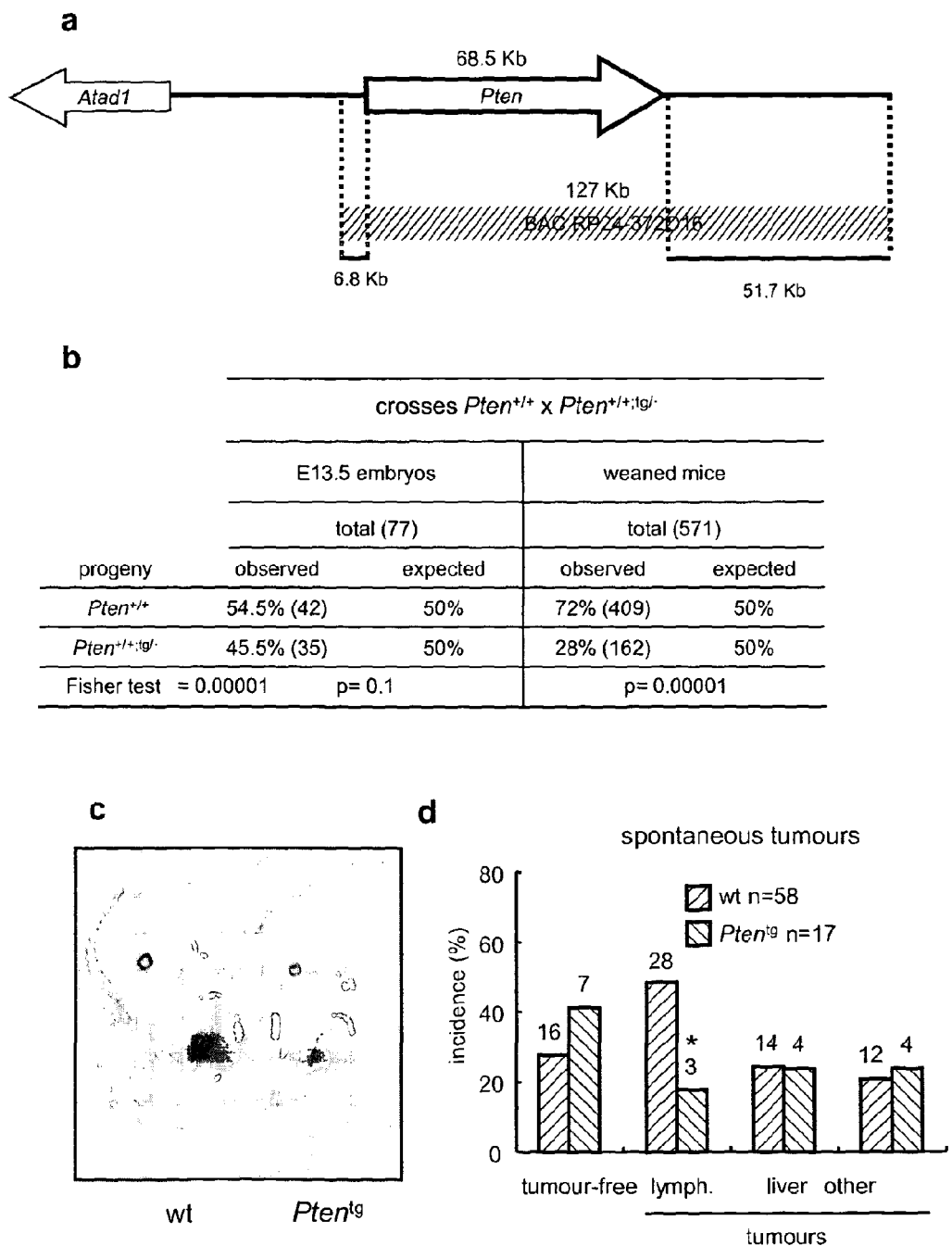

FIG. 5.
a. Scheme of BAC used for the generation of Pten$^{tg}$ mouse.
b. Proportions of embryos at stage E13.5 and weaned wt and Pten$^{tg}$ mice. Statistical significance was determined by the Fisher's exact test.
c. Representative picture of E13.5 embryos of the indicated genotypes.
d. Tumour spectrum of old moribund wt and Pten$^{tg}$ mice. Statistical significance was determined by the Fisher's exact test. *p<0.05.

Figure 6:
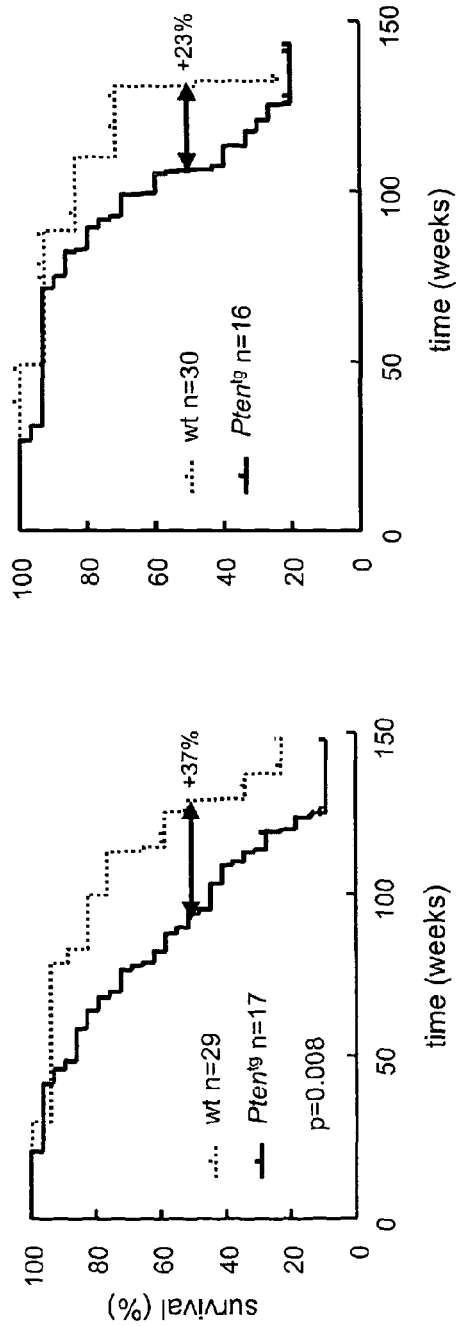
Figure 6:
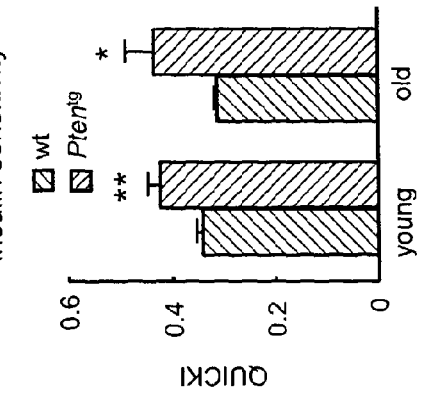
Figure 6:
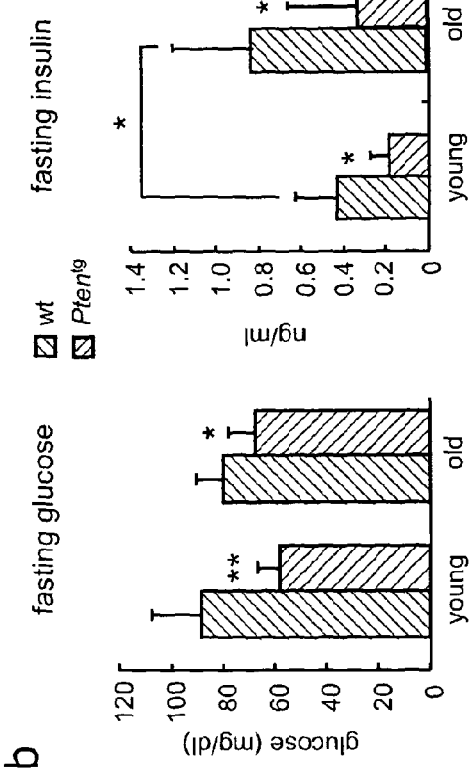
Figure 6:
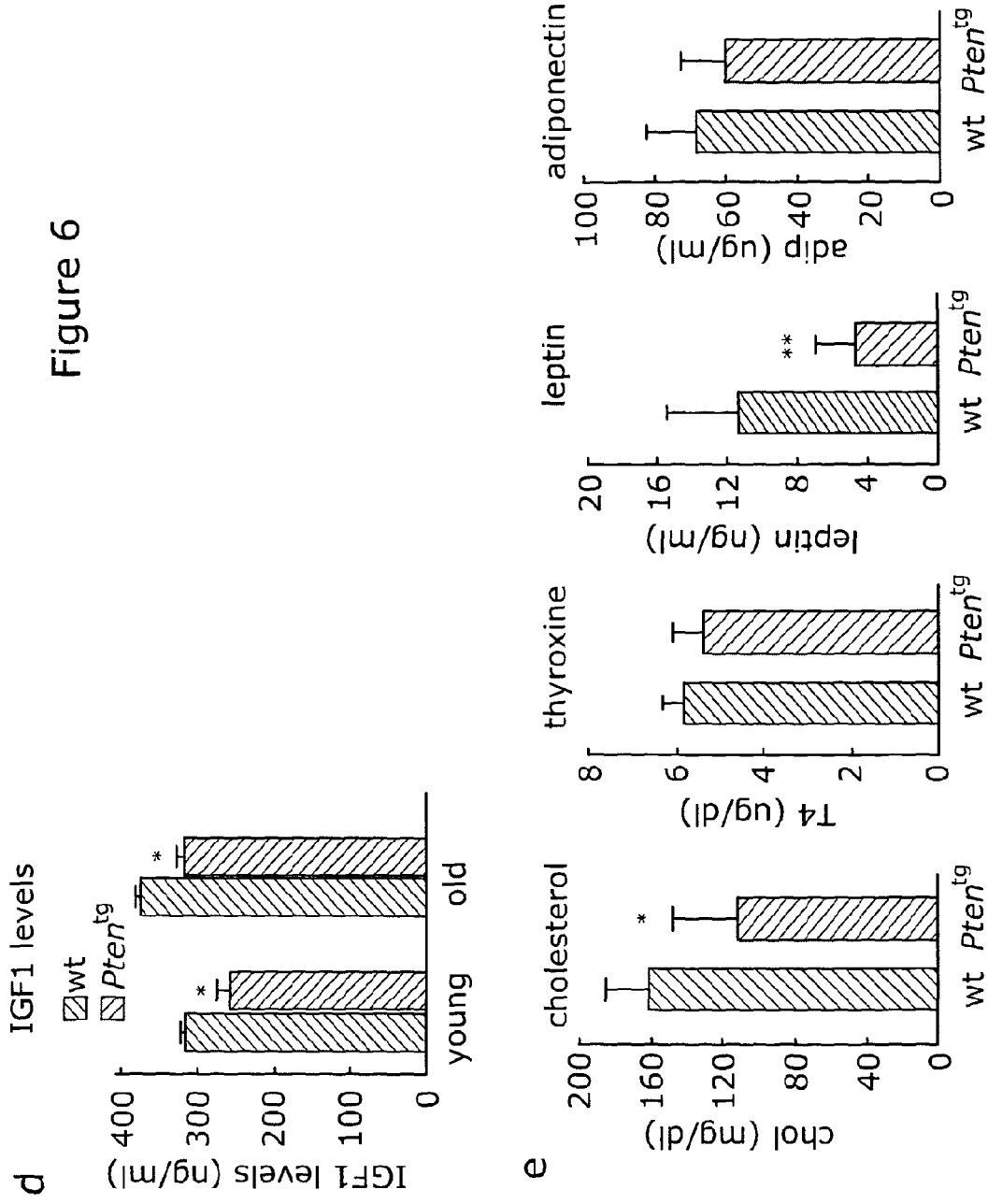

FIG. 6.
a. Kaplan-Meier survival curves of lymphoma-free wt and Pten$^{tg}$ mice. Statistical significance was determined by the logrank test.
b. Levels of fasting glucose and fasting insulin of young (less that 6 months old) and old (1.5-2 years old) wt and Pten$^{tg}$ mice.
c. Quantitative insulin sensitivity check index (QUICKI) of young (less that 6 months old) and old (1.5-2 years old) wt and Pten$^{tg}$ mice.
d. Igf1 serum levels in young (less that 6 months old) and old (1.5 to 2 years old) wt and Pten$^{tg}$ mice.
e. Levels of the indicated metabolites in hormones and serum.
Panels b, c and d represent the mean±sd. Statistical significance was determined by the two-tailed Student's t-test. *p<0.05, **p<0.01.

Figure 7:
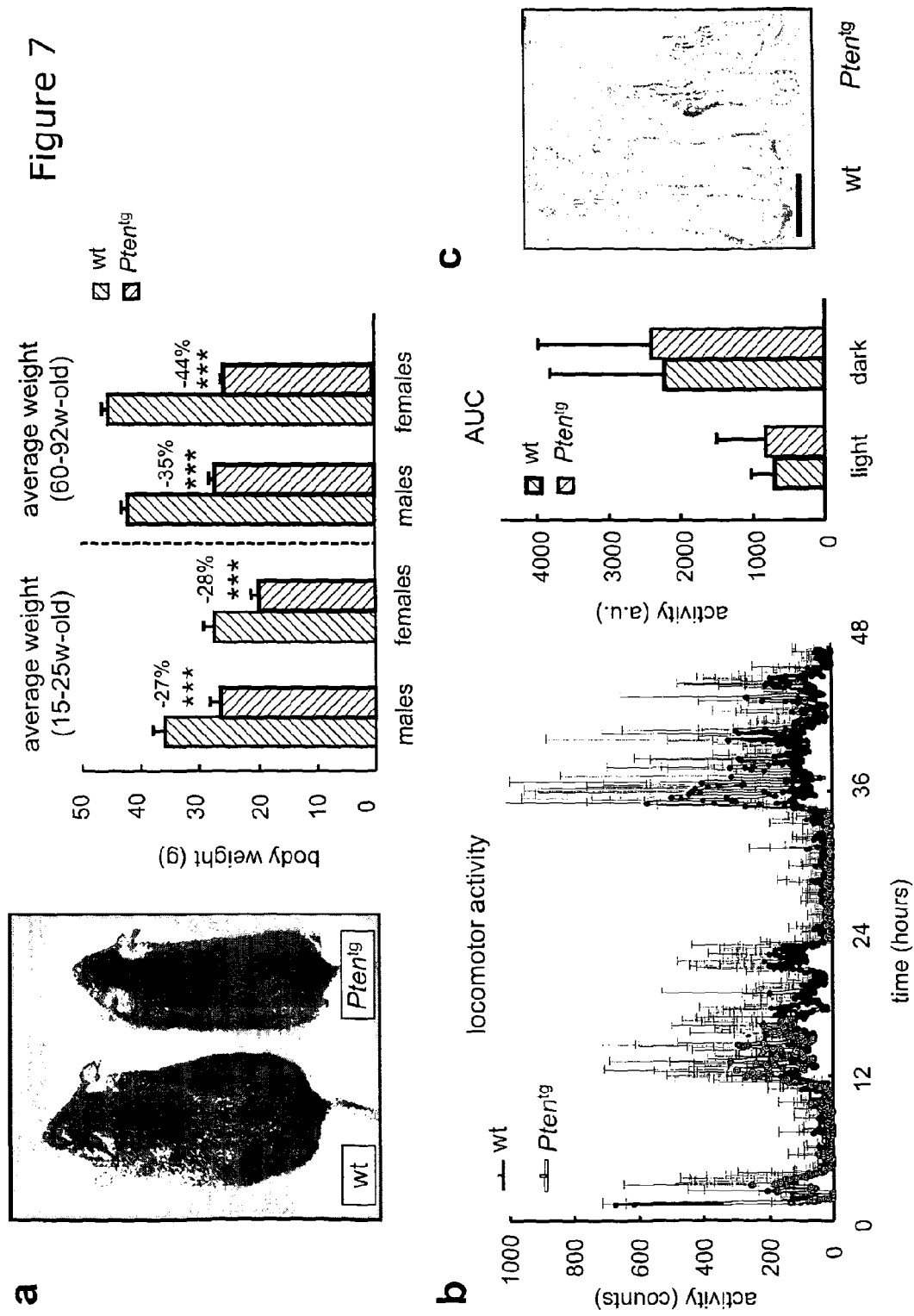
Figure 7:
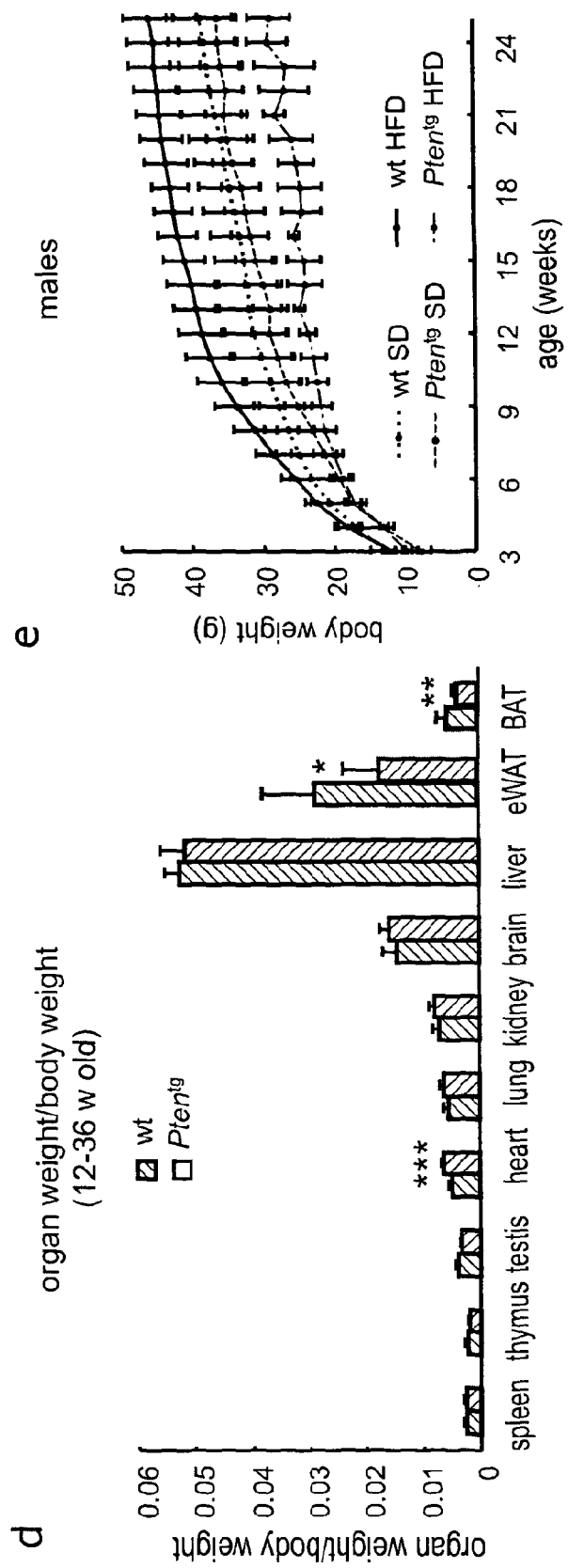

FIG. 7.
a. Representative picture of wt and Pten$^{tg}$ mice and their body weight at the indicated age ranges.
b. Locomotor activity in wt and Pten$^{tg}$ mice. The adjacent bar graph represents the average area under the curve (AUC) over the two nocturnal and two diurnal phases.
c. Representative macroscopic pictures of epididymal WAT. Bar indicates 1 cm.
d. Ratios between organ weight and total body weight (n=6-8 male mice per genotype). eWAT: epididymal WAT.
e. Weight curves of male mice under Standard Diet (SD) or High-Fat Diet (HFD) since weaning (n=15 for each genotype).
Panels c and d represent the mean±sd. Statistical significance was determined by the two-tailed Student's t-test. *p<0.05, p<0.01, *p<0.001.

FIG. 8.
Representative examples of ectopic BAT from Prdm16/Cebpb-programmed wt or Pten$^{tg}$ fibroblasts. Low magnification, bars corresponds to 1 mm; high magnification, bars correspond to 200 μm.

Figure 9:
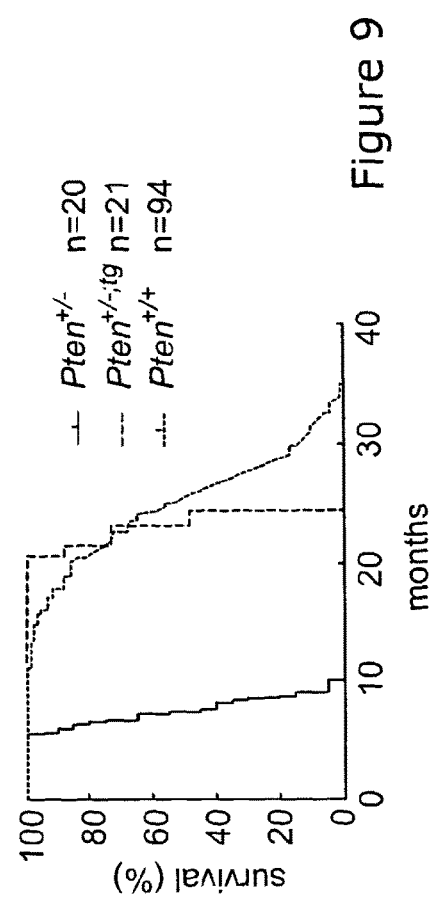

FIG. 9.
Rescue to the early lethality of Pten+/− mice by the transgenic copy of Pten. Kaplan-Meier curves of the indicated cohorts (males and females pooled).

Figure 10:
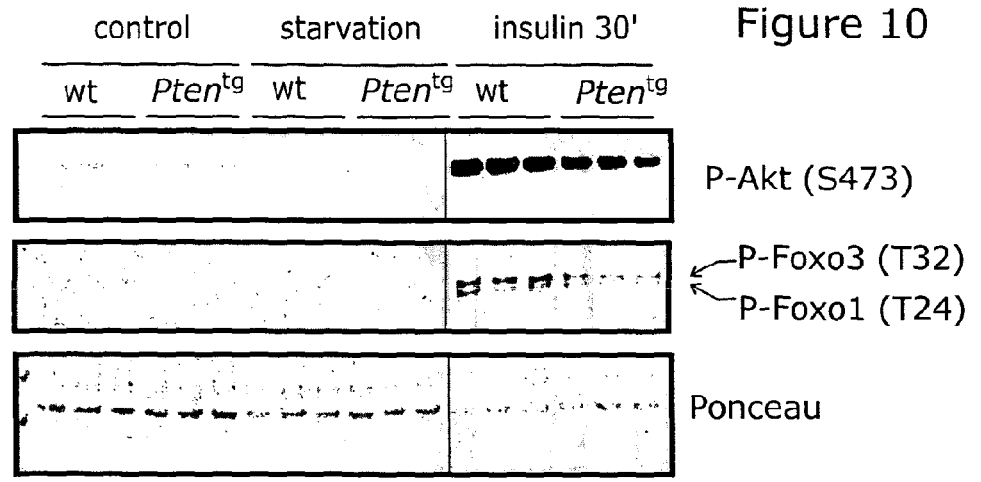

FIG. 10.
Immunoblot of lysates from normal growing cells (control), serum deprived cells (starvation), or starved and then stimulated cells with 1 ug/ml insulin (insulin 30′). Ponceau staining is shown as a loading control.

Figure 11:
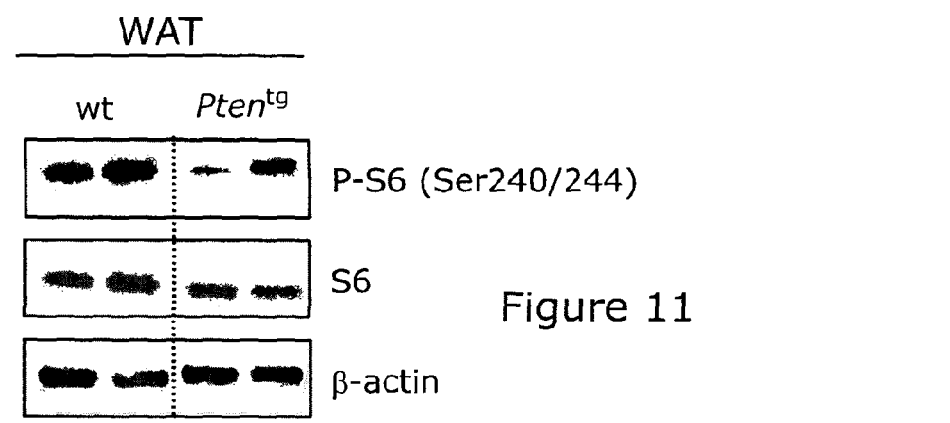

FIG. 11.
Immunoblot of the indicated proteins from WAT extracts (n=2 males per genotype; 4 months old).

Figure 12:
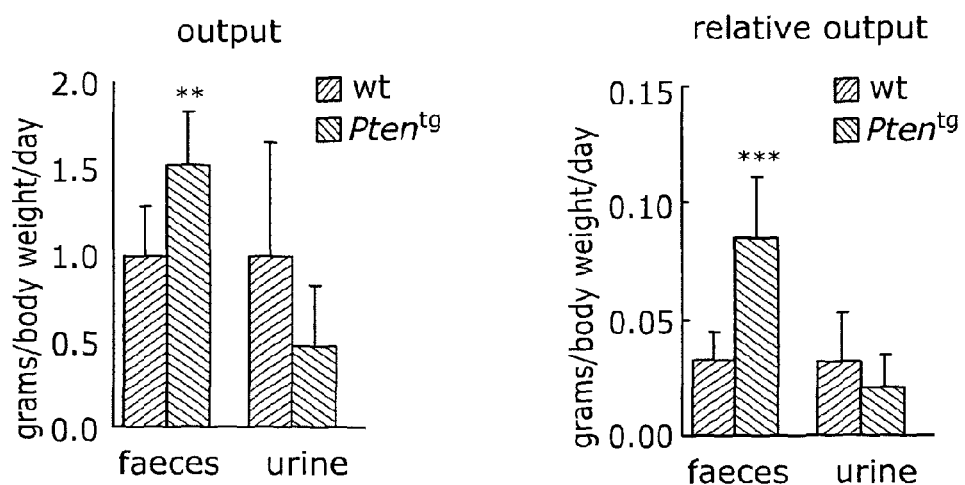

FIG. 12.
Output in absolute values (left) and normalized by body weight (right) (n-8 males per genotype; 3-4 months old)

Figure 13:
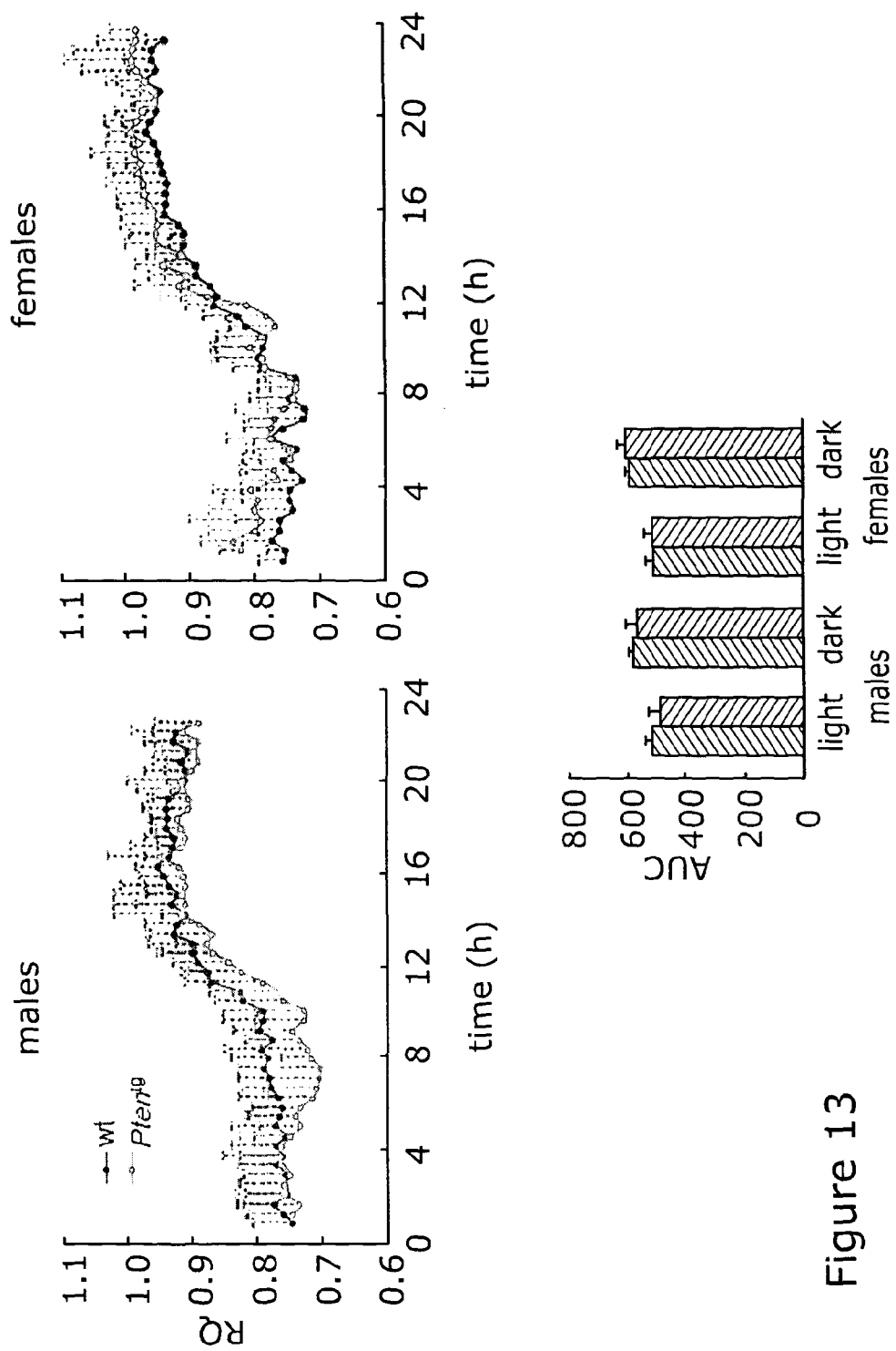

FIG. 13.
Respiratory quotient (VCO$_2$/VO$_2$) measured in adult males and females (6-8 months old; n=8-10 per genotype and per sex). The bar graph represents the average Area Under the Curve (AUC) over the indicated 12 hr period.

Figure 14:
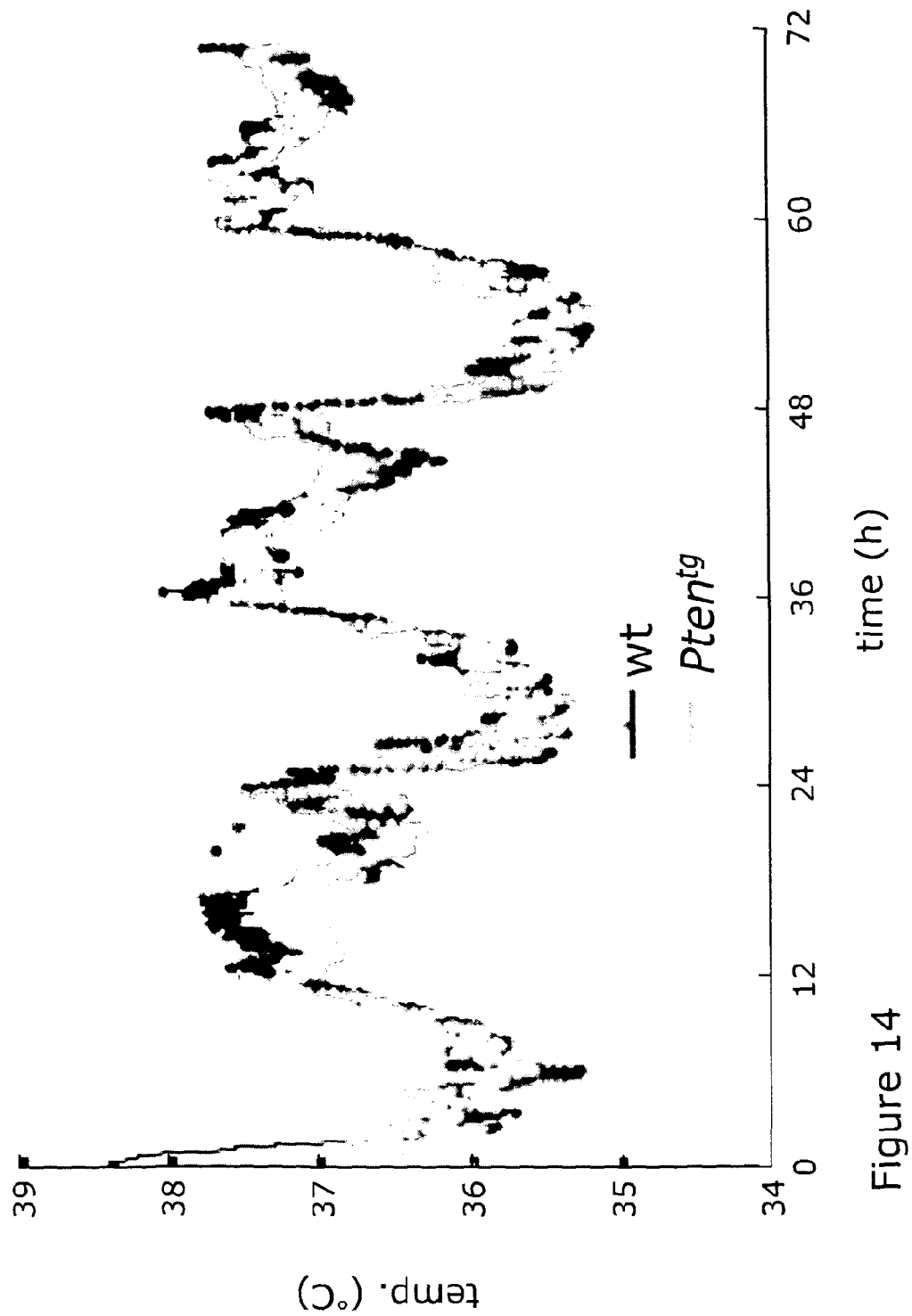

FIG. 14.
Temperature in wt and Pten$^{tg}$ mice. For measuring temperature, mice were implanted intraperitoneally with a PhysioTel®TA-F10 transmitter (Datasciences International, DSI) and temperature was recorded every 2 min at a room temperature of 23 degrees. Values correspond to the mean (n-6 males per genotype; 6 months old).

Figure 15:
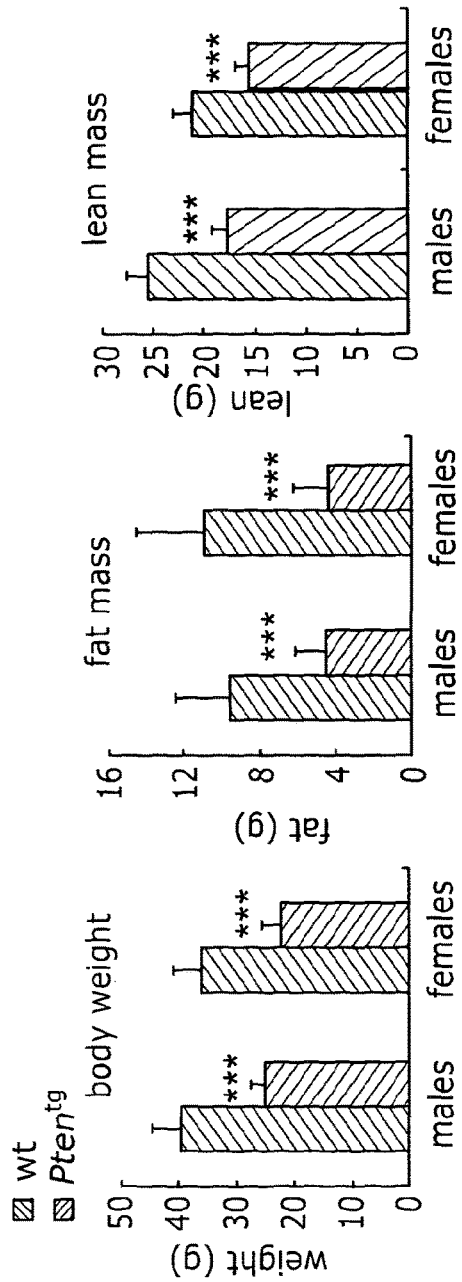

FIG. 15.
Body weight, fat mass (measured by DXA), and lean mass (measured by DXA). Values represented correspond to the mean±sd (n=8-10 mice per genotype and sex; 6-8 months old). Statistical significance was determined by the two-tailed Student's t-test. ***p<0.0001. Main FIG. 3(i) shows the ration between fat mass/(fat mass+lean mass).

Figure 16:
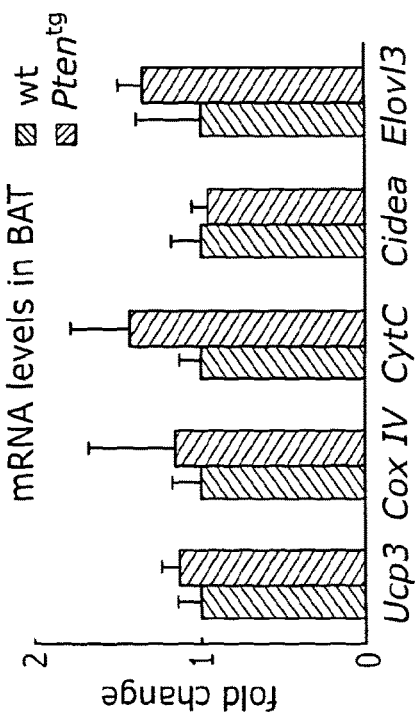

FIG. 16.
Relative gene expression in BAT (4-5 months old; n=3-4 males per genotype). Values represent mean±sd.

Figure 17:
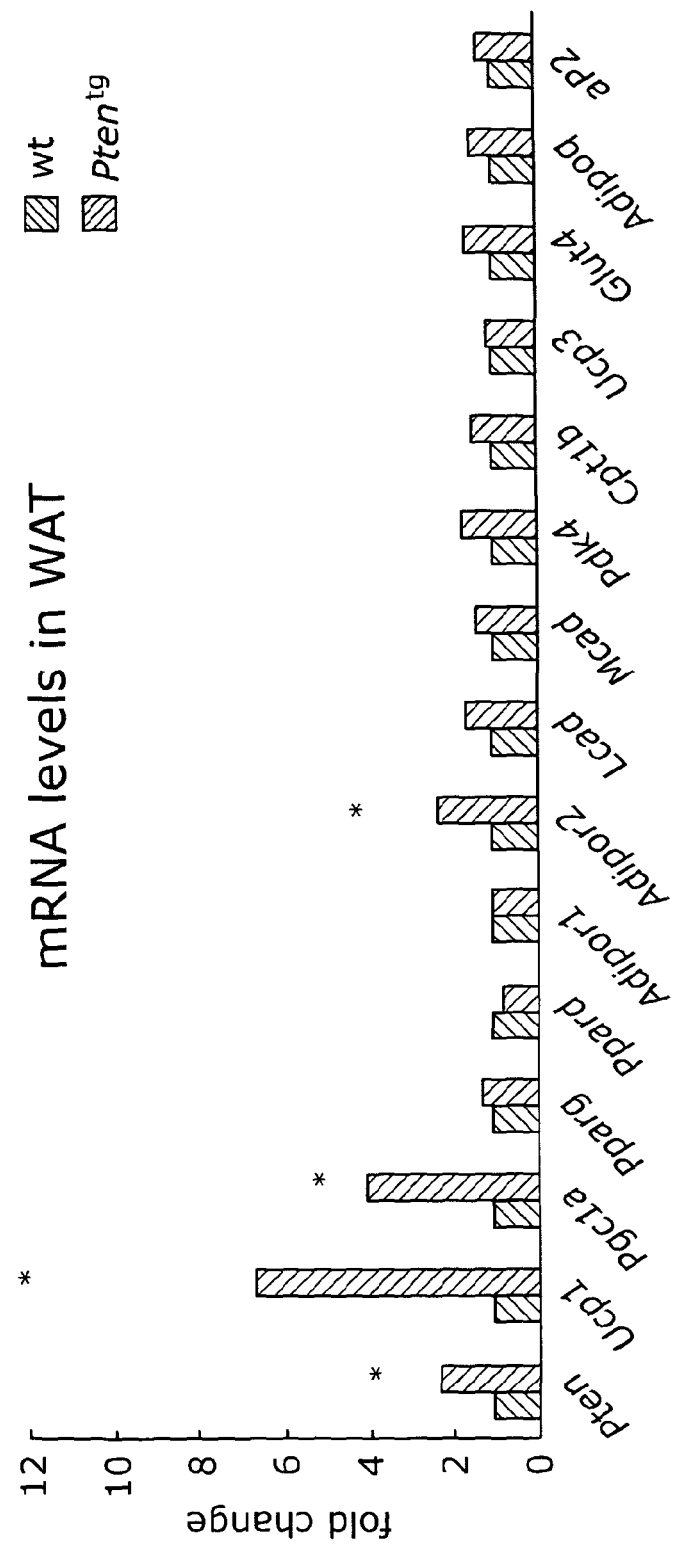

FIG. 17.
Relative gene expression in epididymal WAT (4-5 months old; n=3-6 males per genotype). Values represent mean±sd and statistical significance was determined using the two-tailed student's t-test. *p<0.05

Figure 18:
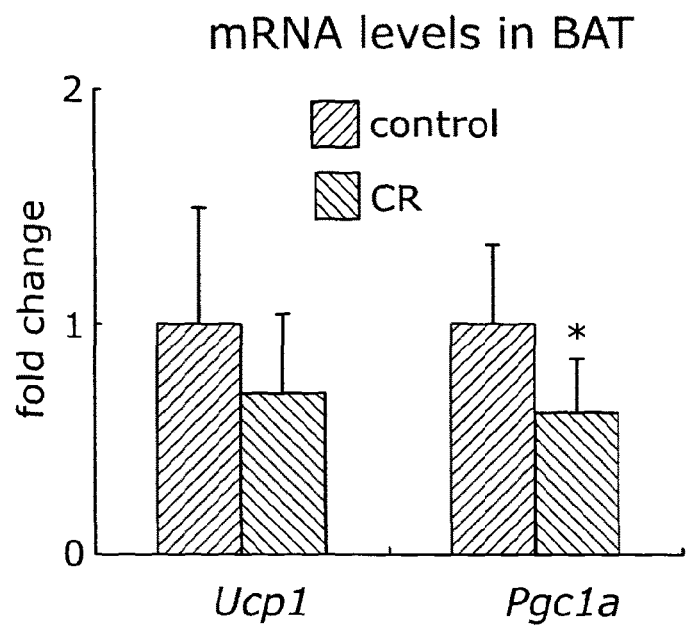

FIG. 18.
Relative gene expression of mice under ad libitum diet (control) or under caloric restriction (CR) during 4 weeks (n=8 males per diet). CR was 25% caloric restriction (diet Bio-Sery F05312). Values represent mean±sd, and statistical significance was determined using the two-tailed student's t-test. *p<0.05

Figure 19:
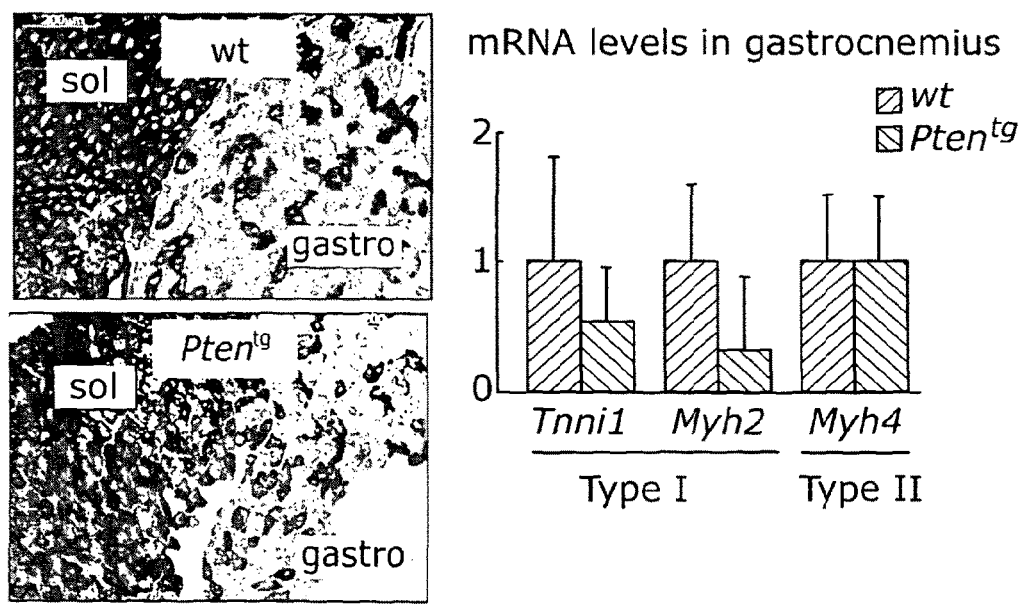

FIG. 19.
Representative succinate dehydrogenase (SDH) histochemical staining on gastrocnemius (gastro) and soleus (sol) muscle sections. SDH-positive myofibers correspond to Type I. Relative gene expression of markers of Type I and Type II myofibers in gastrocnemius. Data correspond to n=4 males per genotype, 1.5-2 years old.

Figure 20:
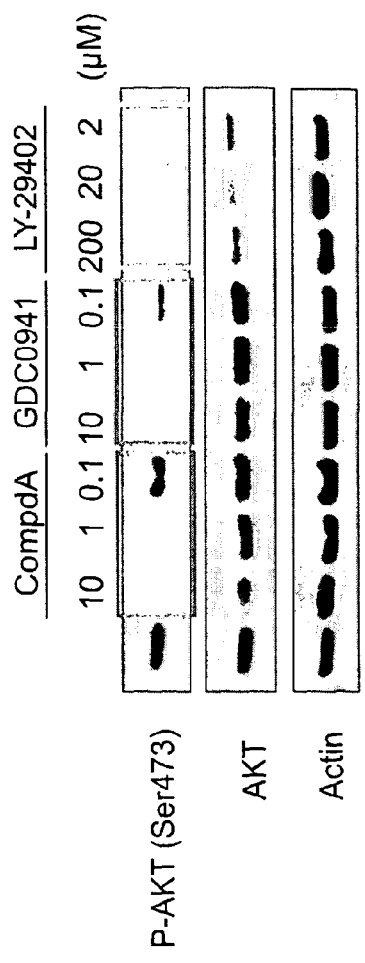

FIG. 20.
General structure of the PI3K small compound inhibitor "Compound A". The properties of this compound are reported in WO 2010/119264 (accessible at http://www.wipo.int/pctdb/en/wo.jsp?WO=2010119264). Also, see hereinbefore.

Figure 21:
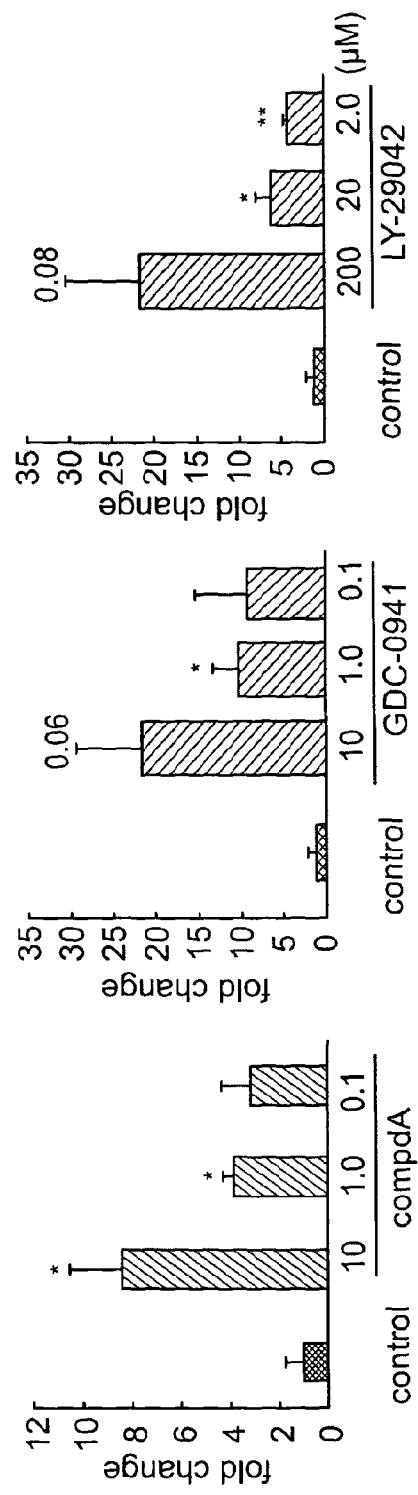

FIG. 21. Activation of pre-brown adipocytes in vitro by Compound A
Pre-brown adiposcytes were treated with Compound A or with the indicated PI3KI for 4 h. After this time, extracts were prepared for analysis of phospho-Akt (upper panels) or for analysis of Ucp1 mRNA levels (lower panels).

Figure 22:
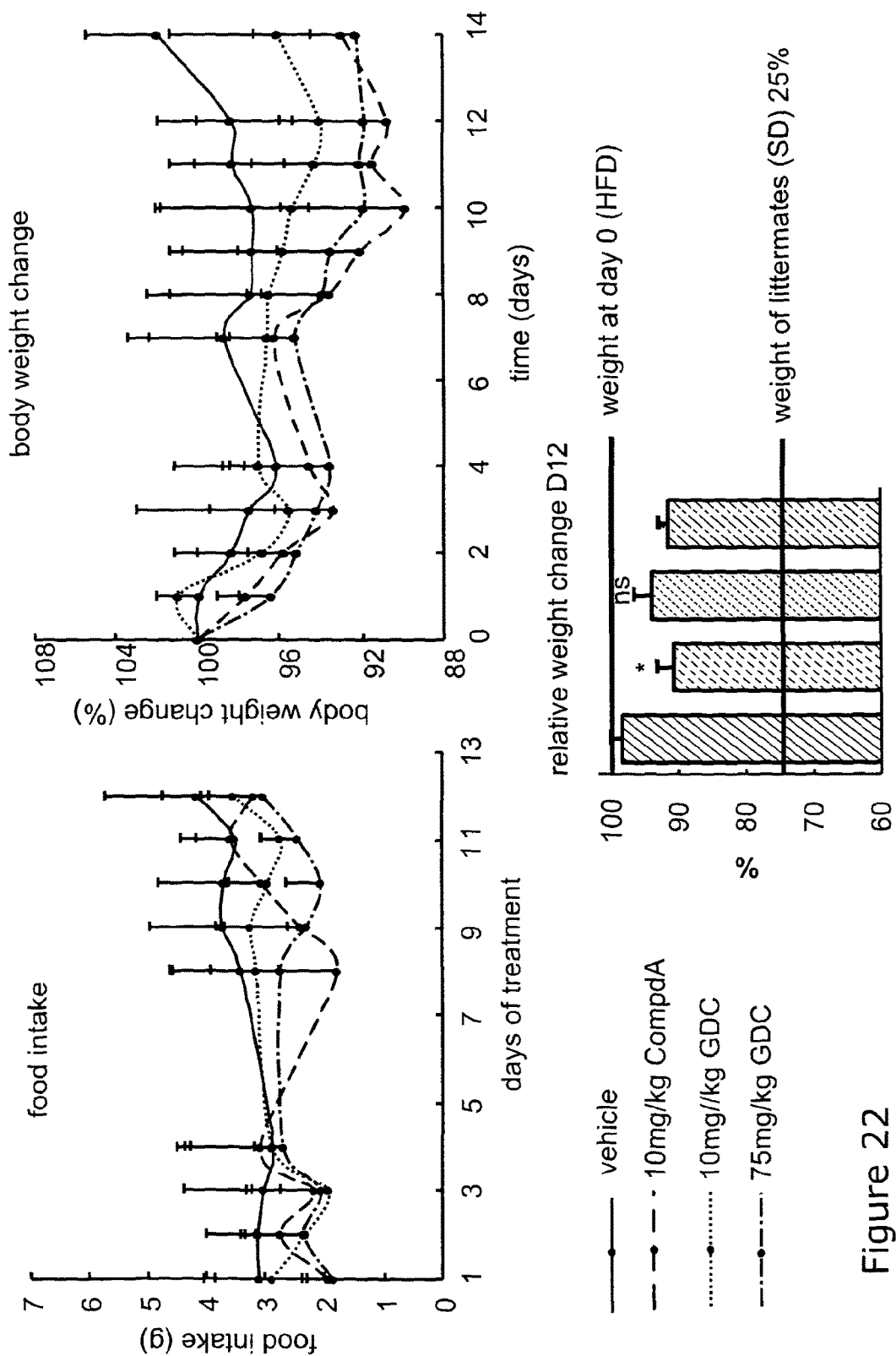

FIG. 22. Body weight loss by Compound A
Obese mice under long-term high-fat (HFD) were dosed with Compound A or with the indicated PI3KI by gavage once per day, during 2 weeks, resting the intervening weekend, and always with ad libitum access to HFD. During the two weeks of treatment, it was scored the amount of food intake (upper left panel) and the change in body weight relative to the initiation of the treatment (upper right panel). The final relative change in body weight is also represented (lower panel). The weight of non-obese littermates (always fed with standard diet, SD) is marked for reference.

Figure 23:
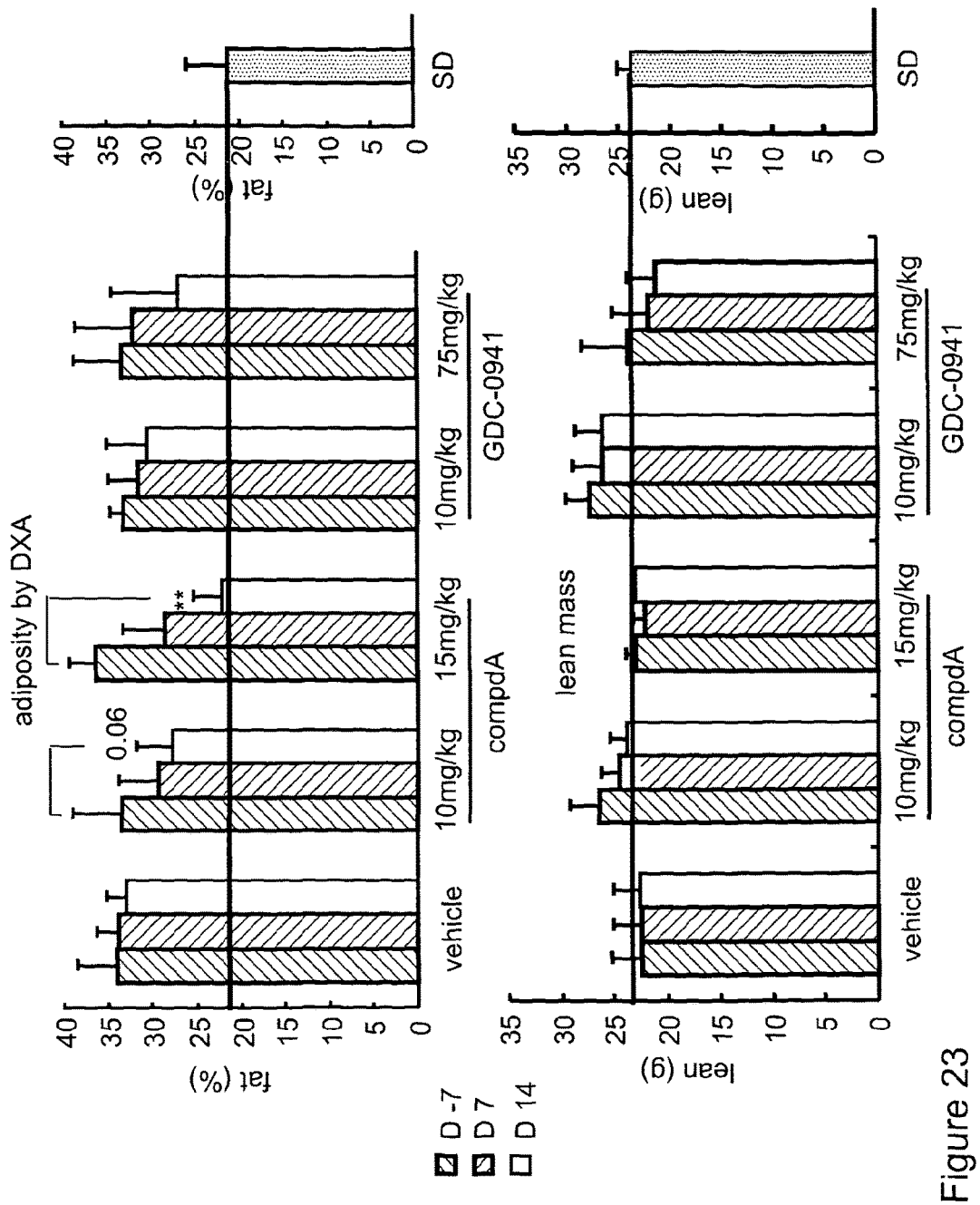
Figure 24:
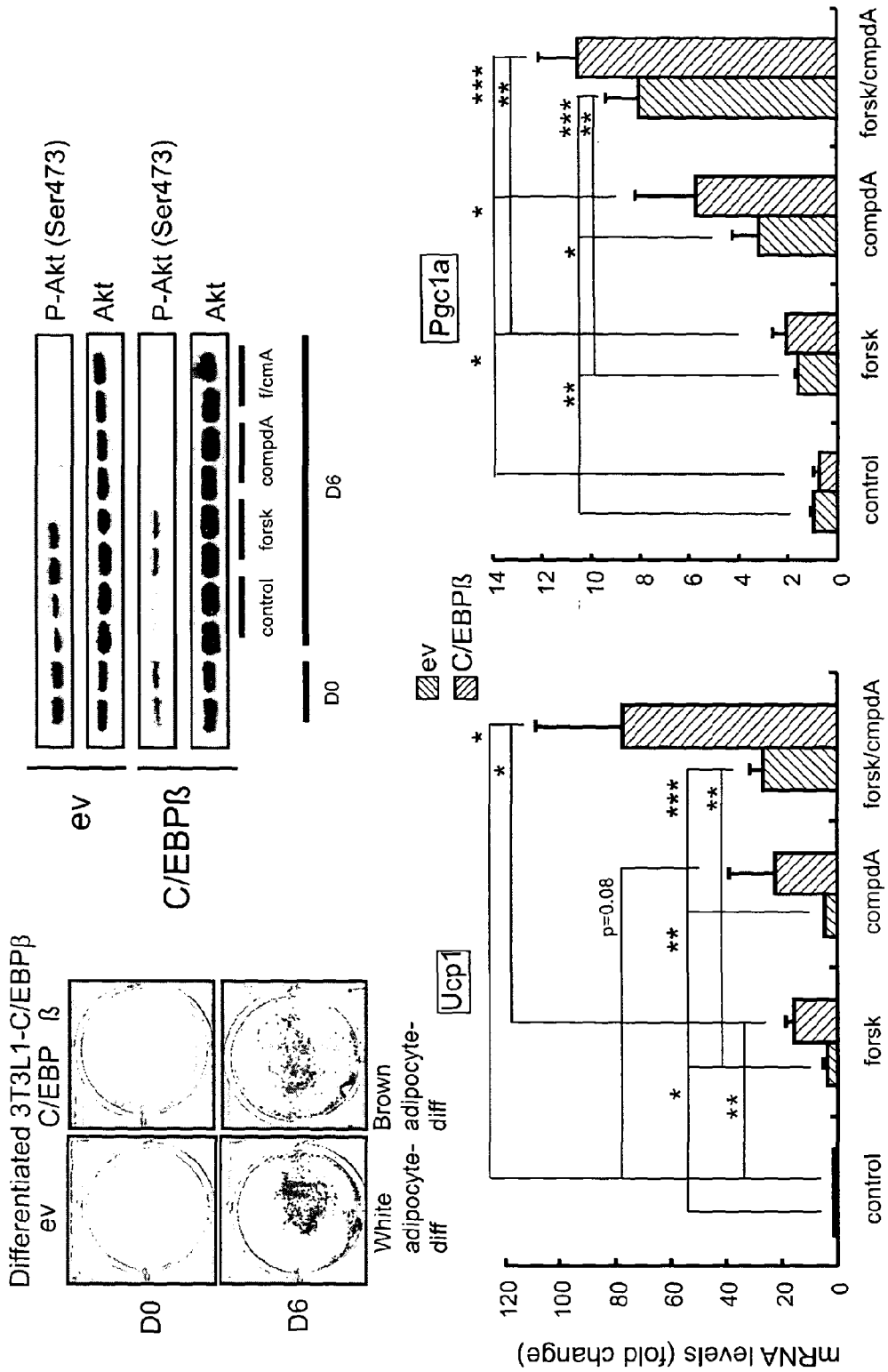
Figure 25:
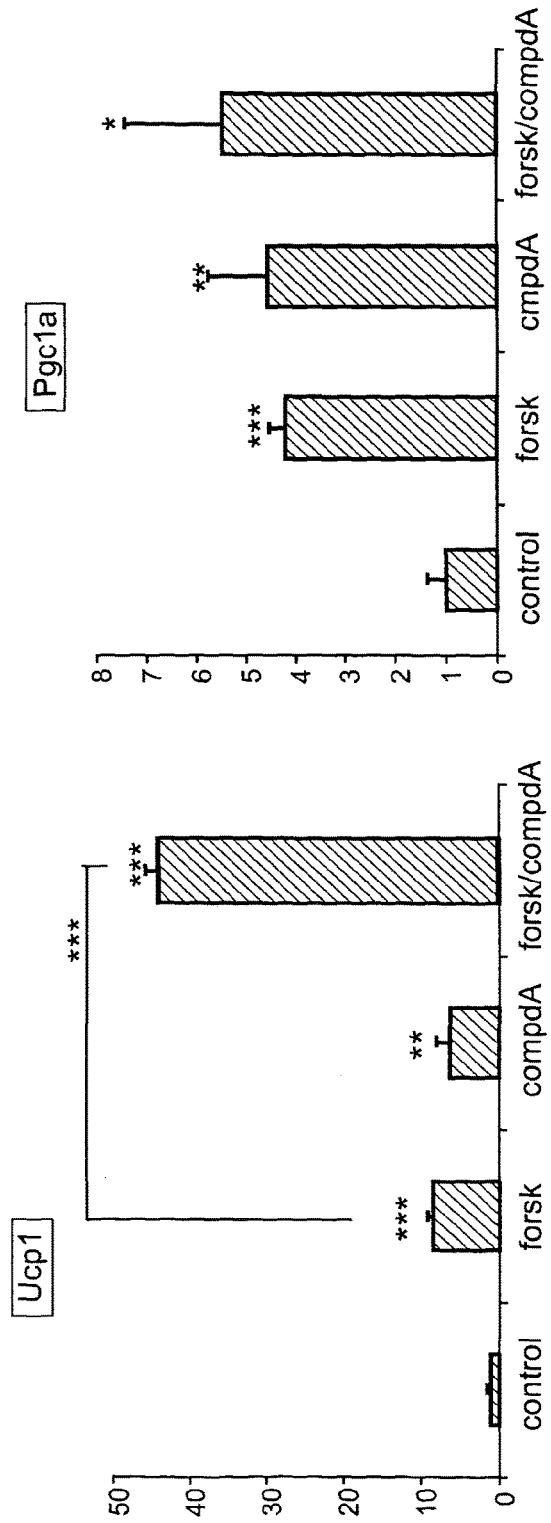
Figure 26:
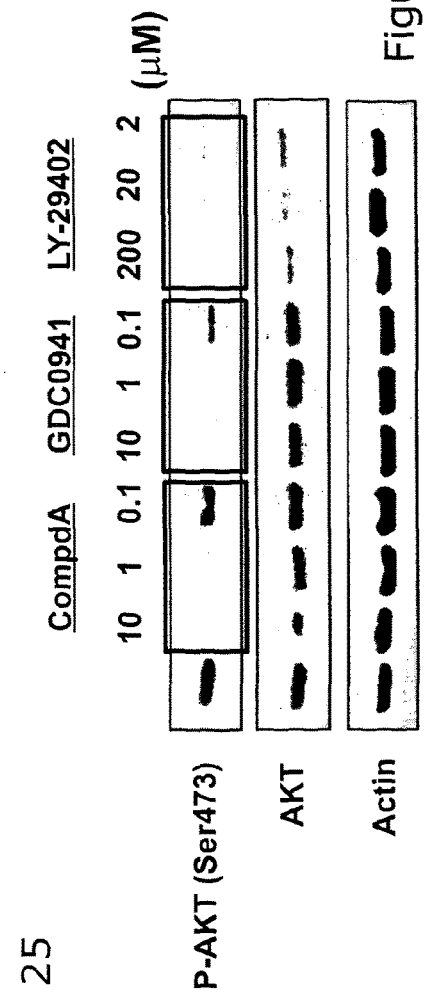
Figure 26:
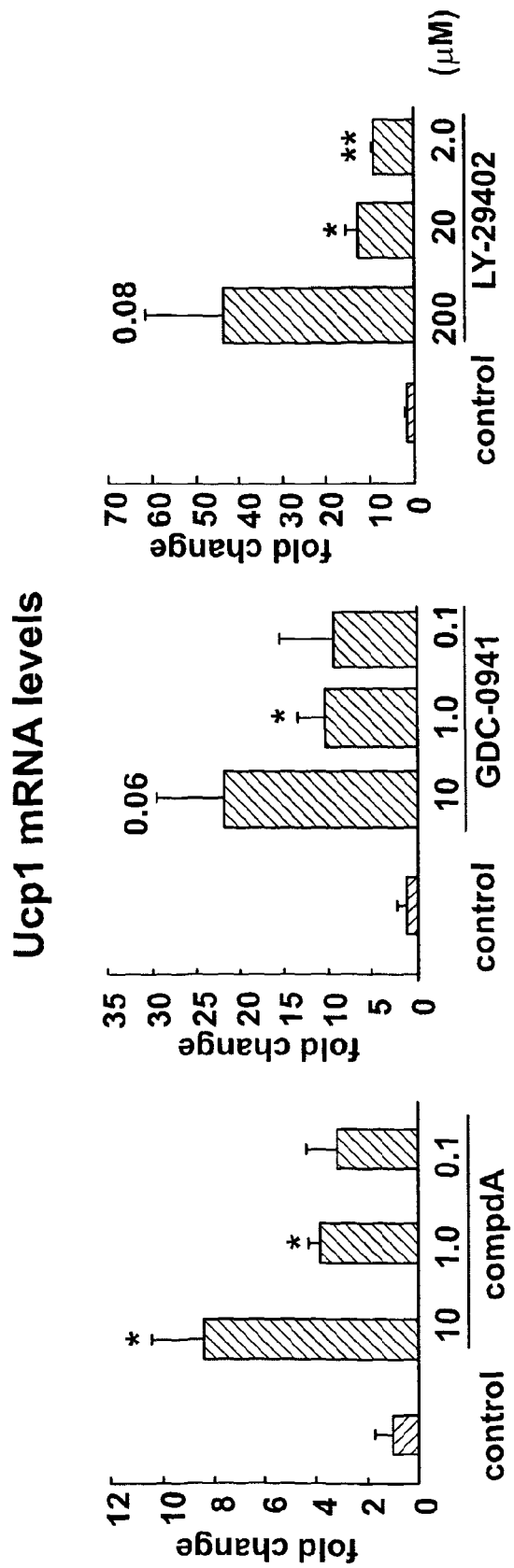
Figure 27:
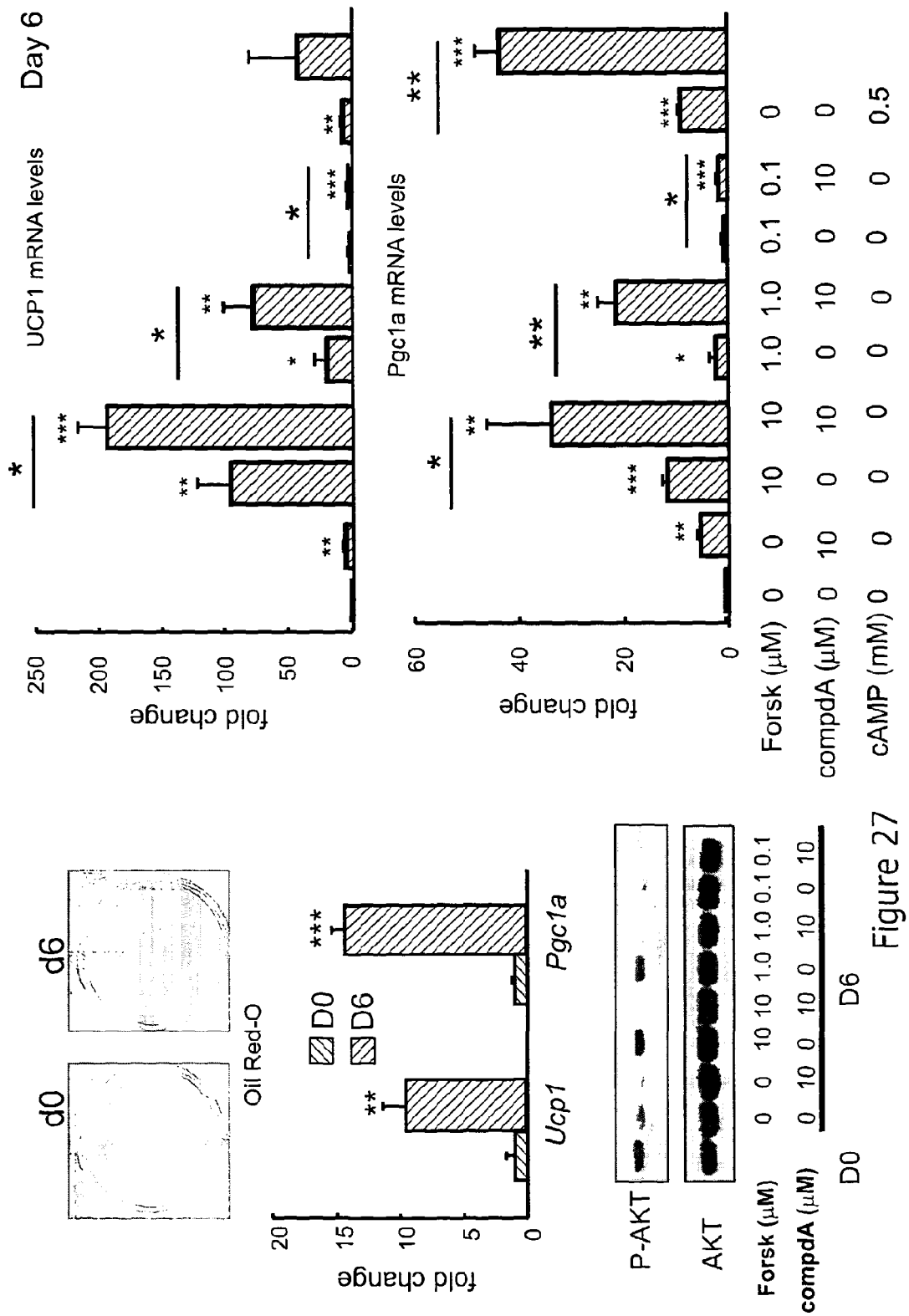
Figure 28:
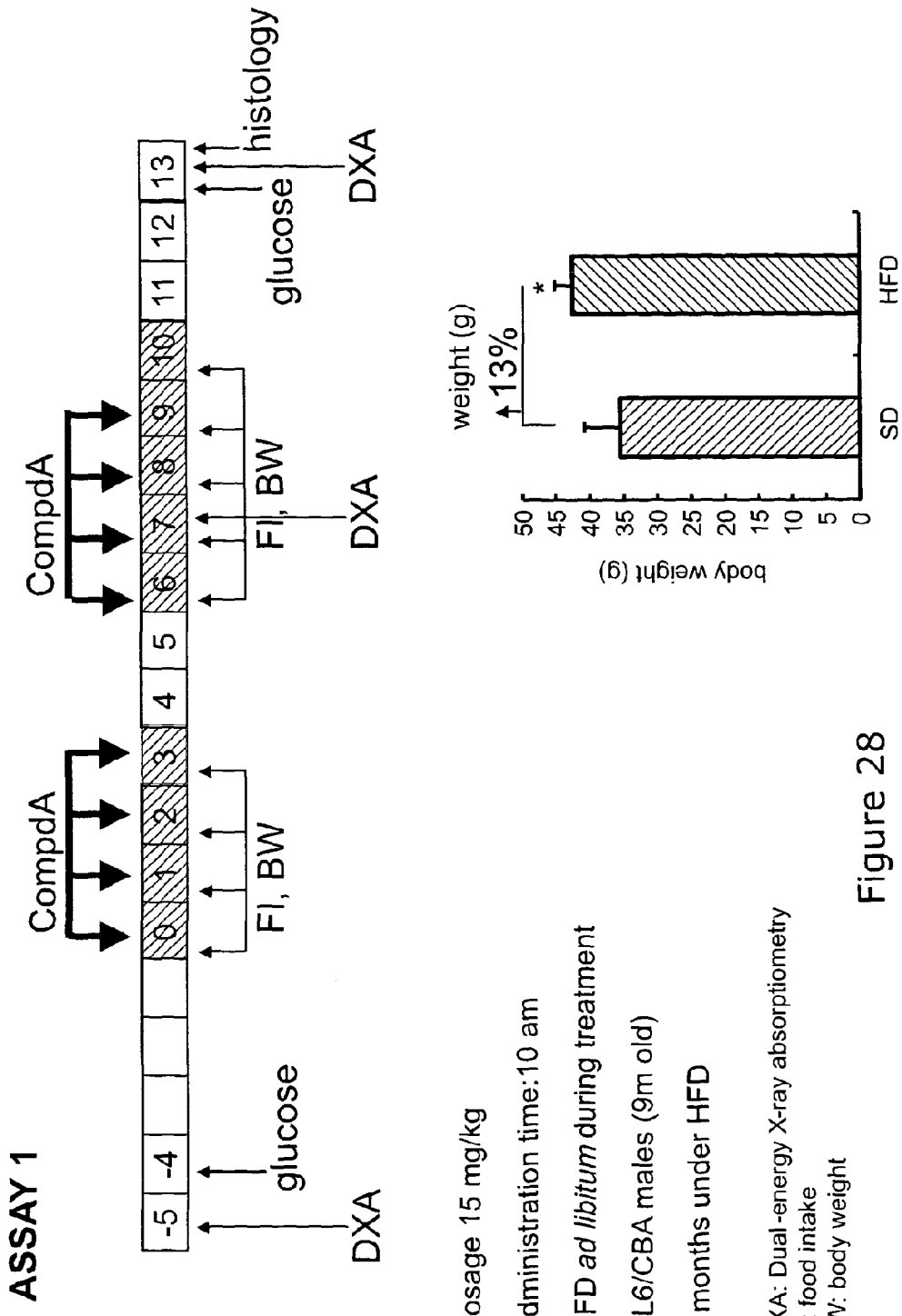
Figure 29:
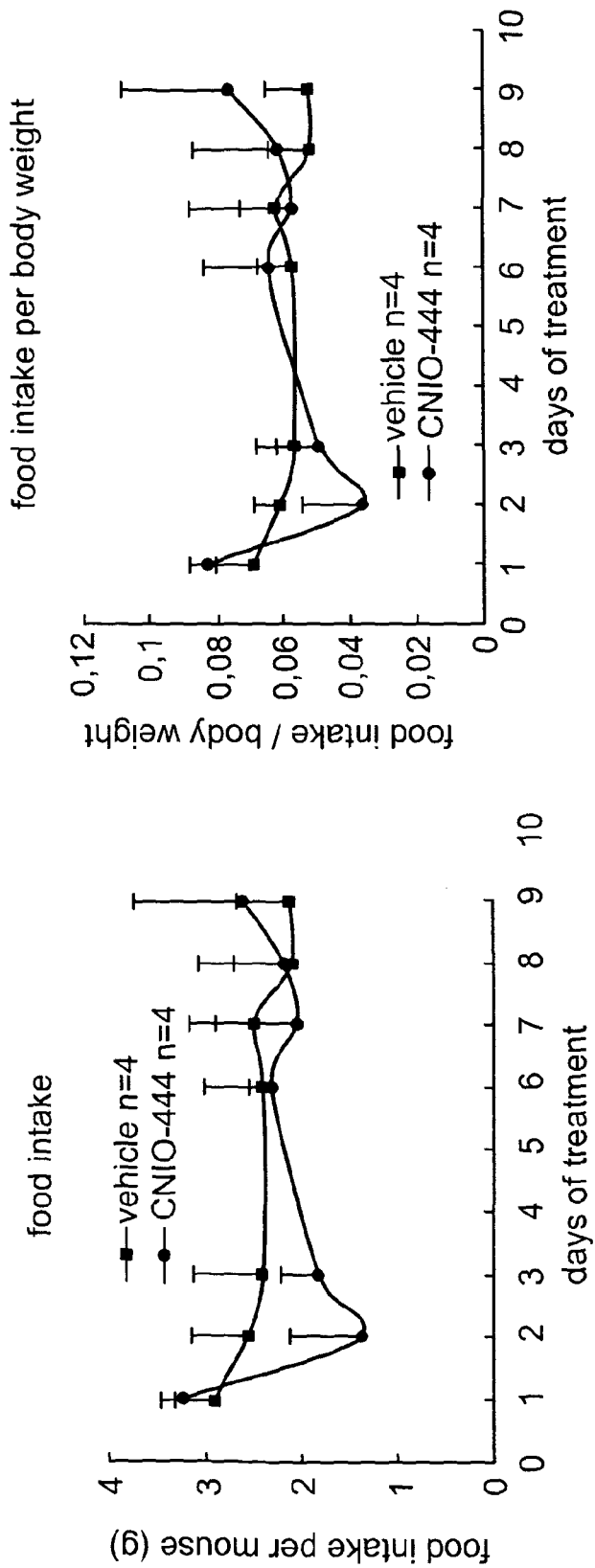
Figure 30:
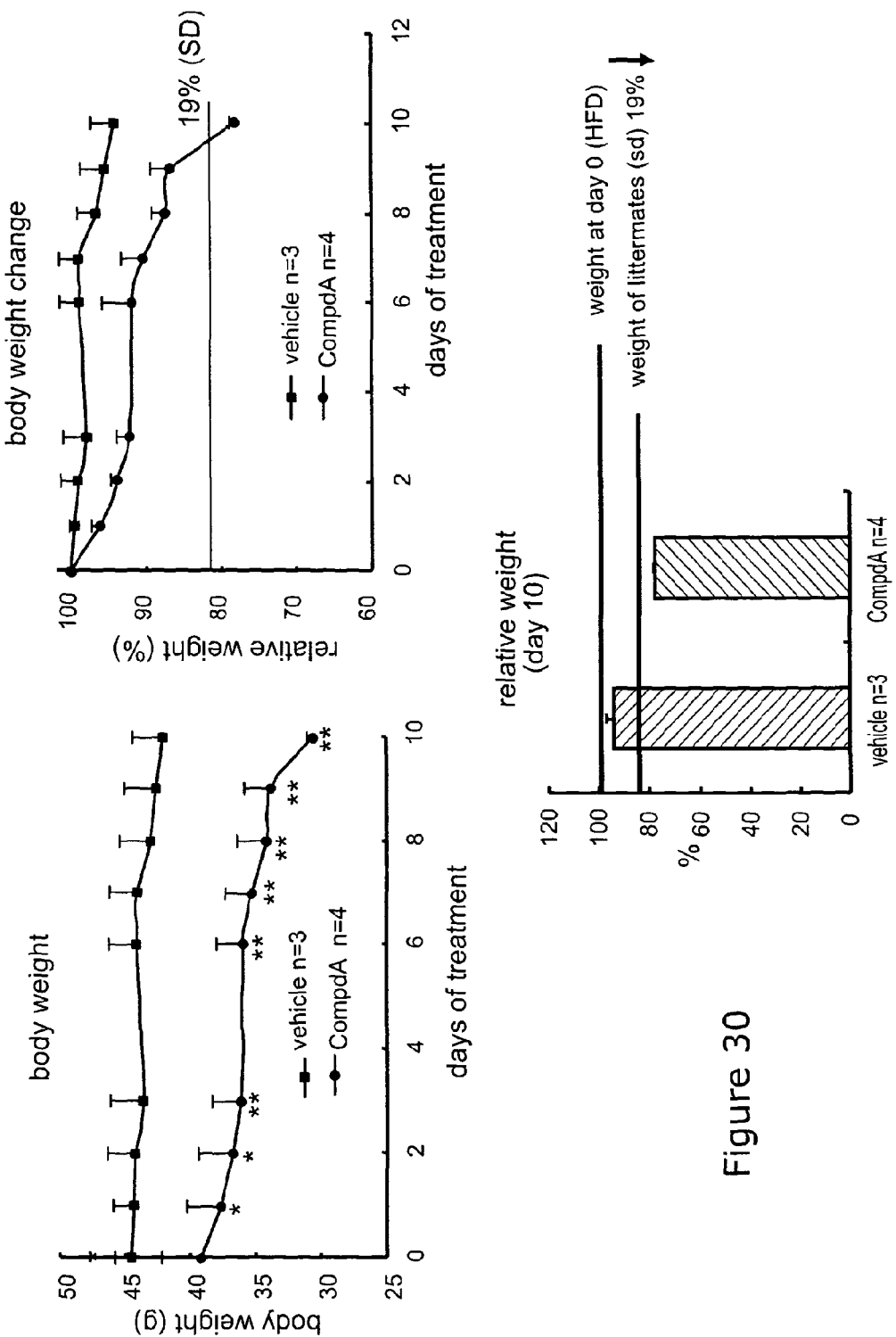
Figure 31:
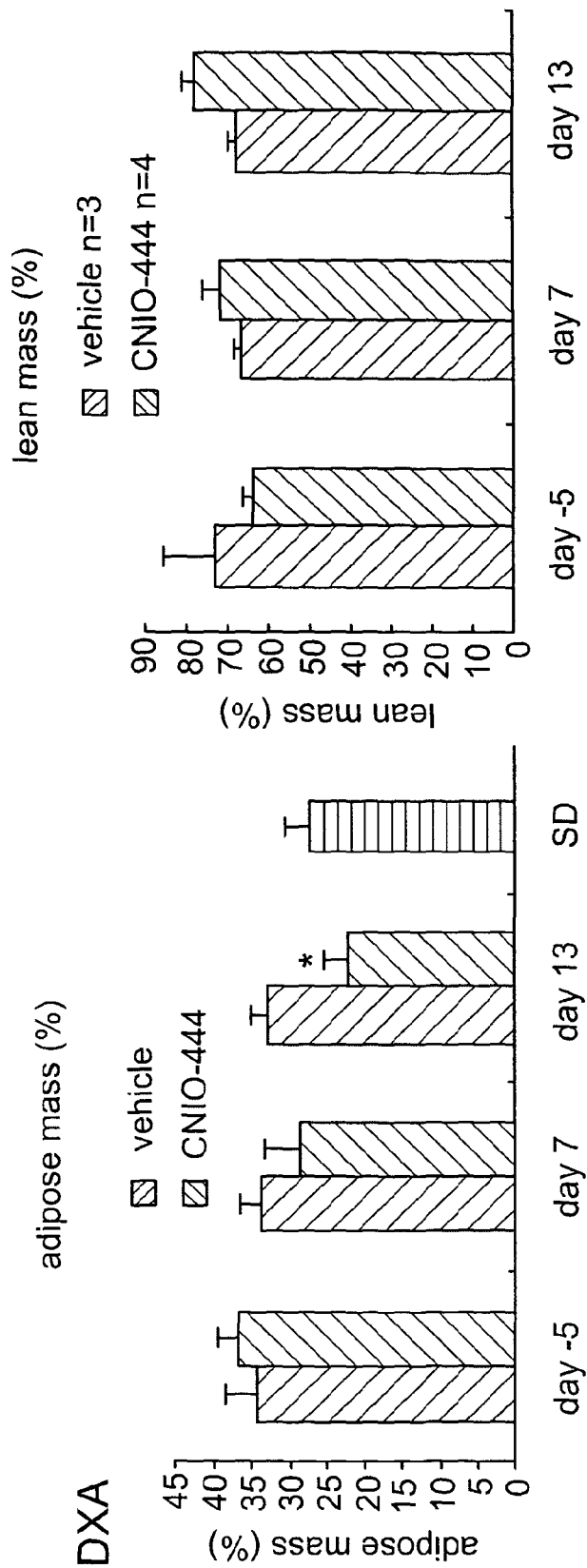
Figure 31:
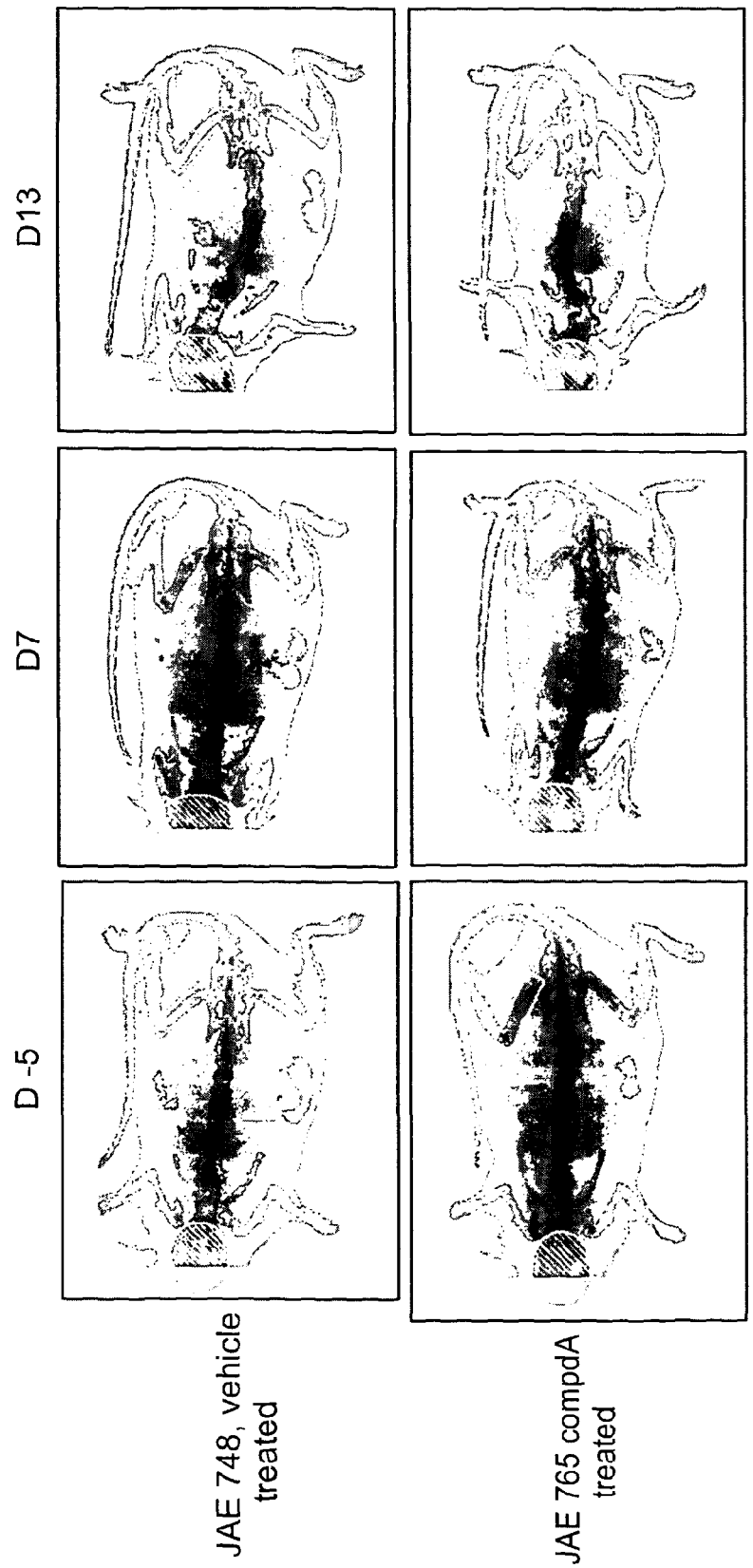
Figure 32:
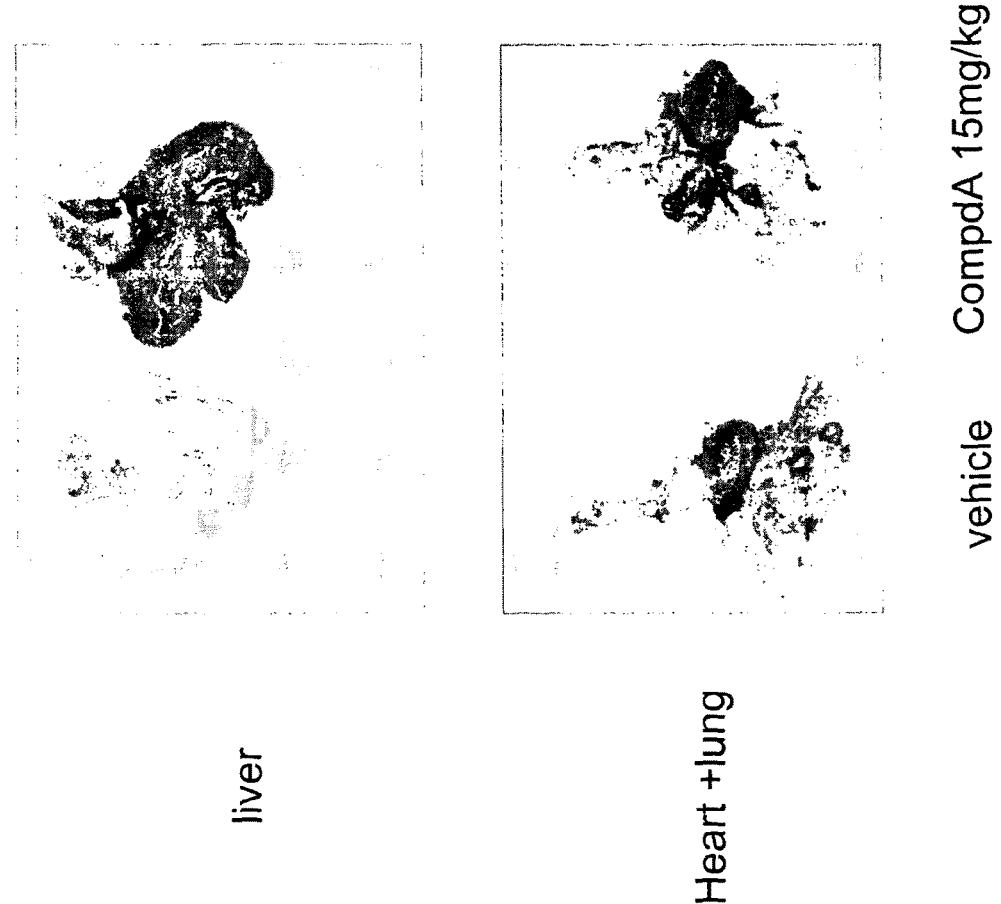
Figure 33:
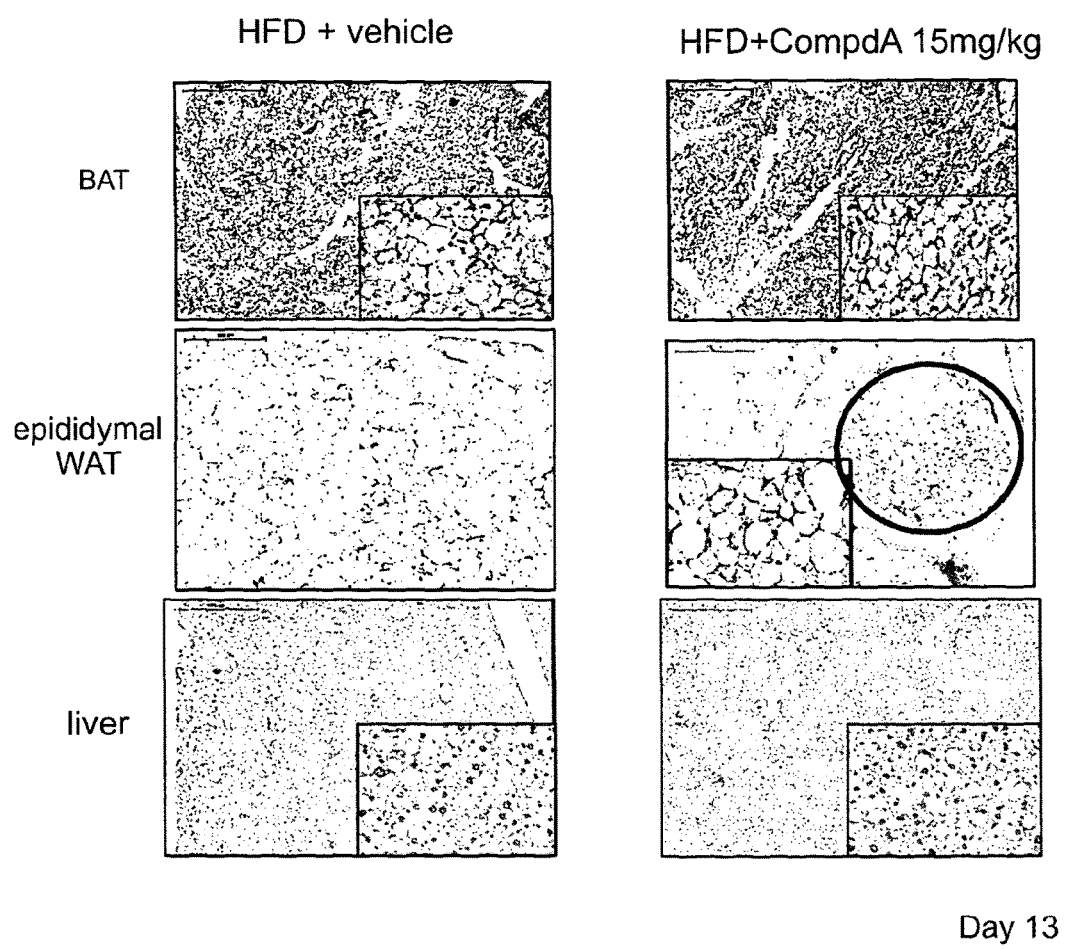
Figure 34:
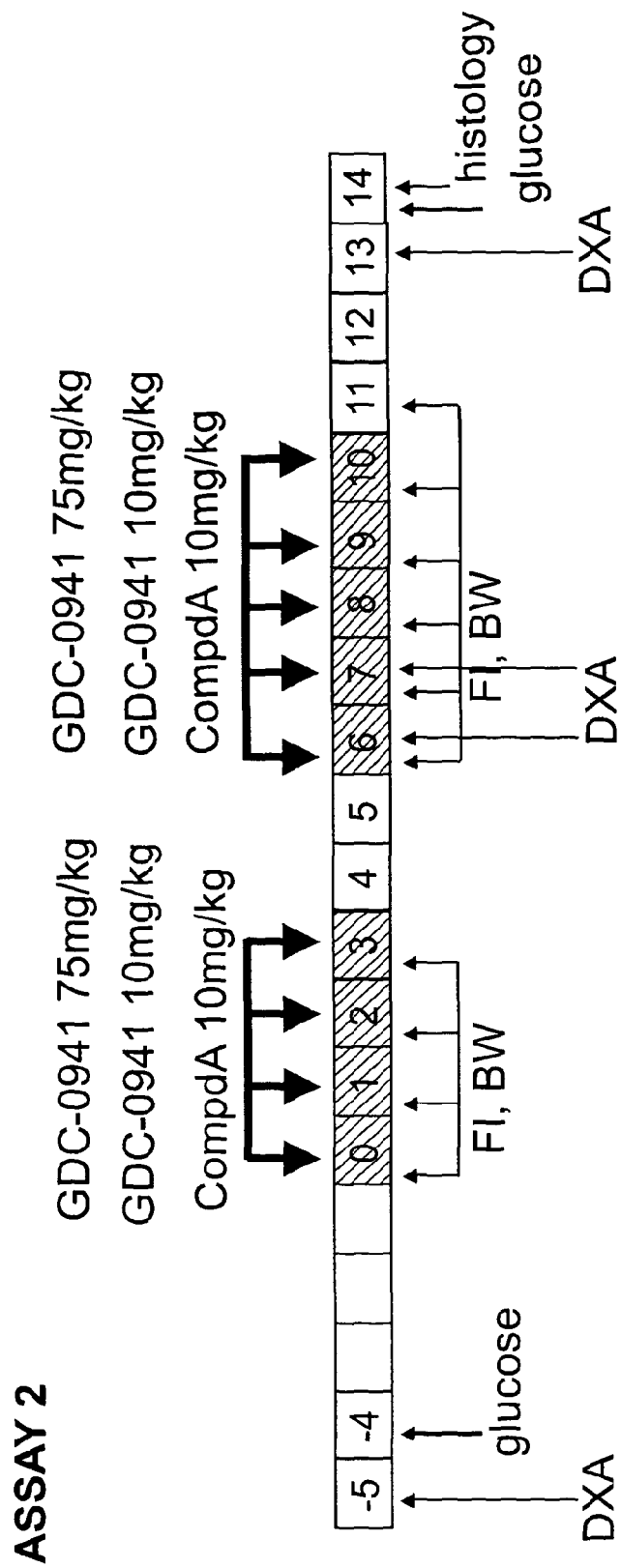
Figure 35:
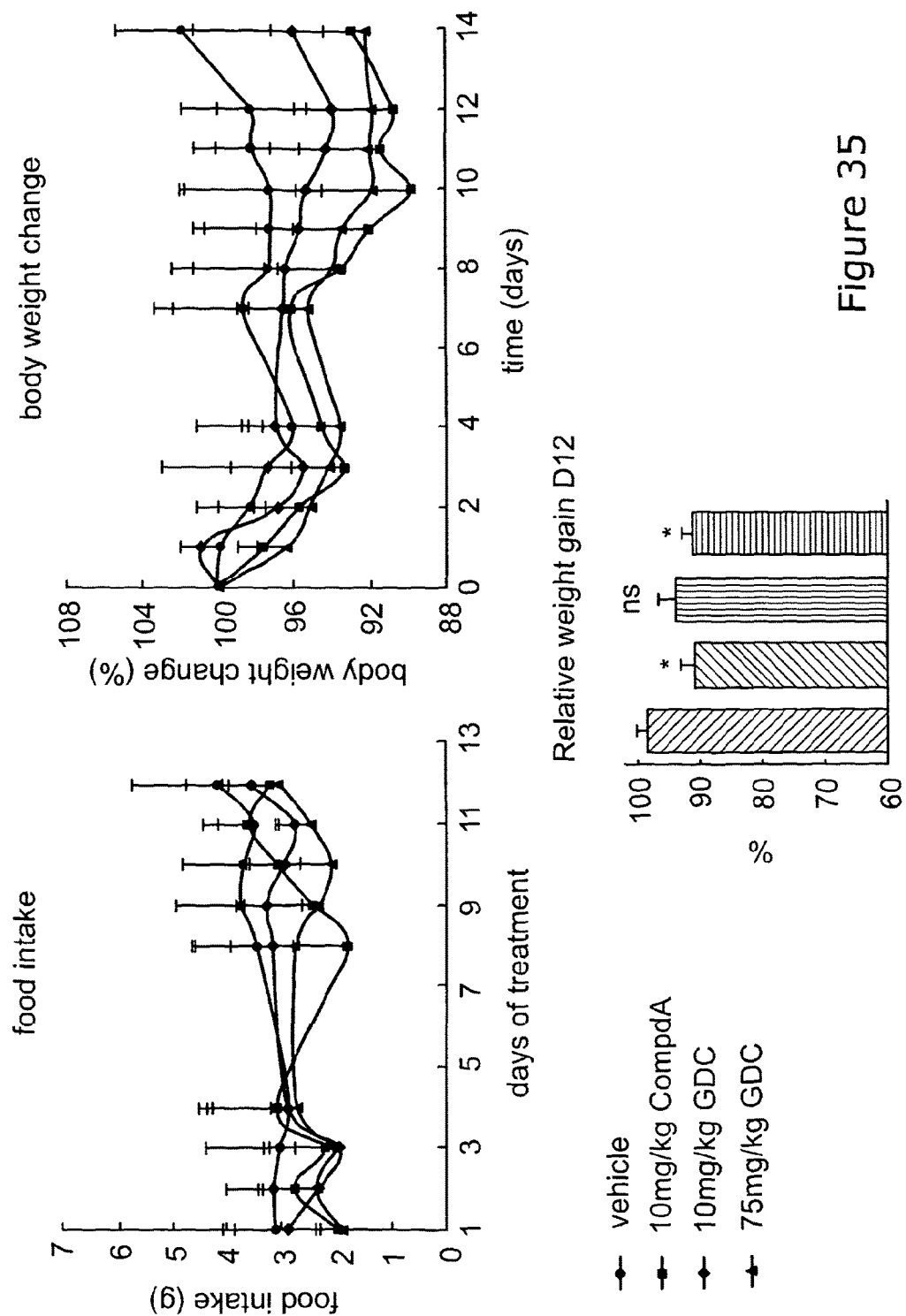
Figure 36:
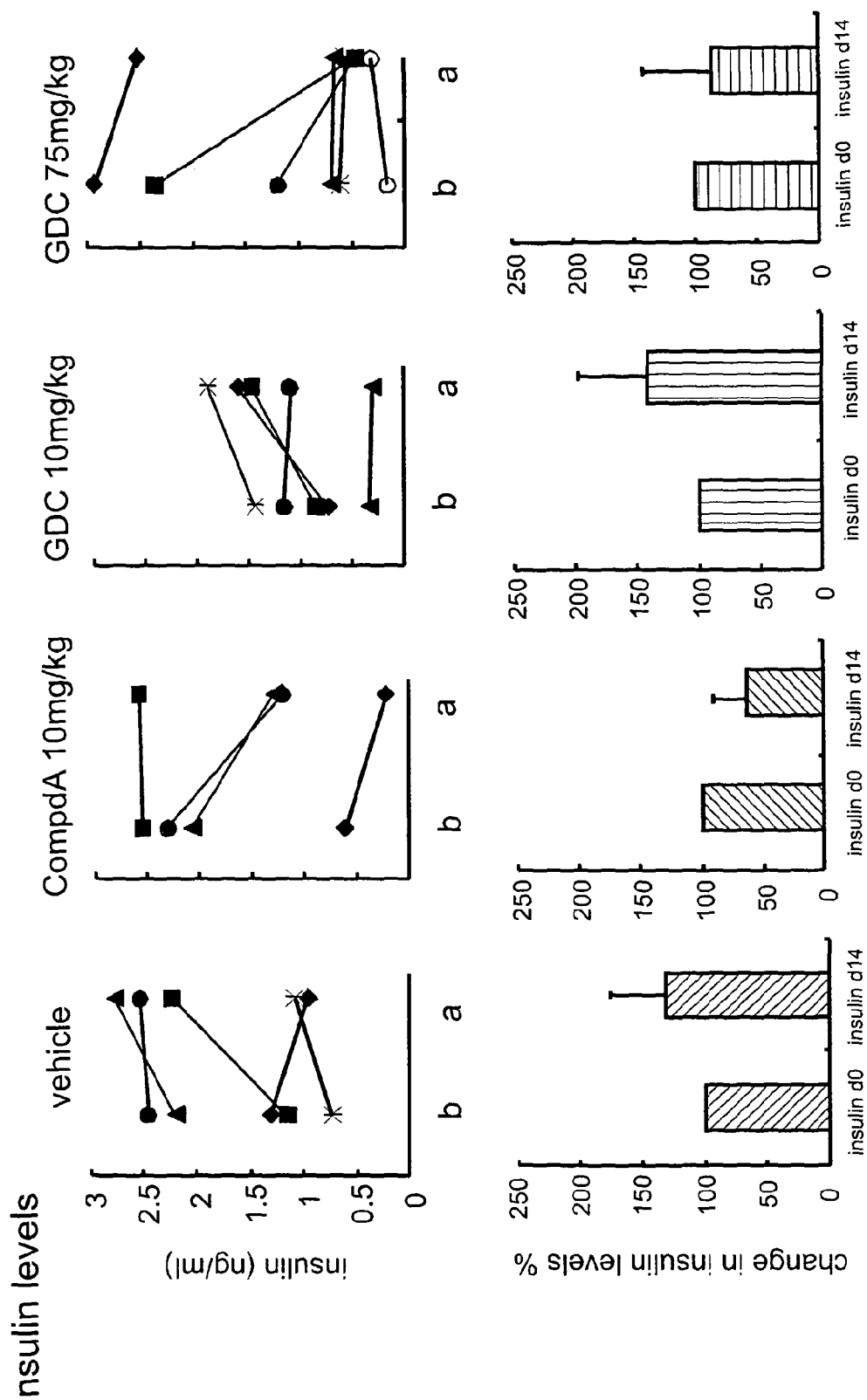
Figure 37:
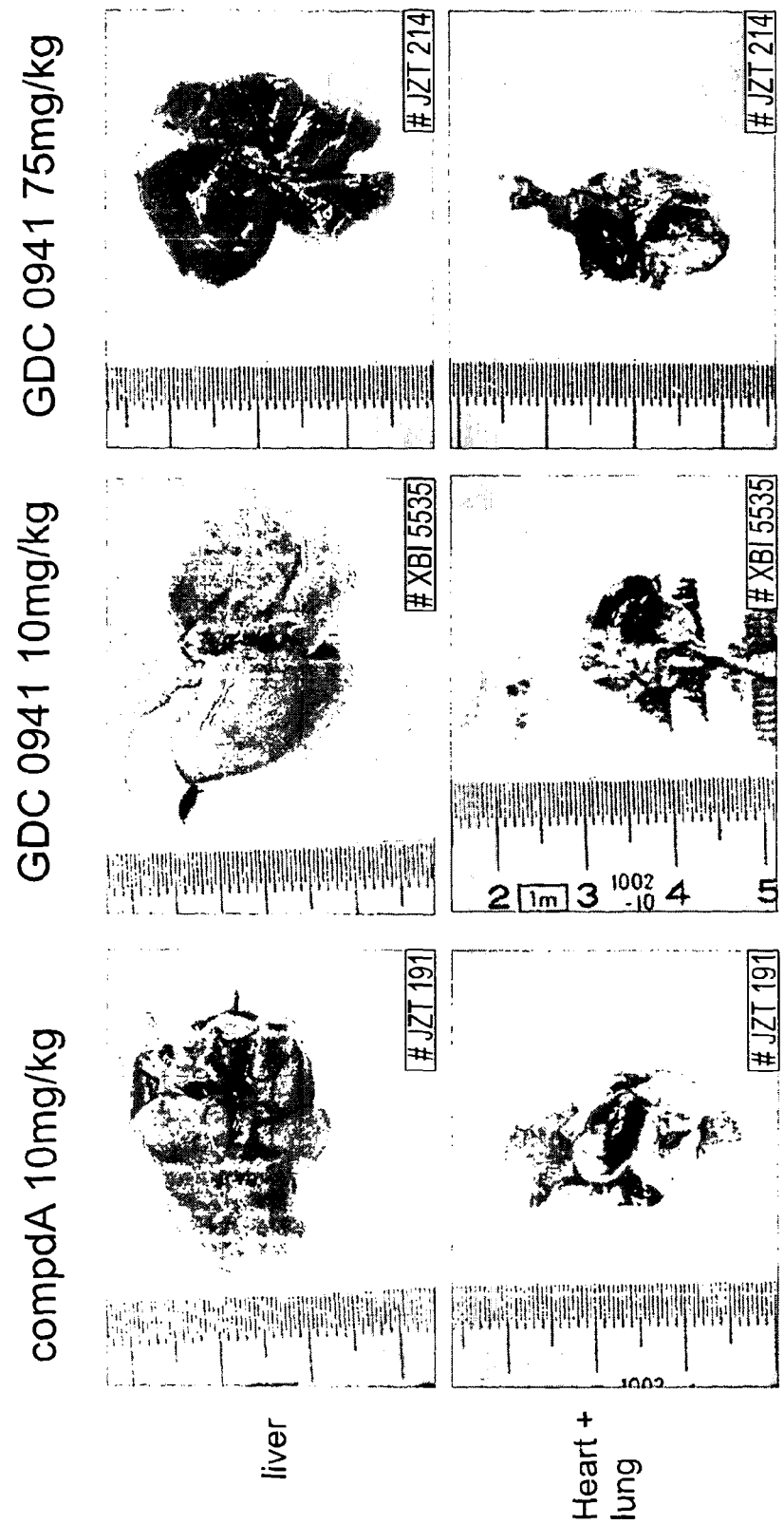
Figure 38:
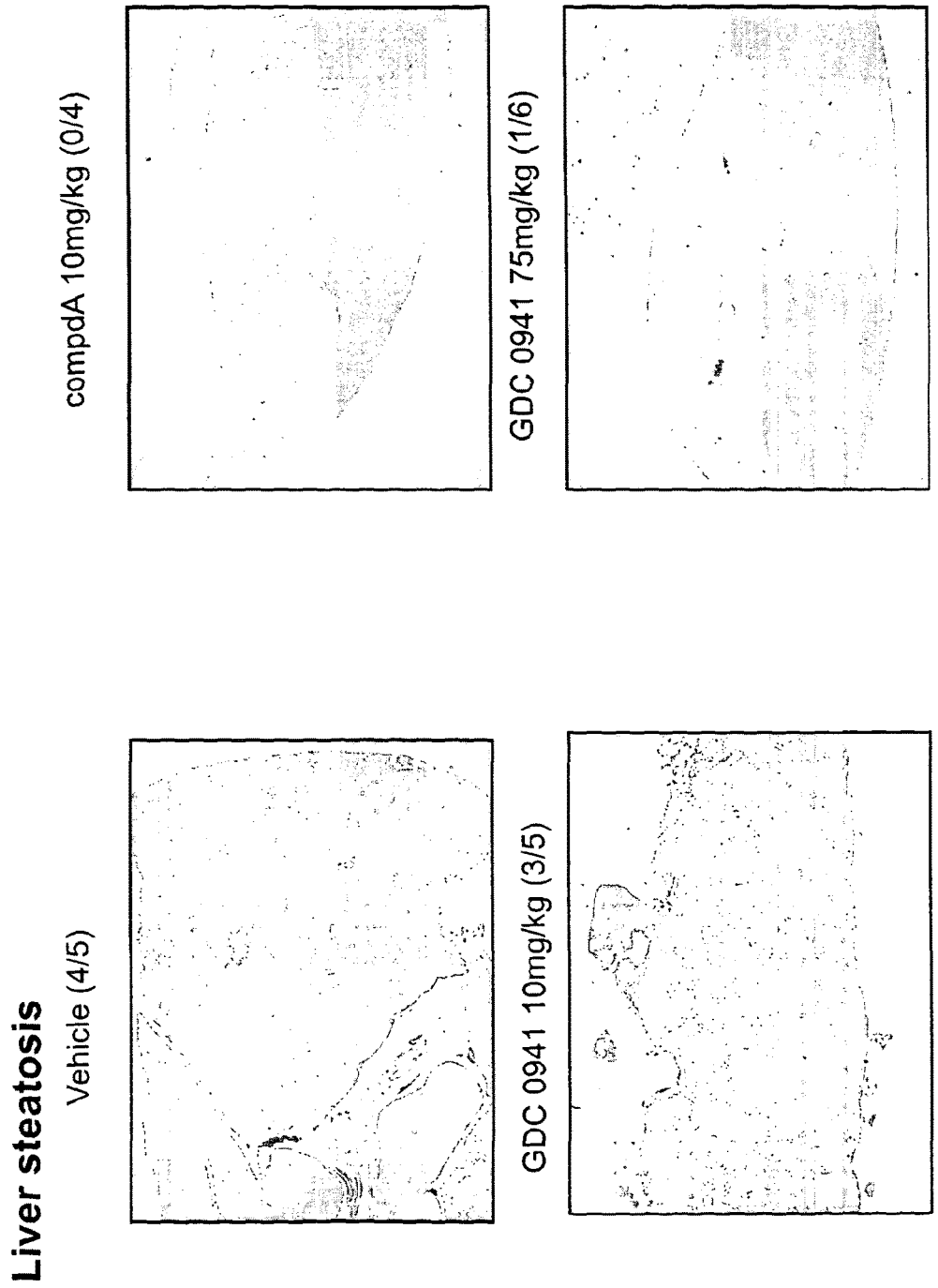
Figure 39:
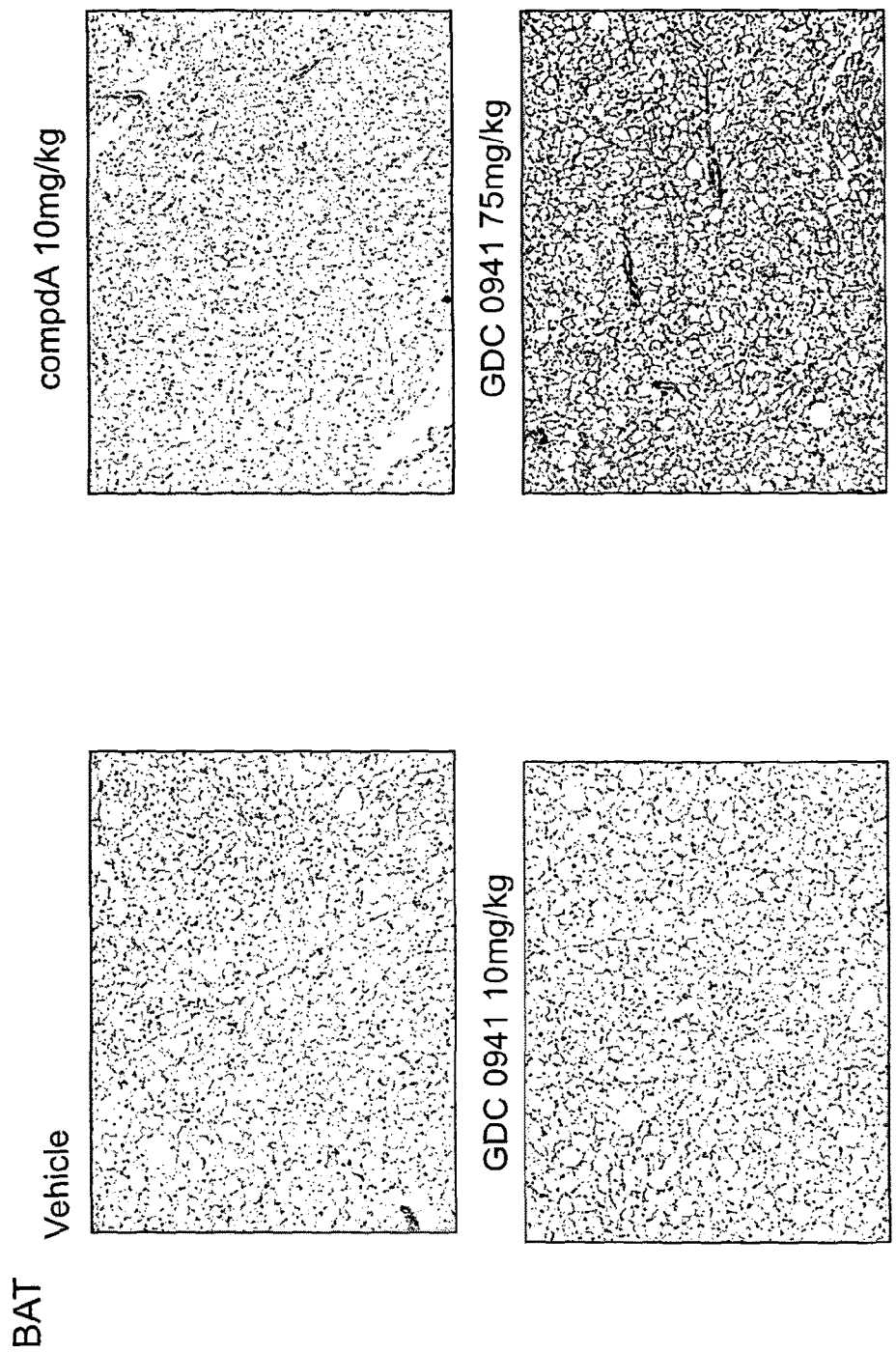
Figure 40:
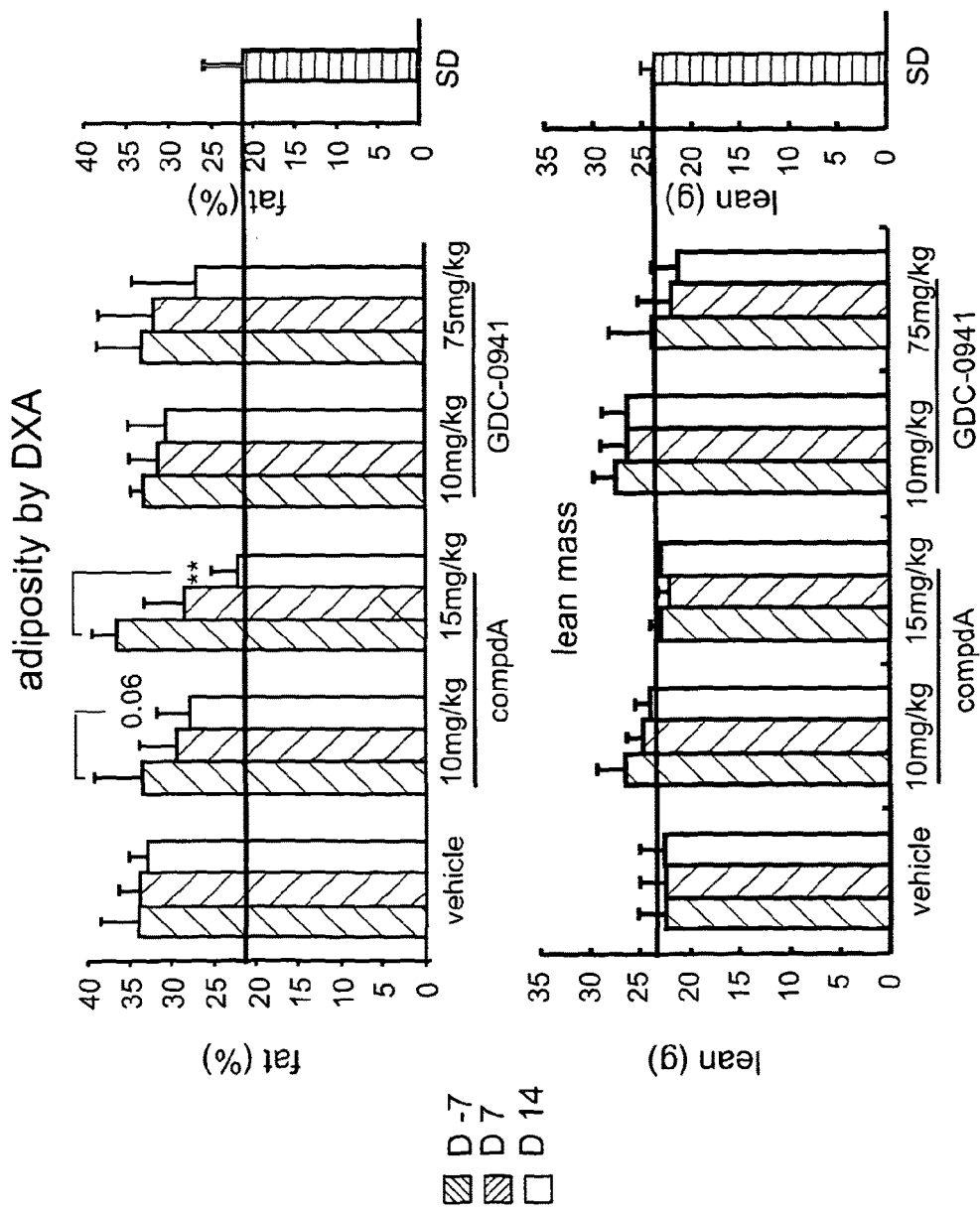

FIG. 23. Loss of adiposity by Compound A
Mice treated as in FIG. 22 were subjected to dual X-ray absorptiometry (DXA) to determine their relative content of fat and lean tissues (the head and the bone mass is not measured). Determinations were performed one week before starting the treatment (day −7 or D−7), in the middle of the 2 weeks treatment (day 7 or D7, and at the end of the treatment (day 14 or D14). The content of fat is expressed as the percentage of fat relative to the combined fat and lean mass (upper panel). The absolute lean mass is also shown (lower panel). The two panels include data from the assay shown in FIG. 22, as well as the data from our previous assay with Compound A at 15 mg/kg. The percentage of fat and the lean mass of non-obese littermates (always fed with standard diet, SD) is shown in orange for reference.

FIGS. 24 to 40 (inclusive). PI3K inhibitors in vitro and in vivo

Figure 41:
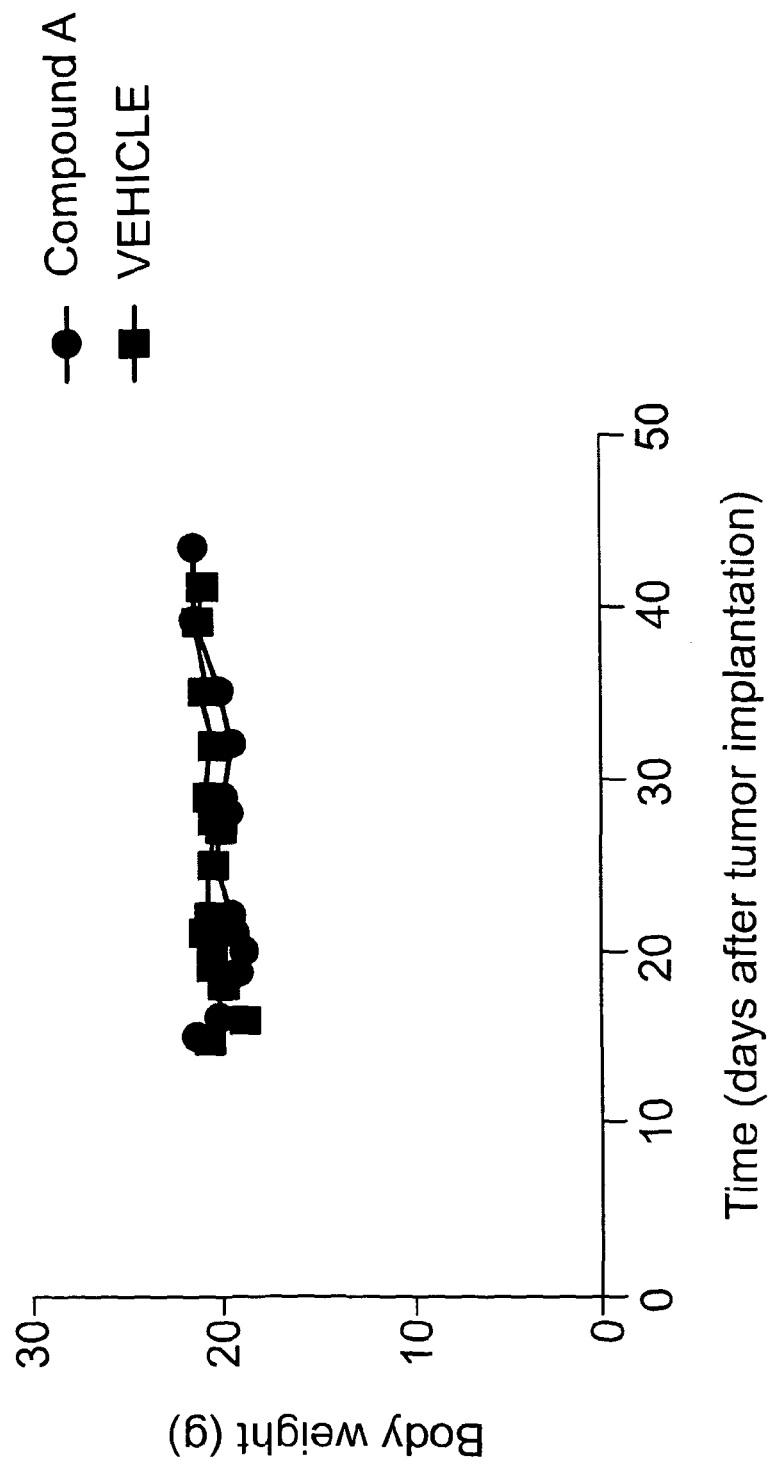

FIG. 41. Body weight evolution of SCID mice bearing human NSCLC A549 lung tumors when treated with Compound A orally, 9 doses of 22 mg/Kg during day 15$^{th}$ and 30$^{th}$, versus compounds treated with vehicle.

The graphic indicates that there are no changes in body weight of mice treated with Compound A during 9 days at 22 mg/kg (the mice are SCID mice implanted with A549 lung tumor xenografts). This indicates that Compound A may require a BAT stimulous with the diet to have an effect. In "normal conditions" no body weight loss is observed.

EXAMPLE A—BIOLOGICAL TESTS

Determination of the activity of PI3 kinase activity of compounds of the invention is possible by a number of direct and indirect detection methods. Certain exemplary compounds described herein were prepared, characterized, and tested for their PI3K binding activity and in vitro activity against tumor cells. The range of PI3K binding activities was less than 1 nM to about 10 µM (i.e. certain compounds of the examples/invention had PI3K binding activity IC$_{50}$ values of less than 10 nM). Compounds of the examples/invention had tumor cell-based activity IC$_{50}$ values less than 100 nM (see Table 4 below).

PI3K Activity Assay

The kinase activity was measured by using the commercial ADP Hunter™ Plus assay available from DiscoveR$_x$ (#33-016), which is a homogeneous assay to measure the accumulation of ADP, a universal product of kinase activity. The enzyme, PI3K (p110α/p85α was purchased from Carna Biosciences (#07CBS-0402A). The assay was done following the manufacturer recommendations with slight modifications: Mainly the kinase buffer was replace by 50 mM HEPES, pH 7.5, 3 mM MgCl$_2$, 100 mM NaCl, 1 mM EGTA, 0.04% CHAPS, 2 mM TCEP and 0.01 mg/ml BGG. The PI3K was assayed in a titration experiment to determine the optimal protein concentration for the inhibition assay. To calculate the IC$_{50}$ of the ETP-compounds, serial 1:5 dilutions of the compounds were added to the enzyme at a fixed concentration (2.5 µg/ml. The enzyme was preincubated with the inhibitor and 30 µM PIP$_2$ substrate (P9763, Sigma) for 5 min and then ATP was added to a final 50 µM concentration. Reaction was carried out for 1 hour at 25° C. Reagent A and B were sequentially added to the wells and plates were incubated for 30 min at 37° C. Fluorescence counts were read in a Victor instrument (Perkin Elmer) with the recommended settings (544 and 580 nm as excitation and emission wavelengths, respectively). Values were normalized against the control activity included for each enzyme (i.e., 100% PI3 kinase activity, without compound). These values were plot against the inhibitor concentration and were fit to a sigmoid dose-response curve by using the Graphad software.

Cellular Mode of Action
Cell Culture:

The cell lines were obtained from the American Type Culture Collection (ATCC). U2OS (human osteosarcoma) was cultured in Dulbecco's modified Eagle's medium (DMEM). PC3 (human prostate carcinoma), MCF7 (human breast cardinoma), HCT116 (human colon carcinoma), 768-0 (human neuroblastoma), U251 (human glyoblastoma) were grown in RPMI. All media were supplemented with 10% fetal bovine serum (FBS) (Sigma) and antibiotics-antimycotics. Cell were maintained in a humidified incubator at 37° C. with 5% CO$_2$ and passaged when confluent using trypsin/EDTA.

U2foxRELOC and U2nesRELOC Assay:

The U2nesRELOC assay and the U2foxRELOC assay have been described previously (1, 2). Briefly, cells were seeded at a density of 1.0×10$^5$ cells/ml into black-wall clear-bottom 96-well microplates (BD Biosciences) After incubation at 37° C. with 5% CO$_2$ for 12 hours, 2 µl of each test compound were transferred from the mother plates to the assay plates. Cells were incubated in the presence of the compounds for one hour. Then cells were fixed and the nucleus stained with DAPI (Invitrogen). Finally the plates were washed with 1×PBS twice and stored at 4° C. before analysis. Compounds of the invention have a range of in vitro cell potency activities from about 1 nM to about 10 µM.

Image Acquirement and Processing:

Assay plates were read on the BD Pathway™ 855 Bioimager equipped with a 488/10 nm EGFP excitation filter, a 380/10 nm DAPI excitation filter, a 515LP nm EGFP emission filter and a 435LP nm DAPI emission filter. Images were acquired in the DAPI and GFP channels of each well using 10× dry objective. The plates were exposed 0.066 ms (Gain 31) to acquire DAPI images and 0.55 ms (Gain 30) for GFP images.

Data Analysis:

The BD Pathway Bioimager outputs its data in standard text files. Data were imported into the data analysis software BD Image Data Explorer. The nuclear/cytoplasmic (Nuc/Cyt) ratios of fluorescence intensity were determined by dividing the fluorescence intensity of the nucleus by the cytoplasmic. A threshold ratio of greater than 1.8 was employed to define nuclear accumulation of fluorescent signal for each cell. Based on this procedure we calculated the percentage of cells per well displaying nuclear translocation or inhibition of nuclear export. Compounds that induced a nuclear accumulation of the fluorescent signal greater than 60% of that obtained from wells treated with 4 nM LMB were considered as hits. In order to estimate the quality of the HCS assay, the Z' factor was calculated by the equation: Z'=1−[(3×std. dev. of positive controls)+(3×std. dev. of negative controls)/(mean of positive controls)−(mean of negative controls)].

PI3K Signalling

AKT Phosphorylation Inhibition. Western Blot Analysis:

Subconfluent cells were incubated under different conditions and washed twice with TBS prior to lysis. Lysis buffer was added containing 50 mM Tris HCl, 150 mM NaCl, 1% NP-40, 2 mM Na$_3$VO$_4$, 100 mM NaF, 20 mM Na$_4$P$_2$O$_7$ and protease inhibitor cocktail (Roche Molecular Biochemicals). The proteins were resolved on 10% SDS-PAGE and transferred to nitrocellulose membrane (Schleicher & Schuell, Dassel, Germany). The membranes were incubated overnight at 4° C. with antibodies specific for Akt, phospho-Ser-473-Akt (Cell Signaling Technology) and α-tubulin (Sigma), they were washed and then incubated with IRDye800 conjugated anti-mouse and Alexa Fluor 680 goat anti-rabbit IgG secondary antibodies. The bands were visualized using an Odyssey infrared imaging system (Li-Cor Biosciences). Compounds of the invention have a range of in vitro cell potency activities from about 1 nM to about 10 µM.

Cytotoxicity Assessment

The compounds were tested on 96-well trays. Cells growing in a flask were harvested just before they became confluent, counted using a haemocytometer and diluted down with media adjusting the concentration to the required number of cells per 0.2 ml (volume for each well). Cells were then seeded in 96-well trays at a density between 1000 and 4000 cells/well, depending of the cell size. Cells were left to plate down and grow for 24 hours before adding the drugs. Drugs were weighed out and diluted with DMSO to get them into solution to a concentration of 10 mM. From here a "mother plate" with serial dilutions was prepared at 200× the final concentration in the culture. The final concentration of DMSO in the tissue culture media should not exceed 0.5%. The appropriate volume of the compound solution (usually 2 microliters) was added automatically (Beckman FX 96 tip) to media to make it up to the final concentration for each drug. The medium was removed from the cells and replaced with 0.2 ml of medium dosed with drug. Each concentration was assayed in triplicate. Two sets of control wells were left on each plate, containing either medium without drug or medium with the same concentration of DMSO. A third control set was obtained with the cells untreated just before adding the drugs (seeding control, number of cells starting the culture). Cells were exposed to the drugs for 72 hours and then processed for MTT colorimetric read-out. Compounds of the invention have a range of in vitro cell potency activities from about 1 nM to about 10 µM.

EXAMPLE B—EXAMPLE OF A COMPOUND OF FORMULA I

Synthesis of Compound A (which Also Corresponds to Example 2-108 Hereinafter)

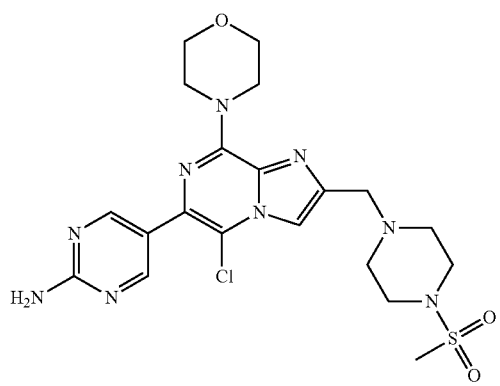 [SMILES: CS(=O)(=O)N1CCN(Cc2cn3c(Cl)c(-c4cnc(N)nc4)nc(N4CCOCC4)c3n2)CC1]

Compound A1 (50 mg, 0.11 mmol) was suspended in DCM (1 mL) and NCS (14 mg, 0.11 mmol) was added. The mixture was stirred at rt for 20 h. The suspension was filtered and rinsed with DCM. The resulting residue was purified by automated chromatography in DCM/MeOH 100 to 90:10 to render the final product Compound A (41 mg, 76%) as white solid.

NMR DMSO δ 8.57 (s, 2H), 7.87 (s, 1H), 6.89 (s, 2H), 4.11 (m, 4H), 3.69 (m, 4H), 3.62 (d, J=14.9, 2H), 3.05 (m, 4H), 2.80 (s, 3H), 2.48 (m, 4H).

LC/MS (Reversed phase HPLC was carried out on a RP-C18 Gemini column (150×4.6 mm, 5 um); 10 min. linear gradient of 50-100% acetonitrile in water+100% acetonitrile in water 2 min:210 nm and 254 or DAD): 2.43 min. [M+1]=508.2

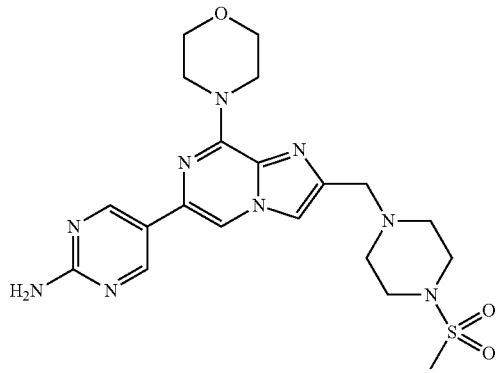

Compound A2 (0.1 g, 0.22 mmol, 1 eq.) was dissolved in DME (1 mL) and 2-aminopyrimidine-5-boronic acid, pinacol ester (58 mg, 0.26 mmol, 1.2 eq), $K_2CO_3$ (90 mg, 0.65 mmol, 3 eq), $PdCl_2(dppf)$ (18 mg, 22 umol, 0.1 eq.) and $H_2O$ (0.5 mL) were added. The mixture was heated under microwave irradiation at 130° C. for 1 h. On cooling, the mixture was purified by column chromatography (Biotage, 25-S, 5% to 10% MeOH in DCM), and the product obtained was precipitated with MeOH and filtered to give the expected product (80 mg, 78%) as a white solid.

DMSO δ 8.77 (s, 2H), 8.41 (s, 1H), 7.76 (s, 1H), 6.83 (s, 2H), 4.22 (d, J=4.5, 4H), 3.77 (m, 4H), 3.66 (s, 2H), 3.11 (d, J=4.8, 4H), 2.87 (s, 3H), 2.55 (s, 4H).

LC/MS (Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 100% of B within 8 min at 50° C., DAD): 2.33 min, [M+1]=474.2

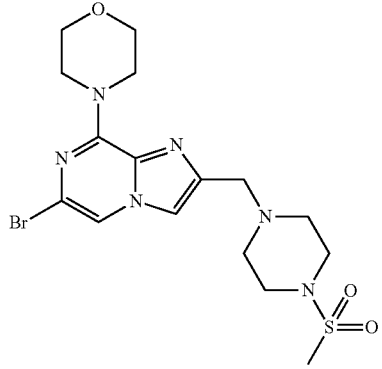

A mixture of Compound A3 (1.5 mmol, 0.5 g), 1-methanesulfonyl-piperazine (1.5 mmol, 0.248 g), $K_2CO_3$ (3 mmol, 0.3 g) in AcCN was heated at 120° C. in a seal tube for 16 h. The mixture was evaporated and the residue was washed with water and then with $Et_2O$ and MeOH, to obtain a brown solid which was dried in vacuo (420 mg) of Compound A2.

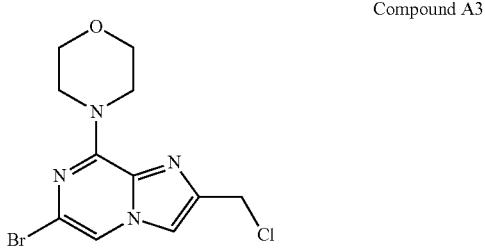 [SMILES: ClCc1cn2cc(Br)nc(N3CCOCC3)c2n1]

Compound A3

A mixture of Compound A4 (8.17 g, 31.52 mmol) and 1,3-dichloroacetone (6.0 g, 47.29 mmol) in 2-propanol (15 mL) was heated in a sealed tube at 55° C. for 2 days. On cooling, the mixture was filtered and rinsed with Et$_2$O and MeOH. The solid was purified by flash chromatography on silica gel (MeOH:DCM, 5:95) and the product obtained was washed with MeOH and dried to give Compound A3 (3.97 g, 38%).

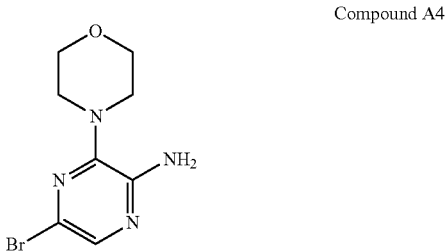 [SMILES: Nc1ncc(Br)nc1N1CCOCC1]

Compound A4

A solution of Compound A5 (15 g, 59.3 mmol) in morpholine (15 ml, 178 mmol) was heated at 120° C. in a Parr reactor for 48 h. A brown solid appears. The solid was suspended in DCM and washed with NaHCO$_3$ aq. sat (twice). The organic phase was dried (NaSO$_4$), filtered and evaporated to dryness to obtain Compound A4, 14.8 g of a brown solid (Y: 96%).

1H NMR (300 MHz, DMSO) d 7.62 (d, J=4.1, 1H), 6.17 (s, 2H), 3.64 (dd, J=30.6, 25.8, 4H), 3.09-2.75 (m, 4H).

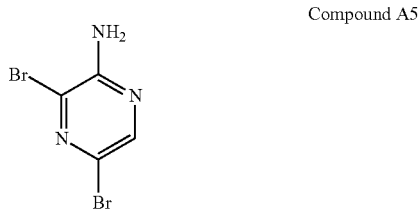

Compound A5

To a mixture of 2-amino pyrazine (50 g, 0.5 mol) in chloroform (1000 ml) cooled to 0° C. was added pyridine (100 ml, 1.21 mol) and bromine (54 ml, 1.05 mmol) dropwise. The mixture was stirred at rt for 16 h, then water was added. The organic phase was extracted, dried (MgSO$_4$), filtered and evaporated to obtain Compound A5, 48 g (Y: 36%) of a yellow solid which was dried in vacuo.

1H NMR (300 MHz, DMSO):8 (s, 1H); 6.9 (broad, 2H)
PI3K Inhibition for Compound A In the biological tests described hereinbefore, Compound A was found to exhibit an IC$_{50}$ value of 2.4 nM and, in the cell assay (p-AKT Western Blot), it was found to exhibit an IC$_{50}$ value of 5 nM.

EXAMPLE C—EXAMPLES OF NEW USE

To augment Pten activity without incurring in overt imbalances, we performed transgenesis with a Bacterial Artificial Chromosome (BAC) carrying a large (127 kb) intact genomic segment that includes the complete murine Pten gene (Supplementary FIG. 5a). In this manner, we obtained a transgenic mouse line, Pten$^{tg}$, that expresses ~2x-fold levels of Pten relative to their wild-type littermates across all examined tissues (2.3±0.4; FIG. 1a). Transgenic mice were fertile and viable. Analysis of the segregation of the Pten$^{tg}$ allele indicated that the frequency of weaned transgenic mice was lower than expected (Supp. FIG. 5b), although embryos at an advanced stage of gestation (E13.5) showed equal proportions of wt and transgenic genotypes (Supp. FIG. 5b). Transgenic E13.5 embryos were smaller than wt embryos (Supp. FIG. 5c) and we surmise that this could cause partial perinatal lethality. The functionality of the transgene was validated genetically by its ability to rescue the completely penetrant embryonic lethality associated to the homozygous deletion of the resident Pten alleles[23]. In particular, upon performing the appropriate crosses, we obtained viable transgenic mice homozygously null for the endogenous alleles (i.e. Pten$^{-/-; tg}$) (FIG. 1b). The impact of Pten overexpression on PI3K signalling was confirmed in primary Mouse embryo fibroblasts (MEFs) under standard culture conditions where the basal levels of Pten protein were clearly augmented in association with lower levels of activated Akt (phospho-Ser473-Akt) (FIG. 1c). Also, insulin-triggered PI3K signalling was attenuated as judged by the levels of phospho-Ser473-Akt and phospho-Thr308-Akt, as well as, phospho-Thr32-Fox03 and phospho-Thr24-Foxo1 (FIG. 1d). Next, we asked whether the Pten transgene was able to protect primary MEFs from oncogenic transformation. For this, we introduced into MEFs the papilloma virus oncoprotein E6, which efficiently inactivates p53, together with either oncogenic EGFR (EGFR$^{L858R}$) or with polyoma virus oncoprotein middle-T, whose oncogenic activities are known to be strictly dependent on PI3K signalling[24,25]. In both cases, Pten$^{tg}$ MEFs were significantly more resistant than wt MEFs to oncogenic transformation (FIG. 1e). Finally, we examined whether tumour suppression, the archetypical activity of Pten, was enhanced in Pten$^{tg}$ mice. This was evaluated, first, using a chemical carcinogenesis assay consisting in intramuscular injection of 3-methyl-cholanthrene (3MC). This aggressive cancer model generates fibrosarcomas in all the treated mice, but Pten$^{tg}$ mice showed a significantly delayed tumour free survival compared to wt mice (FIG. 1f). Additionally, we scored the presence of spontaneous tumours in aged moribund mice and observed that the incidence of lymphomas was significantly decreased in Pten$^{tg}$ mice relative to wt mice (FIG. 1g). The second most frequent tumours in the wt control mice were liver tumours, but in this case the presence of the Pten transgene had no impact on their incidence (Supp. FIG. 5d). These observations are in concordance with the fact that Pten haploinsufficiency does not result in liver tumours but in a multitude of other tumour types, notably including lymphomas [23,26,27]. We conclude that the Pten$^{tg}$ allele is functional and provides protection against neoplastic transformation and cancer.

To address the impact of Pten on health span and longevity, we followed cohorts of Pten$^{tg}$ mice, together with their wt littermates, during their entire lifespan. Importantly, both male and female Pten$^{tg}$ mice showed an increase in longevity as indicated by their Kaplan-Meier survival curves (FIG. 2a) and other indicators, such as maximal lifespan in the case of males (FIG. 2a and Tables 5, 6). Additional statistical tests indicated that the increased survival was dependent on the transgene and independent of other variables, such as the identity of the parents, date of birth, or size of the cohort (Tables 7, 8). Median lifespan was increased by >20% in transgenic mice (27% in males and 21% in females). We wondered whether this effect in longevity was due to the decreased incidence of lymphomas observed in Pten$^{tg}$ mice. However, lymphoma-free Pten$^{tg}$ mice presented a similar increase in longevity when compared with lymphoma-free wt mice (FIG. 6a). This indicates that Pten$^{tg}$ extends longevity independently of its effect on cancer protection, thus suggesting a direct impact on healthspan. In this regard, the accumulation of DNA damage within tissues, and particularly in the liver, is a robust biomarker of aging[12,45]. Immunofluorescence with two markers of DNA damage, γH2AX and 53BP1, indicated a significantly lower level of DNA damage in the liver of old Ptentg mice compared to wt controls (FIG. 2f). We scored the neuromuscular coordination of the mice using the tightrope test, which is another robust biomarker of aging[28]. Old (2 yrs) transgenic mice performed significantly better in this test than their wt controls of the same age (FIG. 2b), which further suggests that Pten$^{tg}$ mice preserve fitness during longer time than wt mice. A feature of long-lived mice with decreased IIS axis activity is their improved insulin sensitivity[18]. This effect, apparently paradoxical, can be explained by feedback mechanisms that keep the pathway within a narrow range of activity, such as the upregulation of the insulin receptor (Insr) or the insulin receptor substrate 2 (Irs2) by Foxo1[13,14,17]. In keeping with this, Pten$^{tg}$ mice had lower fasting levels of glucose and insulin (FIG. 6b) and a significantly lower value of the insulin resistance indexes HOMA-IR (FIG. 2c) and QUICKI (FIG. 6c), which are both derived from the glucose and insulin levels. Incidentally, serum levels of Igf1 were moderately lower in Pten$^{tg}$ mice compared to wt mice, both at young and old age (FIG. 6d). We also examined the level of inhibitory Ser/Thr-phosphorylations in Irs1 in white adipose tissue, which may reflect negative feedback regulation by S6K1[29]. Old Pten$^{tg}$ mice showed reduced levels of phosphorylated Akt and, interestingly, also presented lower levels of phosphorylated-Ser636/639-Irs1 compared to their wt controls (FIG. 2d). The lower phosphorylation of Irs1 at Ser6363/639 may reflect lower levels of negative feedback regulation by S6K1[29] and, in agreement with this, we found lower levels of phosphorylation of the S6K1 substrate S6 in the WAT of Ptentg mice compared to wt controls (FIG. 11). These data support the concept that improved insulin sensitivity in Pten$^{tg}$ mice results from compensatory feedback mechanisms that ensure homeostasis. We conclude that moderate and regulated overexpression of Pten results in extended longevity and healthspan.

Despite intense investigation, understanding of the physiological mechanisms that could be involved in aging retardation by decreased IIS/PI3K activity is still incomplete. Caloric restriction (CR) is a universal anti-aging intervention[2] and it is associated to decreased levels of Igf1 and reduced basal levels of PI3K pathway activity[30-32]. Pten$^{tg}$ mice presented a decreased body weight (FIG. 3a) (27%-28% decrease in young mice and 35-44% in old mice, values correspond to males and females, respectively; FIG. 7a). Interestingly, this lower weight occurred despite the fact that Pten$^{tg}$ mice were hyperphagic (FIG. 3b). We wondered whether this could be a result of increased energy expenditure. Of note, the IIS/PI3K and mTOR/S6K pathways are closely linked[2,33] and mice deficient in S6k1 are longevous[34] and present increased energy expenditure[15]. Incidentally, serum levels of Igf1 were moderately, but Ortega-Molina et al., submitted to Nature[4] Ortega-Molina et al., submitted to Nature[4] significantly, lower in Pten$^{tg}$ mice compared to wt mice, both at young and old age, and cholesterol levels were also lower in Ptentg mice (FIG. 6(e)). All together, we conclude that moderate and regulated overexpression of Pten results in extended survival and improved healthspan. In an effort to shed light into the physiological mechanisms that could be involved in the extended lifespan of Pten$^{tg}$ mice, we have explored their metabolism. Pten$^{tg}$ mice presented a decreased body weight (FIG. 3a) (27% and 28% decrease in young males and females mice, respectively, and 35% and 44% in old males and females; FIG. 7a). Interestingly, this lower weight occurred despite the fact that Pten$^{tg}$ mice were hyperphagic (FIG. 3b and FIG. 12). We wondered whether this could be a result of increased energy expenditure. Indirect calorimetry indicated that Pten$^{tg}$ mice have an increased energy expenditure (FIG. 3c). We fitted a General Model System (GLM) with energy expenditure as a variable dependent of the genotype and of the body weight. ANalysis of COVAriance (ANCOVA) indicated that genotype has a significant impact on energy expenditure, which is independent of the impact of the body weight (Table 9). Indirect calorimetry indicated that Pten$^{tg}$ mice have increased energy expenditure (FIG. 3c), as well as, an elevated respiratory quotient during the active period, i.e. dark, of the daily cycle (FIG. 3d). Locomotor activity was similar between the two cohorts of mice (FIG. 7b), thus implying that an elevated metabolic rate is responsible for the observed increase in energy expenditure. Energy expenditure, by favoring combustion at the expense of conservation, is generally associated with reduced storage of nutrients and protection from metabolic damage. In support of this, we observed that Pten$^{tg}$ mice had decreased total adiposity (41% less fat in young males) (FIG. 3e), lower mass of epidydimal White Adipose Tissue (WAT) relative to body weight (41% lower in young males; FIGS. 7c and 7d), and smaller adipocytes in the epididymal WAT (FIG. 3f). In support of this, Dual energy X172 ray Absorptiometry (DXA) indicated that Ptentg mice had a relative decrease in fat mass and a relative decrease in the fat/lean ratio (FIG. 3d and FIG. 15). Also, compared to wt controls, the weight of the epidydimal WAT relative to body weight was significantly lower in young transgenic males (FIGS. 7c and 7d), and the size of the adipocytes in the epididymal WAT was smaller (FIG. 3e). Pten$^{tg}$ mice under High-Fat Diet (HFD) for 6 months increased their body weight to a similar relative extent as wt mice (FIG. 7e). However, in contrast to wt mice under HFD, Pten$^{tg}$ mice did not developed liver steatosis (FIG. 3g). Together, these results indicate that moderate upregulation of Pten results in increased energy expenditure, lower nutrient overload and improved protection against metabolic damage.

The most efficient mechanism to dissipate energy is through brown adipocytes, located both at the Brown Adipose Tissue (BAT) and, also, intermingled within the WAT[35,36]. Brown adipocytes have gained considerable attention since the recent realization of their relevance in adult humans[37]. Macroscopically, the interscapular BAT of Pten$^{tg}$ mice had a more intense reddish colour compared to wt BAT (FIG. 4a, left); and, histologically, it presented a denser appearance due to reduced size of the multilocular lipid droplets (FIG. 4a, right), which is suggestive of higher lipolytic activity. Energy dissipation in brown adipocytes is mediated by the uncoupling protein Ucp1[35]. Remarkably, the expression levels of Ucp1 were significantly higher in the BAT of Pten$^{tg}$ mice compared to their wt littermates (FIG. 4b). Analysis of a number of genes important for BAT function indicated that most of them were expressed at normal levels in Pten$^{tg}$ BAT, with the notable important exception of Pgc1a (FIG. 4b). In relation to this, it is worth mentioning that mice lacking the insulin receptor (IR) in the BAT also present higher levels of Ucp1 expression[46]. The transcriptional co-activator Pgc1a integrates multiple metabolic responses and is a critical positive regulator of Ucp1 expression[38,39]. Interestingly, Pgc1α together with some genes involved in fatty acid oxidation were also significantly upregulated in the BAT of Pten$^{tg}$ mice (FIG. 4b). Other genes characteristic of brown adipocytes were not significantly altered (FIG. 16). Both Pgc1α and Ucp1 are characteristically expressed in brown, but not in white, adipocytes[38,39] and, therefore, their detection in WAT is indicative of the presence of brown adipocytes within WAT[47,36]. Analysis of epididymal WAT indicated the presence of significantly higher levels of Pgc1a and Ucp1 expression in transgenic mice compared to wt mice (FIG. 17), thus suggesting higher activity in the brown adipocytes that reside within the WAT. Incidentally, we wondered whether caloric restriction (CR) would exert a similar transcriptional response in the BAT, but mice under CR for 4 weeks presented lower, rather than higher, levels of Pgc1a and normal levels of Ucp1 in the BAT (FIG. 18), thus suggesting that the Pten transgene and CR are different in this regardIn the liver, the transcriptional factor Foxo1 is an essential partner for the function of Pgc1α[5,7], and Akt phosphorylates and inhibits both Pgc1α 5 and Foxo proteins[40,33]. Based on this, we examined whether the BAT of Pten$^{tg}$ mice also had lower levels of phosphorylated Akt and Foxo1. Indeed, immunodetection of these proteins revealed that transgenic BAT had lower levels of active Akt (phospho-Ser473-Akt), as well as, lower levels of phosphorylated Foxo1 (phospho-Thr24-Foxo1) (FIG. 4c). In addition to the BAT, muscle is another important organ responsible for energy expenditure. In particular, overexpression of Pgc1a or small compounds that activate Pgc1α through Sirt1 induce a change in muscle myofibers from type II (low oxidative capacity) to type I (high oxidative capacity)[48,49] and, in some cases, this is associated to an increased energy expenditure.[48] Examination of succinate dehydrogenase in the gastrocnemius muscle (containing both types of myofibers), as well as, the mRNA levels characteristic of type I myofibers did not support the concept that the Ptentg mice have a relative increase in type I myofibers (FIG. 19). This reinforces the idea that the increased energy expenditure observed in Pten$^{tg}$ mice is due to a higher activity of brown adipocytes.

The mechanisms of action of Pten go beyond the inhibition of PI3K[49]. To establish the involvement of PI3K on the above reported effects of Pten in BAT, we inhibited PI3K in two different systems of in vitro-cultured brown adipocytes. For this, we used a small compound inhibitor of PI3K developed at the Spanish National Cancer Research Centre (CNIO), named "CNIO-compound A", and abbreviated here as PI3Ki or Compound A (see Methods and FIG. 20). Preadipocytes 3T3-L1 ectopically expressing C/Ebpβ were differentiated into brown adipocytes[50] and treatment with PI3Ki resulted in upregulation of Ucp1 and Pgc1α, both when used alone or in combination with forskolin (an activator of AMP cyclase known to upregulate Ucp1 levels[38]) and together with a severe decrease in the levels of phospho-Akt (FIG. 4d). To further support this, treatment of immortalized neonatal brown adipocytes (three independent lines) with PI3Ki also upregulated the expression of Ucp1 (FIG. 4d). Finally, treatment of mice with PI3Ki resulted in significant upregulation of Ucp1 and Pgc1a in the BAT, as well as Lcad involved in fatty acid oxidation (FIG. 4e and FIG. 4b). These results indicate that downregulation of PI3K is responsible, at least in part, for the effects of Pten overexpression in the BAT of Pten$^{tg}$ mice.

The above results demonstrate that PI3K inhibition has cell autonomous effects that can be recapitulated in vitro with cultured brown adipocytes. To further extend this concept, we took advantage of the transcriptional factor Prdm16 and its cofactor C/Ebpβ, whose combined expression is able to program fibroblasts to form subcutaneous BAT-containing fat pads upon transplantation[8,9]. Immortalized wt and Pten$^{tg}$ MEFs were programmed with retroviruses encoding Prdm16 and C/Ebpβ, and injected subcutaneously into nude mice. Two months later, ectopic fat pads with depots of BAT were identified at the injection sites (FIG. 4f and FIG. 8). Quantification of the amount of BAT formed indicated that Pten$^{tg}$ cells were significantly more efficient at generating BAT than their wt counterparts (FIG. 4g). These results confirm that Pten exerts a cell autonomous effect on BAT, and open a route to improve the generation of ectopic BAT transplants. All together, these observations reveal a novel function of Pten as a positive regulator of energy dissipation in brown adipocytes.

In worms and flies, the IIS longevity pathway is intracellularly mediated by the PI3K/Akt/Foxo pathway. This link, however, was missing in mammals where decreased IIS activity was known to extend longevity but nothing was known about the impact of PI3K signalling in longevity. Our finding that Pten regulates longevity, strongly supports the evolutionary conservation of this intracellular longevity pathway. In a wider scope and together with previous reports 10,11, the four main tumour suppressors, namely, p53, Ink4a, Arf, and Pten, increase organismal survival independently of their effects on cancer protection, thus revealing an intimate connection between longevity and cancer protection. We have also uncovered a role of Pten in the regulation of nutrient combustion by brown adipocytes. This puts forward a new mechanism to explain the longevity effects of decreased IIS/PI3K pathway activity. In particular, increased energy expenditure reduces lipid storage and ameliorates the pathological effects of nutrient overload, which in turn contributes to improve healthspan and prolong longevity. The effects of moderate Pten overexpression are reminiscent of those reported for S6KI deficiency, which also results in enhanced energy expenditure[29] and longevity[34]. Together, these observations support a unified and evolutionary conserved mechanism for the involvement of the IIS/PI3K and mTOR/S6K pathways in mammalian longevity.

Methods

Transgenesis

To generate the Ptentg mouse strain, the Bacterial Artificial Chromosome (BAC) RP24-372016 (obtained from CHORI; http://www.chori.org) (Supp. FIG. 5a) was linearized using PI-SceI (New England Biolabs) and 2 pl of a solution containing 0.4 µg/µl were microinjected into the pronuclei of fertilized oocytes derived from intercrosses between (C57BL6×CBA) F1 mice. Founders were mated with C57BL6 mice and the resulting progeny, which was of genetic background C57BL6/CBA (75%:25%), was analyzed for transmission of the transgene, integrity of the transgene, and number of integration sites. Analysis of integrity and transmission was checked by PCR amplification of the two terminal regions of the genomic insert, namely, T7-O16 (Fw-T7: 5'-CCG CTA ATA CGA CTC ACT ATA GGG-3' (SEQ ID NO: 1); Rv-T7: 5'-TCA TCT CGG CTC CAT CGT TT-3' (SEQ ID NO: 2)) and SP6-O16

(Fw-Sp6: 5'-GTC GAC ATT TAG GTG ACA CTA TAG AAG-3' (SEQ ID NO: 3); Rv-Sp6: 5'-GAT GCT GTG TGC TAC AGG GAT G-3' (SEQ ID NO: 4)). Pten$^{tg}$ mice were backcrossed for one generation with C57BL6 mice, in this manner the background of all the mice used in this study is C57BL6/CBA (75%:25%). Mice were fed either with a standard chow diet (Harlan Teklad 2018, 18% calories from fat) or, when indicated, with a high fat diet (Research Diet D12451, 45% of total calories from fat).

Animal Experimentation

For 3-methyl-cholanthrene (3MC) carcinogenesis, we followed previously described methods[41], Briefly, 2 month old mice (males and females) received a single intramuscular injection at one of the rear legs of a 100 μL solution containing 3MC (Sigma), at a concentration of 100 μg/μL and dissolved in sesame oil (Sigma). For the tightrope assay, mice (males and females) were placed on a bar of circular section (60 cm long and 1.5 cm diameter) and the test was considered successful when a mouse stayed on the bar for 60 seconds in a least one trial out of 5 consecutive trials. All mice were observed weekly by trained personnel. Upon signs of morbidity, mice were closely inspected daily until application of Humane End Point (HEP) criteria (http://dels.nas.edu/global/ilar/Guide). From our experience, the humane end point is applied when the life expectancy of the mice is on average shorter than one week. Mice that died spontaneously (Death In Cage or DIC) had a sudden death and were not preceded by detectable morbidity.

Metabolic Measurements

All the metabolic determinations were performed in male mice. Mice were housed in metabolic cages during 5 days, and food and water intake, as well as, the output of faeces and urine were measured during the last 4 days, Body composition (fat and lean content) was determined by Dual energy X-ray 4bsorptiometry (DXA) (Lunar PIXImus Densitometer, GE Medical Systems). Image acquisition lasted 5 minutes with mice under anaesthesia by inhalation of 2% isofluorane in 100% oxygen. The analysis of lean mass and fat mass was performed using a Region Of Interest (ROI) comprising the entire body. Indirect calorimetry was performed following standard methods using Oxylet System metabolic chambers (Panlab Harvard Apparatus). Mice were in the measurement cages 12 hr previous to data recording. Room temperature was 23° C. and light/dark cycles were of 12 hr. Volume of consumed $O_2$ ($VO_2$) and eliminated $CO_2$ ($VCO_2$) were recorded every 24 min (4 simultaneous metabolic chambers, with a sample period of 4 min per cage, plus 1 min purge per cage). Respiratory Quotient (RQ) was calculated as: $RQ=VCO_2/VO_2$. Energy Expenditure (EE) was calculated as: $EE=(3,815+(1.232\times RQ))\times VO_2\times 1.44$. Total locomotor activity was measured using the Physiocage System (Panlab Harvard Apparatus). Serum Igf1 levels were measured by ELISA (Mouse/Rat IGF-1 ELISA; Demeditec). Fasting serum glucose was measured using Glucocard strips (A. Meranini Diagnosis). Fasting insulin levels were determined by ELISA (Ultra Sensitive Mouse Insulin ELISA kit; Crystal Chem Inc), Insulin sensitivity was evaluated by the HOmeostatic Model Assessment index (HOMA-IR=[(fasting insulin, μU/ml)×(fasting glucose, mg/dl]/405) and the QUantitative Insulin sensitivity ChecK Index (QUICKI=1/(Log(fasting insulin, μU/ml)+Log(fasting glucose, mg/dl)]).

Serum cholesterol and thyroxine were determined using VetScan rotors (Abaxis Veterinary Diagnostics). Serum leptin was determined by ELISA (Crystal Chem. Inc.). Serum adiponectin was determined by ELISA (Invitrogen). Blood was collected from tail tip (glucose and insulin), from the sub-mandibular vein (Igf1, cholesterol and thyroxine), or from post-mortem heart puncture (leptin and adiponectin).

In Vivo Inhibition of PI3K

The low molecular weight Compound A is a potent inhibitor of PI3K isoforms p110a (Ki=2.4 nM) and p110δ (Ki=9.8 nM) (inhibition of the other PI3K isoforms p1103 and p110γ had values of Ki>100 nM, and inhibition of a total of 282 additional kinases including mTOR and DNAPK required concentrations of IC50<1 μM). For in vitro assays Compound A was added at a concentration of 1 μM. For in vivo assays, Compound A" was administered orally by gavage at a dose of 15 mg/kg. Mice were sacrificed 6 h after and tissues were extracted and analyzed. Treated mice were C57BL6 males, 3 months old.

Cellular Assays

Mouse Embryonic Fibroblasts (MEFs) were isolated at E13.5 as previously described[42]. For insulin stimulation, primary MEFs were serum starved (0% FBS) for 12 h, followed by 60 min incubation with PBS and then stimulated with 1 μg/ml of insulin (Sigma) during 30 min. For oncogenic transformation, primary MEFs were retrovirally transduced with pLXSN-neo-E6 and either pWZL-blast-middle-T (kindly provided by Jean Zhao, Dana-Farber Cancer Institute, Boston) or pBABE-puro-EGFRL858R (kindly provided by William Sellers and Matthew Meyerson, Addgene plasmid #11012)[43]. After the corresponding drug selection 20,000 cells were plated in 10 cm diameter plates, and 2 weeks later were fixed and stained with 20% Giemsa. Immortalized brown adipocyte cell lines were obtained from the interscapular BAT of 3-5 day-old neonates, treated with and cultured as previously described[33]. For immortalization, cultures were retrovirally transduced with Large-T antigen (in vector pBABE-puro, kindly provided by James de Caprio, Dana Farber Cancer Institute, Boston). For the reprogramming of 3T3-L1 adipocytes into brownadipocytes, we followed the method previously reported[50]. Briefly, 3T3-L1 cells were retrovirally transduced with pBABE-puro-Cebpb (kindly provided by Roger R. Gomis, IRB, Barcelona). After drug selection with puromycin, cells were grown to confluence and subsequently cultured for 48 h with "differentiation medium" (DMEM 10% FBS, 20 nM insulin, 1 nM T3, 1 μM rosiglitazone, 0.5 mM isobutylmethylxanthine, 125 nM indomethacin, 5 μM dexamethasone). After this, cells were exposed to "maintenance medium" (DMEM 10% FBS, 20 nM insulin, 1 nM T3) for 4 days. For the experiment shown in FIG. 4d, differentiated 3T3-L1/Cebpβ or non-differentiated neonatal immortalized brown adipocytes cultures were PBS washed and treated with "regular medium" (DMEM 10% FBS) containing 10 μM forskolin (Sigma) and/or or 1 μM Compound A for 4 h.

Generation of Ectopic BAT

In vitro programming of MEFs and subsequent transplantation to generate brown adipocytes was performed essentially as previously described[9]. Briefly, primary MEFs were first immortalized with pLXSN-neo-E6, and then retrovirally transduced with pBABE-puro-Prdm16 (kindly provided by Bruce Spiegelman, Addgene plasmid 15504)[8] and pBABE-puro-Cebpb (kindly provided by Roger R. Gomis, IRB, Barcelona). After drug selection, Prdm16/Cebpb-transduced fibroblasts were expanded and injected subcutaneously (10 million cells per injection site) into nude mice (males, 10 weeks old). After 2 months, mice were sacrificed. Grafted adipose pads were often visible. The skin around the injection site was processed for histology. Serial sections were scanned and examined. In some cases, ectopic fat was not identified (see quantification in FIG. 4g). The areas occupied by BAT were quantified, excluding WAT or other, such as granuloma.

Protein Analyses

Lysis buffer (150 mM NaCl, 10 mM Tris pH 7.2, 0.1% SDS, 1.0% Triton X-100, 1% deoxycholate, 5 mM EDTA) was used to prepare protein extracts. Western blot analyses were performed according to standard procedures. Antibodies from Cell Signaling were used for detection of Pten (#9552), P-S473-Akt (#4058), P-T308-Akt (#9275), P-T24/T32-Foxo1/3 (#9464), P-S636/639-Irs1 (#2388). For detection of total Akt1, we used an antibody from Upstate (#07-416), and for β-actin, from Sigma (AC-15).

RNA Analyses

Total RNA from tissues or fibroblasts was extracted using TRIZOL (Invitrogen). Reverse transcription was performed using random primers and Ready-To-Go™ You-Prime First-Strand Beads (GE Healthcare). Quantitative real time-PCR was performed using DNA Master Sybr Green I mix (Applied Biosystems) in an ABI PRISM 7700 thermocycler (Applied Biosystem). Primer sequences are described in Supp. Table SI.

Histological Analyses

Brown adipose tissue, white adipose tissue and liver were fixed overnight in formalin, embedded in paraffin blocks and sectioned. Tissue sections were stained with hematoxilin/eosin. The size of white adipocytes was measured using the ImageJ program and at least 500 cells were measured for each mouse.

Statistical Analyses

Survival curves were compared using the logrank test. For all other comparisons we used, as indicated, the Fisher's exact test or the two-tailed Student's t-test.

EXAMPLE D—FURTHER EXAMPLES OF COMPOUNDS/PI3K INHIBITORS OF FORMULA I

Compounds of the invention/formula I are/were tested and shown to be PI3K inhibitors.

Where compound names are given herein, they are typically generated with ChemDraw.

The invention is illustrated by way of the following examples, in which the following abbreviations (or chemical symbols) may be employed:

"dba" dibenzylidene acetone; "DCM" dichloromethane; "MeOH" methanol; "EtOH" ethanol; "THF" tetrahydrofuran; "DMF" dimethylformamide; "CHCl$_3$" chloroform; "DME" dimethoxyethane; "Et$_2$O" diethyl ether; "Hex" hexane; "EtOAc" ethyl acetate; "Pd(PPh$_3$)$_4$" tetrakis(triphenylphosphine)palladium; "KOAc" potassium acetate; "DIPEA" diisopropylethylamine; "Pd(PPh$_3$)$_4$" tetrakis(triphenylphosphine)-palladium; "Pd(dppf)Cl$_2$.DCM" 1,1'-bis(diphenylphosphino)ferrocenepalladium(II) dichloride, dichloromethane; "min." minutes; and "h." hours.

The intermediate compounds of Table 1 were prepared according to the procedures A-1, A-2 and A-3 described hereinafter. The intermediate compounds of Table 2 were prepared according to the procedures A-4 to A-28 described hereinafter. The final examples of compounds of the invention were prepared according to the procedures B-1 to B-26 (and A-13) described hereinafter. Procedures of methods A and B are described in more detail in the experimental hereinafter. If an experimental procedure is not specifically described, the synthesis is performed in accordance with the methods described herein, optionally with reference to procedures known to the skilled person. A procedure to prepare a final compound may or may not be accompanied by characterising data for that final compound.

TABLE 1

Pyrazine Intermediates

| Exp. No. | Meth. | —R1 | —R2 |
|---|---|---|---|
| I-01 | A-1 | —Br | —Br |
| I-02 | A-2 | morpholinyl | —Br |
| I-03 | A-3 | morpholinyl | indazolyl |
| I-04 | A-3 | morpholinyl | 3-hydroxyphenyl |
| I-53 | A1 | —Cl | —I |
| I-54 | A3 | morpholinyl | 2-aminopyrimidin-5-yl |

TABLE 2
Intermediates
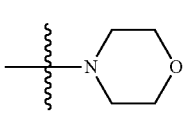
| No. | Exp. Meth. | —R1 | —R2 | —R3 | —R4 | —R5 |
|---|---|---|---|---|---|---|
| I-05 | A4 | —Br | —Me | —H | —H | —Br |
| I-06 | A5 | —Br | —Me | —Br | —H | —Br |
| I-07 | A4 | —Br | —CO$_2$Et | —H | —H | —Br |
| I-08 | A4 | —Br | —CF$_3$ | —H | —H | —Br |
| I-09 | A6 | —Br | —CO$_2$Et | —Br | —H | —Br |
| I-10 | A7 | 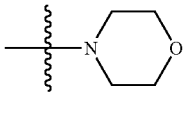 [SMILES: *N1CCOCC1] | —Me | —H | —H | —Br |
| I-11 | A7 | 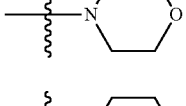 | —Me | —Br | —H | —Br |
| I-12 | A7 | 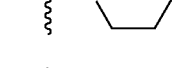 | —CO$_2$Et | —H | —H | —Br |
| I-13 | A8 | 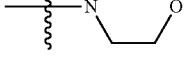 | —CHO | —H | —H | —Br |
| I-14 | A9 | 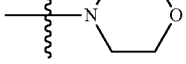 | —CH$_2$OH | —H | —H | —Br |
| I-15 | A7 | 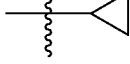 | 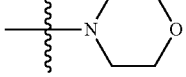 | —H | —H | —Br |
| I-16 | A10 | 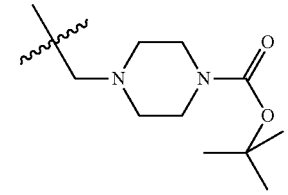 [SMILES: *CN1CCN(C(=O)OC(C)(C)C)CC1] | 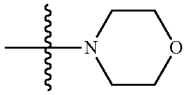 [SMILES: *N1CCOCC1] | —H | —H | —Br |
| I-17 | A11 | 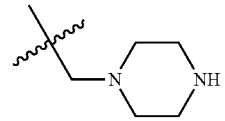 [SMILES: *CN1CCNCC1] | 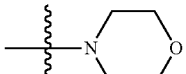 | —H | —H | —Br |
| I-18 | A10 | 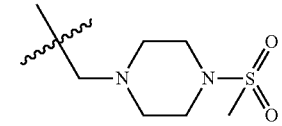 |  | —H | —H | —Br |

TABLE 2-continued

Intermediates

[Structure: imidazo[1,2-a]pyrazine core with substituents R1 (position 8), R2 (position 2), R3 (position 3), R4 (position 5), R5 (position 6)]

| No. | Exp. Meth. | —R1 | —R2 | —R3 | —R4 | —R5 |
|-----|------------|-----|-----|-----|-----|-----|
| I-19 | A10 | morpholin-4-yl | -CH2-N(piperazinyl)-C(=O)CH3 (4-acetylpiperazin-1-ylmethyl) | —H | —H | —Br |
| I-20 | A10 | morpholin-4-yl | -CH2-(4-methylpiperazin-1-yl) | —H | —H | —Br |
| I-21 | A10 | morpholin-4-yl | -CH2-(3-oxopiperazin-1-yl) | —H | —H | —Br |
| I-22 | A10 | morpholin-4-yl | -CH2-morpholin-4-yl | —H | —H | —Br |
| I-23 | A12 | morpholin-4-yl | -C(=O)-(4-methylpiperazin-1-yl) | —H | —H | —Br |
| I-24 | A12 | morpholin-4-yl | -C(=O)-N(piperazinyl)-S(=O)2CH3 (4-(methylsulfonyl)piperazin-1-ylcarbonyl) | —H | —H | —Br |
| I-25 | A12 | morpholin-4-yl | -CH2-(4-Boc-piperazin-1-yl) | —H | —H | —Br |
| I-26 | A7 | morpholin-4-yl | —CF$_3$ | —H | —H | —Br |

TABLE 2-continued

Intermediates

| No. | Exp. Meth. | —R1 | —R2 | —R3 | —R4 | —R5 |
|---|---|---|---|---|---|---|
| I-27 | A14 | morpholin-4-yl | —Me | 1-Boc-piperidin-4-yl-NHC(O)C(Me)- | —H | —Cl |
| I-28 | A4 | morpholin-4-yl | —Me | —CO$_2$Et | —H | —Cl |
| I-29 | A13 | morpholin-4-yl | —Me | —CO$_2$H | —H | —Cl |
| I-30 | A15 | morpholin-4-yl | —CONH$_2$ | —H | —H | —Br |
| I-35 | A4 | morpholin-4-yl | methyl 3-methylbutanoate-3-yl | —H | —H | —Cl |
| I-39 | A18 | morpholin-4-yl | methyl 3-methylbutanoate-3-yl | —H | —CHO | —Cl |
| I-40 | A9 | morpholin-4-yl | methyl 3-methylbutanoate-3-yl | —H | —CH$_2$OH | —Cl |
| I-43 | A4 | —Cl | —Me | —H | —H | —I |

TABLE 2-continued

Intermediates

[Structure: imidazo[1,2-a]pyrazine core with R1 at 8-position, R2 at 2-position, R3 at 3-position, R4 at 5-position, R5 at 6-position]

| No. | Exp. Meth. | —R1 | —R2 | —R3 | —R4 | —R5 |
|---|---|---|---|---|---|---|
| I-44 | A16 | —Cl | —Me | —H | —H | 5-(2-aminopyrimidinyl) |
| I-45 | A4 | morpholin-4-yl | —H | —H | —H | —Br |
| I-46 | A4 | —Cl | —CO₂Et | —H | —H | —I |
| I-47 | A6 | —Cl | —CO₂Et | —Br | —H | —I |
| I-48 | A7 | morpholin-4-yl | —CO₂Et | —Br | —H | —I |
| I-49 | A9 | morpholin-4-yl | —CH₂OH | —Br | —H | —I |
| I-50 | A20 | morpholin-4-yl | —CHO | —Br | —H | —I |
| I-51 | A10 | morpholin-4-yl | (4-(methylsulfonyl)piperazin-1-yl)methyl | —Br | —H | —I |
| I-55 | A4 | morpholin-4-yl | tetrahydro-2H-pyran-4-yl | —H | —H | —Br |
| I-56 | A4 | morpholin-4-yl | —CO₂Et | —Me | —H | —Br |
| I-57 | A4 | morpholin-4-yl | —CH₂Cl | —H | —H | —Br |

TABLE 2-continued
Intermediates
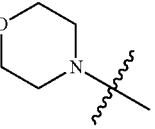
| No. | Exp. Meth. | —R1 | —R2 | —R3 | —R4 | —R5 |
|---|---|---|---|---|---|---|
| I-58 | A21 | 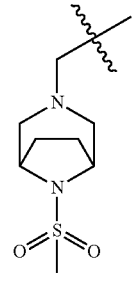 [SMILES: *CN1CC2CCC(C1)N2S(C)(=O)=O] | 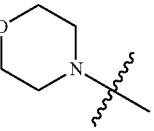 | —H | —H | —Br |
| I-59 | A21 | 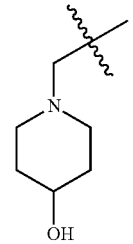 | 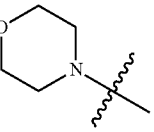 | —H | —H | —Br |
| I-59A | A21 | 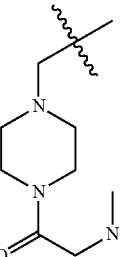 | 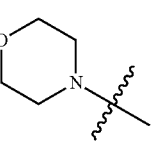 | —H | —H | —Br |
| I-60 | A22 | 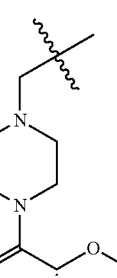 | 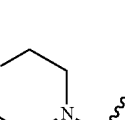 | —H | —H | —Br |
| I-61 | A23 | 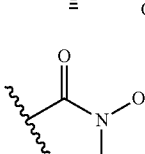 | | —H | —H | —Br |

TABLE 2-continued

Intermediates

| No. | Exp. Meth. | —R1 | —R2 | —R3 | —R4 | —R5 |
|---|---|---|---|---|---|---|
| I-62 | A24 | morpholin-4-yl (N-linked via CMe) | acetyl (C(O)CH₃) | —H | —H | —Br |
| I-63 | A25 | morpholin-4-yl (N-linked via CMe) | 2-cyano-2-(4-Boc-piperazin-1-yl)propan-2-yl | —H | —H | —Br |
| I-64 | A26 | morpholin-4-yl (N-linked via CMe) | 2-(4-Boc-piperazin-1-yl)propan-2-yl | —H | —H | —Br |
| I-65 | A10 | morpholin-4-yl (N-linked via CMe) | —CH₂—N(CH₃)—(1-methanesulfonyl-piperidin-4-yl) | —H | —H | —Br |

TABLE 2-continued

Intermediates

| No. | Exp. Meth. | —R1 | —R2 | —R3 | —R4 | —R5 |
|---|---|---|---|---|---|---|
| I-66 | A10 | morpholine | 1-(methylsulfonyl)-1,4-diazepan-4-yl-methyl | —H | —H | —Br |
| I-67 | A11 | morpholine | 2-(piperazin-1-yl)propan-2-yl | —H | —H | —Br |
| I-68 | A27 | morpholine | 2-(4-(methylsulfonyl)piperazin-1-yl)propan-2-yl | —H | —H | —Br |
| I-69 | A3 | morpholine | —H | —Me | —H | 4-aminophenyl |
| I-70 | A28 | morpholine | —H | —Me | —H | —Br |

TABLE 3

Final Products prepared in accordance with the procedures described herein

| No. | Exp. | —R1 | —R2 | —R3 | —R4 | —R5 |
|---|---|---|---|---|---|---|
| 2-01 | B1 | morpholinyl | —CO₂Et | —H | —H | 3-hydroxyphenyl |
| 2-02 | B1 | morpholinyl | —CO₂H | —H | —H | 3-hydroxyphenyl |
| 2-03 | B1 | morpholinyl | —CHO | —H | —H | 3-hydroxyphenyl |
| 2-04 | B1 | morpholinyl | —CH₂OH | —H | —H | 3-hydroxyphenyl |

TABLE 3-continued

Final Products prepared in accordance with the procedures described herein

| No. | Exp. | —R1 | —R2 | —R3 | —R4 | —R5 |
|---|---|---|---|---|---|---|
| 2-05 | B1 | morpholinyl | piperazine-N-Boc-CH2 | —H | —H | 3-hydroxyphenyl |
| 2-06 | B1 | morpholinyl | piperazine-N-acetyl-CH2 | —H | —H | 3-hydroxyphenyl |
| 2-07 | B1 | morpholinyl | 4-methylpiperazine-CH2 | —H | —H | 3-hydroxyphenyl |

TABLE 3-continued

Final Products prepared in accordance with the procedures described herein

| No. | Exp. | —R1 | —R2 | —R3 | —R4 | —R5 |
|---|---|---|---|---|---|---|
| 2-08 | B1 | morpholine | piperazinone-CH2- | —H | —H | 3-hydroxyphenyl |
| 2-09 | B1 | morpholine | morpholine-CH2- | —H | —H | 3-hydroxyphenyl |
| 2-10 | B1 | morpholine | 4-(methylsulfonyl)piperazine-CH2- | —H | —H | 3-hydroxyphenyl |

TABLE 3-continued

Final Products prepared in accordance with the procedures described herein

| No. | Exp. | —R1 | —R2 | —R3 | —R4 | —R5 |
|---|---|---|---|---|---|---|
| 2-11 | B1 | morpholinyl | piperazinyl-C(O)-C(CH3)- with N-SO2Me | —H | —H | 3-hydroxyphenyl |
| 2-12 | B4 | morpholinyl | —Me | —H | —H | 3-methoxyphenyl |
| 2-13 | B1 | morpholinyl | —CF3 | —H | —H | 3-hydroxyphenyl |
| 2-14 | B1 | morpholinyl | cyclopropyl-C(CH3)- | —H | —H | 3-hydroxyphenyl |

TABLE 3-continued

Final Products prepared in accordance with the procedures described herein

| No. | Exp. | —R1 | —R2 | —R3 | —R4 | —R5 |
|---|---|---|---|---|---|---|
| 2-15 | B1 | morpholinyl | 1-methylpiperazine carbonyl | —H | —H | 1H-indazol-4-yl |
| 2-16 | B1 | morpholinyl | 4-(methylsulfonyl)piperazine carbonyl | —H | —H | 1H-indazol-4-yl |
| 2-17 | B1 | morpholinyl | (4-(methylsulfonyl)piperazin-1-yl)methyl | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-18 | B1 | morpholinyl | piperazine-carbonyl | —H | —H | 1H-indazol-4-yl |
| 2-19 | B1 | morpholinyl | cyclopropyl | —H | —H | 1H-indazol-4-yl |
| 2-20 | B1 | morpholinyl | —CF$_3$ | —H | —H | 1H-indazol-4-yl |
| 2-21 | B2 | morpholinyl | —CONH$_2$ | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-22 | B3 | morpholinyl | —CN | —H | —H | 1H-indazol-4-yl |
| 2-23 | B1 | morpholinyl | —Me | —H | —H | 3-hydroxyphenyl |
| 2-24 | B1 | morpholinyl | —Me | —H | —H | 1H-indazol-4-yl |
| 2-25 | B1 | morpholinyl | —Me | —H | —H | 1H-indol-6-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-26 | B1 | morpholin-4-yl | —Me | —H | —H | pyridin-3-yl |
| 2-27 | B1 | morpholin-4-yl | —Me | —H | —H | 5-methoxypyridin-3-yl |
| 2-28 | B1 | morpholin-4-yl | —Me | —H | —H | 3-(methylsulfonamido)phenyl |
| 2-29 | B1 | morpholin-4-yl | —Me | —H | —H | 4-(3-methylureido)phenyl |

TABLE 3-continued

Final Products prepared in accordance with the procedures described herein

| No. | Exp. | —R1 | —R2 | —R3 | —R4 | —R5 |
|---|---|---|---|---|---|---|
| 2-30 | B11 | morpholinyl | —Me | —H | —H | 5-hydroxypyridin-3-yl |
| 2-31 | B1 | morpholinyl | —Me | —H | —H | pyridin-4-yl |
| 2-32 | B1 | morpholinyl | —Me | —H | —H | 3-methoxyphenyl |
| 2-33 | B4 | morpholinyl | —Me | —H | —Cl | pyridin-4-yl |
| 2-34 | B4 | morpholinyl | —Me | —H | —Cl | pyridin-3-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-35 | B2 | morpholine | —CONH$_2$ | —H | —H | phenyl |
| 2-36 | B14 | morpholine | —Me | —H | —CN | 1H-indazol-4-yl |
| 2-37 | B5 | morpholine | —H | 4-methylpiperazin-1-yl | —H | 3-hydroxyphenyl |
| 2-38 | B5 | morpholine | —H | 4-methylpiperazin-1-yl | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-39 | B5 | morpholinyl | —H | 4-(methylsulfonyl)piperazin-1-yl | —H | 3-hydroxyphenyl |
| 2-40 | B5 | morpholinyl | —H | piperazin-1-yl | —H | 3-hydroxyphenyl |
| 2-41 | B5 | morpholinyl | —H | 4-(methylsulfonyl)piperazin-1-yl | —H | 1H-indazol-4-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-42 | B1 | 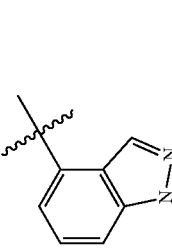 | —Me | —Br | —H | 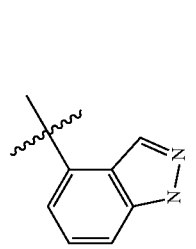 |
| 2-43 | B6 | 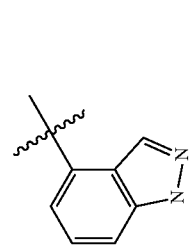 | —Me | 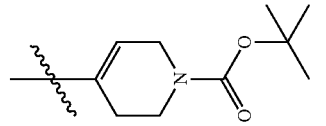 | —H | 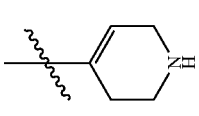 |
| 2-44 | B7 | 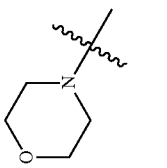 | —Me | 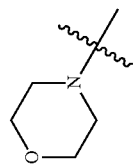 | —H | 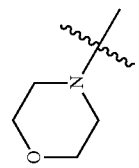 |

TABLE 3-continued
Final Products prepared in accordance with the procedures described herein
| No. | Exp. | —R1 | —R2 | —R3 | —R4 | —R5 |
|---|---|---|---|---|---|---|
| 2-45 | B8 | 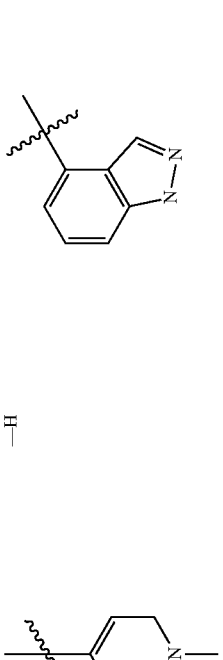 | —Me | 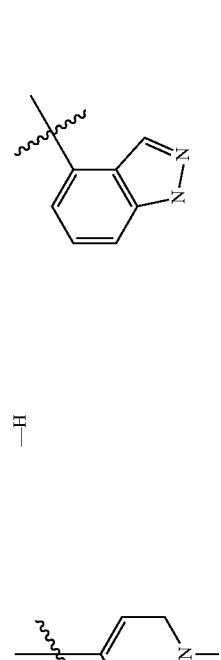 | —H | 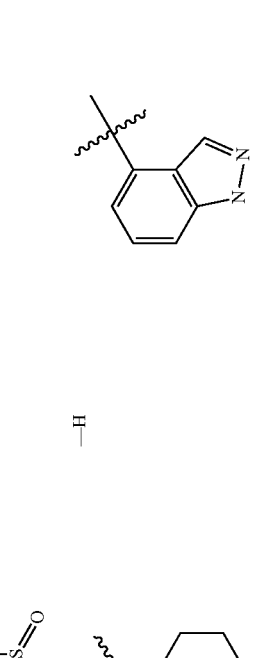 |
| 2-46 | B9 |  | —Me | 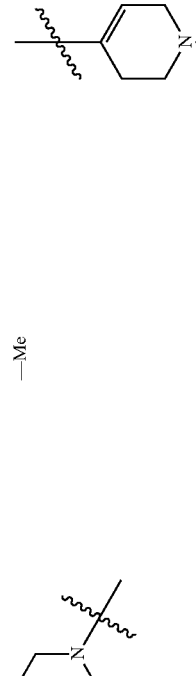 | —H | 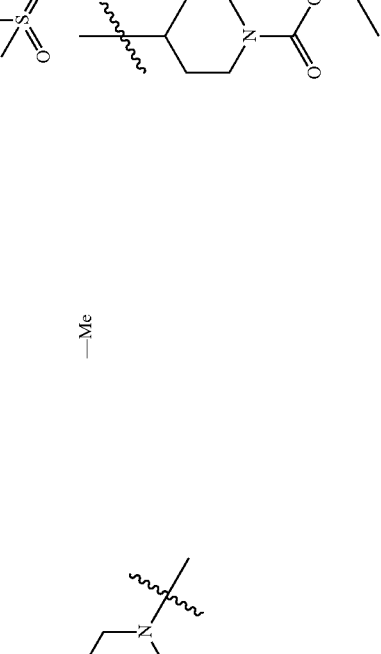 |
| 2-47 | B10 | 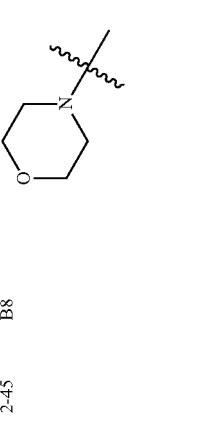 | —Me | 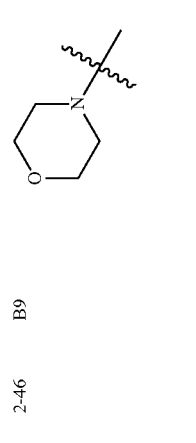 | —H | 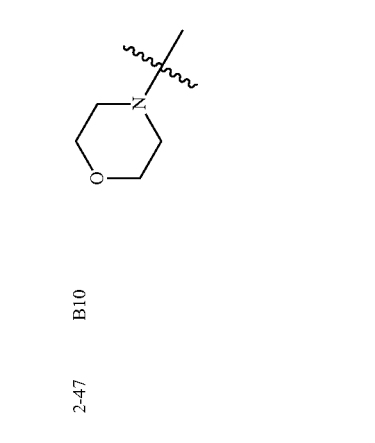 |

TABLE 3-continued

Final Products prepared in accordance with the procedures described herein

| No. | Exp. | —R1 | —R2 | —R3 | —R4 | —R5 |
|---|---|---|---|---|---|---|
| 2-48 | B4 | morpholinyl | —Me | —H | —Cl | 3-methoxyphenyl |
| 2-49 | B11 | morpholinyl | —Me | —H | —Cl | 3-hydroxyphenyl |
| 2-50 | B1 | morpholinyl | 4-(methylsulfonyl)piperazin-1-ylmethyl | —H | —H | 2-aminopyrimidin-5-yl |
| 2-51 | B5 | morpholinyl | —H | piperazin-1-yl | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-52 | B13 | morpholine (N-linked, C-linked) | —CO₂Et | —H | —H | 1H-indazol-4-yl |
| 2-53 | B4 | morpholine (N-linked) | —Me | —H | —I | 3-methoxyphenyl |
| 2-54 | B4 | morpholine (N-linked) | —Me | —H | —Cl | 1H-indazol-4-yl |
| 2-55 | B4 | morpholine (N-linked) | —Me | —H | —Br | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-56 | B4 | morpholine (N-linked) | —Me | —H | —I | pyridin-3-yl |
| 2-57 | B12 | morpholine (N-linked) | —Me | piperidin-4-yl (NH) | —H | 1H-indazol-4-yl |
| 2-58 | B8 | morpholine (N-linked) | —Me | 1-methylpiperidin-4-yl | —H | 1H-indazol-4-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-59 | B9 | 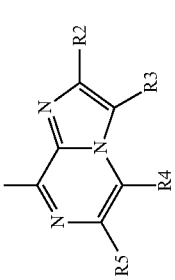 | —Me |  | —H |  |
| 2-60 | B4 | 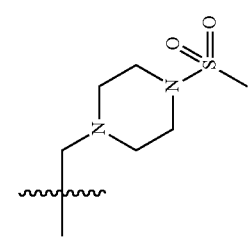 | 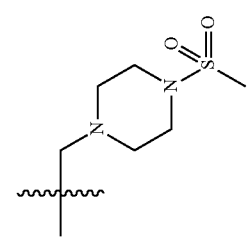 | —H | —Cl | 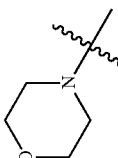 |
| 2-61 | B1 | 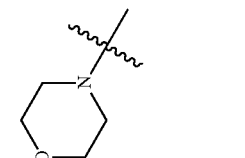 | 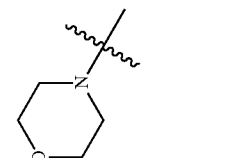 | —H | —H | 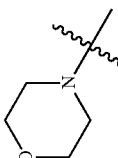 |

TABLE 3-continued

Final Products prepared in accordance with the procedures described herein

| No. | Exp. | —R1 | —R2 | —R3 | —R4 | —R5 |
|---|---|---|---|---|---|---|
| 2-62 | B14 | morpholinyl | —Me | —CN | —H | 3-methoxyphenyl |
| 2-63 | B1 | morpholinyl | —Me | N-(1-Boc-piperidin-4-yl)-2-methylpropanamide | —H | 1H-indazol-4-yl |
| 2-64 | B12 | morpholinyl | —Me | N-(piperidin-4-yl)-2-methylpropanamide | —H | 1H-indazol-4-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-65 | B1 | 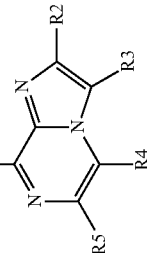 |  | —H | —H |  |
| 2-66 | B1 |  |  | —H | —H |  |
| 2-67 | B1 | 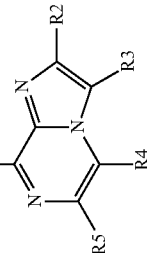 |  | —H | —H |  |

TABLE 3-continued

Final Products prepared in accordance with the procedures described herein

| No. | Exp. | —R1 | —R2 | —R3 | —R4 | —R5 |
|---|---|---|---|---|---|---|
| 2-68 | B1 | morpholine | 4-(methylsulfonyl)piperazin-1-ylmethyl | —H | —H | 4-carbamoylphenyl |
| 2-69 | B1 | morpholine | 4-(methylsulfonyl)piperazin-1-ylmethyl | —H | —H | 2-oxoindolin-5-yl |
| 2-70 | B1 | morpholine | 4-(methylsulfonyl)piperazin-1-ylmethyl | —H | —H | 5-fluoro-1H-indol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-71 | B1 | morpholine (N-linked) | 4-(methylsulfonyl)piperazin-1-ylmethyl | —H | —H | indol-4-yl |
| 2-72 | B1 | morpholine (N-linked) | 4-(methylsulfonyl)piperazin-1-ylmethyl | —H | —H | 3-carbamoylphenyl |
| 2-73 | B4 | morpholine (N-linked) | —Me | —H | —I | indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-74 | B2 | morpholine | —CONHEt | —H | —H | 1H-indazol-4-yl |
| 2-75 | B1 | morpholine | 4-(methylsulfonyl)piperazin-1-ylmethyl | —H | —H | 1H-pyrrolo[2,3-b]pyridin-5-yl |
| 2-76 | B9 | morpholine | —Me | 2-methyl-N-(1-(methylsulfonyl)piperidin-4-yl)propanamido | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-77 | B12 | morpholin-4-yl | —Me | —CONH$_2$ | —H | 1H-indazol-4-yl |
| 2-78 | B5 | morpholin-4-yl | —H | 4-aminopiperidin-1-yl | —H | 1H-indazol-4-yl |
| 2-79 | B15 | morpholin-4-yl | —CONHMe | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-81 | B1 | morpholine | piperazinyl-methyl-N-SO2Me | —H | —H | pyridinyl-NHC(O)CH3 |
| 2-82 | B1 | morpholine | piperazinyl-methyl-N-SO2Me | —H | —H | phenyl-NHC(O)NHCH3 |

TABLE 3-continued

Final Products prepared in accordance with the procedures described herein

| No. | Exp. | —R1 | —R2 | —R3 | —R4 | —R5 |
|---|---|---|---|---|---|---|
| 2-83 | B1 | morpholinyl | piperazinyl-SO2Me | —H | —H | 2-amino-3-(trifluoromethyl)pyridin-5-yl |
| 2-84 | B14 | morpholinyl | piperazinyl-SO2Me | —H | —CN | 1H-indazol-4-yl |
| 2-86 | B15 | morpholinyl | —CONMe2 | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-87 | B16 | morpholinyl | pyrrolidinyl-C(O)-C(CH3)- | —H | —H | 1H-indazol-4-yl |
| 2-88 | B11 | morpholinyl | —Me | —CN | —H | 3-hydroxyphenyl |
| 2-89 | B1 | morpholinyl | 4-(methylsulfonyl)piperazin-1-ylmethyl | —H | —H | 4-aminophenyl |

TABLE 3-continued

Final Products prepared in accordance with the procedures described herein

| No. | Exp. | —R1 | —R2 | —R3 | —R4 | —R5 |
|---|---|---|---|---|---|---|
| 2-90 | B1 | morpholine (N-linked) | CH2-piperazine-N-SO2CH3 | —H | —H | 1H-pyrazol-4-yl |
| 2-91 | B13 | morpholine (N-linked) | —CONH2 | —H | —H | pyridin-4-yl |
| 2-92 | B13 | morpholine (N-linked) | —CONH2 | —H | —H | pyridin-3-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-93 | B13 | morpholin-4-yl | —CONH2 | —H | —H | 2-aminopyrimidin-5-yl |
| 2-94 | B13 | morpholin-4-yl | —CONH2 | —H | —H | 1H-indol-4-yl |
| 2-95 | B13 | morpholin-4-yl | —CONH2 | —H | —H | 5-fluoro-1H-indol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-96 | B4 | morpholinyl | —CONH2 | —H | —Cl | 2-aminopyrimidin-5-yl |
| 2-97 | B17 | morpholinyl | tert-butyl 2,8-diazaspiro[4.5]decane-2-carboxylate-8-yl-methyl | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-98 | B17 | morpholine | N-Boc-2,8-diazaspiro[5.5]... | —H | —H | 1H-indazol-4-yl |
| 2-99 | B17 | morpholine | N-Boc-octahydropyrrolo[3,4-c]pyrrole | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-100 | B17 | morpholine | N-Boc-2,8-diazaspiro[4.5]decane (via CH2 linker) | —H | —H | 1H-indazol-4-yl |
| 2-101 | B4 | morpholine | —CONH2 | —H | —Cl | pyridin-4-yl |
| 2-102 | B4 | morpholine | —CONH2 | —H | —Cl | pyridin-3-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-103 | B4 | morpholin-4-yl | —CONH2 | —H | —H | 3-chloro-1H-indol-4-yl |
| 2-104 | B4 | morpholin-4-yl | —CONH2 | —H | —Cl | 3-chloro-1H-indol-4-yl |
| 2-105 | B4 | morpholin-4-yl | —CONH2 | —H | —H | 3-chloro-5-fluoro-1H-indol-4-yl |
| 2-106 | B4 | morpholin-4-yl | —CONH2 | —H | —Cl | 3-chloro-5-fluoro-1H-indol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-107 | B13 | morpholine | methyl acetate | —H | —H | 1H-indazol-4-yl |
| 2-108 | B4 | morpholine | (4-(methylsulfonyl)piperazin-1-yl)methyl | —H | —Cl | 2-aminopyrimidin-5-yl |
| 2-109 | B4 | morpholine | (4-(methylsulfonyl)piperazin-1-yl)methyl | —H | —Cl | 6-methoxypyridin-3-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-110 | B4 | morpholinyl | CH2-piperazinyl-SO2Me | —H | —Cl | 5-methoxypyridin-3-yl |
| 2-111 | B7 | morpholinyl | CH2-(2,8-diazaspiro[5.5]undecanyl) | —H | —H | 1H-indazol-4-yl |
| 2-112 | B4 | morpholinyl | CH2-piperazinyl-SO2Me | —H | —Cl | 2-methoxypyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-113 | B4 | morpholine | CH₂-piperazine-SO₂CH₃ | —H | —Cl | 5-(2-oxoindolin-5-yl) |
| 2-114 | B4 | morpholine | CH₂-piperazine-SO₂CH₃ | —H | —Cl | 1H-pyrrolo[2,3-b]pyridin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-115 | B4 | morpholinyl | CH₂-piperazinyl-SO₂CH₃ | —H | —Cl | 4-chloro-7-azaindol-5-yl |
| 2-116 | B4 | morpholinyl | CH₂-piperazinyl-SO₂CH₃ | —H | —Cl | 6-aminopyridin-3-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-117 | B7 | 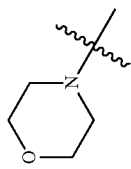 | 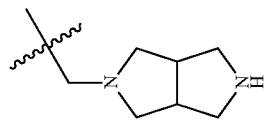 | —H | —H | 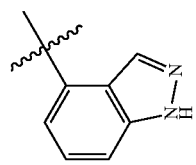 |
| 2-118 | B7 | 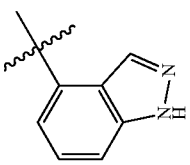 | 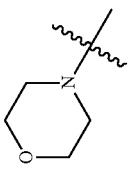 | —H | —H | 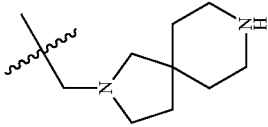 |
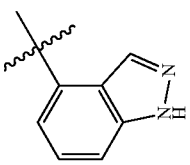

TABLE 3-continued
Final Products prepared in accordance with the procedures described herein
| No. | Exp. | —R1 | —R2 | —R3 | —R4 | —R5 |
|---|---|---|---|---|---|---|
| 2-121 | B4 |  | 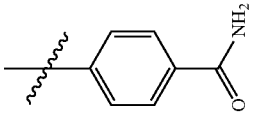 | —H | —Cl |  |
| 2-122 | B4 | 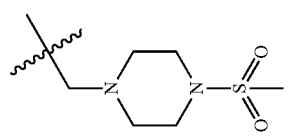 | 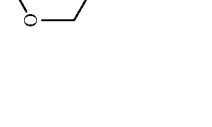 | —H | —H |  |

TABLE 3-continued

Final Products prepared in accordance with the procedures described herein

| No. | Exp. | —R1 | —R2 | —R3 | —R4 | —R5 |
|---|---|---|---|---|---|---|
| 2-123 | B4 | morpholine | CH2-piperazine-SO2CH3 | —H | —Cl | 5-fluoro-1H-indol-4-yl |
| 2-124 | B4 | morpholine | CH2-piperazine-SO2CH3 | —H | —Cl | 3-chloro-5-fluoro-1H-indol-4-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-125 | B1 | 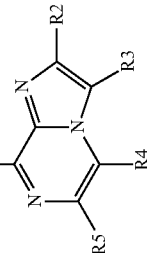 | 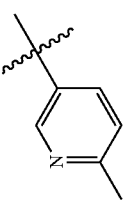 | —H | —H |  |
| 2-126 | B1 | 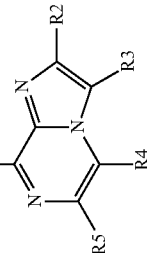 | 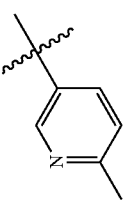 | —H | —H | 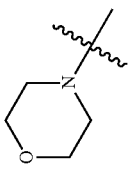 |

TABLE 3-continued
Final Products prepared in accordance with the procedures described herein
| No. | Exp. | —R1 | —R2 | —R3 | —R4 | —R5 |
|---|---|---|---|---|---|---|
| 2-127 | B1 | 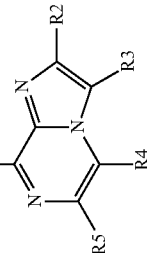 | 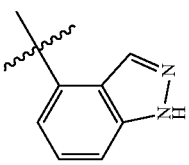 | —H | —H | 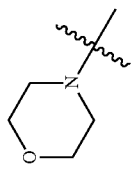 |
| 2-128 | B17 | 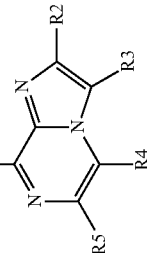 | 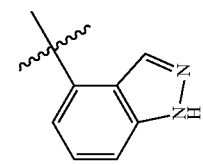 | —H | —H | 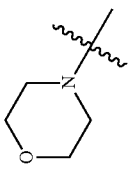 |
| 2-129 | B17 | 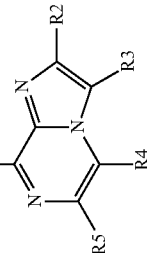 | 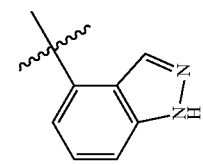 | —H | —H | 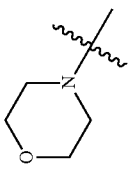 |

TABLE 3-continued

Final Products prepared in accordance with the procedures described herein

| No. | Exp. | —R1 | —R2 | —R3 | —R4 | —R5 |
|---|---|---|---|---|---|---|
| 2-130 | B17 | morpholine | 2-oxo-8-azaspiro[4.5]decan-8-ylmethyl (with NH, C=O) | —H | —H | 1H-indazol-4-yl |
| 2-131 | B17 | morpholine | 3-oxo-2,8-diazaspiro[4.5]decan-8-ylmethyl | —H | —H | 1H-indazol-4-yl |
| 2-133 | B5 | morpholine | —H | 3-aminopiperidin-1-yl | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-134 | B17 | morpholin-4-yl | 2-(methylsulfonyl)-2,8-diazaspiro[4.5]dec-8-ylmethyl | —H | —H | 1H-indazol-4-yl |
| 2-135 | B4 | morpholin-4-yl | [4-(methylsulfonyl)piperazin-1-yl]methyl | —H | —Cl | 6-methylpyridin-3-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-136 | B4 | morpholine | piperazine-N-SO₂Me (CH₂ linker) | —H | —Cl | pyrazine |
| 2-137 | B1 | morpholine | —CO₂Et | —H | —H | 1H-indazol-4-yl |
| 2-138 | B1 | morpholine | —CO₂Et | —H | —H | 2-aminopyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-139 | B16 | morpholine | dimethylaminopropyl amide | —H | —H | 1H-indazol-4-yl |
| 2-140 | B16 | morpholine | methoxypropyl amide | —H | —H | 1H-indazol-4-yl |
| 2-141 | B16 | morpholine | dimethylaminoethyl amide (α,α-dimethyl) | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-142 | B16 | morpholine | -CH2-C(=O)-NH-CH2CH2-morpholine | —H | —H | 1H-indazol-4-yl |
| 2-143 | B7 | morpholine | —Me | 1,2,3,6-tetrahydropyridin-4-yl | —H | 2-aminopyrimidin-5-yl |
| 2-144 | B16 | morpholine | -C(CH3)2-CH2-C(=O)-NH-CH2-phenyl | —H | —CH2OH | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-145 | B17 | morpholine | 2-(methylsulfonyl)-2,7-diazaspiro[3.5]nonan-7-ylmethyl | —H | —H | 1H-indazol-4-yl |
| 2-146 | B16 | morpholine | N-(3-(dimethylamino)propyl)-2-methylpropanamide | —H | —H | pyridin-3-yl |
| 2-147 | B16 | morpholine | N-(2-(dimethylamino)ethyl)-2-methylpropanamide | —H | —H | pyridin-3-yl |
| 2-148 | B16 | morpholine | N-(3-methoxypropyl)-2-methylpropanamide | —H | —H | pyridin-3-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-149 | B17 | morpholine | 3-(methylsulfonyl)-3,9-diazaspiro[5.5]undecane (N9-linked) | —H | —H | 1H-indazol-4-yl |
| 2-150 | B17 | morpholine | 2-(methylsulfonyl)-2,7-diazaspiro[3.5]nonane linked via CH2 | —H | —H | 1H-indazol-4-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-151 | B4 | morpholin-4-yl | —CH₂-(4-methanesulfonyl-piperazin-1-yl) | —H | —Cl | 1H-indol-5-yl |
| 2-152 | B1 | morpholin-4-yl | —CH₂-(4-methanesulfonyl-piperazin-1-yl) | —H | —H | pyridin-3-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-153 | B1 | 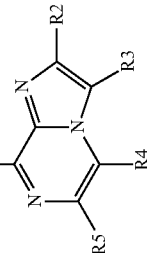 | 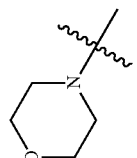 | —H | —H | 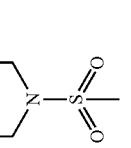 |
| 2-154 | B16 | 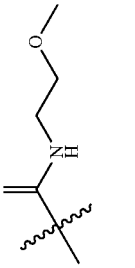 | 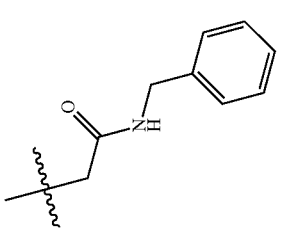 | —H | —H | 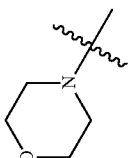 |
| 2-155 | B18 | 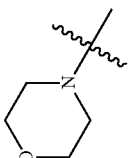 | | —H | | |

TABLE 3-continued

Final Products prepared in accordance with the procedures described herein

| No. | Exp. | —R1 | —R2 | —R3 | —R4 | —R5 |
|---|---|---|---|---|---|---|
| 2-156 | B10 | morpholine | —Me | piperidine-N-isobutyryl | —H | 4-indazolyl |
| 2-157 | B16 | morpholine | acetamido-ethyl-amide | —H | —H | 4-indazolyl |
| 2-158 | B16 | morpholine | acetamido-ethyl-amide | —H | —H | 3-pyridyl |
| 2-159 | B16 | morpholine | morpholino-ethyl-amide | —H | —H | 3-pyridyl |

TABLE 3-continued

Final Products prepared in accordance with the procedures described herein

| No. | Exp. | —R1 | —R2 | —R3 | —R4 | —R5 |
|---|---|---|---|---|---|---|
| 2-160 | B16 | morpholin-4-yl | —C(O)C(CH₃)₂NHCH₂CH₂CH₂N(CH₃)₂ | —H | —H | 2-aminopyrimidin-5-yl |
| 2-161 | B16 | morpholin-4-yl | —C(O)C(CH₃)₂NHCH₂CH₂CH₂OCH₃ | —H | —H | 2-aminopyrimidin-5-yl |
| 2-162 | B16 | morpholin-4-yl | —C(O)C(CH₃)₂NHCH₂CH₂N(CH₃)₂ | —H | —H | 2-aminopyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-163 | B16 | morpholine | methoxyethyl-NH-C(O)-C(CH3)2- | —H | —H | 5-(2-aminopyrimidinyl) |
| 2-164 | B16 | morpholine | morpholinoethyl-NH-C(O)-C(CH3)2- | —H | —H | 5-(2-aminopyrimidinyl) |
| 2-165 | B13 | morpholine | (4-methylsulfonyl-piperazin-1-yl)methyl- | —Me | —H | 5-(2-aminopyrimidinyl) |

TABLE 3-continued

Final Products prepared in accordance with the procedures described herein

| No. | Exp. | —R1 | —R2 | —R3 | —R4 | —R5 |
|---|---|---|---|---|---|---|
| 2-167 | B4 | morpholine (N-linked) | piperidine-N-CH₂- with 4-N-SO₂Me | —H | —Cl | 2-methoxy-4-methylpyridin-5-yl |
| 2-169 | B17 | morpholine (N-linked) | 2,7-diazaspiro[3.5]nonane-CH₂- with N-SO₂Me | —H | —H | 2-aminopyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-170 | B17 | morpholine (N-linked) | hexahydropyrrolo[3,4-c]pyrrole-N-methylsulfonyl, N'-CH2- linked | —H | —H | 5-(2-aminopyrimidinyl) |
| 2-171 | B1 | morpholine (N-linked) | cyclopropyl-CH< | —H | —H | 5-(2-aminopyrimidinyl) |
| 2-172 | B1 | morpholine (N-linked) | —CF3 | —H | —H | 5-(2-aminopyrimidinyl) |

TABLE 3-continued

Final Products prepared in accordance with the procedures described herein

| No. | Exp. | —R1 | —R2 | —R3 | —R4 | —R5 |
|---|---|---|---|---|---|---|
| 2-173 | B4 | morpholine (N-linked) | piperazine-N-CH₂– with N'-SO₂CH₃ | —H | —Cl | 4-methylpyridin-3-yl |
| 2-174 | B1 | morpholine (N-linked) | —H | —H | —H | 2-aminopyrimidin-5-yl |
| 2-175 | B1 | morpholine (N-linked) | morpholine-N-CH₂– | —H | —H | 2-aminopyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-176 | B1 | morpholine | 5-(2-aminopyrimidinyl)methyl | —H | —H | 5-(2-aminopyrimidinyl) |
| 2-177 | B19 | morpholine | 2-hydroxy-2-methylpropyl | —H | —H | 5-(2-aminopyrimidinyl) |
| 2-178 | B1 | morpholine | (4-methylsulfonylpiperazin-1-yl)methyl | —Br | —H | 5-(2-aminopyrimidinyl) |

TABLE 3-continued

Final Products prepared in accordance with the procedures described herein

| No. | Exp. | —R1 | —R2 | —R3 | —R4 | —R5 |
|---|---|---|---|---|---|---|
| 2-179 | B5 | morpholinyl | —H | 4-(methylsulfonyl)piperazin-1-yl | —H | 5-(2-aminopyrimidinyl) |
| 2-180 | B14 | morpholinyl | (4-(methylsulfonyl)piperazin-1-yl)methyl | —H | —CN | 5-(2-aminopyrimidinyl) |
| 2-181 | B1 | morpholinyl | —Me | —H | —H | 5-(2-aminopyrimidinyl) |

TABLE 3-continued

Final Products prepared in accordance with the procedures described herein

| No. | Exp. | —R1 | —R2 | —R3 | —R4 | —R5 |
|---|---|---|---|---|---|---|
| 2-182 | B16 | morpholinyl | 4-(acetamido)piperidine-1-carboxylic acid ethyl ester | —H | —H | 1H-indazol-4-yl |
| 2-183 | B1 | morpholinyl | (4-(methylsulfonyl)piperazin-1-yl)methyl | —Br | —H | 1H-indazol-4-yl |
| 2-184 | B16 | morpholinyl | —CONHMe | —H | —H | 2-aminopyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-185 | B4 | morpholine (N-linked) | —Me | —H | —Cl | 5-(2-aminopyrimidinyl) |
| 2-186 | B16 | morpholine (N-linked) | —C(Me)₂C(O)NHCH₂CH₂OMe | —H | —H | 4-(1H-indazolyl) |
| 2-187 | B14 | morpholine (N-linked) | —Me | —H | —CN | 5-(2-aminopyrimidinyl) |

TABLE 3-continued

Final Products prepared in accordance with the procedures described herein

| No. | Exp. | —R1 | —R2 | —R3 | —R4 | —R5 |
|---|---|---|---|---|---|---|
| 2-188 | B16 | morpholinyl | piperidine-4-ylamido with N-ethoxycarbonyl | —H | —H | 5-(2-aminopyrimidinyl) |
| 2-189 | B4 | morpholinyl | —CONHMe | —H | —Cl | 5-(2-aminopyrimidinyl) |
| 2-190 | B13 | tetrahydropyran-4-yl | —Me | —H | —H | 5-(2-aminopyrimidinyl) |

TABLE 3-continued

Final Products prepared in accordance with the procedures described herein

| No. | Exp. | —R1 | —R2 | —R3 | —R4 | —R5 |
|---|---|---|---|---|---|---|
| 2-191 | B20 | morpholine | tetrahydropyran-4-yl-amide | —H | —H | 2-aminopyrimidin-5-yl |
| 2-192 | B20 | morpholine | trans-4-hydroxycyclohexyl-amide | —H | —H | 2-aminopyrimidin-5-yl |
| 2-193 | B20 | morpholine | 4-Boc-piperazin-1-yl-carbonyl | —H | —H | 2-aminopyrimidin-5-yl |

TABLE 3-continued
Final Products prepared in accordance with the procedures described herein
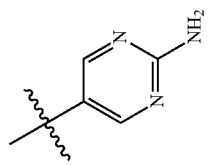
| No. | Exp. | —R1 | —R2 | —R3 | —R4 | —R5 |
|---|---|---|---|---|---|---|
| 2-194 | B4 | 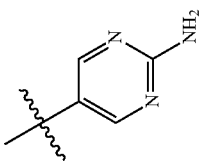 | 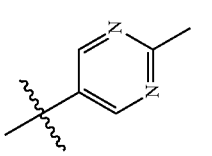 | —H | —Cl | 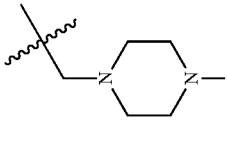 |
| 2-195 | B1 | 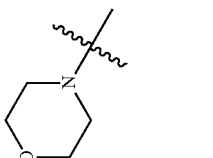 |  | —H | —H | 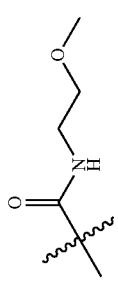 |
| 2-196 | B1 | 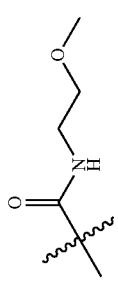 | 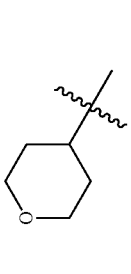 | —H | —H | 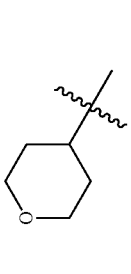 |

TABLE 3-continued

Final Products prepared in accordance with the procedures described herein

| No. | Exp. | —R1 | —R2 | —R3 | —R4 | —R5 |
|---|---|---|---|---|---|---|
| 2-197 | B1 | morpholine | piperidine-N-sulfonylmethyl (CH2-linked) | —H | —H | 1H-indazol-6-yl |
| 2-198 | B1 | morpholine | piperidine-N-sulfonylmethyl (CH2-linked) | —H | —H | 6-amino-5-methylpyridin-3-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-199 | B1 | morpholine | piperazine-N-SO2Me | —H | —H | 2-(methylamino)pyrimidin-5-yl |
| 2-200 | B1 | morpholine | piperazine-N-SO2Me | —H | —H | 2-amino-4-methylpyrimidin-5-yl |

TABLE 3-continued
Final Products prepared in accordance with the procedures described herein
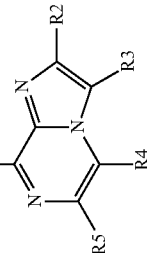
| No. | Exp. | —R1 | —R2 | —R3 | —R4 | —R5 |
|---|---|---|---|---|---|---|
| 2-201 | B1 | 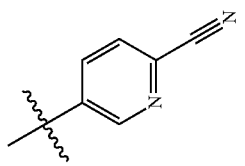 | 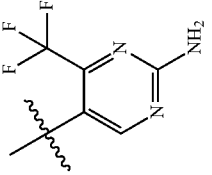 | —H | —H | 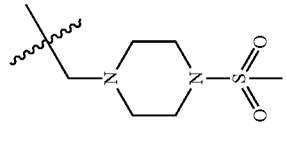 |
| 2-202 | B1 | 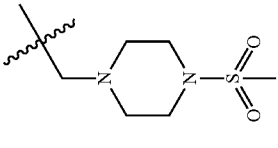 | 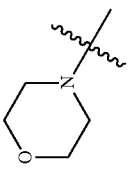 | —H | —H |  |

TABLE 3-continued
Final Products prepared in accordance with the procedures described herein
| No. | Exp. | —R1 | —R2 | —R3 | —R4 | —R5 |
|---|---|---|---|---|---|---|
| 2-203 | B1 | 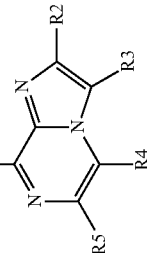 | 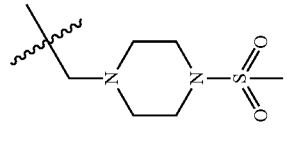 | —H | —H | 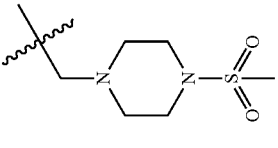 |
| 2-204 | B1 |  | 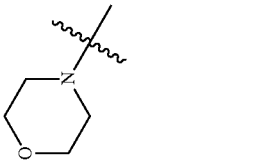 | —H | —H |  |

TABLE 3-continued

Final Products prepared in accordance with the procedures described herein

| No. | Exp. | —R1 | —R2 | —R3 | —R4 | —R5 |
|---|---|---|---|---|---|---|
| 2-205 | B1 | morpholin-4-yl | 4-(methylsulfonyl)piperazin-1-ylmethyl | —H | —H | 2-amino-3-fluoropyridin-5-yl |
| 2-206 | B4 | morpholin-4-yl | 4-(methylsulfonyl)piperazin-1-ylmethyl | —H | —Cl | 2-cyanopyridin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-207 | B4 | morpholine | piperazine-N-SO2Me | —H | —Cl | pyrimidine-NHMe |
| 2-208 | B4 | morpholine | piperazine-N-SO2Me | —H | —Cl | methylpyrimidine-NH2 |

TABLE 3-continued

Final Products prepared in accordance with the procedures described herein

| No. | Exp. | —R1 | —R2 | —R3 | —R4 | —R5 |
|---|---|---|---|---|---|---|
| 2-209 | B4 | morpholine | piperazine-N-SO2Me (CH2 linker) | —H | —Cl | 2-amino-4-(trifluoromethyl)pyrimidin-5-yl (gem-dimethyl linker) |
| 2-210 | B4 | morpholine | piperazine-N-SO2Me (CH2 linker) | —H | —Cl | 2-aminopyridin-4-yl (gem-dimethyl linker) |

TABLE 3-continued
Final Products prepared in accordance with the procedures described herein
| No. | Exp. | —R1 | —R2 | —R3 | —R4 | —R5 |
|---|---|---|---|---|---|---|
| 2-211 | B4 | 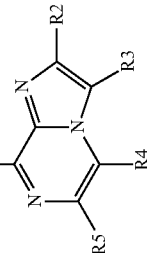 | 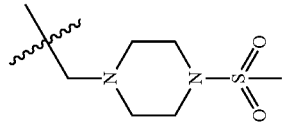 | —H | —Cl | 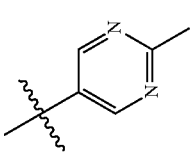 |
| 2-212 | B4 |  |  | —H | —Cl |  |

TABLE 3-continued
Final Products prepared in accordance with the procedures described herein
| No. | Exp. | —R1 | —R2 | —R3 | —R4 | —R5 |
|---|---|---|---|---|---|---|
| 2-213 | B4 |  | 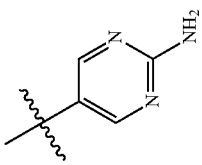 | —H | —Cl | 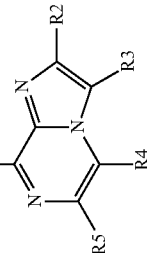 |
| 2-214 | B1 |  | —CO₂Et | —Me | —H | 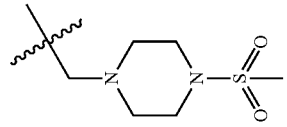 |
| 2-215 | B16 |  |  | —Me | —H |  |

TABLE 3-continued

Final Products prepared in accordance with the procedures described herein

| No. | Exp. | —R1 | —R2 | —R3 | —R4 | —R5 |
|---|---|---|---|---|---|---|
| 2-216 | B20 | morpholinyl | 2-methoxyethylamino-2-methylpropanamide | —Cl | —H | 5-(2-aminopyrimidinyl) |
| 2-217 | B15 | morpholinyl | 2-methylpropanamide (carbamoyl-isopropyl) | —Me | —H | 5-(2-aminopyrimidinyl) |
| 2-218 | B13 | morpholinyl | tert-butyl (2S,5R)-2,5-dimethylpiperazine-1-carboxylate methylene | —H | —H | 5-(2-aminopyrimidinyl) |

TABLE 3-continued
Final Products prepared in accordance with the procedures described herein
| No. | Exp. | —R1 | —R2 | —R3 | —R4 | —R5 |
|---|---|---|---|---|---|---|
| 2-219 | B9 | 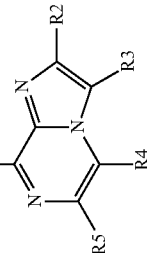 | 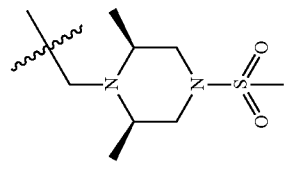 | —H | —H | 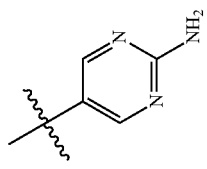 |
| 2-220 | B13 | 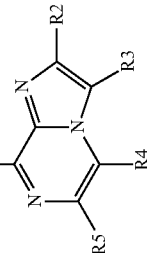 | 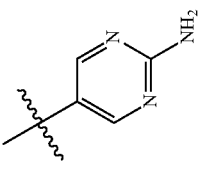 | —H | —H | 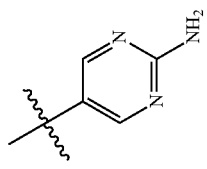 |

TABLE 3-continued
Final Products prepared in accordance with the procedures described herein
| No. | Exp. | —R1 | —R2 | —R3 | —R4 | —R5 |
|---|---|---|---|---|---|---|
| 2-221 | B13 | 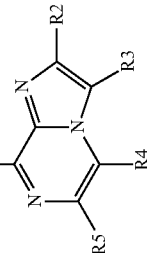 | 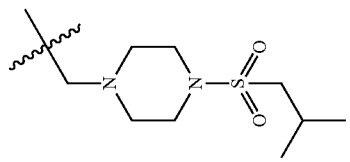 | —H | —H | 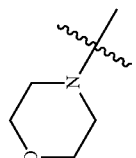 |
| 2-222 | B13 | 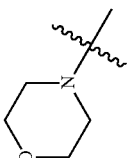 | 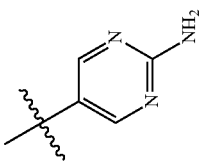 | —H | —H | 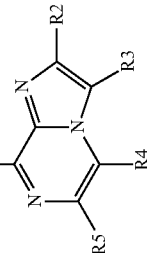 |

TABLE 3-continued

Final Products prepared in accordance with the procedures described herein

| No. | Exp. | —R1 | —R2 | —R3 | —R4 | —R5 |
|---|---|---|---|---|---|---|
| 2-225 | B13 | morpholin-4-yl | piperazine-N-sulfonylphenyl-CH2- | —H | —H | 2-aminopyrimidin-5-yl |
| 2-226 | B13 | morpholin-4-yl | piperazin-1-yl-CH2- | —H | —H | 2-aminopyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-228 | B13 | morpholine | N-methylsulfonyl diazabicyclooctane-CH2- | —H | —H | 5-(2-aminopyrimidinyl) |
| 2-229 | B13 | morpholine | 4-hydroxypiperidine-CH2- | —H | —H | 5-(2-aminopyrimidinyl) |
| 2-230 | B13 | morpholine | 4-(N,N-dimethylglycyl)piperazine-CH2- | —H | —H | 5-(2-aminopyrimidinyl) |

TABLE 3-continued

Final Products prepared in accordance with the procedures described herein

| No. | Exp. | —R1 | —R2 | —R3 | —R4 | —R5 |
|---|---|---|---|---|---|---|
| 2-231 | B13 | morpholine (N-linked) | piperazine-CH2- linked, N-acylated with (S)-2-acetoxypropanoyl | —H | —H | 2-aminopyrimidin-5-yl |
| 2-232 | B13 | morpholine (N-linked) | 2-(piperazin-1-yl)propan-2-yl, N-Boc | —H | —H | 2-aminopyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-233 | B13 | morpholine | CH2-N(Me)-piperidine-N-SO2Me | —H | —H | 2-aminopyrimidin-5-yl |
| 2-234 | B21 | morpholine | CH2-piperazine-C(O)-CH(OH)CH3 | —H | —H | 2-aminopyrimidin-5-yl |

TABLE 3-continued
Final Products prepared in accordance with the procedures described herein
| No. | Exp. | —R1 | —R2 | —R3 | —R4 | —R5 |
|---|---|---|---|---|---|---|
| 2-235 | B13 | 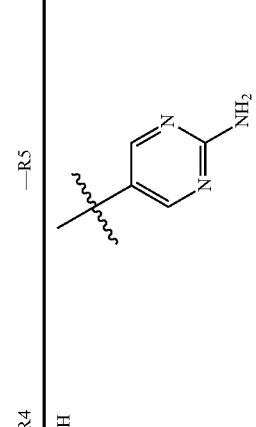 | 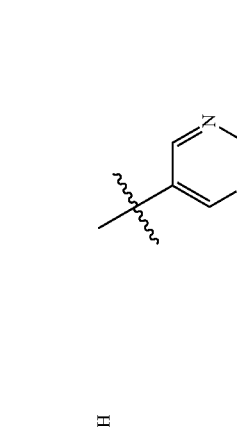 | —H | —H | 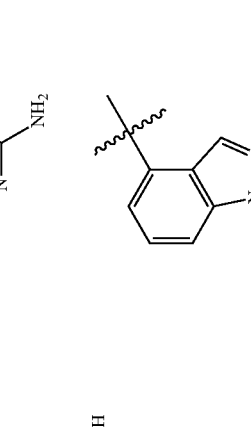 |
| 2-236 | B12 | 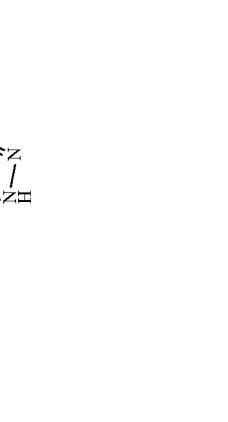 | 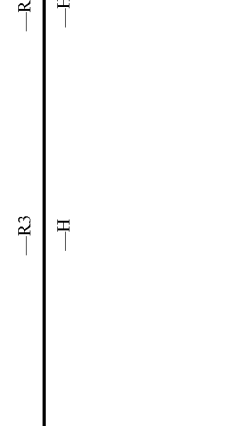 | —H | —H | 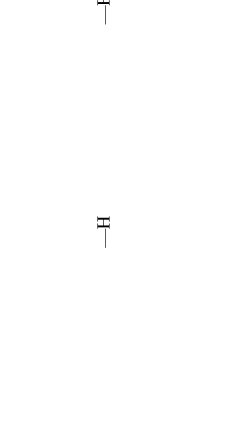 |
| 2-237 | B22 | 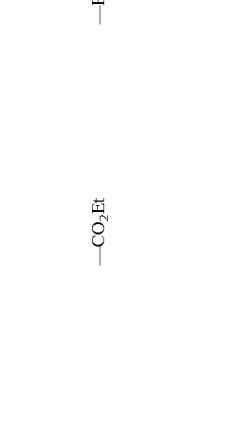 | —Me | —CO$_2$Et | —H |  |

TABLE 3-continued

Final Products prepared in accordance with the procedures described herein

| No. | Exp. | —R1 | —R2 | —R3 | —R4 | —R5 |
|---|---|---|---|---|---|---|
| 2-238 | B23 | morpholine | —Me | —CO₂H | —H | 4-indazolyl |
| 2-239 | B1 | morpholine | —CHO | —H | —H | 4-indazolyl |
| 2-240 | B1 | morpholine | —CH(CH₃)CH₂CO₂Me | —H | —CH₂OH | 4-indazolyl |

TABLE 3-continued

Final Products prepared in accordance with the procedures described herein

| No. | Exp. | —R1 | —R2 | —R3 | —R4 | —R5 |
|---|---|---|---|---|---|---|
| 2-241 | B24 | morpholine | —Me | 1-isobutyryl-1,2,3,6-tetrahydropyridin-4-yl | —H | 1H-indazol-4-yl |
| 2-242 | B1 | morpholine | 2-(4-(methylsulfonyl)piperazin-1-yl)propan-2-yl | —H | —H | 2-aminopyrimidin-5-yl |

TABLE 3-continued

Final Products prepared in accordance with the procedures described herein

| No. | Exp. | —R1 | —R2 | —R3 | —R4 | —R5 |
|---|---|---|---|---|---|---|
| 2-243 | B25 | morpholin-4-yl | —H | —Me | —H | 3-[(4-methylpiperazine-1-carbonyl)]phenyl-NH-C(O)-NH-(4-phenyl) |
| 2-244 | B23 | morpholin-4-yl | —H | —Me | —H | 3-carboxyphenyl-NH-C(O)-NH-(4-phenyl) |

TABLE 3-continued
Final Products prepared in accordance with the procedures described herein
| No. | Exp. | —R1 | —R2 | —R3 | —R4 | —R5 |
|---|---|---|---|---|---|---|
| 2-245 | B26 | 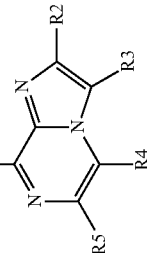 | —H | —Me | —H | 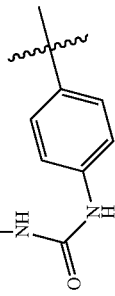 |
| 2-246 | A13 | 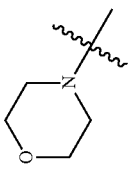 | —CO₂H | —H | —H | 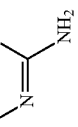 |

Experimental Part

Preparation of the intermediates

Method A1

Preparation of Intermediate I-01

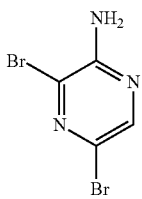

To a mixture of 2-amino pyrazine (50 g, 0.5 mol) in chloroform (1000 ml) cooled to 0° C. was added pyridine (100 ml, 1.21 mol) and bromine (54 ml, 1.05 mmol) dropwise. The mixture was stirred at rt for 16 h, then water was added. The organic phase was extracted, dried (MgSO$_4$), filtered and evaporated to obtain I-01, 48 g (Y: 36%) of a yellow solid which was dried in vacuo.

Preparation of Intermediate I-53

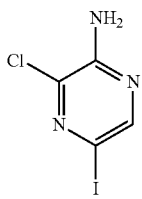

To a mixture of 2-amino-3-chloropyrazine (3.627 g, 28.00 mmol) in acetonitrile (20 mL), N-iodosuccinimide (6.929 g, 30.800 mmol) and trifluoroacetic acid (2.2 mL) were added. The reaction mixture was stirred at rt for 18 h. EtOAc was added and the mixture was washed with Na$_2$S$_2$O$_3$, dried, filtered and evaporated. The residue was purified in by column chromatography (EtOAc:Cyclohexane, 0:100 to 40:60) to render 5.1 g of Intermediate I-53 (71%).

Method A2

Preparation of Intermediate I-02

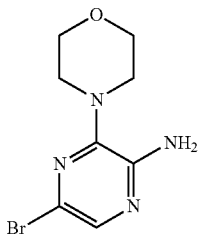 [SMILES: Nc1ncc(Br)nc1N1CCOCC1]

A solution of intermediate I-01(15 g, 59.3 mmol) in morpholine (15 ml, 178 mmol) was heated at 120° C. in a Parr reactor for 48 h. A brown solid appears. The solid was suspended in DCM and washed with NaHCO$_3$ aq. sat (twice). The organic phase was dried (NaSO$_4$), filtered and evaporated to dryness to obtain I-02, 14.8 g of a brown solid (Y: 96%)

Method A3

Preparation of Intermediate I-03

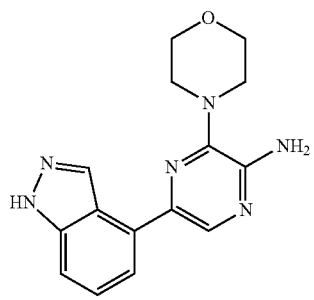 [SMILES: Nc1ncc(-c2cccc3[nH]ncc23)nc1N1CCOCC1]

A mixture of intermediate I-02 (360 mg, 1.35 mmol), indazole-4-boronic acid hydrochloride (600 mg, 2.97 mmol), K$_2$CO$_3$ (2 mL of saturated solution), PdCl$_2$(dppf). DCM (112 mg, 0.135 mmol) in DME (5 mL) was heated under microwave irradiation for 10 min at 130° C. The reaction mixture was filtered through a celite pad, washing with DCM. The filtrate was dried over Na$_2$SO$_4$ and concentrated. The crude was purified by flash column chromatography (Isolute Si II 10 g cartridge) eluting with a gradient of DCM/MeOH (from 100% to 90:10) to yield 250 mg of the intermediate I-03 pure (Y: 62%).

Preparation of Intermediate I-69

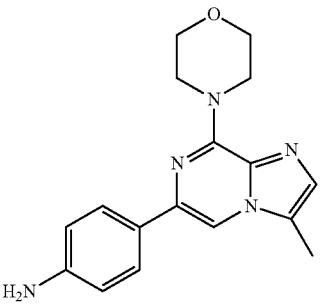 [SMILES: Cc1cnc2c(N3CCOCC3)nc(-c3ccc(N)cc3)cn12]

A mixture of Intermediate I-70 (45 mg, 0.15 mmol), 4-(4,4,5,5-tetramethyl-1,3,2-dioxaborolan-2-yl)aniline (40 mg, 0.18 mmol), PdCl$_2$(dppf) (12 mg, 0.02 mmol) and Na$_2$CO$_3$ (sat aq sol; 0.75 mL) in 1,2-DME (0.75 mL) was heated under microwave irradiation at 130° C. for 1 h. The mixture was diluted with DCM:MeOH, adsorbed on celite and purified by chromatography (Isolute 5 g; MeOH:DCM, 0:100 to 20:809 to give Intermediate I-69 (50 mg, 100%) as a yellow solid.

Method A4

Preparation of Intermediate I-05

Intermediate I-01 (2 g, 7.9 mmol) was solved in 2-chloroacetone (3 ml). The reaction was heated in a sealed tube at 90° C. for 16 h. A precipitate appears. Then Et₂O was added. The precipitate was filtered off as a salt. The resulting solid was suspended in DCM and treated with an aqueous saturated solution of Na₂CO₃. The organic phase was extracted, dried (MgSO₄), filtered and evaporated to obtain the intermediate I-05 (1.2 g of a brown solid, Y: 35%)

Preparation of Intermediate I-28

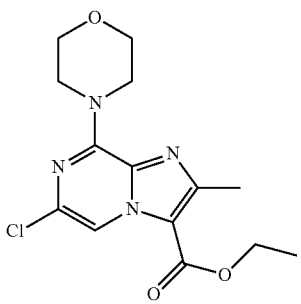 [SMILES: CCOC(=O)c1c(C)nc2c(N3CCOCC3)nc(Cl)cn12]

Intermediate I-02 (1.2 g, 4.7 mmol) and ethyl 2-chloroacetoacetate (2.3 g, 14.2 mmol) were suspended in EtOH (12 mL). The mixture was heated under microwave irradiation for 1 h at 150° C. After cooling down to room temperature, petroleum ether was added and the solid formed was filtered off. The filtrate was evaporated under reduced pressure and the residue was purified by flash chromatography on silica gel (c-Hex/EtAOAc 8:2) to obtain a solid that was washed with petroleum ether to give the desired product I-28 (231 mg, Y: 33%).

Preparation of Intermediate I-35

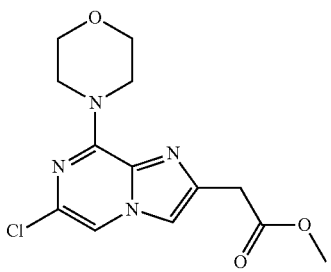 [SMILES: COC(=O)Cc1cn2cc(Cl)nc(N3CCOCC3)c2n1]

Intermediate I-02 (2 g, 7.72 mmol) and methyl 4-chloroacetoacetate (3.56 mL, 30.88 mmol) were heated in two sealed tubes (half of material in each tube) at 90° C. for 2 h. Volatiles were removed under reduced pressure and the residue was purified by flash chromatography on silica gel (c-Hex/EtAOAc 10:0 to 6:4) to obtain a solid that was washed with diethyl ether to render the desired product I-35 (1.17 g, Y: 49%).

Preparation of Intermediate I-57

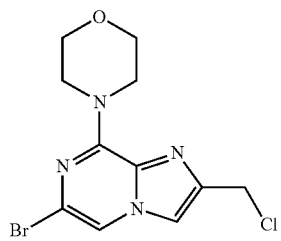 [SMILES: ClCc1cn2cc(Br)nc(N3CCOCC3)c2n1]

A mixture of Intermediate I-02 (8.17 g, 31.52 mmol) and 1,3-dichloroacetone (6.0 g, 47.29 mmol) in 2-propanol (15 mL) was heated in a sealed tube at 55° C. for 2 days. On cooling, the mixture was filtered and rinsed with Et₂O and MeOH. The solid was purified by flash chromatography on silica gel (MeOH:DCM, 5:95) and the product obtained was washed with MeOH and dried to give Intermediate I-57 (3.97 g, 38%).

Method A5

Preparation of Intermediate I-06

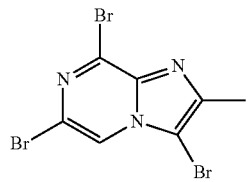

Intermediate I-05 (0.62 g, 2.13 mmol) was dissolved in CHCl₃ (4 mL) and N-bromosuccinimide (455 mg, 2.56 mmol) was added. The reaction mixture was heated under microwave irradiation at 120° C. for 1 h. On cooling, the mixture was adsorbed in silica and purified by Biotage column chromatography (DCM/MeOH from 100% to 95:5) to give intermediate I-06 (720 mg, Y: 91%) as a yellow solid.

Method A6

Preparation of Intermediate I-09

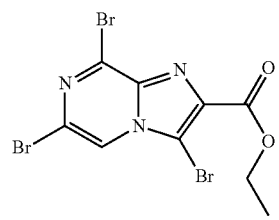 [SMILES: CCOC(=O)c1nc2c(Br)nc(Br)cn2c1Br]

Intermediate I-07 (1.00 g, 2.87 mmol) was dissolved in DCM (28 mL) and N-bromosuccinimide (0.61 g, 3.44 mmol) and trifluoroacetic acid (0.25 mL) were added. The reaction mixture was stirring at rt for 16 h and then heated at 60° C. for 2 h more. The reaction mixture was cooled, and washed with water. The organic phase was dried (Na₂SO₄), filtered and the solvent removed in vacuum. The residue was purified by biotage with a gradient cyclohexane/EtOAc: from 100% to 50:50 The desired fractions were collected to obtained 1.15 g of a white solid as intermediate I-09 (Y: 94%).

Method A7

Preparation of Intermediate I-10

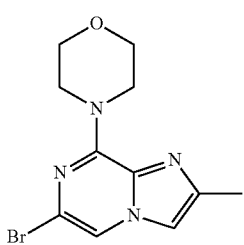 [SMILES: Cc1cn2cc(Br)nc(N3CCOCC3)c2n1]

A mixture of Intermediate I-05 (1.75 g, 6.015 mmol), morpholine (0.526 mL, 6.015 mmol) and DCM (20 mL) was stirred at rt for 16 h. Additional morpholine (0.526 mL, 6.015 mmol) was added and the mixture was stirred at rt for 18 h more. Na₂CO₃ sat. aq. was added. The organic phase was separated, dried (Na₂SO₄), filtered and evaporated till dryness to obtain 1.8 g of intermediate I-10 (Y: quantitative). The resulting product was used in the next step without further purification.

Preparation of Intermediate I-11

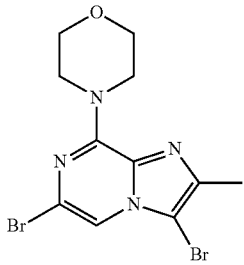 [SMILES: Cc1nc2c(N3CCOCC3)nc(Br)cn2c1Br]

Intermediate I-06 (0.72 g, 1.95 mmol) was dissolved in DCM (6 mL) and morpholine (0.68 mL, 7.79 mmol) was added in one portion. The reaction mixture was stirred at rt for 3 h. The mixture was purified, together with a second batch of the same reaction, by column chromatography (DCM/MeOH from 100% to 50:50) to give the expected product intermediate I-11 (980 mg, Y: 76%) as a clear yellow solid.

Preparation of Intermediate I-48

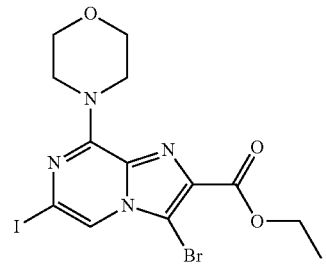 [SMILES: CCOC(=O)c1nc2c(N3CCOCC3)nc(I)cn2c1Br]

To a mixture of Intermediate I-47 (2.25 g, 5.22 mmol) in acetonitrile (20 mL) morpholine (0.59 mL, 6.79 mmol) and N,N-diisopropylethylamine (1.36 mL, 7.84 mmol) were added. The reaction mixture was heated under microwave irradiation at 160° C. for 30 min. On cooling, NH₄Cl was added and the mixture was extracted with DCM. The organic layer was dried (Na₂SO₄), filtered and evaporated. The residue was precipitated with Et₂O and MeOH to render Intermediate I-48 (1.875 g, 75%) as a white solid. The filtrate was evaporated and purified by column chromatography (Cyclohexane:EtOAc, 100:0 to 60:40) to render 620 mg of Intermediate I-48 (24%).

Method A8

Preparation of Intermediate I-13

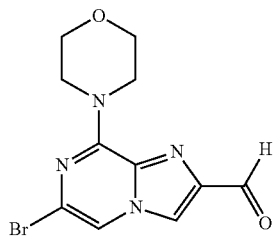 [SMILES: O=Cc1cn2cc(Br)nc(N3CCOCC3)c2n1]

To a solution of intermediate I-12 (2 g, 5.6 mmol) in DCM (50 mL) was added dropwise DIBAL (3.8 mL, 1 M in toluene, 22.75 mmol) at −78° C. stirring at that temperature for 40 min. The reaction was quenched with cold methanol and stirred for 10 min. more. The mixture was poured into a biphasic mixture of saturated NaHCO₃ and DCM and allowed to warm to room temperature with occasional stirring. It was then passed though a Celite bed to remove a gelatinous mass, and the bed was thoroughly washed with DCM. After the organic layer was separated, the aqueous layer was extracted with DCM. The combined organic phase was dried (Na₂SO₄), filtered and concentrated under reduced pressure to obtain a light yellow solid, 1.674 g, Y: 96% as intermediate I-13 which was used in next reaction step without further purification.

Method A9

Preparation of Intermediate I-14

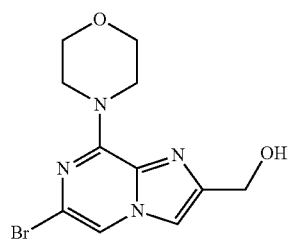 [SMILES: OCc1cn2cc(Br)nc(N3CCOCC3)c2n1]

To a stirred slurry of LiAlH₄ (556 mg, 14.64 mmol) in dry THF was slowly added intermediate I-12 (5.63 mmol) in THF (28 mL) at 0° C. After the addition, the reaction mixture was stirred at room temperature for 2 h and quenched with saturated NH₄Cl/NH₄OH. The mixture was poured into CHCl₃/MeOH (3:1) and it was then passed though a Celite bed to remove a gelatinous mass, and the bed was thoroughly washed with CHCl₃. The organic layer was washed with saturated NaCl. The organic phase was dried (Na₂SO₄), filtered and evaporated under reduced pressure to obtain the expected product I-14 as a light yellow solid (1.02 g, Y: 57% yield) which was used in next reaction step without further purification.

Preparation of Intermediate I-40

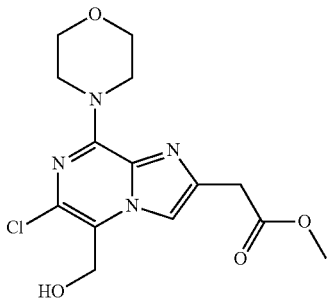 [SMILES: COC(=O)Cc1cn2c(CO)c(Cl)nc(N3CCOCC3)c2n1]

A solution of Intermediate I-39 (1 g, 2.952 mmol) in THF (10 mL) was slowly added to a stirred slurry of NaBH₄ (123 mg, 3.247 mmol) in dry THF (11 mL) at 0° C. The mixture was stirred 2 h at rt. The solvent was removed and the residue was suspended in H₂O and extracted with EtOAc. The organic layer was dried (Na₂SO₄), filtered and evaporated concentrated. The residue was used in the next experiment without further purification.

Preparation of Intermediate I-49

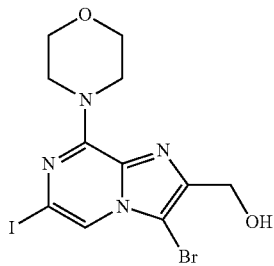 [SMILES: OCc1nc2c(N3CCOCC3)nc(I)cn2c1Br]

To a solution of Intermediate I-48 (1.3 g, 2.7 mmol) in DCM (25 mL) was added diisobutylaluminum hydride (1M in toluene) (2.7 mL, 2.7 mmol) drowise at 0° C. The reaction mixture was stirred at rt for 16 h and more DIBAL (2.7 mL) was added. Stirring was continued at rt for 2 days and another eq. of DIBAL was added (2.7 mL). After 2 days the reaction was quenched with cold MeOH, stirred for 10 min and poured into a biphasic mixture of H₂O/DCM. The suspension was filtered off to render Intermediate I-49 (0.86 g). The organic layer was extracted with DCM, dried, filtered and evaporated to render Intermediate I-49 (320 mg) as a white solid.

Method A10

Preparation of Intermediate I-16

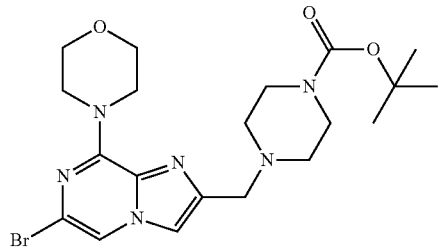 [SMILES: CC(C)(C)OC(=O)N1CCN(Cc2cn3cc(Br)nc(N4CCOCC4)c3n2)CC1]

A mixture of intermediate I-13 (520 mg, 1.67 mmol), 1-boc-piperazine (405 mg, 2.17 mmol) and trimethyl orthoformate (1.83 mL, 16.71 mmol) was stirred in 1,2-dichloroethane (14 mL) for 6 h at room temperature. Then sodium triacetoxyborohydride (425 mg, 2.0 mmol) was added and the reaction mixture was stirred for 48 h at room temperature. The mixture was then quenched with brine and extracted with DCM. The organic phase was dried (Na₂SO₄), filtered and evaporated in vacuo. The residue was purified by silica gel column chromatography in Biotage by eluting it with cyclohexane/ethyl acetate and then with DCM/MeOH to obtain intermediate I-16, 475 mg, Y: 60% as a light yellow solid.

Method A11

Preparation of Intermediate I-17

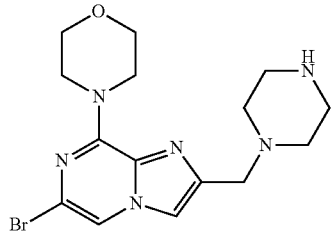 [SMILES: Brc1cn2cc(CN3CCNCC3)nc2c(N2CCOCC2)n1]

Intermediate I-16 (0.380 mg, 0.789 mmol) was dissolved in DCM (10 mL) and 2N HCl (2 mL) was added and the reaction was stirred at rt for 16 h. Because only starting material was observed, the solvent was evaporated and THF 3 mL and 3 mL HCl (2N) were added and the reaction mixture was stirred for 2 h. The solvent was removed in vacuo to obtain intermediate I-17 as a chlorohydrate salt (307 mg, Y: 93%) which was used in the next reaction without further purification.

Method A12

Preparation of Intermediate I-23

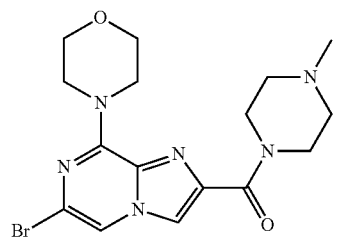 [SMILES: CN1CCN(C(=O)c2cn3cc(Br)nc(N4CCOCC4)c3n2)CC1]

Methylpiperazine (0.282 mmol, 32 μL) and AlMe₃ 2M in hexanes (0.282 mmol, 0.14 mL) in dry DCM (4 mL) was stirred at rt for 15 min. Then intermediate I-12 (100 mg, 0.282 mmol) was added and the mixture was stirred at rt for 3 h and then at 40° C. overnight. The reaction was quenched with sat sol of ammonium chloride and diluted with DCM. The organic phase was dried (Na₂SO₄), filtered and evaporated to afford a residue which was triturated with Et₂O-DCM precipitating an off white solid as an impurity. The filtrate was purified by flash chromatography (Biotage Hex-EtOAc from 100% to 70:30 and then DCM-MeOH/NH₃ 7N 80:20 to obtain 67 mg (Y: 48%) of required product as intermediate I-23.

Method A13

Preparation of Intermediate I-29

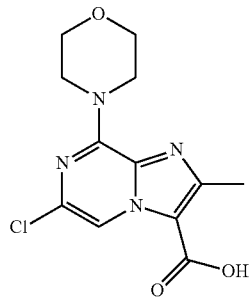 [SMILES: Cc1nc2c(N3CCOCC3)nc(Cl)cn2c1C(=O)O]

2N NaOH (0.85 mL) was added to a stirred mixture of intermediate I-28 in MeOH. The reaction was stirred at 50° C. for 1.5 h and at reflux for 20 min. The solvent was evaporated and water was added and the pH was adjusted to 4 by addition of AcOH. The mixture was diluted with EtOAc (until a clear solution was obtained (ca 250 mL). The layers were separated and the aqueous layer was extracted twice with EtOAc. The organic layer was dried and evaporated. The residue was azeotropically dried with toluene to give 261 mg (Y: 100%) of desired product I-29 which was used in next reaction step without further purification.

Method A14

Preparation of Intermediate I-27

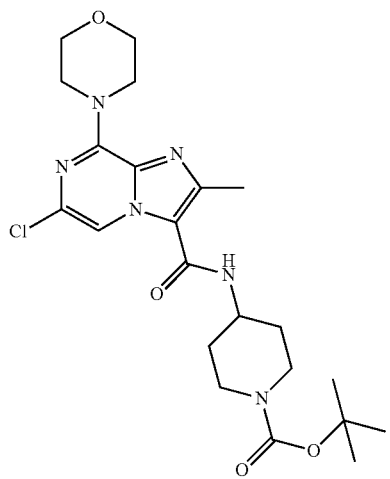 [SMILES: Cc1nc2c(N3CCOCC3)nc(Cl)cn2c1C(=O)NC1CCN(C(=O)OC(C)(C)C)CC1]

4-Amine-1-BOC piperidine was added to a stirred mixture of intermediate I-29, DIPEA and HATU in DMF. The reaction was stirred at rt for 4 h. The reaction mixture was directly chromatographed on silica gel (biotage c-Hex/EtOAc 10 to 100% EtOAc) to obtain the desired product (233 mg, Y: for two steps: 69%).

Method A15

Preparation of Intermediate I-30

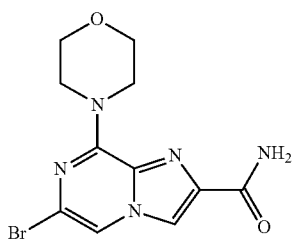 [SMILES: NC(=O)c1cn2cc(Br)nc(N3CCOCC3)c2n1]

Intermediate I-12 (240 mg) in a seal tube, was suspended in a solution of MeOH/NH₃ 7N. The reaction mixture was heated at 100° C. for 16 h. The solvent was evaporated to dryness and the residue was washed with MeOH and Et₂O. the resulting yellow solid was dried in vacuo to obtain 200 mg of desired product I-30. Alternatively, a precipitate may appear, which may be filtered off to obtain the desired product I-30.

Method A16

Preparation of Intermediate I-44

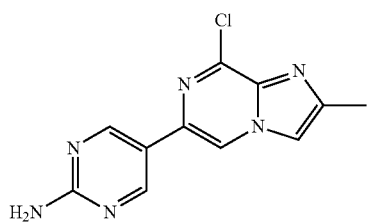 [SMILES: Cc1cn2cc(-c3cnc(N)nc3)nc(Cl)c2n1]

A mixture of Intermediate I-43 (0.15 g, 0.51 mmol), 2-aminopyrimidine-5-boronic acid, pinacol ester (136 mg, 0.613 mmol) and PdCl₂(dppf) (42 mg, 0.051 mmol) and sat. sol. Na₂CO₃ (1.96 mL) in 1,2-DME (1.96 mL) was stirred at r.t. for 1 h 30 min. DCM was added and the mixture was washed with H₂O and sat. NaCl. The organics were dried (Na₂SO₄), filtered and evaporated. The residue was purified by column chromatography (DCM:MeOH, 99:1 to 90:10) to render Intermediate I-44 (10 mg, 8%) as a beige solid.

Method A18

Preparation of Intermediate I-39

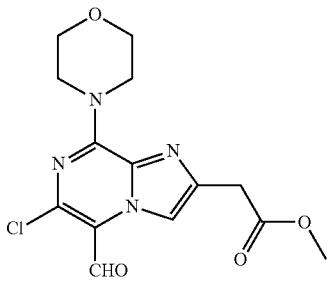 [SMILES: COC(=O)Cc1cn2c(C=O)c(Cl)nc(N3CCOCC3)c2n1]

To a solution of Intermediate I-35 (3.76 g, 12.11 mmol) in DMF (120 mL) was added POCl₃ (3.38 mL, 36.34 mmol) at −20° C. The mixture was stirred at rt overnight under N₂ and diluted with H₂O/ice. The white solid was filtered off and dried to render 2.95 g (63%) of Intermediate I-39. It was used in the next experiment without further purification.

Method A20

Preparation of Intermediate I-50

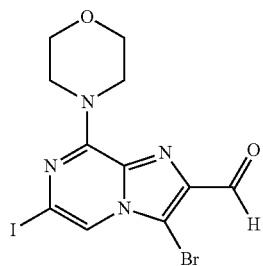 [SMILES: O=Cc1nc2c(N3CCOCC3)nc(I)cn2c1Br]

To a solution of Intermediate I-49 (1.18 g, 2.7 mmol) in CHCl₃ (54 mL) activated MnO₂ (4.0 g, 45.93 mmol) was added. The reaction mixture was refluxed for 8 h. On cooling, the mixture was filtered through celite. The filtrate was evaporated to render Intermediate I-50 (0.67 g). It was used in the next reaction without further purification.

Method A21

Preparation of Intermediate I-58

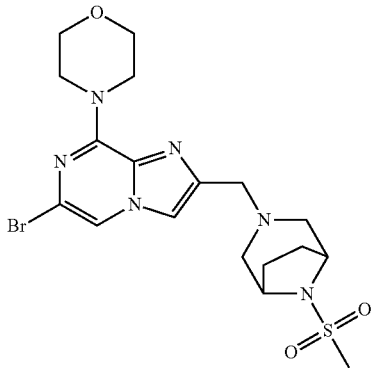 [SMILES: CS(=O)(=O)N1C2CCC1CN(Cc1cn3cc(Br)nc(N4CCOCC4)c3n1)C2]

To a suspension of Intermediate I-57 (0.232 g, 0.7 mmol) and K₂CO₃ (0.193 g, 1.4 mmol) in Acetonitrile (20 mL) was added 8-methanesulfonyl-3,8-diaza-bicyclo [3.2.1]octane ((0.133 g, 0.7 mmol). The reaction mixture was refluxed for 24 h and concentrated. The residue was suspended in DCM and washed with brine. The organic layer was dried, filtered and evaporated. The residue was triturated from MeOH to give Intermediate I-58 (0.189 g, 56%) as a white solid.

Method A22

Preparation of Intermediate I-60

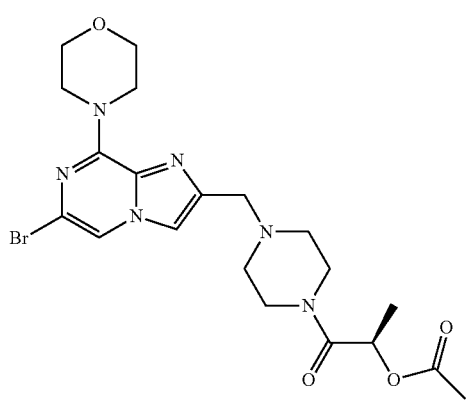 [SMILES: CC(=O)O[C@H](C)C(=O)N1CCN(Cc2cn3cc(Br)nc(N4CCOCC4)c3n2)CC1]

To a solution of Intermediate I-17 (100 mg, 0.297 mmol), BOP (158 mg, 0.356 mmol) and (s)-(−)-2-acetoxypropionic acid (41 mg, 0.356 mmol) in CH₂Cl₂ (3 mL), Et₃N (0.083 mL, 0.594 mmol) was added. The mixture was stirred at RT for 2 days. CH₂Cl₂ was added and the mixture was washed with water. The organic layer was dried over Na₂SO₄, filtered and evaporated. The residue was purified by column chromatography (Biotage, CH₂Cl₂:MeOH, 100:0 to 60:40) to give Intermediate I-60 (130 mg, 88%) as a colourless oil.

Method A23

Preparation of Intermediate I-61

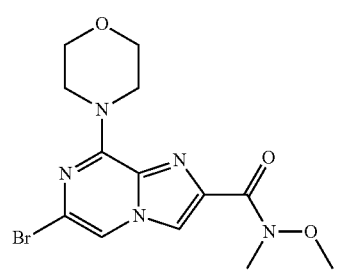 [SMILES: CON(C)C(=O)c1cn2cc(Br)nc(N3CCOCC3)c2n1]

A 2M solution of trimethylaluminum in hexanes (5.5 mL, 11.02 mmol) was added to a mixture of N,O-dimethylhydroxylamine hydrochloride (1.075 g, 11.02 mmol) in DCM (10 mL) and the reaction was stirred at rt for 40 min. A solution of Intermediate I-12 (0.783 g, 2.20 mmol) in DCM (16 mL) was added and the reaction mixture was stirred at 40° C. for 2 h. On cooling, the mixture was carefully quenched with 1N HCl and diluted with DCM. After 30 min stirring layers were separated and the aqueous layer was Method A24

Preparation of Intermediate I-62

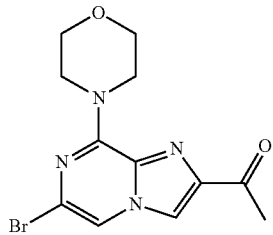 [SMILES: CC(=O)c1cn2cc(Br)nc(N3CCOCC3)c2n1]

To a mixture of Intermediate I-61 (545 mg, 1.47 mmol) in THF (15 mL) was added MeMgBr (2.2 mL, 2.2 mmol) at 0° C. The reaction was stirred at 0° C. for 1 h. Additional MeMgBr (1.1 mL, 1.1 mmol) was added and the reaction was stirred at 0° C. for 1 h. The mixture was quenched with sat NH₄Cl, and extracted with EtOAc (×3). The combined organic layers were dried, filtered and evaporated to give Intermediate I-62 (458 mg, 96%).

Method A5

Preparation of Intermediate I-63

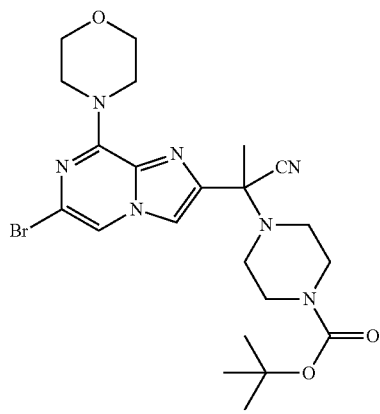 [SMILES: CC(C)(C)OC(=O)N1CCN(C(C)(C#N)c2cn3cc(Br)nc(N4CCOCC4)c3n2)CC1]

To a mixture of Intermediate I-62 (0.1 g, 0.308 mmol) and 1-Boc-piperazine (0.115 g, 0.615 mmol) in DCM (4 mL) was added Ti(iPrO)₄ (0.182 mL, 0.615 mmol). The reaction was stirred at reflux for 2 h. Et₂AlCN (0.62 mL, 0.615 mmol) was added and the reaction mixture was stirred at reflux for 5 h. On cooling, the mixture was quenched with sat NaHCO₃ and extracted with EtOAc (×3). The combined organic layers were washed with brine, dried, filtered and evaporated. The residue was purified by column chromatography (biotage, cHex/EtOAc 10:90 to 0:100) to give Intermediate I-63 (100 mg, 63%).

Method A26

Preparation of Intermediate I-64

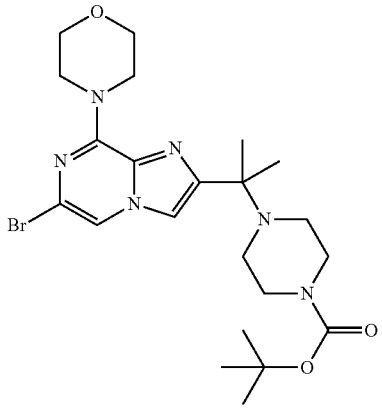 [SMILES: CC(C)(C)OC(=O)N1CCN(C(C)(C)c2cn3cc(Br)nc(N4CCOCC4)c3n2)CC1]

To a stirred solution of MeMgBr (1 mL, 0.96 mmol) was added a solution of Intermediate I-63 (50 mg, 0.096 mmol) in THF (1.5 mL) at 0° C. The reaction was stirred at 0° C. for 4 h and the mixture was poured onto ice cold sat NH₄Cl. The mixture was extracted with EtOAc and the combined organic layers were dried, filtered and evaporated. The residue was purified by column chromatography (biotage, cHex/EtOAc 10:90 to 0:100) to give Intermediate I-64 (22 mg, 45%).

Method A27

Preparation of Intermediate I-68

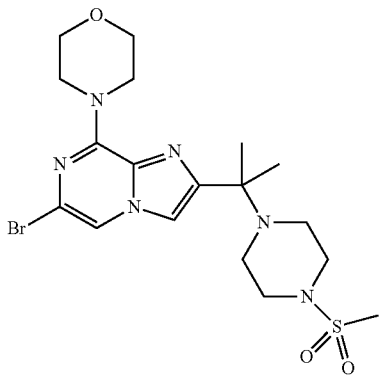 [SMILES: CC(C)(c1cn2cc(Br)nc(N3CCOCC3)c2n1)N1CCN(S(C)(=O)=O)CC1]

MsCl (0.046 mL, 0.589 mmol) was added to solution of Intermediate I-67 (0.175 g, 0.393 mmol) and TEA (0.274 mL, 1.96 mmol) in DCM (4 mL) at 0° C. The reaction mixture was stirred at rt for 3 h and poured onto sat NaHCO₃. The mixture was extracted with DCM and the combined organic layers were dried, filtered and evaporated. The residue was purified on silica gel (DCM:MeOH, 90:10) to afford Intermediate I-68 (133 mg, 70%).

Method A28

Preparation of Intermediate I-70

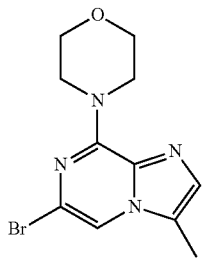 [SMILES: Cc1cnc2c(N3CCOCC3)nc(Br)cn12]

To a solution of Intermediate I-02 (150 mg, 0.58 mmol) in Toluene (6.8 mL), 2-chloro-1,1-dimethoxypropane (0.758 mL, 5.8 mmol) and p-toluenesulfonic acid (18 mg, 0.09 mmol) were added. The reaction mixture was refluxed for 24 h and additional amounts of 2-chloro-1,1-dimethoxypropane (10 eq) and p-toluenesulfonic acid (0.16 eq) were added. The reaction mixture was refluxed for 15 h and the solvent was removed. The residue was purified by column chromatography (Isolute 10 g; AcOEt-cyclohexane 0:100 to 50:50) to give the Intermediate I-70 (55 mg, 32%) as a beige solid.

EXAMPLE B1

Preparation of Final Product 2-01

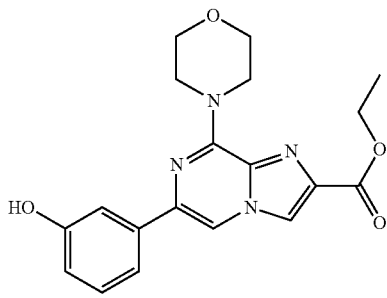 [SMILES: CCOC(=O)c1cn2cc(-c3cccc(O)c3)nc(N3CCOCC3)c2n1]

A mixture of intermediate I-12 (100 mg, 0.282 mmol), 3-hydroxyphenylboronic acid (85 mg, 0.685 mmol), and PdCl$_2$(dppf)·DCM (23 mg. 0.028 mmol) in DME (1.2 mL) was added a saturated aqueous solution of sodium carbonate (1 mL). The mixture was heated to 130° C. under microwave irradiation for 3 min. The reaction mixture was cooled, diluted with chloroform, washed with brine. The organic phase was dried (Na$_2$SO$_4$), filtered and the solvent removed in vacuo. The residue was purified by biotage chromatography with a gradient cyclohexane/EtOAc: from 100% to 50:50. The desired fractions were collected and the solvent evaporated. The resulting solid was crystallised with MeOH to obtain a white solid as final product 2-01 (44 mg, Y: 68% yield).

Preparation of Final Product 2-10

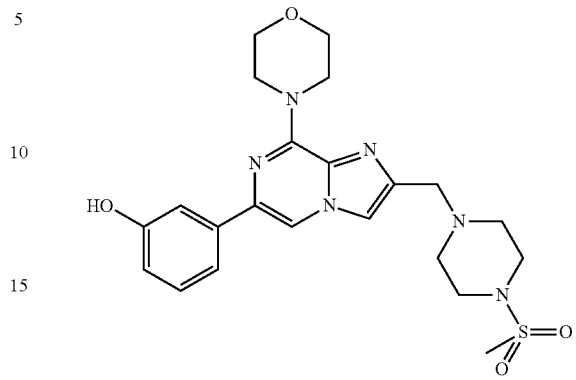

A mixture of intermediate I-18 (200 mg, 0.435 mmol), 3-hydroxyphenylboronic acid (132 mg, 0.985 mmol), and PdCl$_2$(dppf).DCM (36 mg. 0.044 mmol) in DME (1.8 mL) was added an aqueous saturated solution of potassium carbonate (1 mL). The mixture was heated to 130° C. under microwave irradiation for 3 min. The reaction mixture was cooled, diluted with chloroform, washed with brine. The organic phase was dried (Na$_2$SO$_4$), filtered and evaporated. The residue was purified by biotage chromatography and eluted with a gradient DCM/MeOH: from 100% to 50:50. The desired fractions were collected and the resulting residue was purified again with EtOAc and then EtOAc/MeOH 20:1. The desired fractions were collected to obtain a white solid, 27 mg, Y: 13%, as final product 2-10.

Preparation of Final Product 2-11

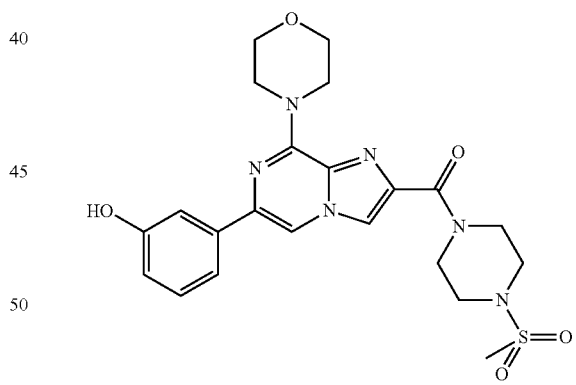

Intermediate I-24 (165 mg, 0.349 mmol), 3-hydroxyphenylboronic acid (0.523 mmol, 72 mg) and PdCl$_2$(dppf).DCM (0.035 mmol, 29 mg) were suspended in a saturated solution of sodium carbonate (1.8 mL) and 1,2-DME (1.8 mL). The mixture was heated under microwave irradiation at 130° C. for 10 min. The mixture was diluted with DCM and washed with water. The organic layer was dried (Na$_2$SO$_4$), filtered and evaporated. The resulting residue was purified by Biotage chromatography (DCM-EtOAc from 50:50 to 100% of EtOAc) to afford a product still impure which was repurified using DCM-MeOH 95:5. The resulting oil was precipitated with DCM-MeOH-Et$_2$O (approx. 10:1:5) to give the desired product 2-11 (63 mg, Y: 36%).

Preparation of Final Product 2-13

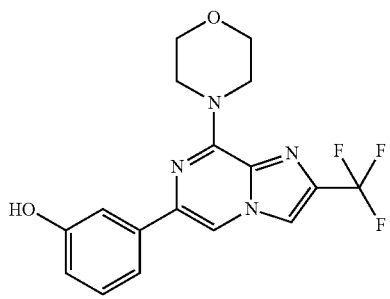 [SMILES: Oc1cccc(-c2cn3cc(C(F)(F)F)nc3c(N3CCOCC3)n2)c1]

A mixture of intermediate I-26 (225 mg, 0.641 mmol), 3-hydroxyphenylboronic acid (194 mg, 1.410 mmol), and PdCl$_2$(dppf).DCM (53 mg, 0.064 mmol) in DME (2.8 mL) was added a saturated aqueous solution of potassium carbonate (0.5 mL). The mixture was heated to 130° C. under microwave irradiation for 3 min. The reaction mixture was cooled, diluted with DCM, washed with brine. The organic phase was dried (Na$_2$SO$_4$), filtered and the solvent removed in vacuum. The resulting residue was purified by biotage chromatography and eluted with a gradient EtOAc/MeOH: from 100% to 50:50. The desired fractions were collected to yield a yellow solid which was crystallised in MeOH to obtain the desired product 2-13 (150 mg, Y: 64%).

Preparation of Final Product 2-14

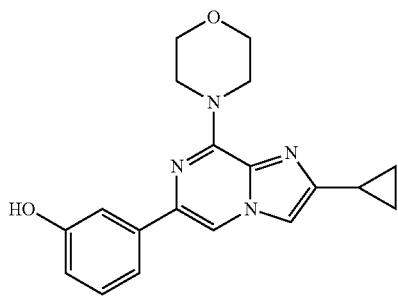 [SMILES: Oc1cccc(-c2cn3cc(C4CC4)nc3c(N3CCOCC3)n2)c1]

Intermediate I-15 (210 mg, 0.650 mmol), 3-hydroxyphenylboronic acid (0.975 mmol, 134 mg) and PdCl$_2$(dppf).DCM (0.065 mmol, 54 mg) were suspended in saturated solution of sodium carbonate (2.6 mL) and 1,2-DME (2.6 mL). The mixture was heated under microwave irradiation at 130° C. for 10 min. The mixture was diluted with DCM and washed with water. The organic layer was dried (Na$_2$SO$_4$), filtered and the solvent was evaporated in vacuo. The resulting residue was purified by flash chromatography (DCM-EtOAc from 100% to 40:60) to afford the desired product 2-14 (69 mg, Y: 31%) as a white solid.

Preparation of Final Product 2-15

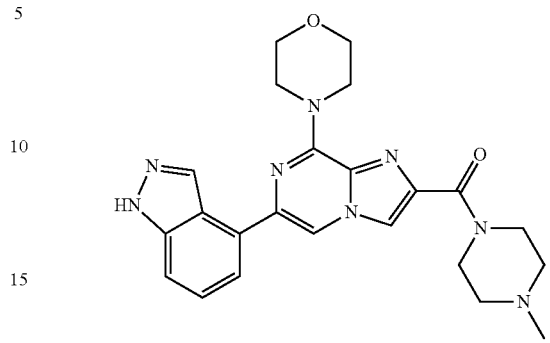

Intermediate I-23 (50 mg, 0.122 mmol), indazole-4-boronic acid hydrochloride (0.183 mol, 36 mg) and PdCl$_2$(dppf).DCM (0.012 mmol, 10 mg) were suspended in a saturated solution of sodium carbonate (0.6 mL) and 1,2-DME (0.6 mL). The mixture was heated under microwave irradiation at 130° C. for 10 min. The mixture was diluted with DCM and washed with brine. The organic layer was dried (Na$_2$SO$_4$), filtered and the solvent was evaporated. The resulting residue was purified by flash chromatography (DCM-MeOH/NH$_3$ 7N from 100% to 90:10). The desired fractions were collected to obtain final product 2-15 (48 mg, Y: 88%) as a white solid.

Preparation of Final Product 2-16

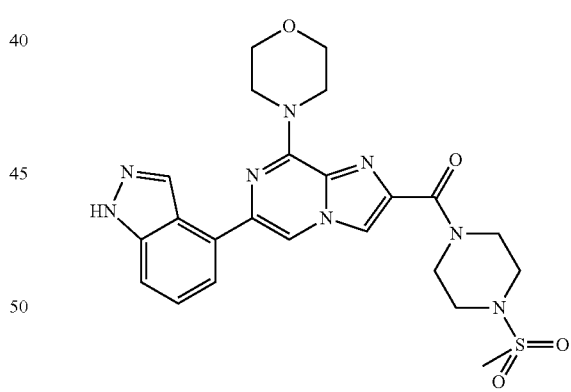

Intermediate I-24 (55 mg, 0.116 mmol), indazole-4-boronic acid hydrochloride (0.174 mmol, 35 mg) and PdCl$_2$(dppf).DCM (0.012 mmol, 10 mg) were suspended in a saturated solution of sodium carbonate (0.6 mL) and 1,2-DME (0.6 mL). The mixture was heated under microwave irradiation at 130° C. for 10 min. The mixture was diluted with DCM and washed with water. The organic layer was dried (Na$_2$SO$_4$), filtered and the solvent evaporated in vacuo. The resulting residue was purified by flash chromatography (EtOAc-MeOH from 100% to 98:2) to obtain the desired final product 2-16 as a white solid (32 mg, Y: 54%).

Preparation of Final Product 2-17

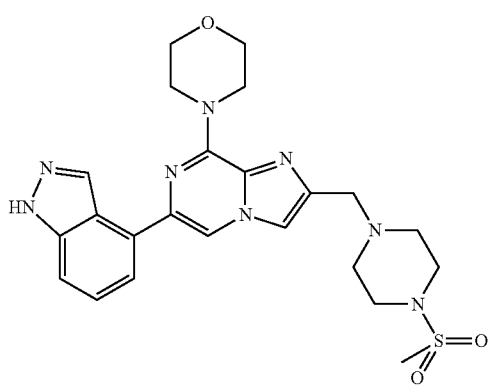 [SMILES: CS(=O)(=O)N1CCN(Cc2cn3cc(-c4cccc5[nH]ncc45)nc(N4CCOCC4)c3n2)CC1]

A mixture of intermediate I-18 (160 mg, 0.348 mmol), PdCl$_2$(dppf).DCM (cat. amount), a saturated solution of K$_2$CO$_3$ (0.5 mL), indazole-4-boronic acid hydrochloride (150 mg, 0.766 mmol), in DME (3.5 mL) was heated under microwave irradiation at 130° C. for 10 min. The mixture was diluted with DCM (30 mL), washed with brine (40 mL). The organic phase was dried (Na$_2$SO$_4$), filtered and concentrated. The crude was purified by Biotage flash column chromatography eluting with a gradient of EtOAc/MeOH (from 100% to 60:40), the resulting solid was triturated with MeOH and filtered to obtain the desired product 2-17 (43 mg) as a white solid.

Preparation of Final Product 2-18

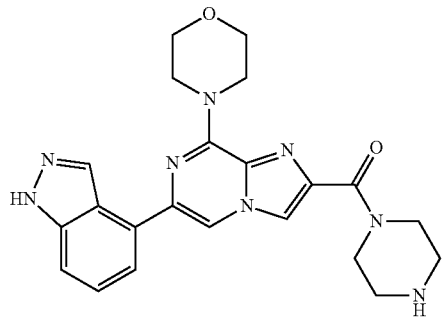 [SMILES: O=C(c1cn2cc(-c3cccc4[nH]ncc34)nc(N3CCOCC3)c2n1)N1CCNCC1]

Intermediate I-25 (150 mg, 0.303 mmol), indazole-4-boronic acid hydrochloride (1.5 equiv, 0.454 mmol, 90 mg) and PdCl$_2$(dppf)$_2$. DCM (0.1 equiv, 0.03 mmol, 25 mg) were suspended in sat sol of sodium carbonate (1.5 mL) and 1,2-DME (1.5 mL). The mixture was heated under microwave irradiation at 130° C. for 10 min. The mixture was diluted with DCM and washed with water. The organic layer was dried over sodium sulfate to yield the crude product which was purified by flash chromatography (EtOAc-MeOH 0-5%) to afford the required (120 mg as yellow solid, 75%). This product (120 mg, 0.225 mmol) was suspended in dry methanol (2.25 mL) and AmberlystR(5) (400 mg) was added. The mixture was slowly stirred at rt for 48 h. The resin was washed with MeOH, and then with MeOH—NH$_3$ 7N. This phase was collected and evaporated to obtain final product 2-18 as a syrup (83 mg, Y: 85%).

Preparation of Final Product 2-19

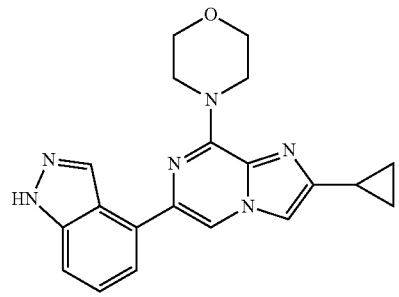 [SMILES: c1cc(-c2cn3cc(C4CC4)nc3c(N3CCOCC3)n2)c2cn[nH]c2c1]

Intermediate I-15 (140 mg, 0.433 mmol), 4-indazoleboronic acid (1.5 equiv, 0.650 mmol, 129 mg) and PdCl$_2$(dppf).DCM (0.043 mmol, 36 mg) were suspended in a saturated solution of sodium carbonate (2 mL) and 1,2-DME (2 mL). The mixture was heated under microwave irradiation at 130° C. for 10 min. The mixture was diluted with DCM and washed with water. The organic layer was dried (Na$_2$SO$_4$), filtered and evaporated. The residue was purified by flash chromatography (DCM-EtOAc from 80:20 to 100% on EtOAc) and then by HPLC to afford final product 2-19 (40 mg, Y: 26%).

Preparation of Final Product 2-20

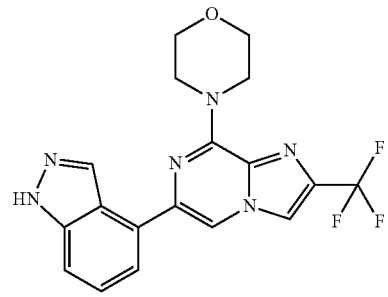 [SMILES: FC(F)(F)c1cn2cc(-c3cccc4[nH]ncc34)nc(N3CCOCC3)c2n1]

A reaction mixture of intermediate I-26 (140 mg, 0.4 mmol), indazole-4-boronic acid hydrochloride (175 mg, 0.87 mmol), K$_2$CO$_3$ (300 mg), PdCl$_2$(dppf).DCM (cat amount) in DME (3 mL) and water (1 mL), was heated under microwave irradiation at 130° C. for 10 min. The dark reaction mixture was diluted with DCM (25 mL), washed with saturated solution of NaHCO$_3$ (2×30 mL) and brine (30 mL). The organic phase was dried (Na$_2$SO$_4$), filtered and concentrated. The resulting residue was purified by flash column chromatography eluting with a gradient system of DCM/MeOH (from 100% to 97:3). The desired fractions were collected and precipitated with DCM/cyclohexane, to obtain the final product 2-20 (40 mg, Y: 26%).

Preparation of Final Product 2-23

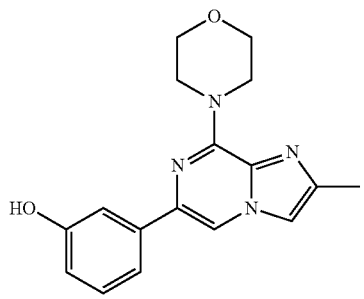 [SMILES: Cc1cn2cc(-c3cccc(O)c3)nc(N3CCOCC3)c2n1]

A mixture of intermediate I-10 (100 mg, 0.337 mmol), 3-hydroxyphenylboronic acid (0.102 g, 0.740 mmol), and PdCl$_2$(dppf).DCM (28 mg, 0.034 mmol) in DME (1.463 mL) was added an aqueous saturated solution of potassium carbonate (0.5 mL). The mixture was heated to 130° C. under microwave irradiation for 10 min. The reaction mixture was cooled, diluted with DCM, washed with brine. The organic phase was dried (Na$_2$SO$_4$), filtered and the solvent removed in vacuum. The residue was purified by biotage chromatography and eluted with a gradient EtOAc/MeOH from 100% to 50:50. The desired fractions were collected and the residue was crystallised in DCM to obtain the desired product 2-23 (44 mg, Y: 42%).

Preparation of Final Product 2-24

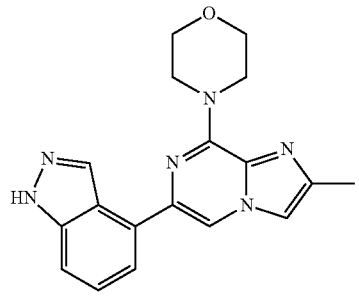 [SMILES: Cc1cn2cc(-c3cccc4[nH]ncc34)nc(N3CCOCC3)c2n1]

A mixture of intermediate I-10 (700 mg, 2.356 mmol), indazole-4-boronic acid hydrochloride (701 mg, 3.534 mmol) and PdCl$_2$(dppf).DCM (190 mg. 0.235 mmol) in DME (11 mL) was added a saturated aqueous solution of potassium carbonate (11 mL). The mixture was heated to 130° C. in the microwave for 0.5 h. The reaction mixture was diluted with EtOAc and washed with water. The organic phase was separated, dried (Na$_2$SO$_4$), filtered and evaporated to give a brown oil. This residue was purified column chromatography (hexane/EtOAc mixtures) to give the desired product 2-24 as green foam (456 mg, 58% yield).

Preparation of Final Product 2-27

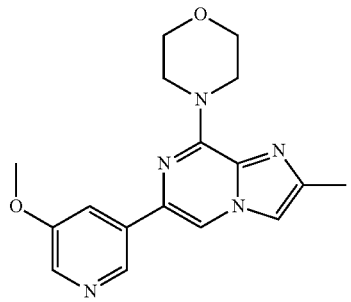 [SMILES: COc1cncc(-c2cn3cc(C)nc3c(N3CCOCC3)n2)c1]

A mixture of intermediate I-10 (200 mg, 0.673 mmol), 3-methoxypyridine-5-boronic acid pinacol ester (348 mg, 1.481 mmol), and PdCl$_2$(dppf).DCM (56 mg. 0.067 mmol) in DME (2.9 mL) was added a saturated solution of sodium carbonate (1 mL). The mixture was heated to 130° C. under microwave irradiation for 10 min. The reaction mixture was cooled, diluted with DCM, washed with brine. The organic phase was dried (Na$_2$SO$_4$), filtered and the solvent removed in vacuum. The residue was purified by biotage chromatography twice and eluted with a gradient EtOAc/MeOH from 100% to 50:50. The desired fractions were collected to obtain 120 mg of the desired product 2-27 as a yellow solid (Y: 55%).

Preparation of Final Product 2-42

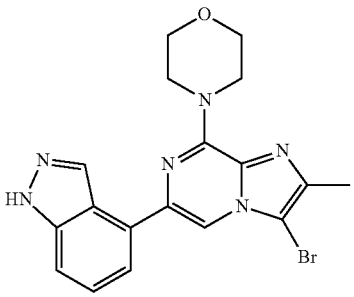 [SMILES: Cc1nc2c(N3CCOCC3)nc(-c3cccc4[nH]ncc34)cn2c1Br]

Intermediate I-11 (1.36 g, 3.62 mmol) was suspended in DME (5 mL) and indazole-4-boronic acid.HCl (0.86 g, 4.34 mmol), PdCl$_2$(dppf).DCM (300 mg, 0.36 mmol), K$_2$CO$_3$ (1.5 g, 10.85 mmol) and H$_2$O (2.5 mL) were added. The reaction mixture was heated under microwave irradiation at 130° C. for 30 min. On cooling, the mixture was evaporated and the residue was purified by column chromatography (DCM/MeOH from 100% to 98:2) to give the expected product 2-42 (230 mg, Y: 15%) as a yellow solid.

Preparation of Final Product 2-71

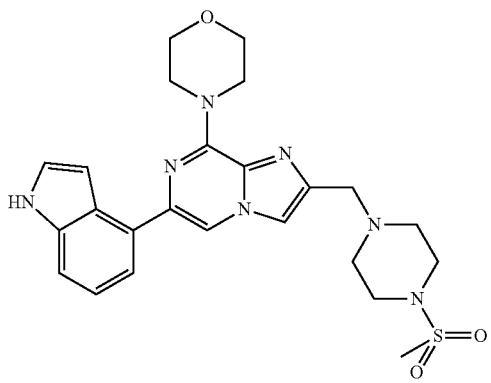 [SMILES: CS(=O)(=O)N1CCN(Cc2cn3cc(-c4cccc5[nH]ccc45)nc(N4CCOCC4)c3n2)CC1]

A mixture of intermediate I-18 (100 mg, 0.218 mmol), PdCl$_2$(dppf).DCM (cat. amount), a saturated solution of K$_2$CO$_3$ (1 mL), indol-4-boronic acid hydrochloride (53 mg, 0.327 mmol), in DME (1 mL) was heated under microwave irradiation at 130° C. for 10 min. The mixture was diluted with DCM (30 mL), washed with brine (40 mL). The organic phase was dried (Na$_2$SO$_4$), filtered and concentrated. The crude was purified by Biotage flash column chromatography eluting with a gradient of DCM/MeOH (from 100% to 50:50) to obtain the desired product 2-71 (39 mg) as a white solid.

Preparation of Final Product 2-70

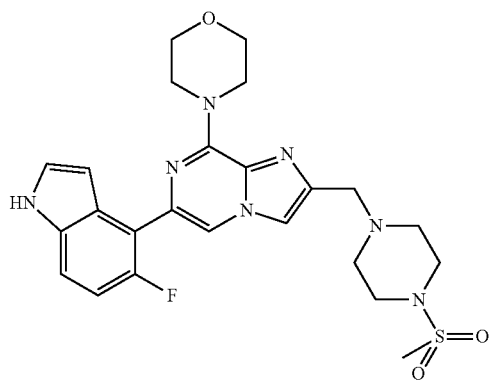 [SMILES: CS(=O)(=O)N1CCN(Cc2cn3cc(-c4c(F)ccc5[nH]ccc45)nc(N4CCOCC4)c3n2)CC1]

A mixture of intermediate I-18 (100 mg, 0.218 mmol), PdCl$_2$(dppf).DCM (cat. amount), a saturated solution of K$_2$CO$_3$ (0.5 mL), 5-fluoro-4-(4,4,5,5-tetramethyl-1,3,2-dioxaborolan-2-yl)-1-tert-butyldimethylsilyl-indole (98 mg, 0.26 mmol, CAS: 1072009-08-5), in DME (1 mL) was heated under microwave irradiation at 130° C. for 1 h. The organic phase was concentrated. The crude was purified by Biotage flash column chromatography eluting with a gradient of DCM/MeOH (from 100% to 90:10) to obtain the desired product 2-70 (39 mg) as a white solid.

Preparation of Final Product 2-35

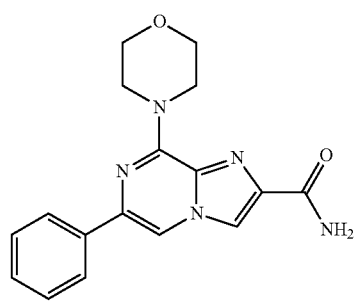 [SMILES: NC(=O)c1cn2cc(-c3ccccc3)nc(N3CCOCC3)c2n1]

Intermediate I-30 (50 mg, 0.15 mmol) was dissolved in DME (1 mL) and phenylboronic acid (22 mg, 0.18 mmol), K$_2$CO$_3$ (64 mg, 0.46 mmol), PdCl$_2$(dppf)-DCM (13 mg, 15 umol) and H$_2$O (0.5 mL) were added. The mixture was heated under microwave irradiation at 130° C. for 1 h. On cooling, the mixture was purified by column chromatography (Biotage, 25-S, 5% to 10% MeOH in DCM), and the product obtained was precipitated with Et$_2$O and filtered to give the expected product 2-35 (45 mg, Y: 91%) as a white solid.

Preparation of Final Product 2-63

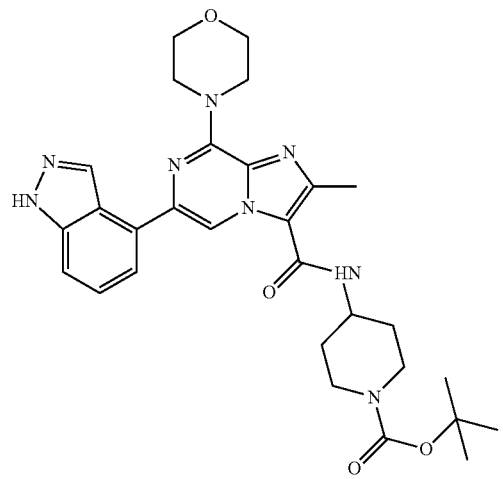 [SMILES: Cc1nc2c(N3CCOCC3)nc(-c3cccc4[nH]ncc34)cn2c1C(=O)NC1CCN(C(=O)OC(C)(C)C)CC1]

PdCl$_2$(dppf) was added to a degassed mixture of intermediate I-27 (100 mg, 0.21 mmol), indazol 4-boronic acid hydrochloride (0.091 g, 0.43 mmol) and an aqueous saturated solution of Na$_2$CO$_3$ (0.25 mL) in DME (1 mL). The vial was sealed and heated at 130° C. under microwaves for 10 min. The mixture was diluted with EtOAc, washed with water, brine, dried and evaporated. The residue was purified by Biotage chromatography in DCM/MeOH 2 to 10% MeOH) to obtain 52 mg of desired compound 2-63.

EXAMPLE B2

Preparation of Final Product 2-21

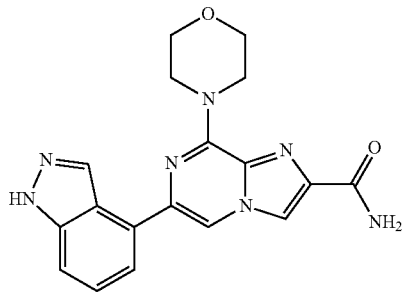 [SMILES: NC(=O)c1cn2cc(-c3cccc4[nH]ncc34)nc(N3CCOCC3)c2n1]

A suspension of final compound 2-52 (160 mg, 0.5 mmol) in MeOH/NH$_3$ 7N was heated in a sealed tube at 90° C. for 16 h. A precipitate appears which was filtered off to obtain 75 mg of the desired product 2-21 as a brown solid (Y: 41%)

Preparation of Final Product 2-77

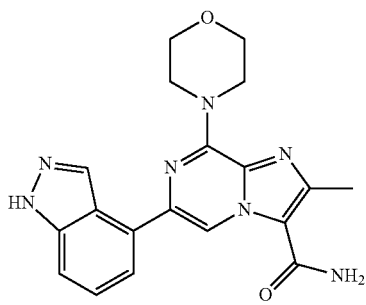 [SMILES: Cc1nc2c(N3CCOCC3)nc(-c3cccc4[nH]ncc34)cn2c1C(N)=O]

To a mixture of intermediate I-32 (70 mg, 0.185 mmol) with dry DMF (3 drops) in benzene (2 mL) was added oxalyl chloride (2 equiv, 0.370 mmol, 31 uL). The mixture was stirred at rt for 3 h, then same amount of reagents was added and stirring continued for 1 h. No reaction observed so volatiles were removed under reduced pressure and the residue was dissolved in dioxane (2 mL) and NH3 in dioxane 0.5N (2 mL) was added. The mixture was stirred at rt overnight and solvent was evaporated under vacuum. The residue was purified by preparative HPLC affording 3 mg of final product 2-77 (Y: 4%).

EXAMPLE B3

Preparation of Final Product 2-22

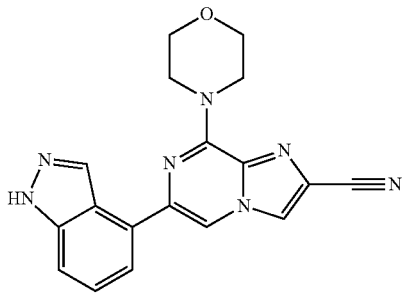 [SMILES: N#Cc1cn2cc(-c3cccc4[nH]ncc34)nc(N3CCOCC3)c2n1]

Final product 2-21 (50 mg, 0.138 mmol) in POCl$_3$ (2 ml) was heated to reflux for 2 h. The solvent was evaporated in vacuo and the residue was suspended in DCM and Na$_2$SO$_4$ aq. solution. The organic phase was extracted, dried (MgSO$_4$), filtered and evaporated to obtain a light brown solid which was washed with Et$_2$O. The precipitate was filtered and dried to obtain the desired product 2-22 (25 mg, Y: 53%) as a pure solid.

EXAMPLE B4

Preparation of Final Product 2-33

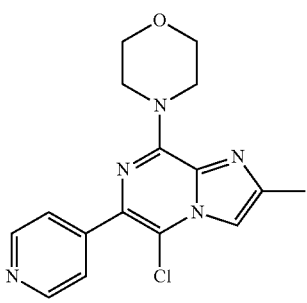 [SMILES: Cc1cn2c(Cl)c(-c3ccncc3)nc(N3CCOCC3)c2n1]

A mixture of final product 2-31 (50 mg, 0.169 mmol) and NCS (18 mg, 0.135 mmol, 0.8 eq) in THF (2 mL) was heated at 60° C. for 18 h. A saturated solution of NaHCO$_3$ was added and the mixture was extracted with EtOAc. The organic phase was separated, dried (Na$_2$SO$_4$), filtered and evaporated till dryness. The residue was purified by using a sep-pack in a manifold, eluent: cyclohexane/EtOAc, 2/1. The desired fractions were collected and the solvent was evaporated till dryness to obtain 15 mg, Y: 27% of desired product 2-33.

Preparation of Final Product 2-54

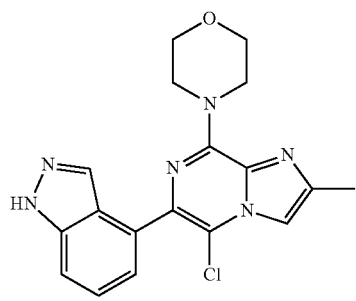 [SMILES: Cc1cn2c(Cl)c(-c3cccc4[nH]ncc34)nc(N3CCOCC3)c2n1]

A mixture of final product 2-24 (60 mg, 0.179 mmol) and NCS (31 mg, 0.233 mmol) in dioxane (2 mL) was heated at 50° C. for 18 h. The organic phase was evaporated till dryness. The residue was purified by using column chromatography (hexane/EtOAc mixtures) and then by HPLC. The desired fractions were collected and the solvent was evaporated till dryness to obtain 9 mg, Y: 14% of desired product 2-54.

Preparation of Final Product 2-56

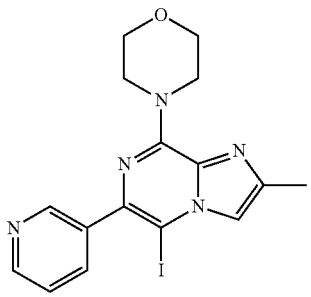 [SMILES: Cc1cn2c(I)c(-c3cccnc3)nc(N3CCOCC3)c2n1]

A mixture of final product 2-31 (0.2 g, 0.677 mmol) and NIS (233 mg, 1.016 mmol) in THF (4 mL) was heated at 65° C. for 18 h. A saturated solution of NaHCO$_3$ was added and the mixture was extracted with EtOAc. The organic phase was separated, dried (Na$_2$SO$_4$), filtered and evaporated till dryness. The residue was purified by using a sep-pack in a manifold and then by HPLC. The desired fractions were collected and the solvent was evaporated till dryness to obtain 2 mg of desired product 2-56.

Preparation of Final Product 2-60

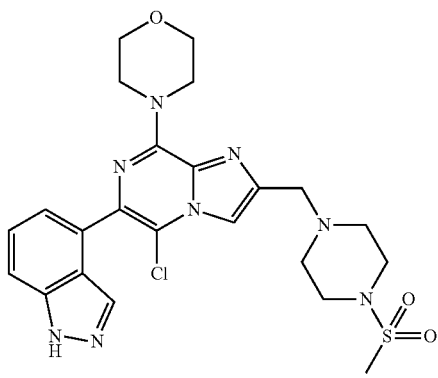 [SMILES: CS(=O)(=O)N1CCN(Cc2cn3c(Cl)c(-c4cccc5[nH]ncc45)nc(N4CCOCC4)c3n2)CC1]

A mixture of final product 2-17 (45 mg, 0.1 mmol) and NCS (20 mg, 0.15 mmol) in acetonitrile (2 mL) was stirred at room temperature for 4 h. A saturated solution of NaHCO$_3$ was added and the mixture was extracted with EtOAc. The organic phase was separated, dried (Na$_2$SO$_4$), filtered and evaporated till dryness. The residue was purified by column chromatograpy (DCM/MeOH 100% to 95:5) and then by HPLC. The desired fractions were collected and the solvent was evaporated till dryness to obtain 10 mg, of desired product 2-60.

Preparation of Final Product 2-12

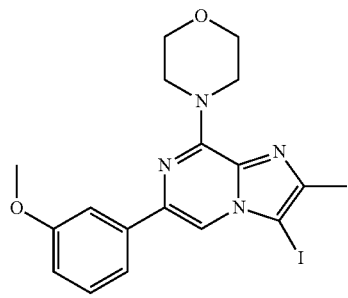 [SMILES: COc1cccc(-c2cn3c(I)c(C)nc3c(N3CCOCC3)n2)c1]

To a solution of final product 2-32 (1.249 mmol) in THF (4.5 mL) was added NIS (1.249 mmol) and the reaction mixture was stirred at rt for 24 h. Excess of NIS (0.31 mmol, 70 mg) was added stirring the reaction for 16 h more. A saturated aqueous solution of NaHCO$_3$ and DCM was added. The organic phase was extracted, dried (Na$_2$SO$_4$), filtered and evaporated. The residue was purified by flash chromatography in Biotage, eluent: CH$_2$Cl$_2$—AcOEt/CH$_2$Cl$_2$ to obtain 38.6 mg of final product 2-12 and 41 mg of the corresponding regioisomer, final product 2.53.

Preparation of Final Product 2-96

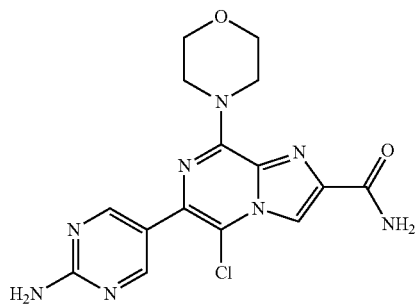 [SMILES: NC(=O)c1cn2c(Cl)c(-c3cnc(N)nc3)nc(N3CCOCC3)c2n1]

Final product 2-93 (30 mg, 88 umol) was suspended in acetonitrile (2 mL) and NCS (12 mg, 88 umol) was added. The mixture was stirred at rt for 15 h and filtered to render a solid that was reprecipitated (DMSO/MeOH/formic acid) affording the final product 2-96 (15 mg, 42%) as a yellow solid with purity of 90% (contaminated with 10% starting material).

Preparation of Final Product 2-108

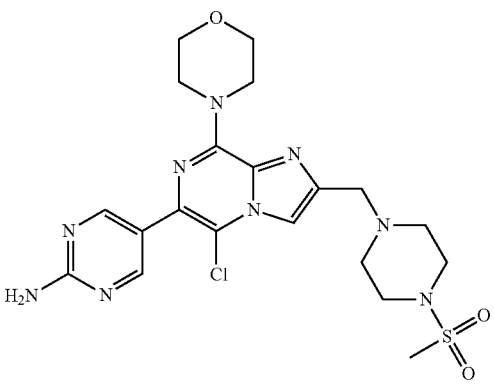 [SMILES: CS(=O)(=O)N1CCN(Cc2cn3c(Cl)c(-c4cnc(N)nc4)nc(N4CCOCC4)c3n2)CC1]

Final product 2-50 (50 mg, 0.11 mmol) was suspended in DCM (1 mL) and NCS (14 mg, 0.11 mmol) was added. The mixture was stirred at rt for 20 h. The suspension was filtered and rinsed with DCM to render the final product 2-108 (41 mg, 76%) as white solid.

Preparation of Final Product 2-112

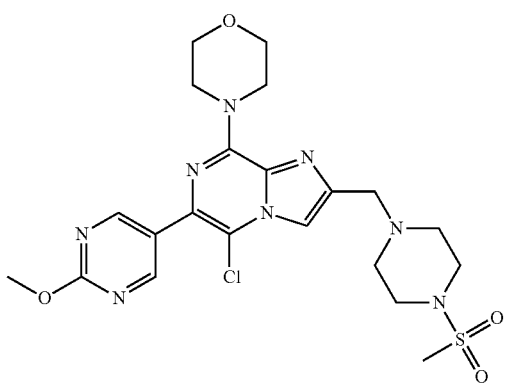 [SMILES: COc1ncc(-c2nc(N3CCOCC3)c3nc(CN4CCN(S(C)(=O)=O)CC4)cn3c2Cl)cn1]

Final product 2-67 (35 mg, 72 μmol) was suspended in DCM (1 mL) and NCS (10 mg, 72 umol) was added. The mixture was stirred at rt for 20 h. NaHCO$_3$ sat sol was added to the mixture and it was extracted with DCM (×2). The combined organic layer was dried, filtered and concentrated. The residue was precipitated with diethyl ether to afford the final product 2-112 (35 mg, 93%) as white solid

EXAMPLE B5

Preparation of Final Product 2-38

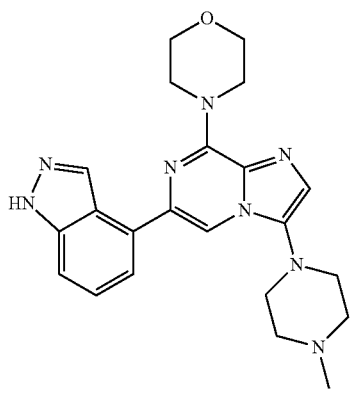 [SMILES: CN1CCN(c2cnc3c(N4CCOCC4)nc(-c4cccc5[nH]ncc45)cn23)CC1]

Benzotriazole (0.7 g, 5.9 mmol) and 1-methylpiperazine (0.660 mL, 5.9 mmol) were stirred in ethanol (20 mL) at rt for 10 min. Glyoxal (0.360 mL of 40% aqueous solution, 2.9 mmol) was added to the reaction mixture, and the stirring was continued for 16 h. The light yellow solution was concentrated under vacuum and precipitated. A light yellow-crystal solid appeared when the resulted oil was washed with diethyl ether to yield a 1.6 g of a solid which was used in next reaction step without further purification. 210 mg (0.44 mmol) of this solid and intermediate I-03 (130 mg, 0.44 mmol) were dissolved in DCE and refluxed for 5 h. The reaction mixture was cooled to rt and then KOH (powder, 250 mg) was added. The mixture was stirred for 20 min at rt, filtered off and washed (DCM). The solvent was concentrated under reduced pressure. The resulting residue was purified by flash column chromatography eluting with a gradient of DCM/MeOH (from 100% to 96:4), yielding final product 2-38, 30 mg, Y: 16%.

Preparation of Final Product 2-41

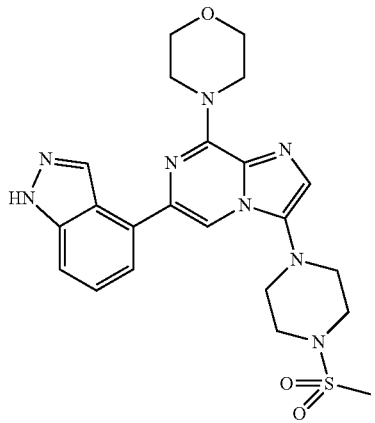 [SMILES: CS(=O)(=O)N1CCN(c2cnc3c(N4CCOCC4)nc(-c4cccc5[nH]ncc45)cn23)CC1]

A mixture of benzotriazole (300 mg, 2.43 mmol) 4-methylsulfonylpiperazine (400 mg, 2.43 mmol) in EtOH (20 mL) was stirred for 20 min. Glyoxal (0.160 mL of a 40% w solution in water, 1.2 mmol) was added, and the resultant mixture was stirred for 16 h. The white solid formed was filtered off, washing with EtOH and diethylether to yield 280 mg that was used in next reaction step without further purification. Another batch of this reaction was progressed. 497 mg (0.844 mmol) of this solid and intermediate I-03 were heated in DCE under reflux for 6 h. The reaction mixture was cooled to rt, KOH (156 mg powder) was added and the resulted mixture was stirred at rt for 1 h. The reaction mixture was filtered off and the filtrate was concerted under vacuum to yield a residue which was purified by flash column chromatography (eluting with a gradient of DCM/MeOH/NH$_3$ 7N (from 100% to 95:5), to yield desired final product 2-41 (50 mg, Y: 12.3%).

EXAMPLE B6

Preparation of Final Product 2-43

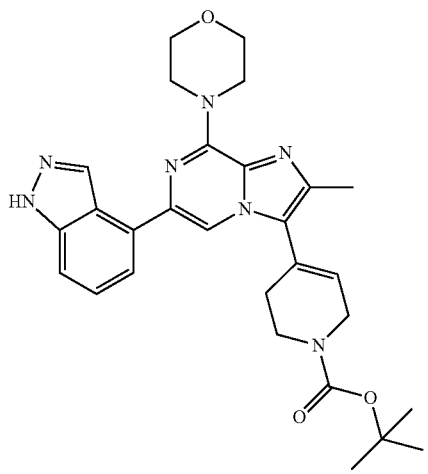 [SMILES: Cc1nc2c(N3CCOCC3)nc(-c3cccc4[nH]ncc34)cn2c1C1=CCN(C(=O)OC(C)(C)C)CC1]

Final product 2-42 (230 mg, 0.56 mmol) was dissolved in 1,4-dioxane (3 mL) and Pd(PPh$_3$)$_4$ (64 mg, 56 umol), Cs$_2$CO$_3$ (363 mg, 1.11 mmol), 1-N-boc-4-(4,4,5,5-tetramethyl-[1,3,2]dioxaborolan-2-yl)-3,6-dihydro-2H-pyridine (198 mg, 0.64 mmol) and H$_2$O (2 mL) were added. The mixture was heated under microwave irradiation at 140° C. for 1 h. On cooling, the solvents were removed and the residue was purified by column chromatography (DCM/MeOH from 98:2 to 94:6) to give the final product 2-43 (260 mg, Y: 91%) as a yellow solid.

EXAMPLE B7

Preparation of Final Product 2-44

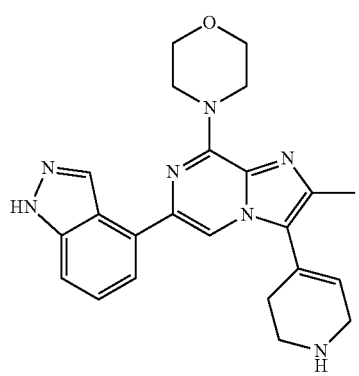 [SMILES: Cc1nc2c(N3CCOCC3)nc(-c3cccc4[nH]ncc34)cn2c1C1=CCNCC1]

Final product 2-43 (200 mg, 0.39 mmol) was dissolved in MeOH (7 mL) and Amberlyst® 15 (1 g, 4.7 mmol) was added. The reaction mixture was stirred at rt for 24 h and filtered. The resin was suspended in MeOH/NH$_3$7N (10 mL), stirred for 10 min and filtered. This treatment was repeated 3 times. The filtrates were together evaporated and the residue was precipitated from DCM (5 mL) and filtered to give the expected product 2-44 (43 mg, Y: 27%), as a white solid.

EXAMPLE B8

Preparation of Final Product 2-45

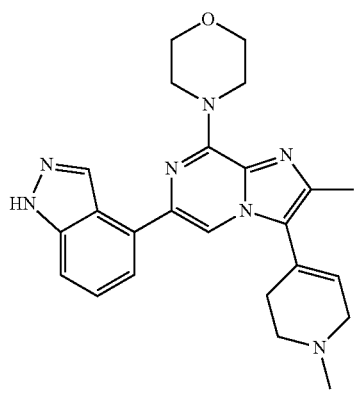 [SMILES: Cc1nc2c(N3CCOCC3)nc(-c3cccc4[nH]ncc34)cn2c1C1=CCN(C)CC1]

Final product 2-44 (35 mg, 84 umol) was suspended in DCM (1.5 mL) and formaldehyde (0.1 mL, 1.26 mmol) and sodium cyanoborohydride (32 mg, 0.5 mmol) were added. The reaction mixture was stirred at rt for 20 h. The reaction was adsorbed in silica and purified by column chromatography (DCM/MeOH from 96:4 to 70:30) and then by HPLC to give the expected product 2-45 (3.2 mg) as a white solid.

Preparation of Final Product 2-58

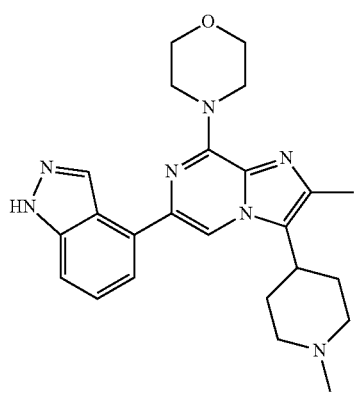 [SMILES: Cc1nc2c(N3CCOCC3)nc(-c3cccc4[nH]ncc34)cn2c1C1CCN(C)CC1]

Final product 2-57 (20 mg, 48 umol) was suspended in DCM (1.5 mL) and formaldehyde (52 μl, 0.72 mmol) and sodium cyanoborohydride (18 mg, 0.29 mmol) were added. The reaction mixture was stirred at rt for 1 h. The reaction was adsorbed in silica and purified by column chromatography (DCM/MeOH from 96:4 to 70:30) and then by HPLC to give the expected product 2-58 (9 mg) as a white solid.

EXAMPLE B9

Preparation of Final Product 2-46

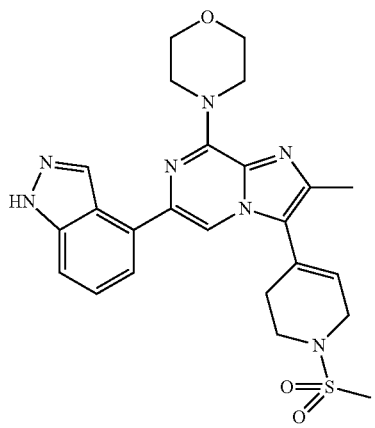 [SMILES: Cc1nc2c(N3CCOCC3)nc(-c3cccc4[nH]ncc34)cn2c1C1=CCN(S(C)(=O)=O)CC1]

Final product 2-44 (30 mg, 72 umol) was suspended in acetonitrile (1 mL) and DIPEA (19 μL, 0.11 mmol) and MeSO$_2$Cl (6 μL, 79 umol) were added. The solution was stirred at rt for 2.5 h. Excess of MeSO$_2$Cl (3 μL, 0.5 eq) was added. The reaction mixture was stirred for 3 days and evaporated. The residue was dissolved in HCl 1M (10 mL) and extracted with DCM (3×7 mL). The organic phase was dried (Na$_2$SO$_4$), filtered and the solvent evaporated in vacuo. The resulting residue was purified by HPLC to give the expected product 2-46 (10 mg, Y: 28%) as a white solid.

EXAMPLE B10

Preparation of Final Product 2-47

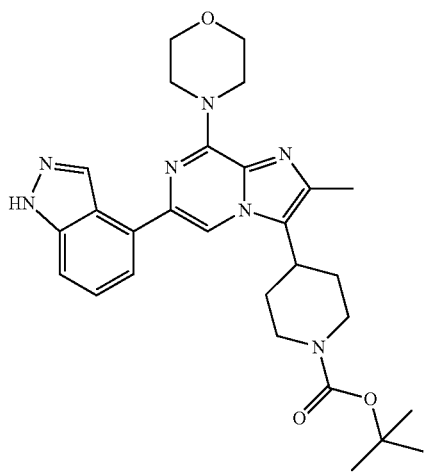 [SMILES: Cc1nc2c(N3CCOCC3)nc(-c3cccc4[nH]ncc34)cn2c1C1CCN(C(=O)OC(C)(C)C)CC1]

Final product 2-43 (50 mg, 97 μmol) was dissolved in MeOH (100 mL) and hydrogenated in the H-Cube (Pd/C 10%, 60° C., Full H$_2$, 1 mL/min). The resulting solution was evaporated and the residue was purified by HPLC to give the expected product 2-47 (14 mg, Y: 28%) as a white solid.

EXAMPLE B11

Preparation of Final Product 2-30

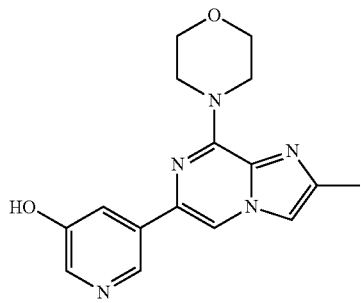 [SMILES: Cc1cn2cc(-c3cncc(O)c3)nc(N3CCOCC3)c2n1]

Boron fluoride-dimethyl sulfide complex (0.226 mL, 2.151 mmol) was added to a stirred solution of final product 2-27 (70 mg, 0.2165 mmol) in DCM (1.3 mL) at rt. The mixture was stirred at rt for 24 h. Additional amount of boron fluoride-dimethyl sulfide complex (2.1 mL) was added, and the mixture was stirred at rt for 48 h more. A saturated solution of NaHCO$_3$ was added and the mixture was extracted with DCM/MeOH 90:1. The organic phase was separated, dried (Na$_2$SO$_4$), filtered and evaporated to dryness. The residue was purified by biotage chromatography and eluted with a gradient DCM/MeOH from 100% to 50:50. The desired fractions were collected to obtain 20 mg of desired product 2-30 as a solid (Y: 30%).

Preparation of Final Product 2-88

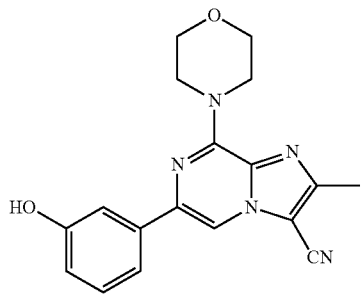 [SMILES: Cc1nc2c(N3CCOCC3)nc(-c3cccc(O)c3)cn2c1C#N]

Boron trifluoride-dimethyl sulfide complex (0.084 mL, 0.8 mmol) was added to a stirred solution of final product 2-62 (28 mg, 0.08 mmol) in DCM (1.5 mL) at rt. The mixture was stirred at rt for 24 h. Additional amount of boron fluoride-dimethyl sulfide complex (total of 0.3 mL) was added, and the mixture was stirred at rt for 48 h more. Then, THF (1 mL) was added and the mixture was heated at 50° C. for 53 h. A saturated solution of NaHCO$_3$ was added and the mixture was extracted with DCM/MeOH 90:1. The organic phase was separated, dried (Na$_2$SO$_4$), filtered and evaporated to dryness. The residue was purified by biotage chromatography and eluted with a gradient DCM/MeOH from 100% to 95:5. The desired fractions were collected to obtain 7 mg of desired product 2-88 as a solid (Y: 26%).

EXAMPLE B12

Preparation of Final Product 2-57

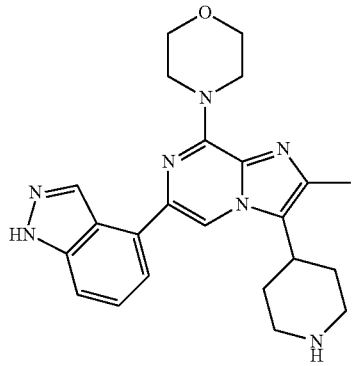 [SMILES: Cc1nc2c(N3CCOCC3)nc(-c3cccc4[nH]ncc34)cn2c1C1CCNCC1]

Final Product 2-47 (174 mg, 0.34 mmol) was dissolvent in MeOH (7 ml) and Amberlyst 15 (1 g) was added. The reaction mixture was stirred at room temperature for 24 h and filtered. The resin was suspended in MeOH/NH$_3$ 7N stirred for 10 min. and the organic phase was collected. The solvent was evaporated and the residue was precipitated with MeOH, and then purified by HPLC to obtain 9 mg as a formate salt of Final product 2-57.

Preparation of Final Product 2-236

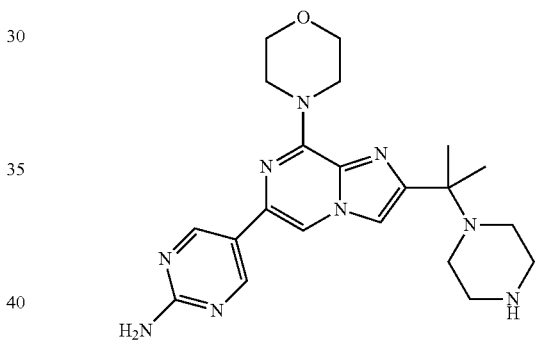

A 4M solution of HCl in dioxane (1 mL) was added at 0° C. to Final product 2-232 (12 mg, 0.023 mmol). The reaction mixture was stirred at rt for 3 h. Solvents were removed and the residue was purified by column chromatography (Isolute SCX-2 cartridge, MeOH to NH$_3$ 7N in MeOH) to give Final product 2-236 (9 mg, 92%).

EXAMPLE B13

Preparation of Final Product 2-52

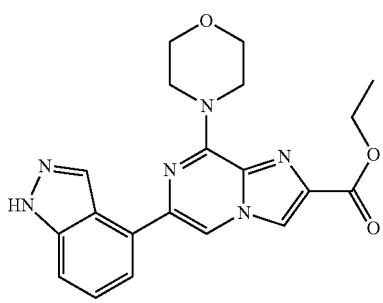 [SMILES: CCOC(=O)c1cn2cc(-c3cccc4[nH]ncc34)nc(N3CCOCC3)c2n1]

To a reaction mixture of intermediate I-12 (150 mg, 0.42 mmol), indazole-4-boronic acid hydrochloride (0.93 mmol, 0.150 mg), and PdCl₂(dppf).DCM (35 mg, 0.042 mmol) in DME (2 ml), was added a saturated solution of potassium carbonate (0.5 ml). The mixture was heated at 130° C. under microwave irradiation for 10 min. A precipitate appears which was filtered, washed with DCM and dried. The resulting solid (0.160 mg, Y: 96%) is the expected final compound 2-52 and was used in next reaction step without further purification.

Preparation of Final Product 2-92

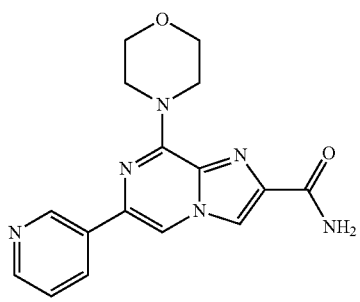 [SMILES: NC(=O)c1cn2cc(-c3cccnc3)nc(N3CCOCC3)c2n1]

Intermediate I-30 (100 mg, 0.31 mmol) was dissolved in DME (2 mL) and pyridine-3-boronic acid (45 mg, 0.37 mmol), K₂CO₃ (127 mg, 0.92 mmol), PdCl₂(dppf)•DCM and water (1 mL) were added. The reaction mixture was heated under microwave irradiation at 130° C. for 1 h. The volatiles were removed under vacuum and the residue was purified by flash chromatography (DCM-MeOH 95:5 to 90:10). The product obtained was precipitated in MeOH affording the final product 2-92 as off-white solid (96 mg, 97%).

Preparation of Final Product 2-93

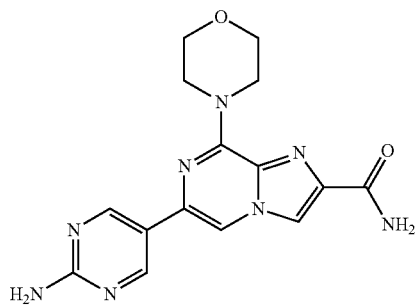

Intermediate I-30 (100 mg, 0.31 mmol) was dissolved in DME (2 mL) and 2-aminopyrimidine-5-boronic acid pinacol ester (81 mg, 0.37 mmol), K₂CO₃ (127 mg, 0.92 mmol), PdCl₂(dppf)•DCM and water (1 mL) were added. The reaction mixture was heated under microwave irradiation at 130° C. for 1 h. The volatiles were removed under vacuum and the residue was purified by flash chromatography (DCM-MeOH 95:5 to 90:10). The product obtained was precipitated in MeOH affording the final product 2-93 as off-white solid (96 mg, 97%).

Preparation of Final Product 2-165

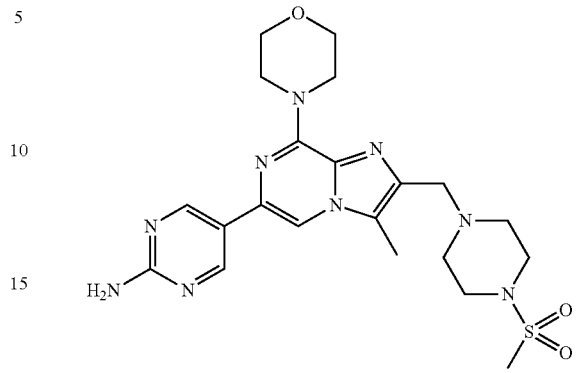

Final product 2-178 (50 mg, 0.087 mmol) was dissolved in 1,4-dioxane (0.3 mL) and Pd(PPh₃)₄ (10 mg, 0.009 mmol), Cs₂CO₃ (57 mg, 0.174 mmol), methylboronic acid (6 mg, 0.1 mmol) and water (0.2 mL) were added. The mixture was heated under microwave irradiation at 140° C. for 1 h. Water was added and the mixture was extracted with DCM. The organics were dried (Na₂SO₄), filtered and evaporated. The residue was purified by column chromatography-TLC in the Chromatotron (DCM:MeOH, 15:1) twice. The desired fractions were collected and evaporated to obtain Final compound 2-165 (22 mg, 52%).

EXAMPLE B14

Preparation of Final Product 2-62

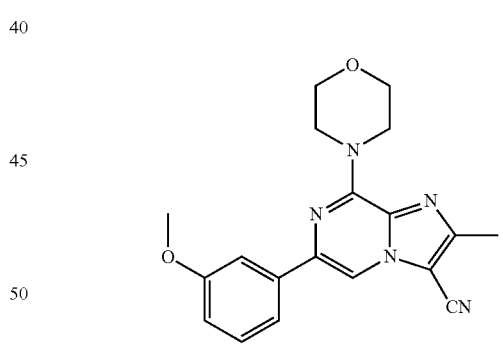

To a solution of final Product 2-12 (0.087 mmol) in DMF dry (1 ml) was added zinc cyanide (0.091 mmol), tris(dibenzylidenaceton)dipalladium (Pd₂ dba₃) (0.004 mmol), 1,1'-bis(diphenylphosphino)ferrocene (DPPF) (0.011 mmol). The mixture was heated at 140° C. for 1 h under microwave irradiation. The solution was diluted with ethyl acetate, washed with water and a saturated solution of NaCl. The organic phase was dried (Na₂SO₄), filtered and the solvent evaporated. The residue was purified by flash column chromatography, eluent: CH₂Cl₂—AcOEt/CH₂Cl₂ 1:100-1:50 to obtain 22.9 mg as a white solid of compound 2-62.

Preparation of Final Product 2-36

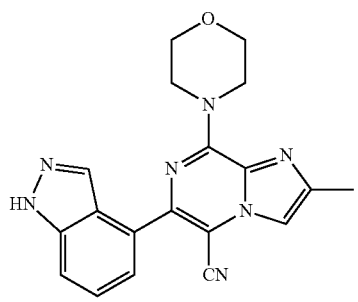 [SMILES: Cc1cn2c(C#N)c(-c3cccc4[nH]ncc34)nc(N3CCOCC3)c2n1]

A mixture of final product 2-73 (38 mg, 0.163 mmol), Zn(CN)₂ (10 mg, 0.087 mmol), diphenylphosphineferrocene (6 mg, 0.01 mmol) and Pd₂(dba)₃ (4 mg, 0.004 mmo) in DMF (0.5 mL) was heated for 1 h at 120° C. under microwave irradiation. Then, more Zn(CN)₂ (10 mg, 0.087 mmol), dppf (6 mg, 0.01 mmol, 0.125 eq) and Pd₂(dba)₃ (4 mg, 0.004 mmol, 0.05 eq) were added and the mixture was heated 1.5 h at 120° C. under microwave irradiation. This excess was added twice. The solvent was removed in vacuo and the residue was purified by column chromatography (EtOAc and EtOAc/MeOH mixtures) and then by HPLC to obtain 1.2 mg of desired product 2-36.

EXAMPLE B15

Preparation of Final Product 2-79

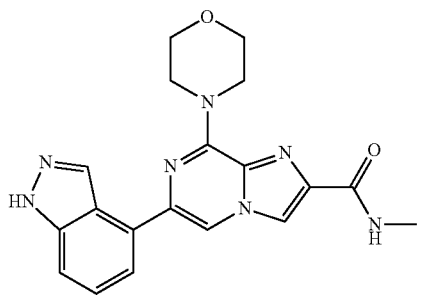 [SMILES: CNC(=O)c1cn2cc(-c3cccc4[nH]ncc34)nc(N3CCOCC3)c2n1]

Final product 2-52 (25 mg, 0.064 mmol) was suspended in EtOH (1.5 mL) and methyl amine (2M in THF, 1.27 mmol, 0.7 mL) was added. The reaction mixture was heated in a sealed tube at 100° C. for 18 h. The reaction mixture was then directly adsorbed in silica to be purified by column chromatography (5% to 10% of MeOH in DCM) rendering 5 mg of the final product 2-79 as a white solid (Y. 21%).

Preparation of Final Product 2-217

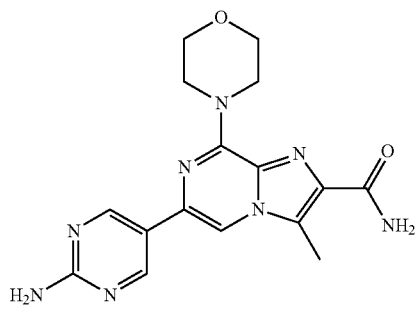 [SMILES: Cc1c(C(N)=O)nc2c(N3CCOCC3)nc(-c3cnc(N)nc3)cn12]

Final product 2-214 (300 mg, 0.78 mmol) was suspended in MeOH/NH₃ 7N (10 mL) and heated under microwave irradiation at 130° C. for 24 h. The mixture was evaporated and purified by column chromatography (MeOH in DCM, 100:0 to 40:60) rendering 80 mg of final product 2-217 as a white solid (Y. 29%).

EXAMPLE B16

Preparation of Final Product 2-87

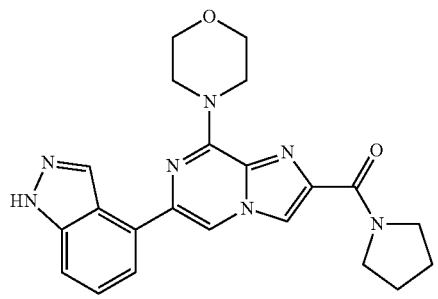 [SMILES: O=C(c1cn2cc(-c3cccc4[nH]ncc34)nc(N3CCOCC3)c2n1)N1CCCC1]

Pyrrolidine (0.54 mmol, 45 µL) was dissolved in EtOH (5 mL) in a sealed tube and AlMe₃ (0.54 mmol, 0.26 mL) was added. The mixture was stirred at rt for 15 min and then, the final product 2-52 (0.27 mmol, 105 mg) was added. The reaction mixture was stirred at rt for 1 h and 4 h at 40° C. On cooling, the reaction was carefully quenched with NH₄Cl sat sol and extracted with CHCl₃-iPrOH 1:1 (×3). The combined organic layer was dried, filtered and concentrated. The crude product was purified by flash chromatography (DCM-MeOH 96:4 to 90:10) rendering the final product 2-87 (15 mg, 13%) as white solid.

Preparation of Final Product 2-139

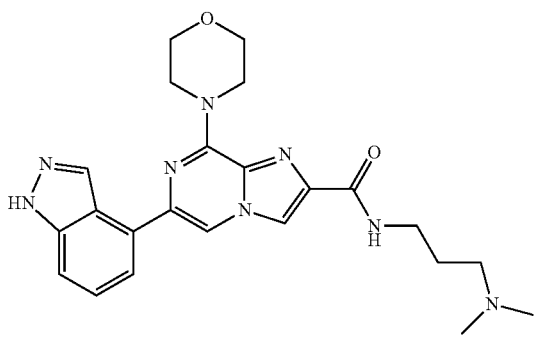 [SMILES: CN(C)CCCNC(=O)c1cn2cc(-c3cccc4[nH]ncc34)nc(N3CCOCC3)c2n1]

Final product 2-52 (0.127 mmol, 50 mg) was dissolved in EtOH (3 mL) and N,N-dimethyl-1,3-propanediamine (1.27 mmol, 0.16 mL) and AlMe₃ (1.27 mmol, 0.64 mL) were added. The mixture was heated at 150° C. for 3 days and under microwave irradiation at 180° C. for 1 h. On cooling, the reaction was carefully quenched with NH₄Cl sat. sol. and extracted with DCM (×2). The combined organic layers were dried, filtered and concentrated. The crude product was purified by flash chromatography (DCM-MeOH:NH₃(7N); 100:0 to 80:20) rendering the final product 2-139 (18 mg, 31%) as white solid.

EXAMPLE B17

Preparation of Final Product 2-97

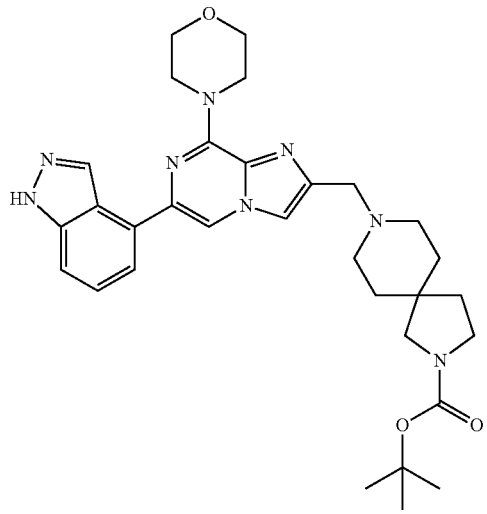 [SMILES: CC(C)(C)OC(=O)N1CCC2(CCN(Cc3cn4cc(-c5cccc6[nH]ncc56)nc(N5CCOCC5)c4n3)CC2)C1]

A mixture of intermediate I-34 (100 mg, 0.28 mmol), AcOH (40 uL, 0.52 mmol), 2,8-diaza-spiro[4.5]decane-2-carboxylic acid tert-butyl ester hydrochloride (90 mg, 0.29 mmol) in DCE (5 mL) was stirred at rt for 40 min. Then, NaBH(OAc)$_3$ (90 mg, 0.40 mmol) was added and stirring continued for 5 h. The reaction mixture was quenched by adding 4N aq sol of KOH and it was extracted with EtOAc (×2). The combined organic layer was washed with brine, dried (Na$_2$SO$_4$), filtered and concentrated the crude product (150 mg, 93%) that was used in next reaction step without further purification. Part of this crude product (50 mg) was further purified by preparative HPLC rendering the final product 2-97 (13 mg).

Method B18

Preparation of Final Product 2-155

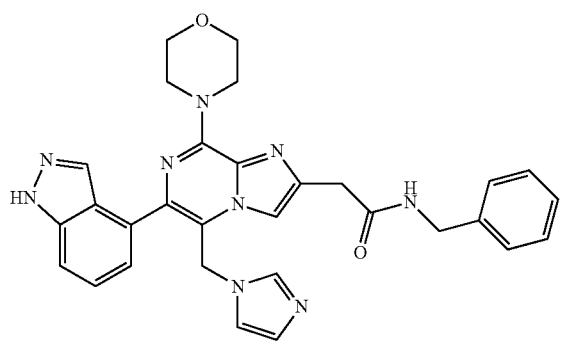 [SMILES: O=C(Cc1cn2c(Cn3ccnc3)c(-c3cccc4[nH]ncc34)nc(N3CCOCC3)c2n1)NCc1ccccc1]

A mixture of iodine (34 mg, 0.133 mmol), triphenylphosphine (29 mg, 0.111 mmol) and imidazole (9 mg, 0.133 mmol) in DMF (2 mL) was stirred at RT for 1 h. Then, Final product 2-144 (55 mg, 0.111 mmol) was added and the mixture was stirred at 70° C. overnight. The mixture was evaporated and the residue was purified by using a sep-pack in a manifold (DCM:MeOH, 92:8) to render 10 mg of Final product 2-155 (16%).

Method B19

Preparation of Final Product 2-177

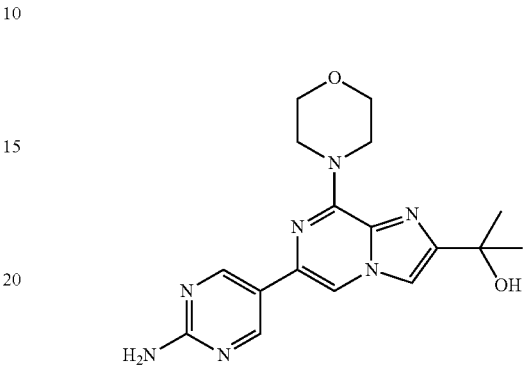

Final product 2-138 (0.3 g, 0.81 mmol) was suspended in THF (6 mL) and MeMgCl (3M, 2.7 mL, 8.1 mmol) was slowly added at 0° C. The reaction mixture was stirred for 4 h and then carefully quenched with H$_2$O. The resulting mixture was purified by column chromatography (DCM:MeOH, 95:5 to 85:15). The product obtained was precipitated with DCM and drops of MeOH and filtered to render Final product 2-177 (20 mg, 7%) as a yellow solid. The filtrate was evaporated and purified by column chromatography (DCM:MeOH, 95:5 to 85:15) and by prep-HPLC to give Final product 2-177 (38 mg, 13%) as a yellow solid.

Method B20

Preparation of Final Product 2-191

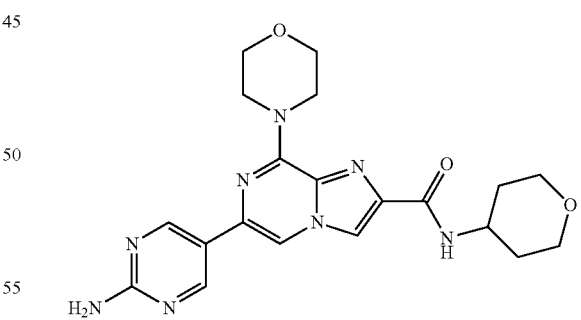

To a solution of Intermediate I-52 (50 mg, 0.146 mmol), BOP (78 mg, 0.176 mmol) and 4-aminotetrahydropyran.HCl (0.024 mL, 0.176 mmol) in DCM (1.5 mL) was added Et$_3$N (0.041 mL, 0.293 mmol). The mixture was stirred at rt for 2 h. DCM was added and the mixture was washed with water. The organic phase was dried, filtered and evaporated. The residue was purified by column chromatography (DCM:MeOH, 100:0 to 60-40) and by prep-HPLC to render 4 mg (6%) of Final product 2-191 as a white solid.

Method B21

Preparation of Final Product 2-234

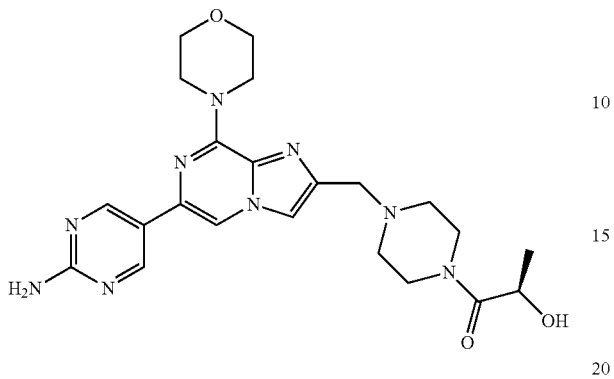

Final product 2-231 (40 mg, 0.078 mmol) was suspended in sodium methoxide 0.5 M in MeOH, 3 mL) and the reaction mixture was stirred at RT for 45 min. H$_2$O (3 mL) was added, the solution was slightly acidified with HCl and extracted with n-BuOH. The organics were dried over Na$_2$SO$_4$, filtered and evaporated. The residue was purified by chromatotron (DCM:MeOH, 10:1). The residue was dissolved in MeOH (4 mL), amberlyst (0.3 g) was added and the mixture was stirred at rt for 2 h, filtered and washed with MeOH. The resine was suspended in NH$_3$/MeOH (7 N, 35 mL) and stirred for 1 h. The mixture was filtered and the filtrate was evaporated. The residue was purified by chromatotron (DCM/MeOH, 10:1) to give Final product 2-234 (12 mg, 33%) as a white solid.

Method B22

Preparation of Final Product 2-237

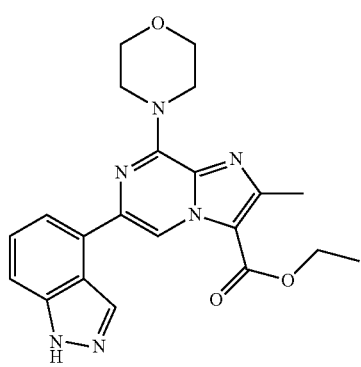 [SMILES: CCOC(=O)c1c(C)nc2c(N3CCOCC3)nc(-c3cccc4[nH]ncc34)cn12]

Intermediate I-28 (500 mg, 1.540 mmol), indazole-4-boronic acid hydrochloride (3.387 mmol, 672 mg) and PdCl$_2$(dppf).DCM (0.154 mmol, 127 mg) were suspended in a saturated solution of sodium carbonate (1.5 mL) and 1,2-DME (7 mL). The mixture was heated under microwave irradiation at 130° C. for 10 min. The mixture was diluted with EtOAc and washed with water. The organic layer was dried (Na$_2$SO$_4$), filtered and the solvent evaporated in vacuo. The resulting residue was purified by flash chromatography (DCM-MeOH from 100:0 to 96:4) to obtain the Final Product 2-237 as a white solid (88 mg, Y: 14%).

Method B23

Preparation of Final Product 2-238

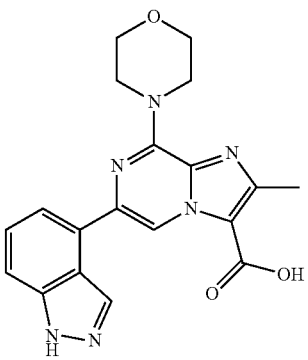 [SMILES: Cc1nc2c(N3CCOCC3)nc(-c3cccc4[nH]ncc34)cn2c1C(=O)O]

Final Product 2-237 (88 mg, 0.217 mmol) was suspended in MeOH (2 mL) and treated with 2N NaOH (0.24 mL, 0.48 mmol). The reaction mixture was refluxed for 4 h. Solvents were evaporated and the residue was dissolved in EtOAc, treated with AcOH and washed with water. The organic layer was dried, filtered and evaporated to give the Final Product 2-238 (82 mg, 100%).

Method B24

Preparation of Final Product 2-241

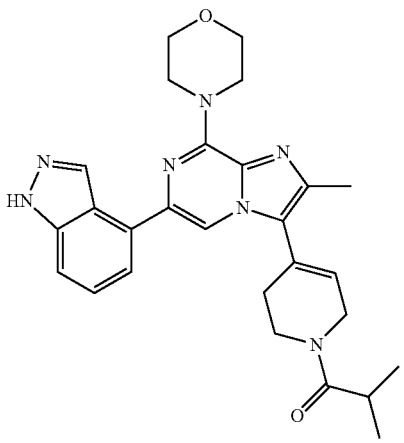 [SMILES: Cc1nc2c(N3CCOCC3)nc(-c3cccc4[nH]ncc34)cn2c1C1=CCN(C(=O)C(C)C)CC1]

To a solution of Final product 2-44 (50 mg, 0.12 mmol) and N,N-diisopropylethylamine (0.031 mL, 0.181 mmol) in acetonitrile (2 mL) was added isobutyryl chloride (0.014 mL, 0.132 mmol). The mixture was stirred at rt for 4 h and evaporated. H$_2$O was added and the mixture was extracted with DCM. The organic layer was dried (Na$_2$SO$_4$), filtered and evaporated to render Final Product 2-241 (51 mg, 87%).

Method B25

Preparation of Final Product 2-243

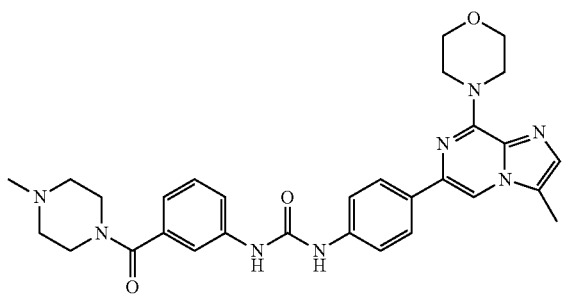 [SMILES: Cc1cnc2c(N3CCOCC3)nc(-c3ccc(NC(=O)Nc4cccc(C(=O)N5CCN(C)CC5)c4)cc3)cn12]

A mixture of Final Compound 2-245/Intermediate I-69 (62 mg, 0.13 mmol), 1-methylpiperazine (0.019 mL, 0.17 mmol), TEA (0.024 mL, 0.17 mmol), HOBT (26 mg, 0.17 mmol) and EDCl (33 mg, 0.17 mmol) in THF (1 mL) was stirred at rt overnight and evaporated. The residue was purified by column chromatography (Isolute 5 g; MeOH:DCM, 1:99 to 20:80 and Flash-NH2 5 g; MeOH:DCM, 0:100 to 2:98) to give the Final Product 2-243 (49 mg, 67%) as a white solid.

Method B26

Preparation of Final Product 2-245

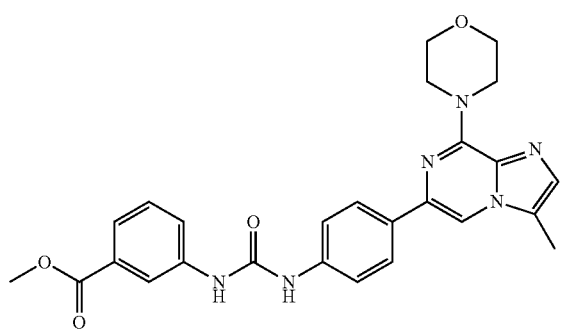 [SMILES: COC(=O)c1cccc(NC(=O)Nc2ccc(-c3cn4c(C)cnc4c(N4CCOCC4)n3)cc2)c1]

To a solution of Intermediate I-69 (50 mg, 0.16 mmol) in DCM (1.3 mL) was added methyl 4-isocyanatobenzoate (31 mg, 0.18 mmol). The reaction mixture was stirred at rt for 5 h. Cyclohexane was added and the mixture was filtered to give Final Product 2-245 (46 mg) as a beige solid. The filtrate was evaporated and the residue was purified by column chromatography (Isolute 5 g; MeOH:DCM, 0:100 to 5:95) to give Final product 2-245 (25 mg) as a light yellow solid. Total yield: 91%.

General Procedure

The HPLC measurement was performed using a HP 1100 from Agilent Technologies comprising a pump (binary) with degasser, an autosampler, a column oven, a diode-array detector (DAD) and a column as specified in the respective methods below. Flow from the column was split to a MS spectrometer. The MS detector was configured with an electrospray ionization source or API/APCI. Nitrogen was used as the nebulizer gas. The source temperature was maintained at 150° C. Data acquisition was performed with ChemStation LC/MSD quad, software.

Method 1

Reversed phase HPLC was carried out on a RP-C18 Gemini column (150×4.6 mm, 5 um); 10 min. linear gradient of 50-100% acetonitrile in water+100% acetonitrile in water 2 min): 210 nm and 254 or DAD.

Method 2

Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 100% of B within 8 min at 50° C., DAD.

Method 3

Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 40% of B within 8 min at 50° C., DAD.

Method 4

Reversed phase HPLC was carried out on a Gemini-NX C18 (100×2.0 mm; 5 um), Solvent A: water with 0.1% formic acid; Solvent B: acetonitrile with 0.1% formic acid. Gradient: 0% of B to 30% of B within 8 min at 50° C., DAD.

Method 5

Reversed phase HPLC was carried out on a Gemini C18 (50×2.0 mm; 3 um), Solvent A: water with 0.1% formic acid; Solvent B: acetonitrile with 0.1% formic acid. Gradient: 10% of B to 95% of B within 4 min at 50° C., DAD.

TABLE 4

Analytical data and PI3Kα activity - $R_t$ means retention time (in minutes), $[M + H]^+$ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | $[M + 1]^+$ | Meth. | PI3Kα IC50 (μM) | 1H NMR (300 MHz; δ in ppm, J in Hz) |
|---|---|---|---|---|---|
| 2-01 | 4.882 | 369.1 | 1 | 0.158 (++) | DMSO δ 9.52 (s, 1H), 8.49 (d, J = 16.6, 2H), 7.32 (m, 3H), 6.78 (dd, J = 7.9, 1.5, |

TABLE 4-continued

Analytical data and PI3Kα activity - $R_t$ means retention time (in minutes), [M + H]$^+$ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]$^+$ | Meth. | PI3Kα IC50 (μM) | $^1$H NMR (300 MHz; δ in ppm, J in Hz) |
|---|---|---|---|---|---|
| | | | | | 1H), 4.32 (dt, J = 13.0, 6.4, 6H), 3.80 (m, 4H), 1.32 (t, J = 7.1, 3H). |
| 2-02 | 9.199 | 341.1 | 1 | 19 | DMSO δ 9.58 (s, 1H), 8.38 (s, 1H), 7.99 (s, 1H), 7.31 (m, 2H), 7.15 (t, J = 7.8, 1H), 6.69 (d, J = 7.8, 1H), 4.22 (m, 4H), 3.72 (m, 4H). |
| 2-03 | 10.433 | 325.1 | 1 | 10 | DMSO) δ 10.01 (s, 1H), 9.53 (s, 1H), 8.60 (s, 1H), 8.51 (s, 1H), 7.38 (m, 2H), 7.25 (t, J = 7.8, 1H), 6.78 (d, J = 7.6, 1H), 4.32 (s, 4H), 3.81 (s, 4H). |
| 2-04 | 8.396 | 327.1 | 1 | 0.639 (++) | $^1$H NMR (300 MHz, DMSO) δ 9.46 (s, 1H), 8.50 (s, 1H), 7.81 (s, 1H), 7.38 (m, 2H), 7.23 (t, J = 7.9, 1H), 6.75 (d, J = 7.8, 1H), 4.59 (s, 2H), 4.23 (m, 4H), 3.78 (m, 4H). |
| 2-05 | 7.277 | 495.3 | 1 | 0.476 | DMSO δ 9.48 (s, 1H), 8.45 (s, 1H), 7.82 (s, 1H), 7.36 (m, 2H), 7.24 (d, J = 7.7, 1H), 6.74 (d, J = 7.5, 1H), 4.23 (m, 4H), 3.78 (m, 4H), 3.62 (s, 2H), 3.35 (m, 4H), 2.40 (m, 4H), 1.38 (s, 9H). |
| 2-06 | 4.707 | 437.2 | 1 | 0.451 (++) | DMSO δ 9.48 (s, 1H), 8.45 (s, 1H), 7.83 (s, 1H), 7.36 (dd, J = 11.7, 5.0, 2H), 7.22 (t, J = 7.9, 1H), 6.74 (d, J = 7.9, 1.6, 1H), 4.23 (m, 4H), 3.77 (m, 4H), 3.62 (s, 2H), 3.40 (m, 4H), 2.41-2.39 (m, 4H), 1.96 (s, 3H). |
| 2-07 | 4.577 | 409.2 | 1 | 27 | DMSO δ 9.48 (s, 1H), 8.45 (s, 1H), 7.80 (s, 1H), 7.37 (dd, J = 12.2, 5.0, 2H), 7.22 (t, J = 7.9, 1H), 6.74 (d, J = 9.5, 1H), 4.24 (m, 4H), 3.78 (m, 4H), 3.58 (s, 2H), 2.42-2.31 (m, 4H), 2.14 (s, 4H), 1.39 (s, 3H). |
| 2-08 | 4.714 | 409.2 | 1 | 0.54 (++) | DMSO δ 9.48 (s, 1H), 8.46 (s, 1H), 7.86 (s, 1H), 7.74 (s, 1H), 7.38 (dd, J = 11.8, 5.0, 2H), 7.23 (t, J = 7.9, 1H), 6.75 (dd, J = 8.0, 1.7, 1H), 4.24 (m, 4H), 3.78 (m, 4H), 3.69 (s, 2H), 3.16 (m, 2H), 2.64 (t, J = 5.3, 2H). |
| 2-09 | 4.601 | 396.2 | 1 | 0.444 (++) | DMSO δ 9.48 (s, 1H), 8.45 (s, 1H), 7.83 (s, 1H), 7.38 (m, 2H), 7.22 (t, J = 7.9, 1H), 6.74 (dd, J = 7.5, 2.0, 1H), 4.24 (m, 4H), 3.78 (m, 4H), 3.58 (m, 6H), 2.45 (m, 4H). |
| 2-10 | 4.409 | 473.2 | 1 | 0.037 (+++) | DMSO δ 9.48 (s, 1H), 8.46 (s, 1H), 7.83 (s, 1H), 7.37 (dd, J = 11.9, 4.9, 2H), 7.23 (t, J = 7.8, 1H), 6.75 (dd, J = 7.9, 1.7, 1H), 4.24 (m, 4H), 3.78 (m, 4H), 3.67 (s, 2H), 3.12 (m, 4H), 2.87 (s, 3H), 2.56 (m, 4H). |
| 2-11 | 6.401 | 487 | 1 | 0.044 | DMSO δ 9.51 (s, 1H), 8.49 (s, 1H), 8.34 (s, 1H), 7.37 (m, 2H), 7.25 (t, J = 7.8, 1H), 6.77 (d, J = 8.1, 1H), 4.25 (s, 6H), 3.80 (s, 6H), 3.22 (s, 4H), 2.92 (s, 3H). |
| 2-12 | 5.599 | 397.1 | 1 | ++ | CDCl$_3$ δ 7.67 (d, J = 0.7, 1H), 7.35 (t, J = 7.9 Hz, 1H), 7.22 (m, 1H), 7.18 (m, 1H), 6.95 (ddd, J = 8.2, 2.6, 0.9 Hz, 1H), 4.28 (m, 4H), 3.85 (s, 3H), 3.84 (m, 4H), 2.46 (s, 3H). |
| 2-13 | 7.691 | 365.1 | 1 | 0.108 (++) | DMSO δ 9.53 (s, 1H), 8.50 (d, J = 13.9, 2H), 7.38 (dd, J = 9.6, 4.9, 2H), 7.26 (t, J = 7.8, 1H), 6.79 (dd, J = 7.9, 1.6, 1H), 4.25 (m, 4H), 3.80 (m, 4H). |
| 2-14 | 7.025 | 337 | 1 | 0.34 (++) | DMSO δ 9.46 (s, 1H), 8.38 (s, 1H), 7.69 (s, 1H), 7.37 (dd, J = 12.3, 5.0, 2H), 7.21 (t, J = 7.9, 1H), 6.73 (dd, J = 7.9, 1.6, 1H), 4.21 (m, 4H), 3.77 (m, 4H), 2.03 (ddd, J = 13.2, 8.3, 4.9, 1H), 0.92 (m, 2H), 0.79 (m, 2H). |
| 2-15 | 3.131 | 447.2 | 1 | 0.741 (++) | DMSO δ 13.25 (s, 1H), 8.65 (s, 1H), 8.55 (s, 1H), 8.40 (s, 1H), 7.67 (d, J = 6.8, 1H), 7.58 (m, 1H), 7.45 (m, 1H), 4.29 (s, 4H), 4.08 (s, 2H), 3.82 (s, 4H), 3.70 (s, 2H), 2.48 (s, 4H), 2.28 (s, 3H). |
| 2-16 | 4.152 | 511.2 | 1 | 0.254 (++) | DMSO δ 13.24 (s, 1H), 8.65 (s, 1H), 8.55 (s, 1H), 8.44 (s, 1H), 7.67 (d, J = 7.0, 1H), 7.58 (d, J = 8.3, 1H), 7.45 (t, J = 7.7, 1H), |

TABLE 4-continued

Analytical data and PI3Kα activity - $R_t$ means retention time (in minutes), [M + H]$^+$ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]$^+$ | Meth. | PI3Kα IC50 (μM) | $^1$H NMR (300 MHz; δ in ppm, J in Hz) |
|---|---|---|---|---|---|
| 2-17 | 3.171 | 497.20 | 1 | 0.095 | 4.29 (s, 6H), 3.82 (s, 6H), 3.23 (s, 4H), 2.92 (s, 3H). DMSO δ 13.20 (s, 1H), 8.58 (d, J = 15.8, 2H), 7.99 (d, J = 37.6, 1H), 7.52 (m, 3H), 4.27 (d, J = 4.4, 4H), 3.81 (m, 4H), 3.70 (s, 2H), 3.14 (t, J = 9.4, 4H), 2.87 (s, 3H), 2.58 (s, 4H). |
| 2-18 | 3.745 | 432.5 | 1 | 0.182 (++) | DMSO δ 8.64 (s, 1H), 8.55 (s, 1H), 8.40 (s, 1H), 8.30 (s, 1H), 7.66 (d, J = 7.1, 1H), 7.58 (d, J = 8.3, 1H), 7.44 (m, 1H), 4.89 (br s, 1H), 4.28 (br s, 4H), 4.07 (br s, 1H), 3.81 (br s, 4H), 3.70 (br s, 1H), 2.92 (brs, 4H) (rotamers observed) |
| 2-19 | 4.151 | 361.2 | 1 | 0.438 | DMSO) δ 13.26 (s, 1H), 8.53 (s, 3H), 7.79 (s, 1H), 7.62 (d, J = 7.1, 1H), 7.55 (d, J = 8.2, 1H), 7.42 (d, J = 7.5, 1H), 4.24 (s, 4H), 3.79 (s, 4H), 2.06 (m, 1H), 0.94 (m, 2H), 0.81 (m, 2H). |
| 2-20 | 4.63 | 389.10 | 1 | 1.8 | DMSO δ 13.26 (s, 1H), 8.59 (m, 3H), 7.67 (d, J = 7.1, 1H), 7.60 (d, J = 8.3, 1H), 7.45 (m, 1H), 4.28 (s, 4H), 3.82 (m, 4H). |
| 2-21 | 5.25 | 364.1 | 1 | — | DMSO δ 13.20 (s, 1H), 8.58 (s, 1H), 8.50 (s, 1H), 8.34 (s, 1H), 7.83 (s, 1H), 7.61 (d, J = 7.1, 1H), 7.52 (d, J = 8.2, 1H), 7.39 (m, 2H), 4.27 (s, 4H), 3.75 (s, 4H). |
| 2-22 | 6.72 | 346 | 1 | 0.618 (++) | DMSO δ 13.19 (s, 1H), 8.73 (s, 1H), 8.58 (s, 1H), 8.47 (s, 1H), 7.61 (d, J = 7.1, 1H), 7.53 (d, J = 8.2, 1H), 7.38 (t, J = 7.7, 1H), 4.21 (s, 4H), 3.75 (m, 4H). |
| 2-23 | 5.438 | 311.1 | 1 | 0.096 (+++) | DMSO δ 9.45 (s, 1H), 8.43 (s, 1H), 7.69 (d, J = 0.7, 1H), 7.38 (m, 2H), 7.22 (t, J = 7.9, 1H), 6.74 (dd, J = 8.0, 1.6, 1H), 4.23 (m, 4H), 3.78 (m, 4H). |
| 2-24 | 5.576 | 335.1 | 1 | 2.6 (+) | DMSO δ 13.19 (s, 1H), 8.58 (s, 1H), 8.55 (s, 1H), 7.79 (s, 1H), 7.64 (d, J = 7.1, 1H), 7.54 (d, J = 8.2, 1H), 7.42 (m, 1H), 4.26 (m, 4H), 3.80 (m, 4H), 2.37 (s, 3H). |
| 2-25 | 6.033 | 334.1 | 1 | 10 | DMSO δ 11.18 (s, 1H), 8.48 (s, 1H), 8.05 (d, J = 0.7, 1H), 7.70 (d, J = 0.7, 1H), 7.58 (d, J = 1.4, 2H), 7.37 (m, 1H), 6.43 (m, 1H), 4.26 (m, 4H), 3.80 (m, 4H), 2.35 (m, 3H). |
| 2-26 | 3.350 | 296.1 | 1 | 10 | DMSO δ 9.09 (m, 1H), 8.56 (s, 1H), 8.48 (dd, J = 4.8, 1.6, 1H), 8.24 (m, 1H), 7.64 (d, J = 0.8, 1H), 7.40 (ddd, J = 8.0, 4.7, 0.7, 1H), 4.19 (m, 4H), 3.71 (m, 4H), 2.29 (s, 3H). |
| 2-27 | 4.651 | 326.1 | 1 | 3.9 (+) | DMSO δ 8.78 (s, 1H), 8.65 (s, 1H), 8.26 (s, 1H), 7.85 (s, 1H), 7.69 (s, 1H), 4.24 (d, J = 4.4, 4H), 3.90 (s, 3H), 3.77 (m, 4H), 2.36 (s, 3H). |
| 2-28 | 5.758 | 388.1 | 1 | 50 | DMSO δ 9.89 (s, 1H), 8.53 (s, 1H), 7.96 (s, 1H), 7.79 (s, 1H), 7.72 (d, J = 7.7, 1H), 7.45 (t, J = 7.9, 1H), 7.26 (d, J = 7.9, 1H), 4.32 (s, 4H), 3.85 (d, J = 4.4, 4H), 3.08 (s, 3H), 2.41 (s, 3H). |
| 2-29 | 4.843 | 367.2 | 1 | 3 | DMSO δ 8.62 (s, 1H), 8.39 (s, 1H), 7.82 (d, J = 8.3, 2H), 7.66 (s, 1H), 7.46 (d, J = 8.2, 3H), 6.03 (s, 1H), 4.22 (s, 4H), 3.77 (s, 4H), 2.65 (d, J = 3.5, 3H), 2.34 (s, 3H). |
| 2-30 | 3.726 | 312.1 | 1 | 0.235 (++) | DMSO δ 9.97 (s, 1H), 8.61 (s, 1H), 8.57 (s, 1H), 8.09 (d, J = 2.4, 1H), 7.70 (d, J = 3.5, 2H), 4.24 (d, J = 4.5, 4H), 3.78 (m, 4H), 2.35 (s, 3H). |
| 2-31 | 3.512 | 296.1 | 1 | 10 | DMSO δ 8.69 (s, 1H), 8.56 (d, J = 5.9, 2H), 7.87 (d, J = 6.0, 2H), 7.66 (s, 1H), 4.20 (m, 4H), 3.71 (m, 4H), 2.30 (s, 3H). |
| 2-32 | NMR | | | — | CDCl$_3$ δ 7.84 (s, 1H), 7.48 (m, 1H), 7.42 (d, J = 7.9, 1H), 7.31 (t, J = 7.9, 1H), 7.26 (s, |

TABLE 4-continued

Analytical data and PI3Kα activity - R$_t$ means retention time (in minutes), [M + H]$^+$ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | R$_t$ | [M + 1]$^+$ | Meth. | PI3Kα IC50 (μM) | $^1$H NMR (300 MHz; δ in ppm, J in Hz) |
|---|---|---|---|---|---|
| | | | | | 1H), 6.87 (dd, J = 8.1, 1.8, 1H), 4.32 (m, 4H), 3.88 (m, 4H), 3.85 (s, 3H), 2.41 (s, 3H). |
| 2-33 | 4.509 | 330.1 | 1 | — | CDCl$_3$ δ 8.62 (dd, J = 4.6, 1.6, 2H), 7.68 (dd, J = 4.5, 1.6, 2H), 7.55 (m, 1H), 4.20 (m, 4H), 3.79 (dd, J = 10.4, 5.7, 4H), 2.38 (t, J = 0.5, 3H). |
| 2-34 | 5.260 | 330.1 | 1 | — | CDCl$_3$ δ 8.99 (d, J = 1.8, 1H), 8.55 (dd, J = 4.8, 1.6, 1H), 8.04 (m, 1H), 7.50 (d, J = 0.6, 1H), 7.31 (m, 1H), 4.22 (m, 4H), 3.80 (m, 4H), 2.40 (d, J = 0.5, 3H). |
| 2-35 | 4.78 | 324.1 | 2 | — | DMSO δ 8.57 (s, 1H), 8.29 (s, 1H), 7.97 (d, J = 7.4, 2H), 7.87 (s, 1H), 7.47 (t, J = 7.3, 3H), 7.37 (t, J = 7.2, 1H), 4.31 (s, 4H), 3.80 (d, J = 4.4, 4H). |
| 2-36 | 4.31 | 360.1 | 2 | — | MeOD δ 8.26 (s, 1H), 7.77 (s, 1H), 7.70 (d, J = 8.9, 1H), 7.62 (d, J = 7.1, 2H), 7.52 (d, J = 8.2, 1H), 4.54 (m, 4H), 3.86 (m, 4H), 2.47 (s, 3H). |
| 2-37 | 3.37 | 395.20 | 1 | ++ | DMSO δ 9.45 (s, 1H), 7.79 (s, 1H), 7.42 (d, J = 6.9, 2H), 7.23 (m, 2H), 6.75 (d, J = 7.4, 1H), 4.26 (m, 4H), 3.77 (m, 4H), 3.02 (m, 4H), 2.56 (m, 4H), 2.27 (s, 3H). |
| 2-38 | 3.06 | 419.2 | 1 | ++ | CDCl$_3$ δ 10.16 (s, 1H), 8.51 (s, 1H), 7.80 (s, 1H), 7.55 (d, J = 6.6, 1H), 7.42 (m, 2H), 7.17 (s, 1H), 4.32 (m, 4H), 3.84 (m, 4H), 3.07 (m, 4H), 2.59 (s, 4H), 2.34 (s, 3H). |
| 2-39 | 4.12 | 459.20 | 1 | ++ | DMSO δ 9.46 (s, 1H), 7.88 (s, 1H), 7.40 (m, 3H), 7.23 (t, J = 7.8, 1H), 6.76 (d, J = 7.3, 1H), 4.27 (s, 4H), 3.77 (s, 4H), 3.38 (s, 4H), 3.13 (s, 4H), 2.98 (s, 3H). |
| 2-40 | 2.90 | 381.20 | 1 | ++ | DMSO δ 9.45 (s, 1H), 7.81 (s, 1H), 7.42 (m, 2H), 7.23 (m, 2H), 6.75 (d, J = 8.8, 1H), 4.26 (s, 4H), 3.77 (m, 4H), 2.93 (s, 8H). |
| 2-41 | 6.065 | 483.2 | 1 | ++ | DMSO δ 13.20 (s, 1H), 8.45 (s, 1H), 7.97 (s, 1H), 7.61 (dd, J = 7.1, 0.6, 1H), 7.57 (d, J = 8.3, 1H), 7.44 (m, 1H), 7.40 (d, J = 3.8, 1H), 4.30 (s, 4H), 3.80 (m, 4H), 3.37 (m, 4H), 3.17 (m, 4H), 2.98 (s, 3H). |
| 2-42 | 7.644 | 413.1 | 1 | — | DMSO δ 13.22 (s, 1H), 8.46 (s, 1H), 8.05 (s, 1H), 7.61 (dd, J = 16.1, 7.7, 2H), 7.43 (t, J = 7.7, 1H), 4.27 (s, 4H), 3.80 (s, 4H), 2.38 (s, 3H). |
| 2-43 | 8.144 | 516.3 | 1 | — | DMSO δ 13.12 (s, 1H), 8.35 (s, 1H), 7.96 (s, 1H), 7.51 (dd, J = 11.0, 7.7, 2H), 7.34 (m, 1H), 6.02 (s, 1H), 4.21 (s, 4H), 4.03 (s, 2H), 3.74 (s, 4H), 3.57 (s, 2H), 2.38 (s, 2H), 2.28 (s, 3H), 1.38 (s, 9H). |
| 2-44 | 3.836 | 416.2 | 1 | 0.731 (++) | DMSO δ 13.13 (s, 1H), 8.34 (s, 1H), 7.95 (s, 1H), 7.50 (m, 2H), 7.35 (t, J = 7.8, 1H), 6.01 (s, 1H), 4.21 (s, 4H), 3.74 (m, 4H), 3.39 (s, 2H), 2.93 (s, 2H), 2.28 (s, 3H), 2.23 (s, 2H). |
| 2-45 | 7.145 | 430.2 | 1 | — | DMSO δ 8.33 (s, 1H), 8.12 (s, 1H), 7.91 (s, 1H), 7.51 (d, J = 5.0, 1H), 7.49 (d, J = 6.2, 1H), 7.35 (dd, J = 8.3, 7.1, 1H), 5.98 (s, 1H), 4.21 (m, 4H), 3.73 (m, 4H), 3.11 (s, 2H), 2.64 (m, 2H), 2.38 (m, 2H), 2.31 (s, 3H), 2.27 (s, 3H). |
| 2-46 | 6.306 | 494.2 | 1 | — | DMSO δ 13.25 (bs, 1H), 8.43 (s, 1H), 8.22 (s, 1H), 7.56 (t, J = 7.0, 2H), 7.41 (dd, J = 8.3, 7.2, 1H), 6.12 (s, 1H), 4.25 (m, 4H), 3.98 (d, J = 2.6, 2H), 3.81 (m, 4H), 3.49 (m, 2H), 3.00 (s, 3H), 2.55 (m, 2H), 2.36 (s, 3H). |
| 2-47 | 7.661 | 518.3 | 1 | — | DMSO δ 13.17 (s, 1H), 8.49 (s, 1H), 8.26 (s, 1H), 7.62 (d, J = 7.1, 1H), 7.56 (d, J = 8.2, 1H), 7.42 (m, 1H), 4.26 (s, 4H), |

TABLE 4-continued

Analytical data and PI3Kα activity - $R_t$ means retention time (in minutes), [M + H]⁺ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| | | | | | 4.09 (d, J = 12.2, 2H), 3.79 (s, 4H), 3.47 (s, 1H), 2.95 (s, 2H), 2.41 (s, 3H), 1.80 (s, 4H), 1.42 (s, 9H). |
| 2-48 | 3.697 | 359.1 | 1 | — | CDCl₃ δ 7.57 (d, J = 0.7, 1H), 7.36 (m, 3H), 6.95 (dt, J = 6.5, 2.6, 1H), 4.28 (m, 4H), 3.87 (m, 7H), 2.47 (d, J = 0.5, 3H). |
| 2-49 | 1.596 | 345.1 | 1 | ++ | DMSO δ 9.54 (s, 1H), 7.87 (s, 1H), 7.25 (t, J = 8.1, 1H), 7.15 (dd, J = 5.1, 3.0, 2H), 6.80 (m, 1H), 4.17 (m, 4H), 3.74 (m, 4H), 2.39 (s, 3H). |
| 2-50 | 2.33 | 474.2 | 2 | 0.001 | DMSO δ 8.77 (s, 2H), 8.41 (s, 1H), 7.76 (s, 1H), 6.83 (s, 2H), 4.22 (d, J = 4.5, 4H), 3.77 (m, 4H), 3.66 (s, 2H), 3.11 (d, J = 4.8, 4H), 2.87 (s, 3H), 2.55 (s, 4H). |
| 2-51 | 4.95 | 405.2 | 1 | — | DMSO δ 13.21 (s, 1H), 8.42 (s, 1H), 7.92 (s, 1H), 7.59 (dd, J = 16.1, 7.7, 2H), 7.43 (m, 1H), 7.29 (s, 1H), 4.30 (s, 4H), 3.79 (m, 4H), 2.94 (m, 8H). |
| 2-52 | NMR | | | 0.676 | DMSO δ 8.66-8.32 (m, 2H), 7.74-7.15 (m, 3H), 4.29 (d, J = 7.3, 5H), 3.76 (s, 4H), 1.25 (t, J = 15.7, 3H). |
| 2-53 | NMR | | | — | CDCl₃ δ 7.67 (d, J = 0.7, 1H), 7.35 (t, J = 7.9 Hz, 1H), 7.22 (m, 1H), 7.18 (m, 1H), 6.95 (ddd, J = 8.2, 2.6, 0.9 Hz, 1H), 4.28 (m, 4H), 3.87 (s, 3H), 3.85 (m, 4H), 2.46 (s, 3H). |
| 2-54 | 1.42 | 369.1 | 2 | 0.266 (++) | CDCl₃ δ 10.06 (s, 1H), 8.19 (d, J = 0.6, 1H), 7.61 (s, 1H), 7.50 (m, 3H), 4.30 (m, 4H), 3.83 (m, 4H), 2.49 (m, 3H). |
| 2-55 | 1.43 | 413.0 | 2 | 12 | CDCl₃ δ 8.13 (s, 1H), 7.66 (s, 1H), 7.54 (dt, J = 7.2, 3.6, 1H), 7.47 (m, 2H), 4.29 (m, 4H), 3.86 (m, 4H), 2.49 (s, 3H). |
| 2-56 | 4.192 | 422.0 | 2 | 0.253 | CDCl₃ δ 9.10 (d, J = 1.8, 1H), 8.54 (dd, J = 4.8, 1.6, 1H), 8.16 (m, 1H), 7.87 (m, 1H), 7.31 (dd, J = 7.9, 4.4, 1H), 4.25 (m, 4H), 3.80 (m, 4H), 2.40 (s, 3H). |
| 2-57 | 3.89 | 418.2 | 1 | 0.144 (++) | DMSO δ 8.50 (d, J = 0.7, 1H), 8.44 (s, 1H), 8.32 (s, 1H), 7.63 (d, J = 7.0, 1H), 7.56 (d, J = 8.3, 1H), 7.42 (dd, J = 8.2, 7.2, 1H), 4.27 (m, 4H), 3.79 (m, 4H), 3.51 (t, J = 12.2, 1H), 3.25 (dd, J = 15.8, 8.2, 2H), 2.95 (t, J = 11.7, 2H), 2.43 (s, 3H), 2.15 (t, J = 11.6, 2H), 1.82 (m, 2H). |
| 2-58 | 2.80 | 432.2 | 2 | ++ | DMSO δ 8.50 (s, 1H), 8.26 (s, 1H), 8.20 (d, J = 7.4, 2H), 7.63 (d, J = 7.1, 1H), 7.55 (t, J = 9.4, 1H), 7.43 (dd, J = 8.2, 7.3, 1H), 4.26 (m, 4H), 3.79 (m, 4H), 3.33 (t, J = 12.3, 1H), 3.17 (d, J = 11.2, 2H), 2.57 (t, J = 11.1, 2H), 2.49 (s, 4H), 2.44 (s, 3H), 2.12 (m, 2H), 1.86 (d, J = 12.1, 2H). |
| 2-59 | 6.37 | 496.2 | 1 | — | DMSO δ 13.17 (s, 1H), 8.50 (s, 1H), 8.27 (s, 1H), 7.63 (d, J = 7.1, 1H), 7.56 (d, J = 8.3, 1H), 7.43 (dd, J = 8.2, 7.2, 1H), 4.27 (s, 4H), 3.80 (m, 4H), 3.72 (d, J = 11.5, 2H), 2.98 (d, J = 13.4, 2H), 2.94 (s, 3H), 2.45 (s, 3H), 1.96 (s, 4H). |
| 2-60 | 4.70 | 4.97 | 2 | ++ | DMSO δ 13.19 (s, 1H), 8.08 (s, 1H), 8.00 (s, 1H), 7.61 (d, J = 8.1, 1H), 7.45 (m, 1H), 7.38 (dd, J = 7.1, 1.0, 1H), 4.19 (m, 4H), 3.76 (m, 4H), 3.14 (m, 4H), 2.88 (s, 3H), 2.59 (m, 4H). |
| 2-61 | 3.14 | 488.2 | 2 | 4.5 | CDCl₃ δ 8.71 (d, J = 2.4, 1H), 8.08 (dd, J = 8.6, 2.5, 1H), 7.82 (s, 1H), 7.49 (s, 1H), 6.83 (d, J = 8.7, 1H), 4.37 (m, 4H), 4.00 (s, 3H), 3.90 (m, 4H), 3.77 (s, 2H), 3.30 (m, 4H), 2.80 (s, 3H), 2.71 (m, 4H). |

TABLE 4-continued

Analytical data and PI3Kα activity - $R_t$ means retention time (in minutes), [M + H]$^+$ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]$^+$ | Meth. | PI3Kα IC50 (μM) | $^1$H NMR (300 MHz; δ in ppm, J in Hz) |
|---|---|---|---|---|---|
| 2-62 | 2.28 | 350.1 | 2 | — | CDCl$_3$ δ 7.99 (s, 1H), 7.48 (m, 2H), 7.37 (t, J = 8.1, 1H), 6.95 (m, 1H), 4.35 (m, 4H), 3.89 (m, 7H), 2.57 (s, 3H). |
| 2-63 | 7.53 | 561.3 | 1 | — | DMSO δ 13.25 (s, 1H), 8.83 (s, 1H), 8.43 (s, 1H), 8.09 (d, J = 7.7, 1H), 7.62 (d, J = 7.1, 1H), 7.58 (d, J = 8.3, 1H), 7.44 (dd, J = 8.1, 7.4, 1H), 4.33-4.21 (m, 4H), 4.13-4.00 (m, 1H), 3.93 (d, J = 13.1, 2H), 3.86-3.76 (m, 4H), 2.98-2.85 (m, 2H), 2.55 (s, 3H), 1.89 (d, J = 10.2, 2H), 1.55-1.42 (m, 2H), 1.41 (s, 9H). |
| 2-64 | 2.94 | 461.2 | 2 | + | DMSO δ 13.27 (s, 1H), 8.81 (s, 1H), 8.58-8.48 (m, 1H), 8.43 (s, 1H), 8.32 (d, J = 7.5, 1H), 8.28-8.20 (m, 1H), 7.63 (d, J = 7.1, 1H), 7.59 (d, J = 8.3, 1H), 7.45 (dd, J = 8.2, 7.2, 1H), 4.32-4.24 (m, 4H), 4.20-4.10 (m, 1H), 3.86-3.78 (m, 4H), 3.15-3.00 (m, 2H), 2.58 (s, 3H), 2.16-2.03 (m, 2H), 1.85-1.68 (m, 2H). Two protons are missing, most likely under the water signal |
| 2-65 | 0.37 | 488.2 | 2 | + | CDCl$_3$ δ 8.71 (d, J = 1.7, 1H), 8.31 (d, J = 2.8, 1H), 7.95 (s, 1H), 7.77 (dd, J = 2.7, 1.8, 1H), 7.51 (s, 1H), 4.38 (m, 4H), 3.96 (s, 3H), 3.91 (m, 4H), 3.77 (s, 2H), 3.30 (m, 4H), 2.80 (s, 3H), 2.72 (m, 4H). |
| 2-66 | 0.367 | 473.2 | 2 | 0.169 | DMSO δ 8.51 (d, J = 2.1, 1H), 8.33 (s, 1H), 7.90 (dd, J = 8.7, 2.4, 1H), 7.76 (s, 1H), 6.50 (d, J = 8.6, 1H), 6.10 (s, 2H), 4.22 (s, 4H), 3.78 (d, J = 4.6, 4H), 3.65 (s, 2H), 3.11 (s, 4H), 2.87 (s, 3H), 2.54 (d, J = 8.2, 4H). |
| 2-67 | 3.44 & 3.99 | 489.2 | 2 | ++ | DMSO δ 9.12 (s, 2H), 8.57 (s, 1H), 7.81 (s, 1H), 4.25 (d, J = 4.4, 4H), 3.97 (s, 3H), 3.77 (m, 4H), 3.68 (s, 2H), 3.11 (d, J = 4.8, 4H), 2.87 (s, 3H), 2.56 (s, 4H). |
| 2-68 | 2.54 & 2.64 | 500.2 | 2 | 11 | DMSO) δ 8.65 (s, 1H), 8.04 (d, J = 8.5, 2H), 8.00 (s, 1H), 7.94 (d, J = 8.5, 2H), 7.83 (s, 1H), 7.38 (s, 1H), 4.27 (s, 4H), 3.79 (m, 4H), 3.68 (s, 2H), 3.12 (s, 4H), 2.87 (s, 3H), 2.56 (s, 4H). |
| 2-69 | 2.75 | 512.2 | 2 | — | DMSO δ 10.47 (s, 1H), 8.43 (s, 1H), 7.81 (s, 1H), 7.80 (d, J = 5.5, 1H), 7.78 (m, 1H), 6.88 (d, J = 8.0, 1H), 4.23 (d, J = 4.5, 4H), 3.78 (m, 4H), 3.66 (s, 2H), 3.55 (s, 2H), 3.11 (d, J = 4.7, 4H), 2.87 (s, 3H), 2.56 (s, 4H). |
| 2-70 | 3.18 | 514 | 2 | — | DMSO δ 11.25 (s, 1H), 8.24 (d, J = 2.1, 1H), 7.93 (s, 1H), 7.41 (m, 2H), 7.02 (dd, J = 11.2, 8.8, 1H), 6.70 (s, 1H), 4.21 (s, 4H), 3.78 (m, 4H), 3.69 (s, 2H), 3.12 (s, 4H), 2.87 (s, 3H), 2.57 (s, 4H). |
| 2-71 | 4.15 & 4.73 | 496.2 | 2 | — | CDCl$_3$ δ 8.51 (s, 1H), 7.97 (s, 1H), 7.53 (dd, J = 7.3, 0.6, 1H), 7.50 (s, 1H), 7.43 (d, J = 8.1, 1H), 7.28 (m, 2H), 6.98 (s, 1H), 4.37 (m, 4H), 3.89 (m, 4H), 3.77 (s, 2H), 3.27 (m, 4H), 2.77 (s, 3H), 2.71 (m, 4H). |
| 2-72 | 3.53 & 3.89 | 500.2 | 2 | — | CDCl$_3$ δ 8.37 (s, 1H), 8.12 (d, J = 7.8, 1H), 8.00 (s, 1H), 7.75 (d, J = 7.6, 1H), 7.51 (dd, J = 13.2, 5.3, 2H), 4.37 (m, 4H), 3.90 (m, 4H), 3.76 (m, 2H), 3.29 (m, 4H), 2.79 (s, 3H), 2.71 (m, 4H). |
| 2-73 | 5.37 | 461.0 | 2 | — | CDCl$_3$ δ 10.14 (m, 1H), 8.06 (d, J = 0.9, 1H), 7.70 (d, J = 0.7, 1H), 7.54 (dt, J = 8.1, 1.0, 1H), 7.46 (t, J = 7.6, 1H), 7.40 (dd, J = 7.0, 1.2, 1H), 4.29 (m, 4H), 3.84 (m, 4H), 2.48 (d, J = 0.4, 3H). |
| 2-74 | 4.55 | 392.1 | 2 | 0.092 | DMSO δ 13.23 (s, 1H), 8.65 (s, 1H), 8.56 (s, 1H), 8.44 (t, J = 6.1, 1H), 8.40 (s, 1H), |

TABLE 4-continued

Analytical data and PI3Kα activity - R_t means retention time (in minutes),
[M + H]+ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | R_t | [M + 1]+ | Meth. | PI3Kα IC50 (μM) | ¹H NMR (300 MHz; δ in ppm, J in Hz) |
|---|---|---|---|---|---|
| | | | | | 7.67 (d, J = 7.1, 1H), 7.58 (d, J = 8.3, 1H), 7.44 (m, 1H), 4.34 (s, 4H), 3.83 (m, 4H), 3.40 (s, 2H), 1.15 (t, J = 7.1, 3H). |
| 2-75 | 2.81 | 497.2 | 2 | 0.113 | DMSO δ 11.65 (s, 1H), 8.75 (d, J = 1.9, 1H), 8.49 (s, 1H), 8.41 (d, J = 1.7, 1H), 7.75 (s, 1H), 7.43 (m, 1H), 6.45 (dd, J = 3.3, 1.8, 1H), 4.21 (s, 4H), 3.73 (s, 4H), 3.61 (s, 2H), 3.06 (s, 4H), 2.80 (s, 3H), 2.50 (s, 4H). |
| 2-76 | 4.67 | 539.1 | 2 | — | DMSO δ 13.27 (s, 1H), 8.82 (s, 1H), 8.44 (s, 1H), 8.18 (d, J = 7.7, 1H), 7.60 (dd, J = 11.7, 7.9, 2H), 7.45 (m, 1H), 4.29 (d, J = 7.8, 4H), 4.03 (s, 1H), 3.82 (s, 4H), 3.58 (d, J = 12.1, 2H), 2.95 (m, 2H), 2.92 (s, 3H), 2.58 (s, 3H), 2.02 (d, J = 10.9, 2H), 1.66 (dd, J = 20.4, 11.1, 2H). |
| 2-77 | 4.12 | 378.1 | 2 | — | DMSO δ 13.25 (s, 1H), 9.06 (s, 1H), 8.44 (s, 1H), 7.60 (dd, J = 11.9, 7.7, 3H), 7.45 (dd, J = 8.3, 7.2, 1H), 4.27 (m, 4H), 3.81 (m, 4H), 2.61 (s, 3H). |
| 2-78 | 2.78 | 419.2 | 2 | — | DMSO δ 13.23 (s, 1H), 8.42 (d, J = 0.8, 1H), 7.87 (s, 1H), 7.63 (d, J = 7.0, 1H), 7.57 (d, J = 8.3, 1H), 7.43 (dd, J = 8.3, 7.2, 1H), 7.28 (s, 1H), 4.30 (m, 4H), 3.79 (m, 4H), 3.32 (s, 2H), 3.25 (dd, J = 28.1, 16.1, 2H), 2.80 (dd, J = 20.2, 9.4, 2H), 1.86 (d, J = 10.1, 2H), 1.53 (m, 2H). |
| 2-79 | 4.23 | 378.1 | 2 | 0.11 | DMSO δ 13.23 (s, 1H), 8.64 (s, 1H), 8.56 (s, 1H), 8.40 (s, 1H), 8.38 (d, J = 5.0, 1H), 7.67 (d, J = 7.1, 1H), 7.58 (d, J = 8.3, 1H), 7.44 (dd, J = 8.2, 7.3, 1H), 4.34 (d, J = 4.4, 4H), 3.83 (m, 4H), 2.84 (d, J = 4.8, 3H). |
| 2-81 | 3.54 and 3.88 | 515.2 | 3 | 0.21 | DMSO δ 10.58 (s, 1H), 8.87 (s, 1H), 8.56 (s, 1H), 8.28 (d, J = 9.1, 1H), 8.14 (d, J = 8.9, 1H), 7.81 (s, 1H), 4.25 (s, 4H), 3.78 (s, 4H), 3.67 (s, 2H), 3.12 (s, 4H), 2.87 (s, 3H), 2.55 (s, 4H), 2.11 (s, 3H). |
| 2-82 | 3.99 and 4.26 | 529.2 | 3 | 0.158 | DMSO δ 8.61 (s, 1H), 8.41 (s, 1H), 7.80 (m, 3H), 7.46 (d, J = 8.7, 2H), 6.02 (d, J = 4.7, 1H), 4.23 (s, 4H), 3.77 (m, 4H), 3.65 (s, 2H), 3.11 (s, 4H), 2.86 (s, 3H), 2.64 (d, J = 4.6, 3H), 2.54 (d, J = 4.6, 4H). |
| 2-83 | 4.79 and 4.96 | 541.2 | 3 | 0.21 | CDCl₃ δ 8.74 (d, J = 1.7, 1H), 8.22 (d, J = 1.9, 1H), 7.81 (s, 1H), 7.47 (s, 1H), 5.08 (s, 2H), 4.36 (m, 4H), 3.90 (m, 4H), 3.76 (s, 2H), 3.29 (m, 4H), 2.79 (s, 3H), 2.70 (m, 4H). |
| 2-84 | 4.43 and 4.75 | 522.2 | 3 | — | DMSO δ 13.33 (s, 1H), 8.23 (s, 1H), 7.95 (s, 1H), 7.72 (d, J = 8.0, 1H), 7.52 (dd, J = 13.2, 7.0, 2H), 4.46 (s, 4H), 3.80 (m, 4H), 3.74 (s, 2H), 3.13 (s, 4H), 2.88 (s, 3H), 2.59 (s, 4H). |
| 2-86 | 4.40 | 392.1 | 1 | 0.891 | CDCl₃ δ 8.49 (s, 1H), 8.04 (s, 1H), 7.93 (s, 1H), 7.47 (m, 2H), 7.39 (m, 2H), 4.36 (m, 4H), 3.84 (m, 4H), 3.47 (s, 3H), 3.10 (s, 3H). |
| 2-87 | 4.87 | 418.2 | 1 | 0.355 | DMSO δ 13.24 (s, 1H), 8.63 (s, 1H), 8.56 (s, 1H), 8.43 (s, 1H), 7.66 (d, J = 7.1, 1H), 7.58 (d, J = 8.3, 1H), 7.44 (dd, J = 8.2, 7.3, 1H), 4.30 (d, J = 4.3, 4H), 3.95 (t, J = 6.6, 2H), 3.81 (m, 4H), 3.53 (t, J = 6.7, 2H), 1.87 (m, 4H). |
| 2-88 | 0.98 | 336.1 | 1 | — | DMSO δ 9.60 (s, 1H), 8.26 (s, 1H), 7.48 (d, J = 6.8, 2H), 7.25 (t, J = 8.1, 1H), 6.80 (d, J = 8.6, 1H), 4.23 (s, 4H), 3.79 (d, J = 4.3, 4H). |
| 2-89 | 0.39 | 472.2 | 3 | 33 | CDCl₃ δ 7.78 (s, 1H), 7.71 (d, J = 8.5, 2H), 7.43 (s, 1H), 6.74 (d, J = 8.5, 2H), 4.33 (m, |

TABLE 4-continued

Analytical data and PI3Kα activity - $R_t$ means retention time (in minutes), [M + H]⁺ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| | | | | | 4H), 3.89 (m, 4H), 3.74 (s, 2H), 3.28 (m, 4H), 2.78 (s, 3H), 2.70 (m, 4H). |
| 2-90 | 2.21 and 3.02 | 447.2 | 3 | 6 | DMSO δ 12.93 (s, 1H), 8.22 (s, 1H), 8.11 (s, 1H), 7.89 (s, 1H), 7.74 (s, 1H), 4.22 (m, 4H), 3.76 (m, 4H), 3.65 (s, 2H), 3.11 (m, 4H), 2.87 (s, 3H), 2.55 (m, 4H). |
| 2-91 | 2.69 | 325.1 | 3 | 3.9 | DMSO δ 8.79 (s, 1H), 8.65 (dd, J = 4.6, 1.6, 2H), 8.31 (s, 1H), 7.93 (dd, J = 4.6, 1.6, 3H), 7.51 (s, 1H), 4.33 (s, 4H), 3.79 (m, 4H). |
| 2-92 | 3.29 | 325.1 | 3 | — | DMSO δ 9.16 (d, J = 1.7, 1H), 8.67 (s, 1H), 8.57 (dd, J = 4.7, 1.6, 1H), 8.31 (m, 2H), 7.90 (s, 1H), 7.49 (dd, J = 7.4, 4.8, 2H), 4.33 (s, 4H), 3.79 (m, 4H). |
| 2-93 | 3.01 | 341.1 | 1 | — | DMSO δ 8.78 (s, 2H), 8.44 (s, 1H), 8.21 (s, 1H), 7.86 (s, 1H), 7.46 (s, 1H), 6.88 (s, 2H), 4.29 (s, 4H), 3.77 (m, 4H). |
| 2-94 | 4.37 | 363.1 | 1 | 0.944 | DMSO δ 11.27 (s, 1H), 8.49 (s, 1H), 8.42 (s, 1H), 7.86 (s, 1H), 7.56 (d, J = 6.8, 1H), 7.45 (t, J = 6.0, 3H), 7.18 (t, J = 7.7, 1H), 6.94 (s, 1H), 4.32 (s, 4H), 3.80 (m, 4H). |
| 2-95 | 4.28 | 381.1 | 1 | 0.891 | DMSO δ 11.27 (s, 1H), 8.41 (s, 1H), 8.29 (t, J = 3.7, 1H), 7.87 (s, 1H), 7.43 (m, 3H), 7.03 (dd, J = 11.3, 8.8, 1H), 6.72 (s, 1H), 4.27 (s, 4H), 3.78 (m, 4H). |
| 2-96 | 3.32 | 375.1 | 1 | — | DMSO δ 8.66 (s, 2H), 8.35 (s, 1H), 7.98 (s, 1H), 7.56 (s, 1H), 6.99 (s, 2H), 4.25 (s, 4H), 3.76 (m, 4H). |
| 2-97 | 0.29 | 573.3 | 4 | 4.5 | DMSO δ 13.21 (s, 1H), 8.60 (s, 1H), 8.55 (s, 1H), 7.90 (s, 1H), 7.64 (d, J = 7.0, 1H), 7.55 (d, J = 8.3, 1H), 7.42 (dd, J = 8.2, 7.3, 1H), 4.27 (m, 4H), 3.80 (m, 4H), 3.62 (s, 2H), 3.26 (t, J = 6.8, 4H), 3.05 (s, 2H), 2.40 (s, 2H), 1.66 (dd, J = 12.0, 6.1, 2H), 1.49 (s, 4H), 1.38 (s, 9H). |
| 2-98 | 3.73 | 587.4 | 1 | 7.2 | DMSO δ 13.19 (s, 1H), 8.61 (s, 1H), 8.55 (s, 1H), 7.93 (s, 1H), 7.64 (d, J = 7.0, 1H), 7.56 (d, J = 8.3, 1H), 7.43 (m, 1H), 4.27 (m, 4H), 3.80 (m, 4H), 3.73 (s, 2H), 3.28 (s, 4H), 2.54 (s, 4H), 1.48 (s, 4H), 1.38 (s, 10H), 1.35 (s, 4H). |
| 2-99 | 3.45 | 545.3 | 1 | 7.9 | DMSO δ 13.21 (s, 1H), 8.60 (s, 1H), 8.55 (s, 1H), 7.91 (s, 1H), 7.64 (d, J = 7.0, 1H), 7.55 (d, J = 8.3, 1H), 7.42 (m, 1H), 4.27 (s, 4H), 3.81 (m, 4H), 3.71 (s, 2H), 3.48 (m, 4H), 3.10 (d, J = 10.9, 2H), 2.76 (s, 2H), 2.58 (dd, J = 14.6, 8.4, 2H), 1.38 (s, 9H). |
| 2-100 | 3.68 | 573.3 | 1 | 5.3 | DMSO δ 13.21 (s, 1H), 8.60 (s, 1H), 8.55 (s, 1H), 7.90 (s, 1H), 7.65 (d, J = 7.1, 1H), 7.55 (d, J = 8.3, 1H), 7.42 (m, 1H), 4.26 (m, 4H), 3.80 (m, 4H), 3.71 (s, 2H), 3.28 (m, 4H), 2.64 (t, J = 6.8, 2H), 2.47 (s, 2H), 1.59 (t, J = 6.8, 2H), 1.44 (s, 4H), 1.38 (s, 9H). |
| 2-101 | 2.60 | 359.1 | 1 | — | DMSO δ 8.70 (dd, J = 4.5, 1.6, 2H), 8.42 (s, 1H), 8.02 (s, 1H), 7.81 (m, 2H), 7.59 (s, 1H), 4.27 (s, 4H), 3.77 (m, 4H). |
| 2-102 | 3.01 | 359.1 | 1 | — | DMSO δ 8.96 (d, J = 1.7, 1H), 8.63 (dd, J = 4.8, 1.5, 1H), 8.40 (s, 1H), 8.17 (m, 1H), 8.01 (s, 1H), 7.58 (s, 1H), 7.53 (dd, J = 7.9, 4.8, 1H), 4.26 (s, 4H), 3.76 (m, 4H). |
| 2-103 | 4.27 | 397.1 | 1 | 34 | DMSO δ 11.57 (s, 1H), 8.36 (s, 1H), 8.06 (s, 1H), 7.86 (s, 1H), 7.54 (d, J = 2.6, 1H), 7.48 (m, 1H), 7.44 (m, 1H), 7.22 (m, 1H), 7.16 (d, J = 6.1, 1H), 4.23 (s, 4H), 3.76 (m, 4H). |

TABLE 4-continued

Analytical data and PI3Kα activity - $R_t$ means retention time (in minutes), [M + H]⁺ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| 2-104 | 4.74 | 431.1 | 1 | 93 | DMSO δ 11.58 (s, 1H), 8.36 (m, 1H), 8.01 (s, 1H), 7.58 (s, 1H), 7.53 (s, 1H), 7.52 (s, 1H), 7.25 (m, 1H), 7.11 (dd, J = 7.2, 0.8, 1H), 4.17 (m, 4H), 3.73 (t, J = 4.7, 4H). |
| 2-105 | 4.34 | 415.1 | 1 | 123 | DMSO δ 11.62 (s, 1H), 8.35 (s, 1H), 8.09 (s, 1H), 7.88 (s, 1H), 7.58 (d, J = 2.7, 1H), 7.49 (dd, J = 8.9, 4.3, 2H), 7.11 (m, 1H), 4.20 (s, 4H), 3.73 (t, J = 4.6, 4H). |
| 2-106 | 4.76 | 449.1 | 1 | 28 | DMSO δ 11.68 (s, 1H), 8.38 (s, 1H), 8.03 (s, 1H), 7.59 (s, 2H), 7.54 (dd, J = 8.9, 4.3, 1H), 7.14 (m, 1H), 4.17 (m, 4H), 3.73 (t, J = 4.7, 4H). |
| 2-107 | 4.61 | 393.1 | 1 | 2.6 | DMSO δ 13.13 (s, 1H), 8.57 (s, 1H), 8.49 (s, 1H), 7.90 (s, 1H), 7.59 (d, J = 7.1, 1H), 7.49 (d, J = 8.3, 1H), 7.36 (m, 1H), 4.18 (m, 4H), 3.81 (s, 2H), 3.74 (m, 4H), 3.59 (s, 3H). |
| 2-108 | 2.43 and 2.58 | 508.2 | 1 | — | DMSO δ 8.57 (s, 2H), 7.87 (s, 1H), 6.89 (s, 2H), 4.11 (m, 4H), 3.69 (m, 4H), 3.62 (d, J = 14.9, 2H), 3.05 (m, 4H), 2.80 (s, 3H), 2.48 (m, 4H). |
| 2-109 | 3.49 | 522.2 | 1 | 1 | DMSO δ 8.57 (s, 1H), 8.06 (m, 2H), 6.93 (d, J = 7.2, 1H), 4.19 (s, 4H), 3.91 (s, 3H), 3.75 (s, 6H), 3.16 (s, 2H), 2.89 (s, 3H), 2.54 (s, 2H). |
| 2-110 | 2.96 | 522.2 | 1 | — | CDCl₃ δ 8.68 (d, J = 1.6, 1H), 8.35 (d, J = 2.8, 1H), 7.79 (s, 1H), 7.63 (dd, J = 2.6, 1.8, 1H), 4.31 (m, 4H), 3.94 (s, 3H), 3.88 (m, 4H), 3.83 (s, 2H), 3.33 (s, 4H), 2.80 (s, 3H), 2.75 (s, 4H). |
| 2-111 | 2.39 | 487.3 | 3 | 0.813 | DMSO δ 8.60 (s, 1H), 8.55 (d, J = 0.5, 1H), 8.38 (s, 1H), 7.89 (s, 1H), 7.64 (d, J = 7.0, 1H), 7.56 (d, J = 8.3, 1H), 7.42 (dd, J = 8.2, 7.3, 1H), 4.26 (m, 4H), 3.80 (m, 4H), 3.63 (s, 2H), 2.96 (s, 4H), 2.45 (s, 4H), 1.54 (s, 4H), 1.48 (s, 4H). |
| 2-112 | 3.10 | 523.2 | 1 | — | DMSO δ 8.94 (s, 2H), 7.95 (s, 1H), 4.15 (s, 4H), 3.93 (s, 3H), 3.69 (m, 6H), 3.06 (s, 3H), 2.82 (s, 4H), 2.51 (m, 4H). |
| 2-113 | 2.95 | 546.2 | 1 | — | DMSO δ 10.52 (s, 1H), 7.97 (s, 1H), 7.58 (m, 2H), 6.91 (d, J = 8.6, 1H), 4.20 (s, 4H), 3.76 (m, 6H), 3.55 (s, 2H), 3.16 (s, 4H), 2.87 (s, 3H), 2.65 (s, 4H). |
| 2-114 | 3.15 | 531.2 | 2 | — | DMSO δ 11.81 (s, 1H), 8.57 (d, J = 2.1, 1H), 8.29 (d, J = 2.0, 1H), 7.97 (s, 1H), 7.54 (m, 1H), 6.54 (dd, J = 3.4, 1.8, 1H), 4.20 (m, 4H), 3.76 (m, 4H), 3.73 (s, 2H), 3.14 (t, J = 7.7, 4H), 2.87 (s, 3H), 2.56 (m, 4H). |
| 2-115 | 3.66 | 565.2 | 2 | — | DMSO δ 12.18 (s, 1H), 8.66 (d, J = 2.0, 1H), 8.22 (d, J = 2.1, 1H), 7.99 (s, 1H), 7.77 (s, 1H), 4.21 (s, 4H), 3.77 (m, 4H), 3.74 (s, 2H), 3.12 (m, 4H), 2.87 (s, 3H), 2.58 (s, 4H). |
| 2-116 | 1.67 | 507.0 | 2 | — | DMSO δ 8.34 (d, J = 2.2, 1H), 7.92 (s, 1H), 7.77 (dd, J = 8.6, 2.4, 1H), 6.52 (d, J = 8.7, 1H), 6.22 (s, 2H), 4.17 (m, 4H), 3.75 (m, 4H), 3.71 (s, 2H), 3.11 (m, 4H), 2.87 (s, 3H), 2.54 (m, 4H). |
| 2-117 | 0.32 | 445.2 | 3 | 0.851 | DMSO δ 8.60 (s, 1H), 8.55 (d, J = 0.6, 1H), 7.90 (s, 1H), 7.64 (d, J = 7.0, 1H), 7.56 (d, J = 8.3, 1H), 7.42 (dd, J = 8.2, 7.3, 1H), 4.27 (m, 4H), 3.80 (m, 4H), 3.72 (s, 2H), 2.96 (m, 4H), 2.65 (t, J = 6.7, 2H), 1.62 (m, 4H). |
| 2-118 | 0.32 and 2.30 | 473.2 | 3 | 1.5 | DMSO δ 8.60 (s, 1H), 8.56 (d, J = 0.6, 1H), 8.35 (s, 1H), 7.91 (s, 1H), 7.64 (d, J = 7.1, 1H), 7.56 (d, J = 8.3, 1H), 7.42 (dd, J = 8.1, |

TABLE 4-continued

Analytical data and PI3Kα activity - $R_t$ means retention time (in minutes), [M + H]$^+$ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]$^+$ | Meth. | PI3Kα IC50 (μM) | $^1$H NMR (300 MHz; δ in ppm, J in Hz) |
|---|---|---|---|---|---|
| | | | | | 7.3, 1H), 4.27 (m, 4H), 3.80 (m, 4H), 3.72 (s, 2H), 2.96 (m, 4H), 2.65 (t, J = 6.8, 2H), 1.62 (m, 6H). |
| 2-121 | 2.91 | 534.2 | 2 | — | DMSO δ 8.04 (s, 1H), 7.98 (s, 1H), 7.96 (d, J = 8.4, 2H), 7.83 (d, J = 8.3, 2H), 7.44 (s, 1H), 4.20 (s, 4H), 3.76 (s, 4H), 3.72 (s, 2H), 3.13 (s, 4H), 2.87 (s, 3H), 2.57 (s, 4H). |
| 2-122 | 3.18 | 548.2 | 2 | 50 | DMSO δ 11.60 (s, 1H), 8.07 (s, 1H), 7.86 (s, 1H), 7.57 (d, J = 2.6, 1H), 7.48 (dd, J = 8.9, 4.3, 1H), 7.10 (m, 1H), 4.13 (s, 4H), 3.72 (t, J = 4.6, 4H), 3.69 (s, 2H), 3.13 (s, 4H), 2.87 (s, 3H), 2.58 (s, 4H). |
| 2-123 | 3.46 | 548.2 | 2 | — | DMSO δ 11.31 (s, 1H), 7.96 (s, 1H), 7.48 (dd, J = 9.0, 4.0, 1H), 7.42 (t, J = 2.7, 1H), 7.03 (dd, J = 10.3, 8.9, 1H), 6.29 (s, 1H), 4.11 (m, 4H), 3.73 (m, 4H), 3.72 (s, 2H), 3.13 (m, 4H), 2.87 (s, 3H), 2.59 (s, 4H). |
| 2-124 | 3.58 | 582.2 | 2 | — | DMSO δ 11.66 (s, 1H), 7.96 (s, 1H), 7.59 (d, J = 2.6, 1H), 7.53 (dd, J = 8.9, 4.3, 1H), 7.13 (m, 1H), 4.12 (ddd, J = 18.3, 13.5, 8.9, 4H), 3.72 (m, 4H), 3.70 (s, 2H), 3.13 (d, J = 4.7, 4H), 2.87 (s, 3H), 2.60 (s, 4H). |
| 2-125 | 3.31 | 459.2 | 3 | — | CDCl$_3$ δ 9.23 (s, 2H), 9.20 (s, 1H), 7.95 (s, 1H), 7.52 (s, 1H), 4.40 (m, 4H), 3.90 (m, 4H), 3.77 (s, 2H), 3.29 (m, 4H), 2.79 (s, 3H), 2.71 (m, 4H). |
| 2-126 | 2.21 | 472.2 | 3 | 0.776 | CDCl$_3$ δ 8.97 (s, 1H), 8.09 (d, J = 5.6, 1H), 7.90 (s, 1H), 7.49 (s, 1H), 7.24 (m, 1H), 4.36 (s, 4H), 3.89 (s, 4H), 3.76 (s, 2H), 3.28 (s, 4H), 2.78 (s, 3H), 2.70 (s, 4H), 2.60 (s, 3H). |
| 2-127 | 4.27 | 497.2 | 3 | 37 | CDCl$_3$ δ 10.38 (s, 1H), 8.31 (s, 1H), 8.13 (s, 1H), 7.90 (m, 2H), 7.52 (d, J = 8.8, 1H), 7.46 (s, 1H), 4.35 (m, 4H), 3.88 (m, 4H), 3.74 (s, 2H), 3.26 (m, 4H), 2.76 (s, 3H), 2.69 (m, 4H). |
| 2-128 | 2.71 and 2.86 | 523.3 | 2 | — | CDCl$_3$ δ 8.54 (d, J = 0.7, 1H), 7.94 (s, 1H), 7.48 (m, 3H), 7.39 (dd, J = 8.2, 6.9, 1H), 4.34 (m, 4H), 3.84 (m, 4H), 3.79 (s, 2H), 3.38 (dd, J = 9.6, 6.6, 2H), 3.16 (dd, J = 9.5, 2.4, 2H), 2.87 (m, 4H), 2.82 (s, 3H), 2.53 (d, J = 6.0, 2H). |
| 2-129 | 2.73 and 3.03 | 551.3 | 2 | 2.5 | CDCl$_3$ δ 8.54 (d, J = 0.7, 1H), 7.96 (s, 1H), 7.49 (m, 3H), 7.41 (dd, J = 8.3, 6.9, 1H), 4.35 (m, 4H), 3.86 (m, 4H), 3.81 (s, 2H), 3.16 (dd, J = 12.8, 6.3, 4H), 2.78 (m, 2H), 2.74 (s, 3H), 2.55 (s, 2H), 1.69 (m, 6H). |
| 2-130 | 2.57 and 2.80 | 487.3 | 2 | 1.4 | CDCl$_3$ δ 8.53 (m, 1H), 7.90 (t, J = 10.1, 1H), 7.49 (m, 3H), 7.38 (m, 1H), 6.23 (m, 1H), 4.33 (m, 4H), 3.85 (m, 4H), 3.73 (s, 2H), 3.31 (m, 2H), 3.00 (m, 2H), 2.27 (m, 2H), 2.03 (m, 4H), 1.48 (m, 2H). |
| 2-131 | 2.57 and 2.71 | 487.3 | 2 | 14 | CDCl$_3$ δ 10.84 (s, 1H), 8.53 (d, J = 0.8, 1H), 7.96 (s, 1H), 7.49 (m, 3H), 7.41 (dd, J = 8.3, 6.9, 1H), 5.89 (s, 1H), 4.35 (m, 4H), 3.86 (m, 4H), 3.71 (s, 2H), 3.18 (s, 2H), 2.55 (d, J = 20.1, 4H), 2.21 (s, 2H), 1.71 (t, J = 5.4, 4H). |
| 2-133 | 4.47 | 419.3 | 3 | — | DMSO δ 13.24 (s, 1H), 8.47 (s, 1H), 8.05 (s, 1H), 7.66 (d, J = 7.0, 1H), 7.57 (d, J = 8.2, 1H), 7.44 (d, J = 7.4, 1H), 7.31 (s, 1H), 4.29 (s, 4H), 3.80 (m, 4H), 3.27 (d, J = 9.8, 2H), 2.96 (dt, J = 17.2, 9.6, 2H), 2.82 (t, J = 8.7, 1H), 1.92 (m, 2H), 1.63 (dd, J = 56.7, 6.4, 2H). |
| 2-134 | 3.04 | 551.3 | 2 | 5.2 | DMSO δ 13.20 (s, 1H), 8.59 (s, 1H), 8.56 (s, 1H), 7.89 (s, 1H), 7.64 (d, J = 7.1, 1H), 7.55 (d, J = 8.3, 1H), 7.42 (dd, J = 8.2, 7.3, |

TABLE 4-continued

Analytical data and PI3Kα activity - $R_t$ means retention time (in minutes), [M + H]$^+$ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]$^+$ | Meth. | PI3Kα IC50 (μM) | $^1$H NMR (300 MHz; δ in ppm, J in Hz) |
|---|---|---|---|---|---|
| | | | | | 1H), 4.27 (m, 4H), 3.80 (m, 4H), 3.58 (s, 6H), 2.99 (s, 3H), 2.40 (s, 4H), 1.71 (s, 4H), 1.39 (s, 2H). |
| 2-135 | 0.56 | 506.2 | 3 | — | CDCl$_3$ δ 8.91 (d, J = 2.0 Hz, 1H), 7.97 (dd, J = 8.1, 2.3 Hz, 1H), 7.71 (s, 1H), 7.22 (d, J = 8.1 Hz, 1H), 4.27 (m, 4H), 3.83 (m, 4H), 3.76 (s, 2H), 3.26 (m, 4H), 2.76 (s, 3H), 2.68 (m, 4H), 2.60 (s, 3H). |
| 2-136 | 3.43 and 3.85 | 493.2 | 3 | | CDCl$_3$ δ 9.23 (s, 1H), 9.20 (s, 2H), 7.76 (s, 1H), 4.32 (m, 4H), 3.87 (m, 4H), 3.80 (s, 2H), 3.30 (m, 4H), 2.79 (s, 3H), 2.71 (m, 4H). |
| 2-137 | 5.00 | 393.2 | 2 | 0.676 | DMSO δ 13.15 (s, 1H), 8.60 (s, 2H), 8.53 (s, 1H), 7.62 (dd, J = 26.6, 4.9 Hz, 2H), 7.44 (m, 1H), 4.34 (s, 6H), 3.83 (s, 4H), 1.35 (t, J = 6.1 Hz, 3H). |
| 2-138 | 3.99 | 370.2 | 2 | 0.012 | CDCl$_3$ δ 8.78 (s, 2H), 8.06 (s, 1H), 7.75 (s, 1H), 5.14 (s, 2H), 4.40 (s, 6H), 3.87 (s, 4H), 1.40 (t, J = 7.0 Hz, 3H). |
| 2-139 | 2.75 and 2.89 | 449.3 | 2 | — | DMSO δ 8.65 (s, 1H), 8.56 (s, 1H), 8.41 (m, 1H), 7.67 (d, J = 7.1 Hz, 1H), 7.59 (d, J = 8.7 Hz, 1H), 7.44 (dd, J = 8.2, 7.3 Hz, 1H), 4.34 (m, 4H), 3.84 (m, 4H), 3.33 (m, 2H), 2.30 (m, 2H), 2.16 (s, 6H), 1.70 (d, J = 7.0 Hz, 2H). |
| 2-140 | 4.60 | 436.2 | 2 | — | DMSO δ 13.24 (s, 1H), 8.65 (s, 1H), 8.56 (s, 1H), 8.41 (s, 1H), 7.68 (d, J = 6.5 Hz, 1H), 7.58 (d, J = 8.4 Hz, 1H), 7.44 (dd, J = 8.3, 7.3 Hz, 1H), 4.34 (m, 4H), 3.83 (m, 4H), 3.38 (m, 4H), 3.26 (s, 3H), 1.80 (m, 2H). |
| 2-141 | 3.94 and 4.24 | 435.3 | 3 | 0.065 | DMSO δ 13.24 (s, 1H), 8.65 (s, 1H), 8.56 (s, 1H), 8.42 (s, 1H), 7.68 (d, J = 7.1 Hz, 1H), 7.58 (d, J = 8.2 Hz, 1H), 7.44 (dd, J = 8.2, 7.2 Hz, 1H), 4.34 (m, 4H), 3.84 (m, 4H), 3.41 (dd, J = 12.7, 6.1 Hz, 2H), 2.27 (m, 2H), 2.24 (s, 6H). |
| 2-142 | 2.90 | 477.3 | 2 | 0.038 | DMSO δ 13.24 (s, 1H), 8.65 (s, 1H), 8.56 (s, 1H), 8.42 (s, 1H), 7.68 (d, J = 6.8 Hz, 1H), 7.58 (d, J = 8.5 Hz, 1H), 7.44 (m, 1H), 4.34 (s, 4H), 3.84 (m, 4H), 3.59 (m, 4H), 3.43 (dd, J = 12.1, 6.7 Hz, 2H), 2.45 (m, 6H). |
| 2-143 | 3.05 | 393.2 | 3 | — | DMSO δ 8.83 (s, 2H), 7.99 (s, 1H), 6.81 (s, 2H), 6.00 (m, 1H), 4.22 (m, 4H), 3.75 (m, 4H), 3.35 (m, 2H), 3.15 (m, 2H), 2.34 (m, 2H), 2.30 (s, 3H). |
| 2-144 | 4.33 | 498.3 | 2 | — | DMSO δ 13.15 (s, 1H), 8.54 (t, J = 5.9 Hz, 1H), 8.08 (s, 1H), 7.96 (s, 1H), 7.59 (d, J = 8.3 Hz, 1H), 7.42 (dd, J = 8.2, 7.2 Hz, 1H), 7.29 (m, 5H), 5.45 (s, 1H), 4.67 (s, 2H), 4.32 (d, J = 5.9 Hz, 2H), 4.19 (m, 4H), 3.74 (m, 6H). |
| 2-145 | 2.91 | 537.3 | 2 | 3 | DMSO δ 13.20 (s, 1H), 8.60 (s, 1H), 8.55 (d, J = 0.7 Hz, 1H), 7.90 (s, 1H), 7.64 (d, J = 7.1 Hz, 1H), 7.55 (d, J = 8.3 Hz, 1H), 7.42 (dd, J = 8.2, 7.2 Hz, 1H), 4.27 (m, 4H), 3.81 (m, 4H), 3.59 (m, 6H), 2.98 (s, 3H), 2.40 (s, 4H), 1.72 (t, J = 4.8 Hz, 4H). |
| 2-146 | 3.24 | 397.2 | 2 | 0.295 | DMSO δ 9.16 (s, 1H), 8.67 (s, 1H), 8.58 (d, J = 4.1 Hz, 1H), 8.43 (t, J = 5.3 Hz, 1H), 8.33 (s, 1H), 8.31 (s, 1H), 7.50 (dd, J = 7.6, 5.0 Hz, 1H), 4.33 (s, 4H), 3.81 (s, 4H), 3.39 (m, 4H), 3.25 (s, 3H), 1.78 (m, 2H). |
| 2-147 | 0.38 and 1.62 | 396.2 | 3 | 0.832 | DMSO δ 9.16 (dd, J = 2.2, 0.6 Hz, 1H), 8.68 (s, 1H), 8.58 (dd, J = 4.8, 1.6 Hz, 1H), 8.33 (q, J = 1.9 Hz, 1H), 8.30 (s, 2H), 7.50 (ddd, J = 8.0, 4.8, 0.6 Hz, 1H), 4.33 (m, |

TABLE 4-continued

Analytical data and PI3Kα activity - R$_t$ means retention time (in minutes),
[M + H]$^+$ means the protonated mass of the compound, method refers to the method used for (LC)MS.
Biological activity in PI3Kα for certain examples is represented in Table 4 by semi-quantative results: IC50 > 1 µM (+), IC50 < 100 nM (+++), 100 nM < IC50 < 1 µM (++).
Biological activity in PI3Kα for certain examples is also represented in Table 4 by quantative results.

| Cpd. Nr. | R$_t$ | [M + 1]$^+$ | Meth. | PI3Kα IC50 (µM) | $^1$H NMR (300 MHz; δ in ppm, J in Hz) |
|---|---|---|---|---|---|
| | | | | | 4H), 3.81 (m, 4H), 3.39 (dd, J = 13.2, 6.7 Hz, 2H), 2.42 (t, J = 6.9 Hz, 2H), 2.19 (s, 6H). |
| 2-148 | 3.04 | 383.2 | 2 | 0.617 | DMSO δ 9.16 (d, J = 1.7 Hz, 1H), 8.67 (s, 1H), 8.58 (dd, J = 4.7, 1.6 Hz, 1H), 8.41 (t, J = 5.0 Hz, 1H), 8.31 (m, 2H), 7.50 (dd, J = 8.0, 4.8 Hz, 1H), 4.33 (m, 4H), 3.81 (m, 4H), 3.48 (m, 4H), 3.28 (s, 3H). |
| 2-149 | 3.08 | 565.3 | 2 | 1.3 | DMSO δ 13.20 (s, 1H), 8.61 (s, 1H), 8.55 (d, J = 0.8 Hz, 1H), 7.91 (s, 1H), 7.64 (dd, J = 7.1, 0.6 Hz, 1H), 7.55 (d, J = 8.3 Hz, 1H), 7.43 (dd, J = 8.3, 7.2 Hz, 1H), 4.28 (m, 4H), 3.81 (m, 4H), 3.66 (s, 2H), 3.08 (m, 4H), 2.84 (s, 3H), 2.50 (s, 4H), 1.49 (s, 8H). |
| 2-150 | 2.97 | 537.3 | 2 | 2.8 | DMSO δ 13.21 (s, 1H), 8.61 (s, 1H), 8.55 (d, J = 0.8 Hz, 1H), 7.90 (s, 1H), 7.65 (dd, J = 7.1, 0.5 Hz, 1H), 7.56 (d, J = 8.3 Hz, 1H), 7.43 (dd, J = 8.3, 7.2 Hz, 1H), 4.27 (m, 4H), 3.80 (m, 6H), 3.13 (s, 4H), 3.05 (m, 4H), 2.82 (s, 3H), 1.77 (m, 4H). |
| 2-151 | 5.73 | 530.2 | 3 | — | DMSO δ 11.22 (s, 1H), 8.19 (s, 1H), 7.93 (s, 1H), 7.47 (s, 2H), 7.41 (m, 1H), 6.51 (m, 1H), 4.20 (m, 4H), 3.77 (m, 4H), 3.72 (s, 2H), 3.13 (m, 4H), 2.87 (s, 3H), 2.57 (m, 4H). |
| 2-152 | 0.32 | 472.2 | 3 | 0.468 | CDCl$_3$ δ 8.55 (s, 1H), 8.43 (d, J = 5.0 Hz, 1H), 7.55 (s, 1H), 7.46 (s, 1H), 7.16 (d, J = 5.0 Hz, 1H), 4.26 (m, 4H), 3.82 (m, 4H), 3.73 (s, 2H), 3.24 (m, 4H), 2.75 (s, 3H), 2.67 (m, 4H), 2.42 (s, 3H). |
| 2-153 | 3.07 | 502.2 | 2 | 2.4 | CDCl$_3$ δ 8.12 (s, 1H), 7.50 (s, 1H), 7.44 (s, 1H), 6.63 (s, 1H), 4.26 (m, 4H), 3.93 (s, 3H), 3.83 (m, 4H), 3.74 (s, 2H), 3.26 (m, 4H), 2.76 (s, 3H), 2.68 (m, 4H), 2.37 (s, 3H). |
| 2-154 | 3.04 | 383.2 | 2 | 0.166 | DMSO δ 9.16 (d, J = 1.7 Hz, 1H), 8.67 (s, 1H), 8.58 (dd, J = 4.7, 1.6 Hz, 1H), 8.41 (t, J = 5.0, 1H), 8.31 (m, 2H), 7.50 (dd, J = 8.0, 4.8, 1H), 4.33 (m, 4H), 3.81 (m, 4H), 3.48 (s, 4H), 3.28 (s, 3H). |
| 2-155 | 3.08 | 548.2 | 2 | — | DMSO δ 13.23 (s, 1H), 8.49 (t, J = 5.9, 1H), 8.07 (s, 1H), 7.84 (s, 1H), 7.78 (s, 1H), 7.62 (d, J = 8.4, 1H), 7.46-7.37 (m, 1H), 7.37-7.20 (m, 5H), 7.16 (d, J = 6.8, 1H), 6.96 (d, J = 3.9, 2H), 5.48 (s, 2H), 4.29 (d, J = 5.9, 2H), 4.22 (s, 4H), 3.81-3.69 (m, 4H), 3.65 (s, 2H). |
| 2-156 | 4.98 | 488.3 | 2 | — | CDCl$_3$ δ 8.53 (s, 1H), 7.80 (s, 1H), 7.62-7.34 (m, 3H), 4.89 (s, 1H), 4.36 (m, 4H), 4.12 (m, 1H), 3.89 (m, 4H), 3.25 (m, 2H), 2.86 (m, 1H), 2.62 (m, 1H), 2.46 (s, 3H), 1.90 (m, 4H), 1.16 (m, 6H). |
| 2-157 | 3.93 | 449.2 | 2 | 0.776 | DMSO δ 13.23 (s, 1H), 8.64 (s, 1H), 8.80 (m, 2H), 8.42 (s, 1H), 8.05 (m, 1H), 7.67 (d, J = 6.8, 1H), 7.57 (d, J = 8.3, 1H), 7.45 (m, 1H), 4.34 (m, 4H), 3.85 (m, 4H), 3.35 (m, 2H), 3.26 (m, 2H), 1.82 (s, 3H). |
| 2-158 | 2.75 | 410.2 | 2 | 2.3 | DMSO δ 9.17 (d, J = 1.6 Hz, 1H), 8.67 (s, 1H), 8.57 (m, 2H), 8.32 (m, 2H), 8.05 (m, 1H), 7.50 (dd, J = 7.7, 5.1, 1H), 4.34 (m, 4H), 3.81 (m, 4H), 3.33 (m, 2H), 3.24 (m, 2H), 1.80 (s, 3H). |
| 2-159 | 0.37 | 438.2 | 3 | 0.398 | DMSO δ 9.16 (d, J = 1.6 Hz, 1H), 8.68 (s, 1H), 8.58 (dd, J = 4.7, 1.6 Hz, 1H), 8.28 (m, 3H), 7.50 (dd, J = 8.0, 4.2, 1H), 4.33 (s, 4H), 3.78 (m, 4H), 3.55 (m, 4H), 3.42 (m, 2H), 2.49 (m, 2H), 2.45 (m, 4H). |

TABLE 4-continued

Analytical data and PI3Kα activity - $R_t$ means retention time (in minutes), [M + H]⁺ means the protonated mass of the compound, method refers to the method used for (LC)MS.
Biological activity in PI3Kα for certain examples is represented in Table 4 by semi-quantitative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| 2-160 | 0.37 | 426.2 | 3 | — | DMSO δ 8.79 (s, 2H), 8.57 (s, 1H), 8.46 (s, 1H), 8.23 (s, 1H), 6.89 (s, 2H), 4.31 (s, 4H), 3.81 (s, 4H), 2.35 (s, 2H), 2.25 (s, 6H), 1.69 (m, 2H), 1.23 (s, 2H). |
| 2-161 | 3.73 | 413.1 | 2 | — | DMSO δ 8.77 (s, 2H), 8.44 (s, 1H), 8.39 (m, 1H), 8.21 (s, 1H), 6.88 (s, 2H), 4.29 (s, 4H), 3.79 (s, 4H), 3.38 (m, 4H), 3.25 (s, 3H), 1.75 (m, 2H). |
| 2-162 | 0.39 and 2.74 | 412.3 | 3 | — | DMSO δ 8.79 (s, 2H), 8.46 (s, 1H), 8.30 (s, 1H), 8.23 (s, 1H), 6.89 (s, 2H), 4.30 (s, 4H), 3.80 (s, 4H), 3.39 (s, 2H), 2.42 (s, 2H), 2.20 (s, 6H). |
| 2-163 | 5.57 | 399.2 | 3 | — | DMSO δ 8.78 (s, 2H), 8.45 (s, 1H), 8.36 (s, 1H), 8.23 (s, 1H), 6.88 (s, 2H), 4.29 (m, 4H), 4.80 (m, 4H), 3.46 (m, 4H), 3.27 (s, 3H). |
| 2-164 | 0.37 and 2.85 | 454.3 | 3 | 0.011 | DMSO δ 8.77 (s, 2H), 8.45 (s, 1H), 8.28 (m, 1H), 8.20 (s, 1H), 6.88 (s, 2H), 4.29 (s, 4H), 3.79 (s, 4H), 3.59 (s, 4H), 3.49 (m, 2H), 2.43 (m, 6H). |
| 2-165 | 0.38 | 488.3 | 3 | — | DMSO δ 8.81 (s, 2H), 8.09 (s, 1H), 6.75 (s, 2H), 4.16 (s, 4H), 3.69 (m, 4H), 3.58 (s, 2H), 3.02 (s, 4H), 2.78 (s, 3H), 2.44 (m, 7H). |
| 2-167 | 3.49 | 536.2 | 2 | — | CDCl₃ δ 8.10 (s, 1H), 7.70 (s, 1H), 6.68 (s, 1H), 4.24 (m, 4H), 3.96 (s, 3H), 3.82 (m, 4H), 3.75 (s, 2H), 3.28 (m, 4H), 2.80 (s, 3H), 2.71 (m, 4H), 2.23 (s, 2H). |
| 2-169 | 0.33 and 3.07 | 514.3 | 3 | 0.11 | DMSO δ 8.76 (s, 2H), 8.40 (s, 1H), 7.70 (s, 1H), 6.82 (s, 2H), 4.22 (m, 4H), 3.76 (m, 4H), 3.69 (s, 2H), 3.32 (s, 4H), 3.04 (s, 4H), 2.81 (s, 3H), 1.74 (m, 4H). |
| 2-170 | 2.14 | 500.3 | 2 | — | DMSO δ 8.76 (s, 2H), 8.40 (s, 1H), 7.75 (s, 1H), 6.82 (s, 2H), 4.22 (m, 4H), 3.76 (m, 4H), 3.68 (s, 2H), 3.38 (m, 2H), 2.96 (dd, J = 9.9, 3.8, 2H), 2.90 (s, 3H), 2.81 (m, 2H), 2.59 (m, 2H). |
| 2-171 | 4.13 | 338.2 | 2 | 0.05 | DMSO δ 8.76 (s, 2H), 8.34 (s, 1H), 7.63 (s, 1H), 6.81 (s, 2H), 4.19 (m, 4H), 3.75 (m, 4H), 2.03 (m, 1H), 0.91 (m, 2H), 0.79 (m, 2H). |
| 2-172 | 4.72 | 366.2 | 2 | 0.032 | DMSO δ 8.79 (s, 2H), 8.47 (d, J = 0.8, 1H), 8.44 (s, 1H), 6.92 (s, 2H), 4.23 (m, 4H), 3.78 (m, 4H). |
| 2-173 | 0.33 and 2.59 | 506.2 | 3 | — | CDCl₃ δ 8.54 (s, 2H), 7.74 (s, 1H), 7.30 (d, J = 4.2, 1H), 4.25 (m, 4H), 3.86 (s, 2H), 3.83 (m, 4H), 3.32 (m, 4H), 2.79 (s, 7H), 2.32 (s, 3H). |
| 2-174 | 3.11 | 298.2 | 2 | 0.191 | DMSO δ 8.78 (s, 2H), 8.46 (s, 1H), 7.89 (d, J = 1.0, 1H), 7.56 (d, J = 1.0, 1H), 6.84 (s, 2H), 4.26 (m, 4H), 3.76 (m, 4H). |
| 2-175 | 0.32 and 2.40 | 397.2 | 3 | 0.083 | DMSO δ 8.76 (s, 2H), 8.40 (s, 1H), 7.75 (s, 1H), 6.83 (s, 2H), 4.22 (m, 4H), 3.76 (m, 4H), 3.57 (m, 6H), 2.44 (m, 4H). |
| 2-176 | 4.29 | 405.2 | 3 | — | DMSO δ 8.75 (s, 2H), 8.37 (s, 1H), 8.19 (d, J = 6.4, 2H), 7.58 (s, 1H), 6.82 (s, 2H), 6.46 (s, 2H), 4.21 (d, J = 4.4, 4H), 3.85 (s, 2H), 3.76 (m, 4H). |
| 2-177 | 3.45 | 356.2 | 2 | — | DMSO δ 8.77 (s, 2H), 8.42 (s, 1H), 7.67 (s, 1H), 6.82 (s, 2H), 5.09 (s, 1H), 4.23 (s, 4H), 3.76 (s, 4H), 1.48 (s, 6H). |
| 2-178 | 2.72 | 553.2 | 2 | — | DMSO δ 8.81 (s, 2H), 8.04 (s, 1H), 6.82 (s, 2H), 4.18 (s, 4H), 3.71 (m, 4H), 3.60 (s, 2H), 3.03 (s, 4H), 2.79 (s, 3H), 2.48 (d, J = 4.7, 4H). |

TABLE 4-continued

Analytical data and PI3Kα activity - $R_t$ means retention time (in minutes), [M + H]⁺ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| 2-179 | 3.76 | 460.2 | 2 | — | DMSO δ 8.88 (s, 2H), 7.91 (s, 1H), 7.30 (s, 1H), 6.89 (s, 2H), 4.25 (s, 4H), 3.75 (m, 4H), 3.39 (m, 4H), 3.12 (m, 4H), 2.99 (s, 3H). |
| 2-180 | 0.32 and 3.18 | 499.2 | 3 | — | DMSO δ 8.74 (s, 2H), 7.88 (s, 1H), 7.23 (s, 2H), 4.44 (s, 4H), 3.77 (s, 4H), 3.70 (s, 2H), 3.12 (s, 4H), 2.87 (s, 3H), 2.56 (s, 4H). |
| 2-181 | 3.17 | 312.2 | 2 | 0.11 | DMSO δ 8.76 (s, 2H), 8.37 (s, 1H), 7.61 (s, 1H), 6.80 (s, 2H), 4.21 (s, 4H), 3.75 (s, 4H), 2.33 (s, 3H). |
| 2-182 | 5.08 | 519.2 | 2 | 0.245 | DMSO δ 13.24 (s, 1H), 8.64 (s, 1H), 8.55 (s, 1H), 8.43 (s, 1H), 8.12 (d, J = 8.6, 1H), 7.67 (d, J = 7.1, 1H), 7.58 (d, J = 8.1, 1H), 7.43 (d, J = 8.2, 1H), 4.33 (s, 4H), 4.05 (m, 6H), 3.83 (m, 4H), 2.91 (m, 1H), 1.77 (m, 2H), 1.56 (m, 2H), 1.20 (t, J = 7.1, 3H). |
| 2-183 | 3.45 | 576.2 | 2 | 0.17 | DMSO δ 13.22 (s, 1H), 8.46 (s, 1H), 8.11 (s, 1H), 7.65 (d, J = 7.1, 1H), 7.60 (d, J = 8.3, 1H), 7.46 (d, J = 7.3, 1H), 4.30 (m, 4H), 3.82 (m, 4H), 3.71 (s, 2H), 3.11 (m, 4H), 2.86 (s, 3H), 2.58 (m, 4H). |
| 2-184 | 3.05 | 355.2 | 2 | — | DMSO δ 8.64 (s, 2H), 8.30 (s, 1H), 8.22 (s, 1H), 8.07 (s, 1H), 6.74 (s, 2H), 4.16 (m, 4H), 3.65 (m, 4H), 2.68 (d, J = 3.9, 3H). |
| 2-185 | 4.10 | 346.2 | 2 | — | DMSO δ 8.62 (s, 2H), 7.85 (d, J = 0.8, 1H), 6.94 (s, 2H), 4.17 (m, 4H), 3.74 (m, 4H), 2.38 (d, J = 0.5, 3H). |
| 2-186 | 4.15 | 422.2 | 2 | 0.066 | DMSO δ 13.17 (s, 1H), 8.58 (s, 1H), 8.49 (s, 1H), 8.35 (s, 1H), 8.31 (m, 1H), 7.61 (d, J = 7.2, 1H), 7.51 (d, J = 8.2, 1H), 7.39 (d, J = 7.2, 1H), 4.27 (m, 4H), 3.77 (m, 4H), 3.42 (m, 4H), 3.21 (s, 4H). |
| 2-187 | 4.02 | 337.2 | 2 | — | DMSO δ 8.74 (s, 2H), 7.83 (s, 1H), 7.20 (s, 2H), 4.43 (s, 4H), 3.76 (m, 4H), 2.37 (s, 3H). |
| 2-188 | 4.03 | 496.2 | 2 | 0.003 | DMSO δ 8.77 (s, 2H), 8.44 (s, 1H), 8.25 (s, 1H), 8.09 (d, J = 8.5, 1H), 6.88 (s, 2H), 4.28 (s, 4H), 4.04 (m, 5H), 3.79 (m, 4H), 2.87 (s, 2H), 1.78 (d, J = 9.9, 2H), 1.57 (dt, J = 12.2, 8.4, 2H), 1.19 (t, J = 7.1, 3H). |
| 2-189 | 3.39 | 389.2 | 2 | — | DMSO δ 8.65 (s, 2H), 8.46 (s, 1H), 8.33 (s, 1H), 6.99 (s, 2H), 4.26 (s, 4H), 3.78 (m, 4H), 2.83 (d, J = 4.8, 3H). |
| 2-190 | 3.11 | 311.2 | 2 | — | CDCl₃ δ 8.83 (d, J = 1.8, 2H), 8.14 (s, 1H), 7.44 (s, 1H), 5.43 (s, 2H), 4.10 (dd, J = 11.4, 3.4, 2H), 3.84 (m, 1H), 3.67 (t, J = 11.5, 2H), 2.49 (s, 3H), 2.15 (m, 2H), 1.90 (m, 2H). |
| 2-191 | 3.53 | 425.2 | 2 | 0.013 | DMSO δ 8.71 (s, 2H), 8.38 (s, 1H), 8.18 (s, 1H), 8.03 (d, J = 8.4, 1H), 6.81 (s, 2H), 4.22 (m, 4H), 3.96 (s, 1H), 3.83 (d, J = 11.1, 2H), 3.73 (m, 4H), 3.33 (m, 2H), 1.66 (m, 4H). |
| 2-192 | 3.40 | 439.2 | 2 | 0.01 | DMSO δ 8.70 (s, 2H), 8.37 (s, 1H), 8.15 (s, 1H), 7.83 (d, J = 8.5, 1H), 6.80 (s, 2H), 4.50 (d, J = 4.4, 1H), 4.20 (s, 4H), 3.72 (m, 4H), 3.33 (m, 1H), 1.75 (m, 4H), 1.42 (m, 2H), 1.18 (m, 2H). |
| 2-193 | 4.64 | 510.3 | 2 | — | DMSO δ 8.77 (s, 2H), 8.44 (s, 1H), 8.22 (s, 1H), 6.89 (s, 2H), 4.24 (m, 4H), 4.02 (m, 2H), 3.78 (m, 4H), 3.63 (m, 2H), 3.41 (m, 4H), 1.42 (s, 9H). |
| 2-194 | 3.77 | 433.3 | 2 | — | DMSO δ 8.66 (s, 2H), 8.50 (s, 1H), 8.36 (s, 1H), 7.00 (s, 2H), 4.25 (m, 4H), 3.78 (m, 4H), 3.48 (m, 4H), 3.28 (s, 3H). |
| 2-195 | 4.52 | 382.2 | 2 | — | DMSO δ 8.76 (s, 2H), 8.37 (s, 1H), 7.65 (s, 1H), 6.81 (s, 2H), 4.23 (m, 4H), 3.92 (d, J = 9.5, 2H), 3.77 (m, 4H), 3.46 (t, J = 10.8, |

TABLE 4-continued

Analytical data and PI3Kα activity - R_t means retention time (in minutes), [M + H]+ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | R_t | [M + 1]+ | Meth. | PI3Kα IC50 (μM) | 1H NMR (300 MHz; δ in ppm, J in Hz) |
|---|---|---|---|---|---|
| | | | | | 2H), 2.93 (m, 1H), 1.91 (d, J = 12.5, 2H), 1.69 (m, 2H). |
| 2-196 | 2.58 | 473.2 | 2 | 0.021 | DMSO δ 9.20 (s, 2H), 8.67 (s, 1H), 7.83 (s, 1H), 4.26 (m, 4H), 3.78 (m, 4H), 3.68 (s, 2H), 3.12 (m, 4H), 2.87 (s, 3H), 2.66 (s, 3H), 2.56 (m, 4H). |
| 2-197 | 2.96 | 497.2 | 2 | — | DMSO δ 13.13 (s, 1H), 8.64 (s, 1H), 8.16 (s, 1H), 8.08 (s, 1H), 7.85 (s, 1H), 7.81 (d, J = 8.6, 1H), 7.69 (d, J = 8.5, 1H), 4.28 (m, 4H), 3.81 (m, 4H), 3.68 (s, 2H), 3.12 (s, 4H), 2.87 (s, 3H), 2.57 (s, 4H). |
| 2-198 | 0.37 | 487.2 | 2 | — | DMSO δ 8.39 (s, 1H), 8.35 (s, 1H), 7.76 (s, 2H), 5.96 (s, 2H), 4.22 (m, 4H), 3.77 (m, 4H), 3.66 (s, 2H), 3.11 (m, 4H), 2.87 (s, 3H), 2.56 (m, 4H), 2.11 (s, 3H). |
| 2-199 | 0.37 and 2.47 | 488.2 | 2 | — | DMSO δ 8.82 (s, 2H), 8.40 (s, 1H), 7.77 (s, 1H), 7.31 (q, J = 4.9, 1H), 4.23 (m, 4H), 3.76 (m, 4H), 3.66 (s, 2H), 3.10 (m, 4H), 2.87 (s, 3H), 2.84 (d, J = 4.8, 3H), 2.53 (m, 4H). |
| 2-200 | 0.36 and 1.99 | 488.2 | 2 | 0.032 | DMSO δ 8.24 (s, 1H), 8.05 (s, 1H), 7.81 (s, 1H), 6.67 (s, 2H), 4.17 (m, 4H), 3.75 (m, 4H), 3.67 (s, 2H), 3.11 (m, 4H), 2.87 (s, 3H), 2.55 (m, 4H), 2.39 (s, 3H). |
| 2-201 | 0.35 and 2.88 | 483.2 | 2 | 3.3 | DMSO δ 9.33 (d, J = 2.3, 1H), 8.84 (s, 1H), 8.56 (dd, J = 8.2, 2.2, 1H), 8.13 (d, J = 8.2, 1H), 7.86 (s, 1H), 4.28 (s, 4H), 3.78 (m, 4H), 3.69 (s, 2H), 3.12 (m, 4H), 2.87 (s, 3H), 2.56 (m, 4H). |
| 2-202 | 0.36 and 2.75 | 542.2 | 2 | — | DMSO δ 8.56 (s, 1H), 8.08 (s, 1H), 7.86 (s, 1H), 7.45 (s, 2H), 4.16 (m, 4H), 3.72 (m, 4H), 3.67 (s, 2H), 3.11 (m, 4H), 2.87 (s, 3H), 2.52 (m, 4H). |
| 2-203 | 0.36 | 473.2 | 2 | — | DMSO δ 8.55 (s, 1H), 7.94 (d, J = 5.4, 1H), 7.86 (s, 1H), 7.07 (s, 1H), 6.97 (d, J = 6.9, 1H), 5.97 (s, 2H), 4.26 (m, 4H), 3.78 (m, 4H), 3.67 (s, 2H), 3.12 (m, 4H), 2.87 (s, 3H), 2.56 (m, 4H). |
| 2-204 | 0.35 | 488.2 | 2 | 10 | DMSO δ 9.11 (s, 1H), 8.60 (s, 1H), 8.43 (d, J = 5.7, 1H), 7.95 (s, 1H), 7.18 (d, J = 5.8, 1H), 4.21 (m, 4H), 3.99 (s, 3H), 3.79 (m, 4H), 3.67 (s, 2H), 3.12 (m, 4H), 2.87 (s, 3H), 2.56 (m, 4H). |
| 2-205 | 0.36 and 2.23 | 491.2 | 2 | — | DMSO δ 8.43 (s, 1H), 8.38 (s, 1H), 7.85 (d, J = 12.7, 1H), 7.75 (s, 1H), 6.39 (s, 2H), 4.23 (m, 4H), 3.77 (m, 4H), 3.66 (s, 2H), 3.11 (m, 4H), 2.87 (s, 3H), 2.52 (m, 4H). |
| 2-206 | 3.20 | 517.2 | 2 | 3.7 | DMSO δ 9.16 (d, J = 1.4, 1H), 8.44 (dd, J = 8.1, 2.2, 1H), 8.18 (d, J = 8.2, 1H), 8.05 (s, 1H), 4.22 (m, 4H), 3.76 (m, 4H), 3.73 (s, 2H), 3.12 (m, 4H), 2.87 (s, 3H), 2.56 (m, 4H). |
| 2-207 | 2.72 and 2.85 | 522.2 | 2 | 0.011 | DMSO δ 8.70 (s, 2H), 7.95 (s, 1H), 7.45 (m, 1H), 4.19 (m, 4H), 3.75 (m, 4H), 3.71 (s, 2H), 3.12 (m, 4H), 2.86 (s, 3H), 2.83 (d, J = 6.3, 3H), 2.56 (m, 4H). |
| 2-208 | 0.36 and 2.32 | 522.2 | 2 | — | DMSO δ 8.15 (s, 1H), 7.93 (s, 1H), 6.76 (s, 2H), 4.15 (m, 4H), 3.74 (m, 4H), 3.72 (s, 2H), 3.12 (m, 4H), 2.87 (s, 3H), 2.57 (m, 4H), 2.19 (s, 3H). |
| 2-209 | 2.96 and 3.09 | 576.2 | 2 | — | DMSO δ 8.56 (s, 1H), 7.96 (s, 1H), 7.59 (s, 2H), 4.14 (m, 4H), 3.72 (m, 6H), 3.12 (m, 4H), 2.87 (s, 3H), 2.54 (m, 4H). |
| 2-210 | 0.37 and 1.70 | 507.2 | 2 | — | DMSO δ 7.98 (m, 2H), 6.84 (m, 2H), 6.04 (s, 2H), 4.20 (m, 4H), 3.76 (m, 4H), 3.72 (s, 2H), 3.12 (m, 4H), 2.87 (s, 3H), 2.53 (m, 4H). |

TABLE 4-continued

Analytical data and PI3Kα activity - $R_t$ means retention time (in minutes), [M + H]⁺ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]⁺ | Meth. | PI3Kα IC50 (μM) | ¹H NMR (300 MHz; δ in ppm, J in Hz) |
|---|---|---|---|---|---|
| 2-211 | 0.36 | 522.2 | 2 | — | DMSO δ 8.53 (d, J = 5.8, 1H), 8.40 (s, 1H), 7.94 (s, 1H), 7.20 (d, J = 5.9, 1H), 4.14 (m, 4H), 3.86 (s, 3H), 3.73 (m, 6H), 3.12 (m, 4H), 2.87 (s, 3H), 2.57 (m, 4H). |
| 2-212 | 2.85 | 507.2 | 2 | — | MeOD δ 9.13 (s, 2H), 8.02 (s, 1H), 4.30 (m, 4H), 3.85 (dd, J = 9.2, 4.5, 4H), 3.82 (s, 2H), 3.27 (m, 4H), 2.86 (s, 3H), 2.77 (s, 3H), 2.71 (m, 4H). |
| 2-213 | 3.24 | 531.2 | 2 | — | MeOD δ 8.10 (s, 1H), 7.99 (s, 1H), 7.92 (s, 1H), 7.84 (d, J = 8.4, 1H), 7.56 (d, J = 8.2, 1H), 4.27 (m, 4H), 3.83 (m, 6H), 3.27 (m, 4H), 2.84 (s, 3H), 2.68 (m, 4H). |
| 2-214 | 4.16 | 384.2 | 2 | — | DMSO δ 8.91 (s, 2H), 8.23 (s, 1H), 6.89 (s, 2H), 4.32 (m, 6H), 3.78 (m, 4H), 2.74 (s, 3H), 1.33 (t, J = 7.1, 3H). |
| 2-215 | 0.35 | 413.2 | 2 | — | DMSO δ 8.90 (s, 2H), 8.27 (s, 1H), 8.20 (s, 1H), 6.86 (s, 2H), 4.28 (m, 4H), 3.78 (m, 4H), 3.45 (m, 4H), 3.28 (s, 3H), 2.75 (s, 3H). |
| 2-216 | 3.76 | 433.2 | 2 | — | DMSO δ 8.91 (s, 2H), 8.44 (s, 1H), 8.20 (s, 1H), 6.92 (s, 2H), 4.29 (s, 4H), 3.79 (s, 4H), 3.45 (m, 4H), 3.25 (s, 3H). |
| 2-217 | 4.79 | 355.2 | 3 | — | DMSO δ 8.90 (s, 2H), 8.18 (s, 1H), 7.77 (s, 1H), 7.35 (s, 1H), 6.85 (s, 2H), 4.28 (s, 4H), 3.77 (m, 4H), 2.74 (s, 3H). |
| 2-218 | 3.53 and 3.76 | 524.3 | 2 | 0.028 | DMSO δ 8.75 (s, 2H), 8.38 (s, 1H), 7.78 (s, 1H), 6.82 (s, 2H), 4.25 (s, 4H), 4.00 (s, 2H), 3.76 (s, 6H), 2.36 (s, 2H), 1.34 (s, 9H), 1.15 (d, J = 5.8, 6H). |
| 2-219 | 0.39 | 502.2 | 3 | 0.003 | DMSO δ 8.76 (s, 2H), 8.39 (s, 1H), 7.80 (s, 1H), 6.82 (s, 2H), 4.25 (s, 4H), 4.02 (s, 2H), 3.76 (m, 4H), 3.34 (m, 2H), 2.84 (s, 3H), 2.53 (m, 2H), 1.20 (d, J = 5.8, 6H). |
| 2-220 | 0.43 | 488.2 | 3 | 0.013 | DMSO δ 8.77 (s, 2H), 8.41 (s, 1H), 7.76 (s, 1H), 6.83 (s, 2H), 4.23 (m, 4H), 3.77 (m, 4H), 3.65 (s, 2H), 3.18 (m, 4H), 3.04 (q, J = 7.4, 2H), 2.51 (m, 4H), 1.20 (t, J = 7.4, 3H). |
| 2-221 | 3.73 and 4.03 | 516.3 | 3 | 0.011 | DMSO δ 8.76 (s, 2H), 8.41 (s, 1H), 7.76 (s, 1H), 6.83 (s, 2H), 4.22 (m, 4H), 3.76 (m, 4H), 3.66 (s, 2H), 3.14 (m, 4H), 2.88 (m, 2H), 2.51 (m, 4H), 2.11 (m, 1H), 1.01 (d, J = 6.5, 6H). |
| 2-222 | 4.07 | 445.1 | 3 | 0.082 | DMSO δ 8.57 (s, 2H), 8.21 (s, 1H), 7.60 (s, 1H), 6.63 (s, 2H), 4.03 (s, 4H), 3.61 (s, 2H), 3.56 (m, 4H), 2.89 (m, 4H), 2.76 (m, 4H). |
| 2-225 | 4.23 | 536.3 | 3 | — | DMSO δ 8.74 (s, 2H), 8.35 (s, 1H), 7.70 (m, 6H), 6.82 (s, 2H), 4.20 (s, 4H), 3.74 (m, 4H), 3.60 (s, 2H), 2.90 (s, 4H), 2.50 (m, 4H). |
| 2-226 | 0.36 | 396.3 | 4 | 0.077 | DMSO δ 8.76 (s, 2H), 8.40 (s, 1H), 7.72 (s, 1H), 6.82 (s, 2H), 4.22 (s, 4H), 3.76 (m, 4H), 3.55 (s, 2H), 3.35 (s, 1H), 2.69 (m, 4H), 2.37 (m, 4H). |
| 2-228 | 0.35 and 2.84 | 500.4 | 3 | 0.108 | DMSO δ 8.77 (s, 2H), 8.40 (s, 1H), 7.80 (s, 1H), 6.83 (s, 2H), 4.21 (m, 4H), 3.76 (m, 4H), 3.63 (s, 2H), 3.38 (s, 2H), 3.19 (dd, J = 10.7, 2.3, 2H), 2.96 (d, J = 10.0, 2H), 2.85 (s, 3H), 1.99 (m, 2H), 1.66 (q, J = 6.1, 2H). |
| 2-229 | 0.35 and 0.87 | 411.3 | 3 | 0.114 | DMSO δ 8.76 (s, 2H), 8.40 (s, 1H), 7.72 (s, 1H), 6.82 (s, 2H), 4.52 (d, J = 4.1, 1H), 4.22 (s, 4H), 3.76 (m, 4H), 3.56 (s, 2H), 3.42 (m, 1H), 2.75 (m, 2H), 2.10 (t, J = 9.7, 2H), 1.69 (m, 2H), 1.40 (m, 2H). |

TABLE 4-continued

Analytical data and PI3Kα activity - $R_t$ means retention time (in minutes), [M + H]$^+$ means the protonated mass of the compound, method refers to the method used for (LC)MS.
Biological activity in PI3Kα for certain examples is represented in Table 4 by semi-quantative results: IC50 > 1 μM (+), IC50 < 100 nM (+++), 100 nM < IC50 < 1 μM (++).
Biological activity in PI3Kα for certain examples is also represented in Table 4 by quantative results.

| Cpd. Nr. | $R_t$ | [M + 1]$^+$ | Meth. | PI3Kα IC50 (μM) | $^1$H NMR (300 MHz; δ in ppm, J in Hz) |
|---|---|---|---|---|---|
| 2-230 | 0.34 | 481.4 | 3 | 0.034 | DMSO δ 8.77 (s, 2H), 8.41 (s, 1H), 7.76 (s, 1H), 6.83 (s, 2H), 4.23 (s, 4H), 3.76 (m, 4H), 3.62 (s, 2H), 3.52 (m, 2H), 3.44 (m, 2H), 3.05 (s, 2H), 2.43 (m, 4H), 2.16 (s, 6H). |
| 2-231 | 0.34 | 510.4 | 3 | 0.085 | DMSO δ 8.77 (s, 2H), 8.41 (s, 1H), 7.77 (s, 1H), 6.83 (s, 2H), 5.34 (q, J = 6.8, 1H), 4.23 (s, 4H), 3.77 (m, 4H), 3.64 (s, 2H), 3.45 (m, 4H), 2.49 (m, 2H), 2.41 (m, 2H), 2.02 (s, 3H), 1.28 (d, J = 6.7, 3H). |
| 2-232 | 0.42 and 3.03 | 524.2 and 424.2 | 2 | — | MeOD δ 8.80 (s, 2H), 8.18 (s, 1H), 7.70 (s, 1H), 7.54 (m, 2H), 4.31 (s, 4H), 3.85 (s, 4H), 3.40 (s, 4H), 2.52 (s, 4H), 1.54 (s, 6H), 1.42 (s, 9H). |
| 2-233 | 2.40 and 2.87 | 502.2 | 3 | — | DMSO δ 8.80 (s, 2H), 8.44 (s, 1H), 7.77 (s, 1H), 6.86 (s, 2H), 4.25 (m, 4H), 3.79 (m, 6H), 3.59 (s, 3H), 2.87 (m, 3H), 2.72 (m, 2H), 2.28 (s, 3H), 1.91 (m, 2H), 1.54 (m, 2H). |
| 2-234 | 0.39 | 468.2 | 3 | — | DMSO δ 8.77 (s, 2H), 8.42 (s, 1H), 7.77 (s, 1H), 6.85 (s, 2H), 4.85 (d, J = 7.0, 1H), 4.40 (m, 1H), 4.23 (m, 4H), 3.78 (m, 4H), 3.64 (s, 2H), 3.44 (m, 4H), 2.40 (m, 4H), 1.16 (d, J = 6.5, 3H). |
| 2-235 | 0.41 and 2.71 | 488.2 | 3 | — | DMSO δ 8.76 (s, 2H), 8.42 (s, 1H), 7.76 (s, 1H), 6.84 (s, 2H), 4.23 (m, 4H), 3.78 (m, 6H), 3.34 (m, 4H), 2.89 (s, 3H), 2.73 (m, 4H), 1.79 (m, 2H). |
| 2-236 | 0.41 | 424.2 | 3 | — | MeOD δ 8.71 (s, 2H), 8.07 (s, 1H), 7.58 (s, 1H), 4.20 (m, 4H), 3.75 (m, 4H), 3.21 (s, 2H), 2.73 (m, 4H), 2.50 (m, 4H), 1.39 (s, 6H). |
| 2-237 | 4.70 | 407.1 | 5 | — | DMSO δ 13.29 (s, 1H), 9.17 (s, 1H), 8.45 (s, 1H), 7.63 (m, 2H), 7.47 (m, 1H), 4.42 (q, J = 7.1, 2H), 4.28 (m, 4H), 3.82 (m, 4H), 2.64 (s, 3H), 1.40 (t, J = 7.1, 3H). |
| 2-238 | 4.07 | 379.1 | 5 | — | |
| 2-239 | 3.92 | 349.1 | 5 | — | |
| 2-240 | 3.65 | 423.2 | 5 | — | |
| 2-241 | 4.34 | 486.3 | 5 | — | |
| 2-242 | 0.40 and 3.01 | 502.3 | 3 | 0.016 | DMSO δ 8.77 (s, 2H), 8.37 (s, 1H), 7.72 (s, 1H), 6.82 (s, 2H), 4.25 (s, 4H), 3.77 (m, 4H), 3.07 (s, 4H), 2.84 (s, 3H), 2.54 (m, 4H), 1.47 (s, 6H). |
| 2-243 | 2.97 | 555.1 | 2 | — | DMSO δ 8.89 (d, J = 10.8, 2H), 8.18 (s, 1H), 8.02 (d, J = 8.7, 2H), 7.54 (dd, J = 8.5, 6.5, 4H), 7.34 (d, J = 8.9, 2H), 4.27 (m, 4H), 3.78 (m, 4H), 3.49 (m, 4H), 2.50 (s, 3H), 2.31 (m, 4H), 2.19 (s, 3H). |
| 2-244 | 4.58 | 473.4 | 2 | 0.144 | DMSO δ 9.22 (s, 1H), 9.07 (s, 1H), 8.22 (s, 1H), 8.03 (d, J = 8.6, 2H), 7.88 (d, J = 8.7, 2H), 7.57 (m, 5H), 7.41 (m, 1H), 4.24 (m, 4H), 3.78 (m, 4H), 2.50 (s, 3H). |
| 2-245 | 5.33 | 487.3 | 2 | — | DMSO δ 9.14 (s, 1H), 8.96 (s, 1H), 8.19 (s, 1H), 8.02 (d, J = 8.7, 2H), 7.90 (d, J = 8.7, 2H), 7.58 (m, 5H), 7.36 (s, 1H), 4.27 (m, 4H), 3.81 (s, 3H), 3.78 (m, 4H), 2.50 (s, 3H). |

TABLE 5

IC50 of AKT Phosphorylation Inhibition of some representative compounds of the examples (µM), as tested in the cell assay procedure described above.

| Cpd. Nr. | p-AKT cell |
| --- | --- |
| 2-01 | 0.132 |
| 2-10 | 0.048 |
| 2-13 | 0.714 |
| 2-16 | 0.503 |
| 2-17 | 0.391 |
| 2-50 | 0.008 |
| 2-66 | 0.014 |
| 2-67 | 0.198 |
| 2-74 | 0.037 |
| 2-75 | 0.077 |
| 2-79 | 0.042 |
| 2-142 | 0.116 |
| 2-154 | 1.05 |
| 2-164 | 0.034 |
| 2-171 | 0.379 |
| 2-172 | 0.149 |
| 2-175 | 0.469 |
| 2-186 | 0.281 |
| 2-188 | 0.060 |
| 2-191 | 0.034 |
| 2-192 | 0.070 |
| 2-196 | 0.134 |
| 2-219 | 0.244 |
| 2-220 | 0.098 |
| 2-221 | 0.135 |
| 2-222 | 0.095 |

REFERENCES

1. Kenyon, C. J. The genetics of ageing. Nature 464, 504-512 (2010).
2. Fontana, L., Partridge, L. & Longo, V. D. Extending healthy life span-¬from yeast to humans. Science 328, 321-326 (2010).
3. Chalhoub, N. & Baker, S. J. PTEN and the PI3-kinase pathway in cancer. Annu Rev Pathol4, 127-150 (2009).
4. Daitoku, H., Yamagata, K., Matsuzaki, H., Hatta, M. & Fukamizui, A. Regulation of PGC-I promoter activity by protein kinase B and the forkhead transcription factor FKHR. Diabetes 52, 642-649 (2003).
5. Puigserver, P. et al. Insulin-regulated hepatic gluconeogenesis through FOXO1-PGC-1alpha interaction. Nature 423, 550-555 (2003).
6. Li, X., Monks, B., Ge, Q. & Birnbaum, M. J. Akt/PKB regulates hepatic metabolism by directly inhibiting PGC-I alpha transcription coactivator. Nature 447, 1012-1016 (2007).
7. Matsumoto, M., Pocai, A., Rossetti, L., Depinho, R. A. & Accili, D. Impaired regulation of hepatic glucose production in mice lacking the forkhead transcription factor Foxo1 in liver. Cell Metab 6, 208-216 (2007).
8. Seale, P. et al. Transcriptional control of brown fat determination by PRDMI6. Cell Metab 6, 38-54 (2007).
9. Kajimura, S. et al. Initiation of myoblast to brown fat switch by a PRDMI6-C/EBPbeta transcriptional complex. Nature 460, 1154-1158 (2009).
10. Serrano, M. & Blasco, M. A. Cancer and ageing: convergent and divergent mechanisms. Nat Rev Mol Cell Bioi 8, 715-722 (2007).
11. Matheu, A. et al. Delayed ageing through damage protection by the Arf/p53 pathway. Nature 448, 375-379 (2007).
12. Matheu, A. et al. Anti-aging activity of the Ink4/Arf locus. Aging Cell 8, 152-161 (2009).
13. Puig, O. & Tjian, R. Transcriptional feedback control of insulin receptor by dFOXO/FOXO1. Genes Dev 19, 2435-2446 (2005).
14. Matsumoto, M., Han, S., Kitamura, T. & Accili, D. Dual role of transcription factor FoxOI in controlling hepatic insulin sensitivity and lipid metabolism. J Clin Invest 116, 2464-2472 (2006).
15. Urn, S. H., D'Alessio, D. & Thomas, G. Nutrient overload, insulin resistance, and ribosomal protein S6 kinase 1, S6KI. Cell Metab 3, 393¬402 (2006).
16. Carracedo, A. & Pandolfi, P. P. The PTEN-PI3K pathway: of feedbacks and cross-talks. Oncogene 27, 5527-5541 (2008).
17. Kamagate, A. et al. Forkhead Box 01 Links Hepatic Insulin Action to Endoplasmic Reticulum Stress, Endocrinology advanced online publication.
18. Bartke, A. Impact of reduced insulin-like growth factor-IIinsulin signaling on aging in mammals: novel findings. Aging Cell 7, 285-290 (2008).
19. Morris, 1. Z., Tissenbaum, H. A. & Ruvkun, G. A phosphatidylinositol-3¬OH kinase family member regulating longevity and diapause in Caenorhabditis elegans. Nature 382, 536-539 (1996).
20. Mihaylova, V. T., Borland, C. Z., Manjarrez, L., Stern, M. J. & Sun, H. The PTEN tumor suppressor homolog in Caenorhabditis elegans regulates longevity and dauer formation in an insulin receptor-like signaling pathway. Proc Natl Acad Sci USA 96, 7427-7432 (1999).
21. Dorman, J. B., Albinder, B., Shroyer, T. & Kenyon, C. The age-1 and daf-2 genes function in a common pathway to control the lifespan of Caenorhabditis elegans. Genetics 141, 1399-1406 (1995).
22. Renner, O. & Camero, A. Mouse models to decipher the PI3K signalling network in human cancer. Curr Mol Med 9, 612-625 (2009).
23. Di Cristofano, A., Pesce, B., Cordon-Cardo, C. & Pandolfi, P. P. Pten is essential for embryonic development and tumour suppression. Nat Genet. 19,348-355 (1998).
24. Zhao, J. J. et al. The p110alpha isoform of PI3K is essential for proper growth factor signalling and oncogenic transformation. Proc Natl Acad Sci USA 103, 16296-16300 (2006).
25. Utermark, T., Schaffhausen, B. S., Roberts, T. M. & Zhao, J. J. The p 11 Oalpha isoform of phosphatidylinositol 3-kinase is essential for polyomavirus middle T antigen-mediated transformation. J Virol81, 706¬7076 (2007).
26. Podsypanina, K. et al. Mutation of Pten/Mmacl in mice causes neoplasia in multiple organ systems. Proc Natl Acad Sci USA 96, 1563-1568 (1999).
27. Stambolic, V. et al. High incidence of breast and endometrial neoplasia resembling human Cowden syndrome in pten$^{+/-}$ mice. Cancer Res 60, 3605-3611 (2000).
28. Ingram, D. K. & Reynolds, M. A. Assessing the predictive validity of psychomotor tests as measures of biological age in mice. Exp Aging Res 12, 155-162 (1986).
29. Urn, S. H. et al. Absence of S6KI protects against age- and diet-induced obesity while enhancing insulin sensitivity. Nature 431, 200-205 (2004).
30. Jiang, W., Zhu, Z. & —Thompson, H. J. Dietary energy restriction modulates the activity of AMP-activated protein kinase, Akt, and mammalian target of rapamycin in mammary carcinomas, mammary gland, and liver. Cancer Res 68, 5492-5499 (2008).

31. Moore, T. et al. Dietary energy balance modulates signaling through the Akt/mammalian target of rapamycin pathways in multiple epithelial tissues. Cancer Pre v Res (Phila Pa.) 1, 65-76 (2008).
32. Hempenstall, S., Picchio, L., Mitchell, S. E., Speakman, J. R. & Selman, C. The impact of acute caloric restriction on the metabolic phenotype in male C57BL/6 and DBN2 mice. Mech Ageing Dev 131, 111-118 (2010).
33. van der Horst, A. & Burgering, B. M. Stressing the role of Foxo proteins in lifespan and disease. Nat Rev Mol Cell Riol8, 440-450 (2007).
34. Selman, C. et al. Ribosomal protein S6 kinase 1 signalling regulates mammalian life span. Science 326, 140-144 (2009).
35. Kozak, L. P. & Anunciado-Koza, R. UCPI: its involvement and utility in obesity. Int Obes (Lond) 32 Suppl 7, S32-38 (2008).
36. Nedergaard, J. & Cannon, B. The changed metabolic world with human brown adipose tissue: therapeutic visions. Cell Metab 11, 268-272 (2010).
37. Lidell, M. E. & Enerback, S. Brown adipose tissue—a new role in humans? Nat Rev Endocrinol 6, 319-325 (2010).
38. Puigserver, P. et al. A cold-inducible coactivator of nuclear receptors linked to adaptive thermogenesis. Cell 92, 829-839 (1998).
39. Puigserver, P. & Spiegelman, B. M. Peroxisome proliferator-activated receptor-gamma coactivator 1 alpha (PGC-1 alpha): transcriptional coactivator and metabolic regulator. Endocr Rev 24, 78-90 (2003).
40. Kops, G. J. et al. Direct control of the Forkhead transcription factor AFX by protein kinase B. Nature 398, 630-634 (1999).
41. Matheu, A" Klatt, P, & Serrano, M. Regulation of the INK4a1ARF locus by histone deacetylase inhibitors. J Bioi Chem 280,42433-42441 (2005).
42. Palmero, I. & Serrano, M, Induction of senescence by oncogenic Ras, Methods Enzymol333, 247-256 (2001).
43. Greulich, H. et al. Oncogenic transformation by inhibitor-sensitive and -resistant EGFR mutants, PLoS Med 2, e313 (2005).
44. Hipkiss, 2008, Energy metabolism, altered proteins, sirtuins and ageing: converging mechanisms?, Biogerontology, 9:49-55.
45. Wang, C. et al. DNA damage response and cellular senescence in tissues of aging mice. *Aging Cell* 8, 311-323 (2009).
46. Guerra, C. et al. Brown adipose tissue-specific insulin receptor knockout shows diabetic phenotype without insulin resistance. *J Clin Invest* 108, 1205-1213 (2001).
47. Kozak, L. P. & Anunciado-Koza, R. UCP1: its involvement and utility in obesity. *Int J Obes* (*Lond*) 32 Suppl 7, S32-38 (2008).
48. Feige, J. N. et al. Specific SIRT1 activation mimics low energy levels and protects against diet-induced metabolic disorders by enhancing fat oxidation. *Cell Metab* 8, 347-358 (2008).
49. Song, M. S. et al. Nuclear PTEN Regulates the APC-CDH1 Tumor-Suppressive Complex in a Phosphatase-Independent Manner. *Cell* 144, 187-199 (2011).
50. Karamanlidis, G., Karamitri, A., Docherty, K., Hazlerigg, D. G. & Lomax, M. A. C/EBPbeta reprograms white 3T3-L1 preadipocytes to a Brown adipocyte pattern of gene expression. *J Biol Chem* 282, 24660-24669 (2007).

EXAMPLE E

Introduction

Two additional assays were conducted to further support the ability of Compound A to activate brown adipocytes in vitro and to decrease body weight in obese mice. A further purpose of these assays was to demonstrate the activity of Compound A using other PI3K inhibitors. This allows us to test whether the biological effects of Compound A are shared by other unrelated PI3K inhibitors, in which case it reinforces the idea that the effects of Compound A are truly mediated by PI3K inhibitors and not (for example) by a putative non-PI3K target of Compound A. Finally, it allows the efficiency of different PI3K inhibitors on obesity to be compared.

Materials and Methods

Methods

Isolation and Treatment of Pre-Brown Adipocytes

Immortalized brown adipocytes were obtained from the interscapular BAT of 3-5 day-old neonates and immortalized by retroviral transduction of Large-T antigen (in vector pBABE-puro, kindly provided by James de Caprio, Dana Farber Cancer Institute, Boston). The resulting pre-brown adipocytes were grown in DMEM 10% FBS. For treatment, cultures were PBS washed and treated with regular medium (DMEM 10% FBS) containing "Compound A" or the indicated PI3Ki, for 4 h, at the indicated concentrations.

Analyses of Proteins and RNA

For immunoblots, pre-brown adipocytes were lysed in lysis buffer (150 mM NaCl, 10 mM Tris pH 7.2, 0.1% SDS, 1.0% Triton X-100, 1% deoxycholate, 5 mM EDTA). Immunoblots were performed according to standard procedures using the following antibodies: for detection of P-S473-Akt, Cell Signaling catalogue number #4058; for detection of total Akt, Upstate catalogue number #07-416; and for β-actin, Sigma catalogue number AC-15.

For RNA analyses, total RNA from pre-brown adipocytes was extracted using TRIZOL (Invitrogen). Reverse transcription was performed using random primers and Ready-To-Go™ You-Prime First-Strand Beads (GE Healthcare). Quantitative real time-PCR was performed using DNA Master Sybr Green I mix (Applied Biosystems) in an ABI PRISM 7700 thermocycler (Applied Biosystem). The housekeeping gene used for input normalization of all the qRT-PCR data is -actin. Primer sequences used are:

| Ucp1-Fw | 5'-ACTGCCACACCTCCAGTCATT-3' (SEQ ID NO: 5) |
| Ucp1-Rv | 5'-CTTTGCCTCACTCAGGATTGG-3' (SEQ ID NO: 6) |
| Actin-Fw | 5'-GGCACCACACCTTCTACAATG-3' (SEQ ID NO: 7) |
| Actin-Rv | 5'-GTGGTGGTGAAGCTGTAGCC-3' (SEQ ID NO: 8) |

Body Weight Analyses

Mice were fed either with a standard chow diet (Harlan Teklad 2018, 18% calories from fat) or, when indicated, with a high fat diet (Research Diets D12451, 45% of total calories from fat). To measure food intake, mice were housed in metabolic cages during 5 days, and food and water intake, as well as, the output of faeces and urine were measured during the last 4 days. Body composition (fat and lean content) was determined by Dual energy X-ray Absorptiometry (DXA) (Lunar PIXImus Densitometer, GE Medical Systems). Image acquisition lasted 5 minutes with mice under anesthesia by inhalation of 2% isofluorane in 100% oxygen. The analysis of lean mass and fat mass was performed using a Region Of Interest (ROI) comprising the entire body.

Results and Discussion

In FIGS. 21, 2 and 23 Compound A as referred to hereinbefore is referenced.

In FIG. 21, pre-brown adipocytes (proliferating brown adipocytes explanted from newborn mice and immortalized with large-T antigen) were treated with different concentrations of PI3K inhibitors and their ability to inhibit the phosphorylation of Akt (a bona fide readout of PI3K activity) was scored (FIG. 21, upper panel). The activity of Compound A is within the range of activity of the other two tested inhibitors, producing a measurable inhibition a 1 microM and a complete inhibition at 10 microM.

To evaluate whether Compound A was able to activate the energy dissipating activity of brown adipocytes, the mRNA expression levels of Ucp1 were scored (FIG. 21, lower panels). As shown in the graphs, Compound A potently induced Ucp1 mRNA levels with an activity similar to the other inhibitors (the three inhibitors up-regulated Ucp1 mRNA levels 8-20x-fold at a dose of 10-20 microM).

In addition, cohorts of obese mice were treated (n=4-7 per group, obesity induced by chronic high-fat diet, weight gain relative to mice under standard diet was of 25) with Compound A or one of the other PI3K is %. The dose of Compound A in this assay was one-third lower than in the previous assay (i.e. 10 mg/kg), thus a slower rate of weight loss was anticipated. A slower rate of weight loss might be considered safer. Mice were dosed in the same manner as before (gavage once a day for 2 weeks, resting during the week end). Mice had ad libitum access to high-fat food during the entire duration of the assay. Food intake was scored and did not change significantly during treatment (FIG. 22, upper left panel). Body weight was significantly decreased (approx. 10%) in the group of mice treated with 10 mg/kg of Compound A (FIG. 22, upper right panel and lower panel). The group of mice treated with 10 mg/kg of the other PI3Ki also showed a tendency to lose weight. A higher dose of this last PI3Ki (75 mg/kg) was as effective as 10 mg/kg of Compound A. Dual X-ray densitometry indicated that weight loss induced by Compound A was due to a loss of fat mass and not to a loss of lean mass (FIG. 23, note that this figure combines the data of the current assay; that is, 10 mg/kg of Compound A and 10 mg/kg or 75 mg/kg of the other PI3Ki, together with data from the previous assay, 15 mg/kg of Compound A).

Together, these results demonstrate that Compound A activates energy dissipation in brown adipocytes in vitro and further confirm that Compound A induces weight loss in obese mice without affecting food intake or lean mass. Also, these activities are shared with other unrelated PI3K is, thus demonstrating that these effects are mediated by the inhibition of PI3K in obese mammals and/or mammals experiencing positive energy balance.

The data on "lack" of weight loss activity of Compound A on NON-OBESE mice are important (see the FIG. 41). This "lack" of effect is very important because it reinforces the concept that the PI3K inhibitor (Compound A) only acts in the context of nutritional stress by overfeeding, i.e. high fat diet. This type of stress is known to activate the BAT in the same way as thermal stress (these are the two stresses that activate the BAT, namely, diet-induced and cold-induced BAT activation).

Tables

TABLE 1

Perinatal lethality of Pten-tg mice crosses: $Pten^{+/+} \times Pten^{+/+; tg/*}$

| | E13.5 embryos | | weaned mice | |
|---|---|---|---|---|
| | observed (n) | expected | observed (n) | expected |
| $Pten^{+/+}$ | 55% (42) | 50% | 72% (409) | 50% |
| $Pten^{+/+; tg/*}$ | 45% (35) | 50% | 28% (162) | 50% |
| Fisher s test | p = 0.1 | | p = 0.00001 | |

TABLE 2

Pathological findings upon necropsy and histology

COHORT OF WT MICE

| | | | | | observed pathologies | |
|---|---|---|---|---|---|---|
| ID | sex | age in months | endpoint[a] | censoring | probable cause of death | other pathologies |
| ID#006 | Male | 18.9 | HEP | VALID | lymphoma | glomerulosclerosis |
| ID#007 | Female | 26.1 | HEP | VALID | lymphoma | endometrial cystic hyperplasia |
| ID#018 | Female | 21.1 | HEP | VALID | histiocytic sarcoma | hepatosteatosis and hepatitis |
| ID#035 | Male | 26.4 | HEP | VALID | histiocytic sarcoma | testicular atrophy |
| ID#036 | Male | 26.0 | HEP | VALID | liver carcinoma | pancreatitis |
| ID#037 | Male | 25.1 | HEP | VALID | lungcarcinoma | thyroid adenoma, liver adenoma, hepatosteatosis |
| m#049 | Male | 20.6 | HEP | VALID | liver carcinoma | hapatosteatosis, thyroid hyperplasia, nephropathy, testicular atrophy |
| ID#050 | Male | 20.6 | HEP | VALID | liver carcinoma | low grade PIN, thyroid hyperplasia, nephropathy, pancreatitis |
| m#055 | Female | 13.0 | HEP | NON-VALID | | dermatitis |
| ID#056 | Female | 26.1 | DIC | VALID | n.d. | |
| ID#057 | Male | 33.8 | HEP | VALID | lymphoma | low grade PIN, testicular atrophy |
| ID#058 | Male | 17.9 | DIC | VALID | n.d. | |

TABLE 2-continued

| | | | | | Pathological findings upon necropsy and histology | |
|---|---|---|---|---|---|---|
| ID#059 | Male | 31.9 | HEP | VALID | lymphoma | thyroid adenoma, lung adenoma, liver carcinoma, hemangioma, pancreatitis |
| ID#062 | Male | 28.8 | HEP | VALID | lymphoma | low grade PIN, glomerulosclerosis, hepatitis |
| ID#063 | Male | 26.5 | HEP | NON VALID | | dermatitis |
| m#065 | Male | 28.0 | HEP | VALID | histiocytic sarcoma | testicular atrophy |
| ID#068 | Female | 30.6 | HEP | VALID | sepsis | thyroid hyperplasia |
| ID#070 | Male | 14.8 | DIC | VALID | n.d. | |
| m#071 | Male | 23.6 | HEP | NON VALID | | dermatitis |
| m#073 | Female | 28.8 | HEP | VALID | lymphoma | thyroid hyperplasia |
| ID#074 | Female | 32.7 | HEP | VALID | n.d. | |
| m#076 | Female | 33.9 | HEP | VALID | lymphoma | |
| ID#077 | Female | 27.4 | HEP | VALID | lymphoma | liver adenoma, lung carcinoma, thyroid hyperplasia, pancreatitis |
| ID#080 | Female | 19.0 | HEP | VALID | lung carcinoma | Harderian gland carcinoma, liver carcinoma, thyroid adenoma, nephropathy, cystic endometrial hyperplasia |
| ID#081 | Female | 22.8 | HEP | VALID | corneal ulcer | thyroid adenoma |
| ID#082 | Male | 27.5 | HEP | VALID | renal failure | lung carcinoma, liver carcinoma, nulmonary edema, nancreatitis |
| ID#084 | Female | 24.2 | DIC | VALID | n.d. | |
| ID#085 | Female | 21.3 | HEP | VALID | cardiovascular failure | thyroid hyperplasia, cystic endometrial hyperplasia, glomerulosclerosis |
| ID#088 | Male | 27.6 | HEP | VALID | cardiovascular failure | thyroid adenoma, pancreatitis |
| ID#090 | Female | 33.4 | HEP | VALID | pituitary adenoma | thyroid adenoma |
| ID#091 | Female | 7.1 | HEP | NON VALID | | dystocia |
| ID#092 | Female | 24.7 | HEP | VALID | lung carcinoma | liver adenoma |
| ID#094 | Female | 31.5 | DIC | VALID | n.d. | |
| ID#095 | Female | 32.2 | HEP | VALID | multiple neoplasias | lymphoma, pituitary carcinoma, thyroid carcinoma, lungcarcinoma, cystic endometrial hyperplasia |
| ID#097 | Female | 24.4 | HEP | VALID | lymphoma | pituitary adenoma |
| ID#098 | Female | 27.8 | HEP | VALID | pituitary adenoma | lymphoma, thyroid carcinoma, endometrial hyperplasia |
| ID#099 | Female | 18.2 | HEP | NON VALID | | dermatitis |
| ID#100 | Male | 20.2 | HEP | VALID | renal failure | thyroid adenoma, hepatosteatosis, nephropathy, testicular atrophy |
| ID#101 | Female | 24.3 | HEP | VALID | histiocytic sarcoma | |
| ID#102 | Female | 17.4 | HEP | NON VALID | | dermatitis |
| ID#103 | Female | 29.1 | HEP | VALID | pituitary carcinoma | intestinal adenoma |
| ID#104 | Female | 27.1 | HEP | VALID | fibrosarcoma | lymphoma |
| ID#105 | Male | 9.6 | EXP | NON VALID | | |
| ID#106 | Female | 25.1 | HEP | VALID | lymphoma | |
| ID#131 | Male | 11.2 | HEP | VALID | n.d. | |
| ID#133 | Female | 28.9 | HEP | VALID | lymphoma | thyroid adenoma, liver adenoma |
| ID#136 | Male | 26.2 | HEP | VALID | cardiovascular failure | thyroid hyperplasia |
| ID#137 | Male | 17.6 | HEP | VALID | renal failure | low grade PIN, liver adenoma |
| ID#139 | Female | 28.2 | HEP | VALID | histiocytic sarcoma | thyroid adenoma, mammary gland adenoma, pancreatitis, nephropaty cystic endometrial hyperplasia |
| ID#141 | Male | 21.9 | HEP | VALID | cardiovascular failure | thyroid adenoma, nephropathy, hepatitis |
| ID#144 | Female | 22.8 | HEP | VALID | cardiovascular failure | |
| ID#145 | Female | 25.6 | HEP | VALID | lymphoma | lung carcinoma, liver carcinoma, pancreatitis, thyroid hyperplasia |
| ID#147 | Male | 5.4 | EXP | NON VALID | | |

TABLE 2-continued

| | | | | | Pathological findings upon necropsy and histology | |
|---|---|---|---|---|---|---|
| ID#148 | Female | 32.1 | DIC | VALID | n.d. | |
| ID#149 | Male | 16.2 | HEP | VALID | histiocytic | thyroid hyperplasia |
| ID#150 | Male | 28.5 | HEP | VALID | renal failure | Peyer s patches hyperplasia, cardiac hypertrophy, thyroid hyperplasia, nephropathy, prostatitis, testicular atrophy |
| ID#153 | Female | 34.0 | ALIVE | VALID | | |
| ID#154 | Female | 16.4 | HEP | NON VALID | | dermatitis |
| ID#155 | Male | 13.5 | HEP | VALID | pneumonia | |
| ID#156 | Male | 26.7 | HEP | VALID | lymphoma | lung carcinoma |
| ID#158 | Male | 32.7 | HEP | VALID | n.d. | |
| ID#159 | Female | 25.4 | HEP | VALID | lymphoma | mammary gland carcinoma, lung adenoma, thyroid adenoma, pancreatitis |
| ID#160 | Female | 20.6 | HEP | VALID | histiocytic sarcoma | cystic endometrial hyperplasia |
| ID#161 | Female | 24.4 | DIC | VALID | n.d. | |
| ID#162 | Male | 18.1 | HEP | VALID | n.d. | |
| ID#163 | Female | 21.0 | HEP | VALID | lymphoma | |
| ID#164 | Female | 30.9 | HEP | VALID | pituitary carcmoma | hepatosteatosis, pancreatitis, nephropathy |
| ID#165 | Female | 29.9 | HEP | VALID | cardiovascular failure | pituitary carcinoma, pulmonary edema |
| ID#209 | Male | 23.5 | HEP | VALID | lymphoma | low grade PIN, thyroid adenoma, Dnacreatitis, testicular atrophy |
| ID#210 | Male | 22.5 | EXP | NON VALID | | |
| ID#211 | Male | 28.2 | HEP | VALID | histiocytic sarcoma | lung carcinoma, thyroid hyperplasia |
| ID#212 | Male | 30.0 | HEP | VALID | n.d. | |
| ID#213 | Female | 24.4 | DIC | VALID | n.d. | |
| ID#214 | Female | 19.3 | HEP | NON VALID | | dermatitis |
| ID#215 | Female | 22.7 | HEP | VALID | lymphoma | |
| ID#217 | Female | 3.9 | EXP | NON VALID | | |
| ID#222 | Male | 25.3 | HEP | VALID | cardiovascular failure | low grade PIN, hepatosteatosis, nephritis, pancreatitis |
| ID#227 | Male | 16.1 | HEP | VALID | cardiovascular failure | intestinal carcinoma, testicular atrophy |
| ID#232 | Male | 30.3 | HEP | VALID | n.d. | |
| ID#234 | Female | 22.8 | DIC | VALID | n.d. | |
| ID#237 | Male | 29.9 | HEP | VALID | hepatocellular carcinoma | low grade PIN, testicular atrophy |
| ID#241 | Female | 28.3 | HEP | VALID | pituitary adenoma | hepatosteatosis, cystic endometrial hyperplasia |
| ID#243 | Male | 23.8 | HEP | VALID | n.d. | |
| ID#247 | Male | 28.9 | HEP | VALID | histiocytic sarcoma | thyroid hyperplasia, pituitary hyperplasia, neDhropathy |
| ID#248 | Male | 24.5 | HEP | VALID | n.d. | |
| ID#249 | Female | 20.6 | HEP | NON VALID | | dermatitis |
| ID#250 | Female | 6.1 | EXP | NON VALID | | |
| ID#251 | Female | 25.1 | HEP | VALID | n.d. | |
| ID#252 | Female | 27.3 | HEP | VALID | histiocytic sarcoma | pituitary carcinoma, thyroid hyperplasia, pancreatitis |
| ID#254 | Female | 25.3 | HE? | VALID | pituitary carcinoma | endometrial cystic hyperplasia, pancreatitis |
| ID#271 | Female | 26.9 | HEP | VALID | lymphoma | pituitary adenoma, thyroid hyperplasia |
| ID#272 | Male | 4.8 | EXP | NON VALID | | |
| ID#274 | Female | 28.0 | HEP | VALID | n.d. | |
| ID#279 | Female | 22.2 | HEP | VALID | histiocytic sarcoma | |
| ID#289 | Male | 18.0 | HEP | VALID | lymphoma | prostate hyperplasia |
| ID#306 | Female | 19.1 | HEP | NON VALID | | dermatitis |
| ID#307 | Female | 26.6 | HEP | VALID | lymphoma | pituitary adenoma, thyroid adenoma |
| ID#320 | Female | 17.2 | DIC | VALID | n.d. | |
| ID#321 | Male | 21.3 | HEP | VALID | lymphoma | liver carcinoma, hepatosteatosis |
| ID#322 | Male | 21.6 | HEP | VALID | n.d. | |
| ID#323 | Female | 20.5 | HEP | VALID | n.d. | |
| ID#330 | Male | 26.4 | HEP | VALID | n.d. | |
| ID#349 | Female | 27.2 | HEP | VALID | n.d. | |

TABLE 2-continued

Pathological findings upon necropsy and histology

| ID | sex | age | endpoint | censoring | | |
|---|---|---|---|---|---|---|
| ID#352 | Female | 25.9 | DIC | VALID | n.d. | |
| ID#353 | Male | 27.2 | HEP | VALID | seminal vesicles enlarged | low grade PIN |
| ID#355 | Male | 26.9 | HEP | VALID | liver carcinoma | Peyer s patches hyperplasia |
| ID#380 | Male | 10.5 | EXP | NON VALID | | |
| ID#408 | Female | 24.3 | DIC | VALID | n.d. | |
| ID#411 | Female | 16.5 | HEP | NON VALID | | dermatitis |
| ID#431 | Female | 23.8 | HEP | VALID | lymphoma | pancreatitis, hepatosteatosis |
| ID#452 | Female | 20.8 | DIC | VALID | n.d. | |
| ID#461 | Male | 15.7 | HEP | VALID | n.d. | |

COHORT OF PTEN-tg MICE

| | | | | | observed pathologies | |
|---|---|---|---|---|---|---|
| ID | sex | age | endpoint | censoring | probable cause of death | other pathologies |
| ID#004 | Male | 29.7 | HEP | VALID | n.d. | pancreatitis, thyroid hyperplasia |
| ID#005 | Male | 31.6 | HEP | VALID | thyroid adenoma | hepatitis |
| ID#019 | Female | 31.3 | HEP | VALID | pneumonia | nephropathy, pancreatitis, hepatosteatosis |
| ID#038 | Female | 6.9 | HEP | NON VALID | | dystocia |
| ID#051 | Male | 6.9 | HEP | NON VALID | | mal-occlusion |
| ID#052 | Male | 38.4 | HEP | VALID | liver carcinoma | low grade PIN, testicular atrophy |
| ID#054 | Male | 26.4 | HEP | VALID | nephropathy | pancreatitis |
| ID#060 | Male | 28.8 | DIC | VALID | n.d. | |
| ID#064 | Male | 33.0 | HEP | VALID | lymphoma | lung adenoma |
| ID#069 | Female | 6.2 | HEP | NON VALID | | dystocia |
| ID#072 | Male | 32.2 | HEP | VALID | cardiovascular failure | pancreatitis, thyroid hyperplasia |
| ID#078 | Female | 30.1 | HEP | VALID | pituitary carCInoma | corneal ulcer, liver adenoma, thyroid hyperplasia, lymphoma |
| ID#083 | Male | 29.7 | HEP | VALID | n.d. | |
| ID#086 | Female | 30.4 | HEP | VALID | liver carcinoma | thyroid hyperplasia |
| ID#093 | Male | 37.0 | HEP | VALID | cardiovascular failure | luing carcinoma, nephropathy, pituitary hyperplasia |
| ID#096 | Female | 25.3 | DIC | VALID | n.d. | |
| ID#130 | Male | 18.1 | DIC | VALID | n.d. | |
| ID#132 | Male | 34.2 | HEP | VALID | n.d. | |
| ID#135 | Female | 35.6 | HE? | VALID | cardiovascular failure | cystic endometrial hyperplasia, pancreatitis, nephropathy, pituitary adenoma |
| ID#138 | Male | 26.1 | HEP | VALID | liver carcinoma | pancreatitis, glomerulosclerosis |
| ID#142 | Male | 23.9 | HEP | VALID | cardiovascular failure | thyroid hyperplasia, hepatitis |
| ID#143 | Male | 25.4 | EXP | NON VALID | | |
| ID#146 | Female | 11.3 | HEP | VALID | ovary tumor | hepatitis |
| ID#151 | Male | 23.0 | DIC | VALID | n.d. | |
| ID#152 | Female | 33.3 | HE? | VALID | lymphoma | thyroid hyperplasia |
| ID#157 | Male | 28.9 | HEP | VALID | cardiovascular failure | pancreatitis, nephropathy, thyroid hvperolasia, urothelial hyperplasia |
| ID#216 | Female | 32.4 | HEP | VALID | lymphoma | |
| ID#218 | Female | 33.8 | ALIVE | VALID | | |
| ID#220 | Male | 29.1 | HEP | VALID | corneal ulcer | pancreatitis |
| ID#229 | Male | 32.1 | HEP | VALID | renal failure | thyroid hyperplasia |
| ID#231 | Male | 26.0 | HEP | VALID | cardiovascular failure | liver carcinoma, nephropathy, testicular atrophy |
| ID#263 | Male | 19.1 | HEP | VALID | thyroid carcmoma | hepatitis |
| ID#270 | Female | 27.9 | DIC | VALID | n.d. | |
| ID#280 | Female | 26.1 | HEP | VALID | cardiovascular failure | cystic endometrial hyperplasia, nephropathy |
| ID#311 | Female | 27.7 | HEP | VALID | n.d. | |
| ID#334 | Female | 20.4 | HEP | VALID | liver carcinoma | pancreatitis |
| ID#338 | Female | 25.8 | HEP | VALID | vasculitis | thyroid hyperplasia |
| ID#346 | Male | 3.0 | EXP | NON VALID | | |
| ID#347 | Male | 3.0 | EXP | NON VALID | | |
| ID#348 | Male | 3.0 | EX? | NON VALID | | |
| ID#350 | Female | 28.5 | DIC | VALID | n.d. | |
| ID#360 | Male | 2.7 | EXP | NON VALID | | |
| ID#365 | Female | 29.8 | ALIVE | VALID | | |
| ID#382 | Female | 27.5 | HEP | VALID | cardiovascular failure | fibrosarcoma, pituitary adenoma |
| ID#393 | Male | 20.1 | EXP | NON VALID | | |
| ID#410 | Male | 19.3 | EXP | NON VALID | | |

TABLE 2-continued

Pathological findings upon necropsy and histology

| ID | Sex | Age | Status | Validity | Finding 1 | Finding 2 |
|---|---|---|---|---|---|---|
| ID#412 | Female | 28.5 | ALIVE | VALID | | |
| ID#425 | Female | 18.7 | HEP | NON VALID | | mal-occlusion |
| ID#427 | Female | 28.0 | ALIVE | VALID | | |
| ID#43 0 | Female | 28.0 | ALIVE | VALID | | |
| ID#463 | Male | 25.0 | HEP | NON VALID | | dermatitis |
| ID#468 | Male | 23.1 | HE? | VALID | n.d. | n.d. |
| ID#469 | Male | 19.8 | HEP | VALID | liver carcinoma | nephropathy |
| ID#472 | Female | 26.5 | ALIVE | VALID | | |
| ID#501 | Female | 24.5 | ALIVE | VALID | | |
| ID#531 | Male | 22.2 | HE? | NON VALID | | dermatitis |
| ID#535 | Female | 12.6 | EXP | NON VALID | | |
| ID#599 | Female | 19.8 | ALIVE | VALID | | |
| ID#613 | Female | 18.3 | ALIVE | VALID | | |
| ID#614 | Female | 18.3 | ALIVE | VALID | | |
| ID#616 | Female | 17.5 | ALIVE | VALID | | |
| ID#651 | Male | 14.4 | HEP | NON VALID | | dermatitis |
| ID#681 | Female | 5.3 | HEP | NON VALID | | malformation |

[a] HEP: Humane End Point; mice were euthanized after clear signs of morbidity and discomfort according to the Guidelines for Humane Endpoints for Animals Used in Biomedical Research' (http://dels.nas.edu/global/ilar/Guide). Cages were supervised daily by trained personnel. DIC: Dead In Cage; mice were found dead in their cages without previous signs of morbidity. EXP: mice were used for experimentation.

TABLE 3

Cohorts used in survival curves

| genotype | sex | re-cruited | non-valid | studied | deaths | alive | HEp[a] | DIC[b] |
|---|---|---|---|---|---|---|---|---|
| wt | male | 49 | 7 | 42 | 42 | 0 | 40 | 2 |
| | female | 63 | 11 | 52 | 52 | 0 | 42 | 10 |
| | m + f | 112 | 18 | 94 | 94 | 0 | 82 | 12 |
| Pten-tg | male | 32 | 11 | 21 | 21 | 0 | 18 | 3 |
| | female | 31 | 5 | 26 | 15 | 11 | 12 | 3 |
| | m + f | 63 | 16 | 47 | 36 | 11 | 30 | 6 |

[a] HEP: Humane End Point; mice were euthanized after clear signs of morbidity and discomfort according to the Guidelines for Humane Endpoints for Animals Used in Biomedical Research. Cages were supervised daily by trained personnel.
[b] DIC: Dead In Cage; mice were found dead in their cages without previous signs of morbidity

TABLE 4

"Non-valid" mice

| cause | genotype | males | females | total non-valid |
|---|---|---|---|---|
| experimentation | wt | 5 | 2 | 7 |
| | Pten-tg | 7 | 1 | 8 |
| mal-occlusion | wt | 0 | 0 | 0 |
| or malformation | Pten-tg | 1 | 2 | 3 |
| dystocia | wt | n.a. | 1 | 1 |
| | Pten-tg | n.a. | 2 | 2 |
| dem1atitis | wt | 2 | 8 | 10 |
| | Pten-tg | 3 | 0 | 3 |
| total non-valid | wt | 7 | 11 | 18 |
| | Pten-tg | 11 | 5 | 16 |

TABLE 5

Log-rank test comparisons and hazards

| sex | comparison | log-rank test $X^2$ | p | hazard ratio | 95% CI of ratio |
|---|---|---|---|---|---|
| male | wt vs Pten-tg | 8.166 | 0.0043 | 2.152 | 1.272-3.640 |
| female | wt vs Pten-tg | 8.788 | 0.003 | 2.131 | 1.292-3.514 |
| m + f | wt vs Pten-tg | 16.71 | <0.0001 | 2.117 | 1.478-3.034 |

TABLE 6

Survival data[a]

| sex | genotype | n | range | median survival | mean longevity ± s.d. all (p-value)[b] | mean longevity ± s.d. oldest 20% (p-value)[b] | mean longevity ± s.d. oldest 10% (p-value)[b] |
|---|---|---|---|---|---|---|---|
| males | wt | 42 | 11.2-33.8 | 25.2 | 23.8 ± 5.6 | 30.8 ± 1.8 | 32.2 ± 1.5 |
| | Pten-tg | 21 | 18.1-38.4 | 28.9 | 28.1 ± 5.6 (0.005) | 35.7 ± 2.5 (0.003) | 37.7 ± 1.0 (0.010) |
| females | wt | 52 | 17.2-35.0 | 25.8 | 26.1 ± 4.0 | 32.2 ± 1.6 | 33.4 ± 1.1 |
| | Pten-tg | 26 | 11.3-35.6 | 30.1 | 27.6 ± 5.8 (0.26) | 33.8 ± 1.6 (0.16) | 34.5 ± 1.6 (0.34) |
| m + f | wt | 94 | 11.2-35.0 | 25.5 | 25.1 ± 4.9 | 31.6 ± 1.8 | 33.1 ± 1.0 |
| | Pten-tg | 47 | 11.3-38.4 | 29.1 | 27.9 ± 5.6 (0.005) | 34.9 ± 22 (0.0008) | 36.3 ± 1.8 (0.0016) |

[a] All data in months.
[b] Student's s t-test.

TABLE 7

Cox regression analysis[a]

| covariate | B | SE | Wald | df | sig. | exp(B) | 95% CI Low to High |
|---|---|---|---|---|---|---|---|
| DOB | 0.000 | 0.000 | 0.001 | | 0.978 | 1.000 | 1.000-1.000 |
| MOM | −0.044 | 0.038 | 1.348 | | 0.246 | 0.957 | 0.888-1.031 |
| DAD | −0.020 | 0.033 | 0.365 | | 0.546 | 0.981 | 0.920-1.045 |
| SEX | −0.216 | 0.219 | 0.972 | | 0.324 | 0.806 | 0.525-1.237 |
| GEN | 0.887 | 0.266 | 11.149 | | 0.001 | 2.429 | 1.443-4.089 |

[a]DOB: Date of birth, MOM: Mother, DAD: Father. The variables sex and genotype (GEN) were replaced with a set of indicator variables to denote the presence or absence of category membership. B is the un-standardised regression coefficient and its standard error (SE), its Wald test statistic value (Wald), the degrees of freedom (df), and the significance (Sig.). Exp(B) for the covariate of interest is the predicted change of the hazard ratio for a unit increase in the predictor and the 95% confidence interval (CI) for exp (B). n = 66 for wt and n = 26 for Pten-tg mice.

TABLE 8

Median survival and log-rank tests with randomly selected subsets of wt mice of the same size group as the corresponding Pten-tg mice group males

| | wt random sub-group (n = 21) | Pten-tg group (n = 21) | | |
|---|---|---|---|---|
| | median survival | median survival | log-rank test | |
| ID# | (months) | (months) | $X^2$ | p |
| 1 | 26.40 | 28.90 | 4.765 | 0.0291 |
| 2 | 23.80 | 28.90 | 8.093 | 0.0044 |
| 3 | 21.90 | 28.90 | 11.75 | 0.0006 |
| 4 | 26.00 | 28.90 | 6.474 | 0.0109 |
| 5 | 25.10 | 28.90 | 5.204 | 0.0225 |
| 6 | 26.40 | 28.90 | 5.713 | 0.0168 |
| 7 | 26.00 | 28.90 | 6.070 | 0.0138 |
| 8 | 23.80 | 28.90 | 8.033 | 0.0046 |
| 9 | 26.40 | 28.90 | 3.957 | 0.0467 |
| 10 | 26.00 | 28.90 | 5.623 | 0.0177 | females

| | wt random sub-group (n = 26) | Pten-tg group (n = 26) | | |
|---|---|---|---|---|
| | median survival | median survival | log-rank test | |
| ID# | (months) | (months) | $X^2$ | p |
| 1 | 24.90 | 30.10 | 21.85 | <0.0001 |
| 2 | 24.90 | 30.10 | 19.06 | <0.0001 |
| 3 | 24.55 | 30.10 | 23.57 | <0.0001 |
| 4 | 25.35 | 30.10 | 20.59 | <0.0001 |
| 5 | 25.20 | 30.10 | 23.11 | <0.0001 |
| 6 | 24.35 | 30.10 | 25.43 | <0.0001 |
| 7 | 24.90 | 30.10 | 24.72 | <0.0001 |
| 8 | 24.75 | 30.10 | 21.30 | <0.0001 |
| 9 | 24.75 | 30.10 | 21.06 | <0.0001 |
| 10 | 25.10 | 30.10 | 22.84 | <0.0001 |

TABLE 9

Analysis of covariance (ANCOVA) using a General Linear Model (GLM) for the relation between Energy Expenditure (EE) and the covariates genotype and body weight (BW)[a]

males (wt: n = 8; tg: n = 8)

| | GEN (p value) | BW (p value) |
|---|---|---|
| EE l + d | 5.716e−05 | 0.006506 |
| EE light | 0.0001072 | 0.0123942 |
| EE dark | 0.0002687 | 0.0135485 |

Regression curves:
EE l + d = 8918.64 + 479.04*(GEN(0, 1)) + 286.09 * BW; Adjusted $R^2$: 0.7398, p-value: 6.241e−05
EE light = 3852.40 + 163.19*(GEN(0, 1)) + 138.96 * BW; Adjusted $R^2$: 0.7079; p-value: 0.0001324
EE dark = 5066.24 + 315.85*(GEN(0, 1)) + 147.13 * BW; Adjusted $R^2$: 0.6709; p-value: 0.0002874 females (wt: n = 8; tg: n = 9)

| | GEN (p value) | BW (p value) |
|---|---|---|
| EE l + d | 8.256e−07 | 1.30ge−05 |
| EE light | 1.161e−06 | 2.122e−05 |
| EE dark | 6.918e−06 | 7.243e−05 |

Regression curves:
EE l + d = 8812.15 + 499.74*(GEN(0, 1)) + 384.08 * BW; Adjusted $R^2$: 0.8736; p-value: 2.027e−07
EE light = 3355.83 + 239.52*(GEN(0, 1)) + 211.16 * BW; Adjusted $R^2$: 0.8654; p-value: 3.135e−07
EE dark = 5456.32 + 260.22*(GEN(0, 1)) + 172.91 * BW; Adjusted $R^2$: 0.8276; p-value: 1.774e−06

[a]Normal distribution of every variable was assessed by Kolmogorov-Smirnov test. Variance equality around the regression line of each group was confirmed for each variable using F-test. Analysis of covariance (ANCOVA) using generalized linear models (GLMs) were used to compare total energy expenditure (EE l + d), EE during the light phase (EE light), or EE during the dark phase (EE dark) between wild-type (wt = O) and Pten-tg (tg = I) mice after adjustment for body weight (BW). No interactions between the predicting variables were found. Statistical analyses were perfomled with R software (http://www.r-project.org/).

TABLE 10

Primer sequences used in qRT-PCR

| | |
|---|---|
| Adipoq-Fw | 5'-GGATGCTACTGTTGCAAGCTC-3' (SEQ ID NO: 9) |
| Adipoq-Rv | 5'-TCCTGTCATTCCAACATCTCC-3' (SEQ ID NO: 10) |
| aP2-Fw | 5'-GCAGACGACAGGAAGGTGA-3' (SEQ ID NO: 11) |
| aP2-Rv | 5'-CTTGTGGAAGTCACGCCTTT-3' (SEQ ID NO: 12) |
| Cidea-Fw | 5'-ATCACAACTGGCCTGGTTACG-3' (SEQ ID NO: 13) |
| Cidea-Rv | 5'-TACTACCCGGTGTCCATTTCT-3' (SEQ ID NO: 14) |
| Cox7a1-Fw | 5'-CAGCGTCATGGTCAGTCTGT-3' (SEQ ID NO: 15) |
| Cox7a1-Rv | 5'-AGAAAACCGTGTGGCAGAGA-3' (SEQ ID NO: 16) |
| Cox8b-Fw | 5'-GAACCATGAAGCCAACGACT-3' (SEQ ID NO: 17) |
| Cox8b-Rv | 5'-GCGAAGTTCACAGTGGTTCC-3' (SEQ ID NO: 18) |

TABLE 10-continued

Primer sequences used in qRT-PCR

| | | |
|---|---|---|
| CoxIVb-Fw | 5'-AGATGAACCATCGCTCCAAC-3' | (SEQ ID NO: 19) |
| CoxIVb-Rv | 5'-ATGGGGTTGCTCTTCATGTC-3' | (SEQ ID NO: 20) |
| Cytc-Fw | 5'-GGAGGCAAGCATAAGACTGG-3' | (SEQ ID NO: 21) |
| Cytc-Rv | 5'-TCCATCAGGGTATCCTCTCC-3' | (SEQ ID NO: 22) |
| Elovl3-Fw | 5'-GATGGTTCTGGGCACCATCTT-3' | (SEQ ID NO: 23) |
| Elovl3-Rv | 5'-CGTTGTTGTGTGGCATCCTT-3' | (SEQ ID NO: 24) |
| Glut4-Fw | 5'-ACGGTCTTCACGTTGGTCTC-3' | (SEQ ID NO: 25) |
| Glut4-Rv | 5'-CTCAAAGAAGGCCACAAAGC-3' | (SEQ ID NO: 26) |
| mCpt1-Fw | 5'-TTGCCCTACAGCTCTGGCATTTCC-3' | (SEQ ID NO: 27) |
| mCpt1-Rv | 5'-GCACCCAGATGATTGGGATACTGT-3' | (SEQ ID NO: 28) |

TABLE 10-continued

Primer sequences used in qRT-PCR

| | | |
|---|---|---|
| Pgc1a-Fw | 5'-AAGTGTGGAACTCTCTGGAACTG-3' | (SEQ ID NO: 29) |
| Pgc1a-Rv | 5'-GGGTTATCTTGGTTGGCTTTATG-3' | (SEQ ID NO: 30) |
| Pparg-Fw | 5'-AGGCCGAGAAGGAGAAGCTGTTG-3' | (SEQ ID NO: 31) |
| Pparg-Rv | 5'-TGGCCACCTCTTTGCTCTGCTC-3' | (SEQ ID NO: 32) |
| Pten-Fw | 5'-CAAATATTATTGCTATGGGATTTCCTGC-3' | (SEQ ID NO: 33) |
| Pten-Rv | 5'-GCTGTGGTGGGTTATGGTCTTC-3' | (SEQ ID NO: 34) |
| Ucp1-Fw | 5'-ACTGCCACACCTCCAGTCATT-3' | (SEQ ID NO: 35) |
| Ucp1-Rv | 5'-CTTTGCCTCACTCAGGATTGG-3' | (SEQ ID NO: 36) |
| Ucp3-Fw | 5'-ACTCCAGCGTCGCCATCAGGATTCT-3' | (SEQ ID NO: 37) |
| Ucp3-Rv | 5'-TAAACAGGTGAGACTCCAGCAACTT-3' | (SEQ ID NO: 38) |

The invention claimed is:

1. A method of treating obesity, comprising administering to a subject in need thereof a an effective amount of a compound of the formula

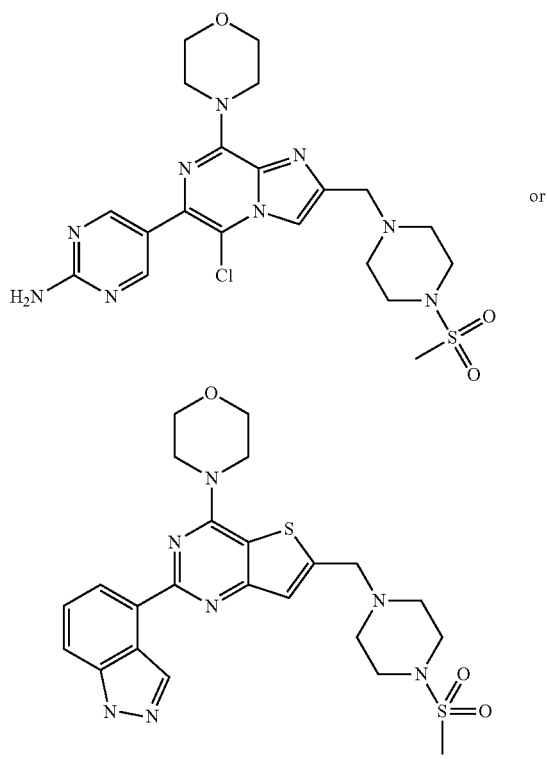

or a pharmaceutically acceptable salt thereof.

2. A method according to claim 1, wherein:
(a) biological energy expenditure is increased,
(b) total adiposity is decreased;
(c) brown adipocyte number is increased;
(d) brown adipose tissue (BAT) weight is increased; and/or
(e) white adipose tissue (WAT) weight is decreased,
compared to an otherwise equivalent individual that has not been treated with the phosphoinositide 3-kinase inhibitor.

3. A method according to claim 1, wherein:
(a) the expression of peroxisome proliferator-activated receptor gamma coactivator 1-a (Pgc1a) is increased in brown adipocytes;
(b) the expression of uncoupling protein 1 (Thermogenin/Ucp1) is increased in brown adipocytes;
(c) the level of active v-akt murine thymoma viral oncogene homolog 1 (Akt/PKB) is decreased in brown adipocytes;
(d) the level of active forkhead box protein O1 (FOXO1) is increased in brown adipocytes;
(e) the level of active forkhead box protein O3 (FOX03) is increased in brown adipocytes; and/or
(f) the level of Ser/Thr phosphorylated Irs1 is decreased in white adipocytes.

4. A method according to claim 3 wherein the brown adipocytes are situated in Brown Adipose Tissue (BAT) and/or White Adipose Tissue (WAT).

5. A method according to claim 1 wherein the compound is administered in combination (either concurrently or consecutively) with an anti-obesity medication.

6. A method according to claim 1, where the treating obesity promotes weight loss in an individual.

7. A method of treating obesity, comprising administering to a patient in need thereof from about 5 mg/kg per day to about 80 mg/kg per day of a compound of the formula

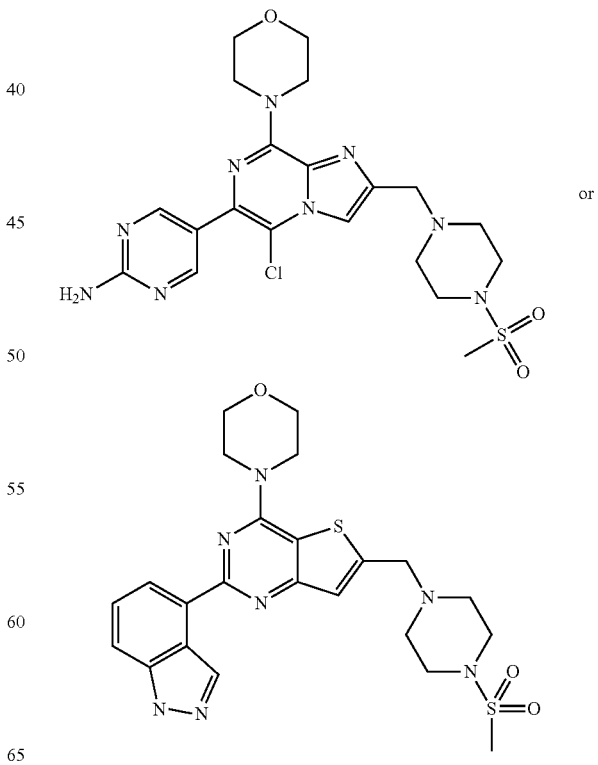

or a pharmaceutically acceptable salt thereof.

8. A method according to claim 1, wherein the compound is administered in combination (either concurrently or consecutively) with an anti-obesity medication selected from the group consisting of orlistat, sibutramine, rimonabant, metformin, exenatide, pramlintide and lorcaserin.

9. A method according to claim 1, wherein:
(a) biological energy expenditure is increased,
(b) total adiposity is decreased;
(c) brown adipocyte number is increased;
(d) brown adipose tissue (BAT) weight is increased; and/or
(e) white adipose tissue (WAT) weight is decreased, compared to an otherwise equivalent individual that has not been treated with the phosphoinositide 3-kinase inhibitor.

10. A method according to claim 1, wherein:
(a) the expression of peroxisome proliferator-activated receptor gamma coactivator 1-a (Pgc1a) is increased in brown adipocytes;
(b) the expression of uncoupling protein 1 (Thermogenin/Ucp1) is increased in brown adipocytes;
(c) the level of active v-akt murine thymoma viral oncogene homolog 1 (Akt/PKB) is decreased in brown adipocytes;
(d) the level of active forkhead box protein O1 (FOXO1) is increased in brown adipocytes;
(e) the level of active forkhead box protein O3 (FOX03) is increased in brown adipocytes; and/or
(f) the level of Ser/Thr phosphorylated Irs1 is decreased in white adipocytes.

11. A method according to claim 3 wherein the brown adipocytes are situated in Brown Adipose Tissue (BAT) and/or White Adipose Tissue (WAT).

12. A method according to claim 1 wherein the compound is administered in combination (either concurrently or consecutively) with an anti-obesity medication.

* * * * *

SEQUENCE LISTING

```
<160> NUMBER OF SEQ ID NOS: 38

<210> SEQ ID NO 1
<211> LENGTH: 24
<212> TYPE: DNA
<213> ORGANISM: Mus musculus

<400> SEQUENCE: 1
ccgctaatac gactcactat aggg                                         24

<210> SEQ ID NO 2
<211> LENGTH: 20
<212> TYPE: DNA
<213> ORGANISM: Mus musculus

<400> SEQUENCE: 2
tcatctcggc tccatcgttt                                              20

<210> SEQ ID NO 3
<211> LENGTH: 27
<212> TYPE: DNA
<213> ORGANISM: Mus musculus

<400> SEQUENCE: 3
gtcgacattt aggtgacact atagaag                                      27

<210> SEQ ID NO 4
<211> LENGTH: 22
<212> TYPE: DNA
<213> ORGANISM: Mus musculus

<400> SEQUENCE: 4
gatgctgtgt gctacaggga tg                                           22
```

<210> SEQ ID NO 5
<211> LENGTH: 21
<212> TYPE: DNA
<213> ORGANISM: Artificial Sequence
<220> FEATURE:
<223> OTHER INFORMATION: synthetic primer Ucp1-Fw

<400> SEQUENCE: 5
actgccacac ctccagtcat t                                    21

<210> SEQ ID NO 6
<211> LENGTH: 21
<212> TYPE: DNA
<213> ORGANISM: Artificial Sequence
<220> FEATURE:
<223> OTHER INFORMATION: synthetic primer Ucp1-Rv

<400> SEQUENCE: 6
ctttgcctca ctcaggattg g                                    21

<210> SEQ ID NO 7
<211> LENGTH: 21
<212> TYPE: DNA
<213> ORGANISM: Artificial Sequence
<220> FEATURE:
<223> OTHER INFORMATION: synthetic primer Actin-Fw

<400> SEQUENCE: 7
ggcaccacac cttctacaat g                                    21

<210> SEQ ID NO 8
<211> LENGTH: 20
<212> TYPE: DNA
<213> ORGANISM: Artificial Sequence
<220> FEATURE:
<223> OTHER INFORMATION: synthetic primer Actin-Rv

<400> SEQUENCE: 8
gtggtggtga agctgtagcc                                      20

<210> SEQ ID NO 9
<211> LENGTH: 21
<212> TYPE: DNA
<213> ORGANISM: Artificial Sequence
<220> FEATURE:
<223> OTHER INFORMATION: synthetic primer Adipoq-Fw

<400> SEQUENCE: 9
ggatgctact gttgcaagct c                                    21

<210> SEQ ID NO 10
<211> LENGTH: 21
<212> TYPE: DNA
<213> ORGANISM: Artificial Sequence
<220> FEATURE:
<223> OTHER INFORMATION: synthetic primer Adipoq-Rv

<400> SEQUENCE: 10
tcctgtcatt ccaacatctc c                                    21

<210> SEQ ID NO 11
<211> LENGTH: 19
<212> TYPE: DNA
<213> ORGANISM: Artificial Sequence
<220> FEATURE:
<223> OTHER INFORMATION: synthetic primer aP2-Fw

```
<400> SEQUENCE: 11
gcagacgaca ggaaggtga                                              19

<210> SEQ ID NO 12
<211> LENGTH: 20
<212> TYPE: DNA
<213> ORGANISM: Artificial Sequence
<220> FEATURE:
<223> OTHER INFORMATION: synthetic primer aP2-Rv

<400> SEQUENCE: 12
cttgtggaag tcacgccttt                                             20

<210> SEQ ID NO 13
<211> LENGTH: 21
<212> TYPE: DNA
<213> ORGANISM: Artificial Sequence
<220> FEATURE:
<223> OTHER INFORMATION: synthetic primer Cidea-Fw

<400> SEQUENCE: 13
atcacaactg gcctggttac g                                           21

<210> SEQ ID NO 14
<211> LENGTH: 21
<212> TYPE: DNA
<213> ORGANISM: Artificial Sequence
<220> FEATURE:
<223> OTHER INFORMATION: synthetic primer Cidea-Rv

<400> SEQUENCE: 14
tactacccgg tgtccatttc t                                           21

<210> SEQ ID NO 15
<211> LENGTH: 20
<212> TYPE: DNA
<213> ORGANISM: Artificial Sequence
<220> FEATURE:
<223> OTHER INFORMATION: synthetic primer Cox7a1-Fw

<400> SEQUENCE: 15
cagcgtcatg gtcagtctgt                                             20

<210> SEQ ID NO 16
<211> LENGTH: 20
<212> TYPE: DNA
<213> ORGANISM: Artificial Sequence
<220> FEATURE:
<223> OTHER INFORMATION: synthetic primer Cox7a1-Rv

<400> SEQUENCE: 16
agaaaaccgt gtggcagaga                                             20

<210> SEQ ID NO 17
<211> LENGTH: 20
<212> TYPE: DNA
<213> ORGANISM: Artificial Sequence
<220> FEATURE:
<223> OTHER INFORMATION: synthetic primer Cox8b-Fw

<400> SEQUENCE: 17
gaaccatgaa gccaacgact                                             20

<210> SEQ ID NO 18
```

```
<211> LENGTH: 20
<212> TYPE: DNA
<213> ORGANISM: Artificial Sequence
<220> FEATURE:
<223> OTHER INFORMATION: synthetic primer Cox8b-Rv

<400> SEQUENCE: 18
gcgaagttca cagtggttcc                                               20

<210> SEQ ID NO 19
<211> LENGTH: 20
<212> TYPE: DNA
<213> ORGANISM: Artificial Sequence
<220> FEATURE:
<223> OTHER INFORMATION: synthetic primer CoxIVb-Fw

<400> SEQUENCE: 19
agatgaacca tcgctccaac                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic primer CoxIVb-Rv

<400> SEQUENCE: 20
atggggttgc tcttcatgtc                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic primer Cytc-Fw

<400> SEQUENCE: 21
ggaggcaagc ataagactgg                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic primer Cytc-Rv

<400> SEQUENCE: 22
tccatcaggg tatcctctcc                                               20

<210> SEQ ID NO 23
<211> LENGTH: 21
<212> TYPE: DNA
<213> ORGANISM: Artificial Sequence
<220> FEATURE:
<223> OTHER INFORMATION: synthetic primer Elovl3-Fw

<400> SEQUENCE: 23
gatggttctg ggcaccatct t                                             21

<210> SEQ ID NO 24
<211> LENGTH: 20
<212> TYPE: DNA
<213> ORGANISM: Artificial Sequence
<220> FEATURE:
<223> OTHER INFORMATION: synthetic primer Elovl3-Rv

<400> SEQUENCE: 24
```
cgttgttgtg tggcatcctt                                             20

<210> SEQ ID NO 25
<211> LENGTH: 20
<212> TYPE: DNA
<213> ORGANISM: Artificial Sequence
<220> FEATURE:
<223> OTHER INFORMATION: synthetic primer Glut4-Fw

<400> SEQUENCE: 25
acggtcttca cgttggtctc                                             20

<210> SEQ ID NO 26
<211> LENGTH: 20
<212> TYPE: DNA
<213> ORGANISM: Artificial Sequence
<220> FEATURE:
<223> OTHER INFORMATION: synthetic primer Glut4-Rv

<400> SEQUENCE: 26
ctcaaagaag gccacaaagc                                             20

<210> SEQ ID NO 27
<211> LENGTH: 24
<212> TYPE: DNA
<213> ORGANISM: Artificial Sequence
<220> FEATURE:
<223> OTHER INFORMATION: synthetic primer mCpt1-Fw

<400> SEQUENCE: 27
ttgccctaca gctctggcat ttcc                                        24

<210> SEQ ID NO 28
<211> LENGTH: 24
<212> TYPE: DNA
<213> ORGANISM: Artificial Sequence
<220> FEATURE:
<223> OTHER INFORMATION: synthetic primer mCpt1-Rv

<400> SEQUENCE: 28
gcacccagat gattgggata ctgt                                        24

<210> SEQ ID NO 29
<211> LENGTH: 23
<212> TYPE: DNA
<213> ORGANISM: Artificial Sequence
<220> FEATURE:
<223> OTHER INFORMATION: synthetic primer Pgc1a-Fw

<400> SEQUENCE: 29
aagtgtggaa ctctctggaa ctg                                         23

<210> SEQ ID NO 30
<211> LENGTH: 23
<212> TYPE: DNA
<213> ORGANISM: Artificial Sequence
<220> FEATURE:
<223> OTHER INFORMATION: synthetic primer Pgc1a-Rv

<400> SEQUENCE: 30
gggttatctt ggttggcttt atg                                         23

<210> SEQ ID NO 31
<211> LENGTH: 23
<212> TYPE: DNA

```
<213> ORGANISM: Artificial Sequence
<220> FEATURE:
<223> OTHER INFORMATION: synthetic primer Pparg-Fw

<400> SEQUENCE: 31
aggccgagaa ggagaagctg ttg                                       23

<210> SEQ ID NO 32
<211> LENGTH: 22
<212> TYPE: DNA
<213> ORGANISM: Artificial Sequence
<220> FEATURE:
<223> OTHER INFORMATION: synthetic primer Pparg-Rv

<400> SEQUENCE: 32
tggccacctc tttgctctgc tc                                        22

<210> SEQ ID NO 33
<211> LENGTH: 28
<212> TYPE: DNA
<213> ORGANISM: Artificial Sequence
<220> FEATURE:
<223> OTHER INFORMATION: synthetic primer Pten-Fw

<400> SEQUENCE: 33
caaatattat tgctatggga tttcctgc                                  28

<210> SEQ ID NO 34
<211> LENGTH: 22
<212> TYPE: DNA
<213> ORGANISM: Artificial Sequence
<220> FEATURE:
<223> OTHER INFORMATION: synthetic primer Pten-Rv

<400> SEQUENCE: 34
gctgtggtgg gttatggtct tc                                        22

<210> SEQ ID NO 35
<211> LENGTH: 21
<212> TYPE: DNA
<213> ORGANISM: Artificial Sequence
<220> FEATURE:
<223> OTHER INFORMATION: synthetic primer Ucp1-Fw

<400> SEQUENCE: 35
actgccacac ctccagtcat t                                         21

<210> SEQ ID NO 36
<211> LENGTH: 21
<212> TYPE: DNA
<213> ORGANISM: Artificial Sequence
<220> FEATURE:
<223> OTHER INFORMATION: synthetic primer Ucp1-Rv

<400> SEQUENCE: 36
ctttgcctca ctcaggattg g                                         21

<210> SEQ ID NO 37
<211> LENGTH: 25
<212> TYPE: DNA
<213> ORGANISM: Artificial Sequence
<220> FEATURE:
<223> OTHER INFORMATION: synthetic primer Ucp3-Fw

<400> SEQUENCE: 37
actccagcgt cgccatcagg attct                                     25
```

```
<210> SEQ ID NO 38
<211> LENGTH: 25
<212> TYPE: DNA
<213> ORGANISM: Artificial Sequence
<220> FEATURE:
<223> OTHER INFORMATION: synthetic primer Ucp3-Rv

<400> SEQUENCE: 38
taaacaggtg agactccagc aactt                                    25
```